United States Patent [19]
Kamireddy et al.

[11] Patent Number: 5,597,573
[45] Date of Patent: Jan. 28, 1997

[54] LIPID-A ANALOGS: NEW MONOSACCHARIDE AND DISACCHARIDE INTERMEDIATES FOR ELICITING THERAPEUTIC ANTIBODIES AND FOR ANTITUMOR AND ANTIVIRAL ACTIVITIES

[75] Inventors: Balreddy Kamireddy, Hockessin, Del.; Michael J. Darsley, Rockville, Md.; David M. Simpson, Adelphi, Md.; Richard J. Massey, Rockville, Md.

[73] Assignee: Igen, Inc., Gaithersburg, Md.

[21] Appl. No.: 405,438

[22] Filed: Mar. 14, 1995

Related U.S. Application Data

[63] Continuation-in-part of PCT/US89/01950, May 4, 1989, and a continuation-in-part of Ser. No. 761,868, Sep. 3, 1991, and a continuation-in-part of Ser. No. 37,261, Mar. 26, 1993, abandoned, which is a continuation-in-part of Ser. No. 871,229, Apr. 17, 1992, abandoned, which is a continuation-in-part of Ser. No. 861,362, Mar. 27, 1992, abandoned.

[51] Int. Cl.$^6$ .......................... A61K 39/02; A61K 31/70; C07H 17/02
[52] U.S. Cl. ...................... 424/234.1; 424/283.1; 514/25; 536/17.1; 536/17.3; 536/17.4; 536/18.7
[58] Field of Search .................. 424/234.1, 283.1; 514/25; 536/17.1, 17.3, 17.4, 18.7

[56] References Cited

U.S. PATENT DOCUMENTS

| | | |
|---|---|---|
| 3,188,309 | 6/1965 | Mukaiyama et al. . |
| 4,659,567 | 4/1987 | Tramontano et al. . |
| 4,792,446 | 12/1988 | Kim et al. . |
| 4,888,281 | 12/1989 | Schochetman et al. . |
| 4,912,094 | 3/1990 | Myers et al. . |
| 4,929,604 | 5/1990 | Munford et al. . |
| 5,041,427 | 8/1991 | Takayama et al. . |
| 5,066,794 | 11/1991 | Shiba . |
| 5,134,230 | 7/1992 | Kusama et al. . |

FOREIGN PATENT DOCUMENTS

| | | |
|---|---|---|
| 0309411 | 3/1989 | European Pat. Off. . |
| 59-48497 | 3/1984 | Japan . |
| 3-135990 | 6/1991 | Japan . |
| WO84/04526 | 11/1984 | WIPO . |

OTHER PUBLICATIONS

Galanos et al (1977) Microbiology pp. 269–276.
Apicella et al (1985) Infect. Immun. 50(1):9–14.
Banerji et al (1979) J. Immunol. 123(6):2558–2562.
Karch et al (1983) J. Immunol 131(1):6–8.
Hermentin et al (1988) Behring Inst. Mitt., No. 82:197–215.
Louis et al (1979) Springer Semin. Immuno Pathol. 2:215–228.
Gould et al (1989) J. Natl Cancer Inst. 81(10):775–781.

(List continued on next page.)

*Primary Examiner*—Kay K. A. Kim
*Attorney, Agent, or Firm*—Curtis, Morris & Safford; Barry Evans; Pamela G. Salkeld

[57] ABSTRACT

The present invention relates to novel amidine components of formula (II):

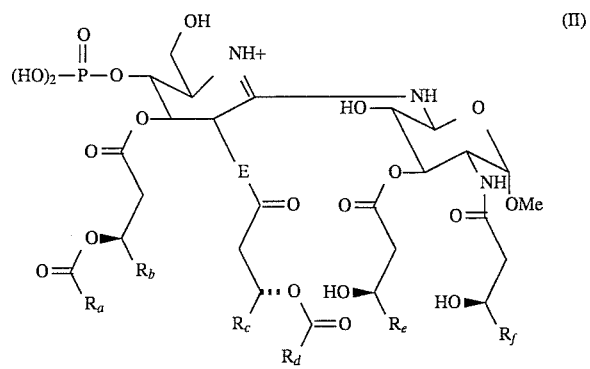

A method for eliciting antibodies in an animal which bind to Lipid A or LPS comprising administering to the animal as an immunogen a composition comprising such a compound is also disclosed.

6 Claims, 53 Drawing Sheets

R=C$_{11}$H$_{23}$

OTHER PUBLICATIONS

Osband et al (1990) Immunology Today 11(6):193–195.
Harris et al (1993) TIBTECH 11:42–44.
Waldmann Science 252:1657–1662 (1991).
Adorini, L. et al., Proc. Natl. Acad. Sci. USA, 85, 5181–5185 (1988).
Alving, C. R., J. Immunol. Meth., 140, 1–13 (1991).
Alving, C. R. and Richards, R. L., J. Immunol. Lett., 25, 275–280 (1990).
Arata, S., Mashimo, J., Kasai, N., et al., FEMS Microbiol Lett., 44, 231 (1987).
Arata S., Mashimo, J., Kasai, N., et al., FEMS Microbiol Lett., 49, 479 (1988).
Anderson, et al., CRU, 10, 27 (1977).
Atherton, E. and Sheppard, R. J., Chem. Soc. Commun., 1151–1152 (1981).
Berzofsky, J. A., Science, 229, 932–940 (1985).
Blundell, J. et al., Nature, 304, 273–275 (1983).
Brade, L., Rietschel, E.Th., Kusumoto, S., et al., Infec. Immunity, 51, 110 (1986).
Brade, L., Bradenberg, K., Kuhn, H. M. et al., Infec. Immunity, 55, 2636 (1987).
Buchner, H., Berl Klin Wochenschr, 47, 1084 (1987).
Carr, C. J. and Morrison, D., Rev. Inf. Dis., 6, 497–500 (1984).
Charon, D. and Szabo, Carbohydrate Res., 11, C9 and C13–C15 (1983).
Clackson, T., Hoogenboom, H. R., Griffiths, A. D. et al., Nature, 352, 624–628 (1991).
Cohen, C. J., Janis, R. A., Taylor, D. G., et al. In Calcium Antagonist and Cardiovascular Disease.
Coley, W. B, JAMA, 31, 389–95 and 456–65 (1988).
Corvol, P. et al., J. Biol. Chem., 262, 2913–2918 (1987).
Erwin, L. A. and Munford, S. R., J. of Biol. Chem., 265, 16444–16499 (1990).
Fersht, A. R. and Kirby, A. J., J. Am. Chem. Soc., 90, 5833 (1968).
Fersht, A., Enzyme Structure and Mechanism, 2d ed., 433–436 (W. H. Freeman and Co.)(1985).
Finam, M. J. and Kishi, Y., Tetrahedron Lett, 23, 2714 (1982).
Flick and Gifford, J. Immun. Meth., 68, 167–75 (1984).
Frisch, B. et al., Eur. J. Immunol., 21, 185–193 (1979).
Galanos, C., Luderitz, O. and Westphal, O., Eur. J. Biochem., 24, 116–122 (1971).
Galanos, C., Reitschel, E. T., Luderittz, O., and Westphal, O., Intern Rev Biochem, Biochemistry of Lipids II, Goodwin, T. W. (Ed.) 14, 239 (University Park Press)(1977).
Galanos, C., Reitschel, E. T., Luderittz, O. et al., Eur. J. Biochem., 31, 230 (1972).
Galanos, C., Luderitz, O., Freudenberg, M., et al., Eur. J. Biochem., 160, 55 (1986).
Galanos, C., Luderitz, O., Rietschel, E. T. et al., Eur. J. Biochem., 148, 1 (1985).
Galanos, C., Lehman, V., Luderitz, O., et al., Eur. J. Biochem., 140, 221 (1984).
Geysen, H. M., et al., J. Immun. Meth., 102, 259–274 (1987).
Geysen, H. M., et al., Proc. Nat'l Acad. Sci. USA, 82, 178–182 (1985).
Geysen, H. M., et al., Science, 235, 1184 (1978).
Golenbock et al., J. Biol. Chem. 266, 19490–19448 (1991).
Greenman, R. L., Shein, R. M., Martin, M. A., et al., JAMA, 266, 1097–1102 (1991).

Hagen, F. S. et al., Biochem. 30, 8415–8423 (1991).
Hall, C. L. and Munford, R. S., Proc. Nat'l. Acad. Sci. USA, 80, 6671 (1983).
Homma, J. Y., Matsuura, M. and Kumuzawa, Y., Drugs of the future, 14, 645 (1989).
Homma, J. Y., Matsuura, M., Kanegsaki, S., et al., J. Biochem., 98, 395 (1985).
Ho, D., J. Virol., 61, 2024 (1987).
Hopp, T. P. and Woods, K. R., Proc. Nat'l Acad. Sci. USA, 78, 3824–3828 (1981).
Huse, W., Sastry, L., Iverson, S., et al., Science, 246, 1275–1281 (1989).
Ikeda, S., Nishimura, C., Nakatsuka, et al., Antiviral Research, 9, 37 (1988).
Ikeda, S., Nishimura, C., Matsuura, M., et al., Antiviral Research, 13, 327–334 (1990).
Ikeda, S., Kumazawa, Y., Nishimura, C., et al., Int. J. Immunopharmacol., 10, 331 (1988).
Ikeda, S., Kumuzawa, Y., Nishimura, C., et al., Antiviral Research, 10, 167–178 (1988).
Imoto, M., Yoshimura, H., Sekiguchi, N., et al., Tetrahedron Lett., 26, 1545 (1985).
Imoto, M., Kusumoto, S., Shiba, T., et al., Tetrahedron Lett., 26, 907 (1985).
Imoto, M., Kusumoto, S., Shiba, T., et al., Tetrahedron Lett., 24, 4017 (1983).
Imoto, M., Yoshimura, H., Kusumoto, S., et al., Proc. Jpn Acad., 60B, 285 (1984).
Imoto, M., Yoshimura, H., Yamamoto, M., et al., Tetrahedron Lett., 25, 2667–2670 (1984).
Inage, M., Chaki, H., Imoto, M., et al., Tetrahedron Lett., 24, 2011 (1983).
Inage, M., Chaki, H., Kusumoto, S., et al., Tetrahedron Lett., 22, 2281 (1981).
Inage, M., Chaki, H., Kusumoto, S., et al., Tetrahedron Lett., 21, 3889 (1980).
Inage, M., Chaki, H., Kusumoto, S., et al., Chem. Lett., 1373–6 (1980).
Jeannin et al., Gastroenterology, 101, 726–733 (1991).
Jencks, W. P., Adv. Enzymol., 43, 219 (1975).
Jacobs, et al., J. Am. Chem. Soc., 109, 2174–2176 (1987).
Kanegasaki, S., Tanamoto, K., Yasuda, T., et al., J. Biochem., 99, 1203 (1986).
Kanegasaki, S., Yasuhiko, K., Matsuura, J., et al., Eur. J. Biochem., 143, 237–242 (1984).
Kasai, N., Arata, S., Mashimo, J., et al., Infec. Immunity, 51, 43 (1986).
Kasai, N., Arata, S., Mashimo, J., et al., Biochem. Biophys. Res. Commun, 28, 607 (1985).
Katsuki, T. and Sharpless., J. Am. Chem. Soc., 102, 5974 (1980).
Katz, D. M., et al., Biochemistry, 18, 690–697 (1979).
Ketchan, Jambotkar and Martinelli., J. Org. Chem., 27, 4666 (1962).
Kiso, M., Tanaka, S., Fujita, M., et al., J. Carbohy. Res., 162, 127 (1987).
Kiso, M., Fujita, M., Hayashi, E., et al., J. Carbohy. Chem., 6, 691 (1987).
Kiso, M., Fujita, M., Tanahashi, M., et al., J. Carbohy. Res., 177, 51 (1988).
Kiso, M., Ishida, H. and Hasegawa, A., Agri. Biol. Chem., 48, 251 (1984).
Kiso, M. and Hasegawa, Bacterial Endotoxin–Chemical, Biological And Clinical Aspects, Homma, Y, J., Kanegasaki, O., et al., (Eds.), 39, (verlag Chemie)(1984).

Kiso, M., Tanaka, S., Tanahashi, M., et al.,, Carbohy. Res., 148, 221 (1986).
Kiso, M., Nishiguchi, H., Nishihori, K., et al., Carbohy. Res., 88, C10 (1981).
Kiso, M., Tanaka, S., Fujishima, M., et al., Carbohy. Res., 162, 247 (1987).
Kotani, S., Takada, H., Tsujimoto, M., et al., Infect. Immun., 45, 293 (1984).
Kotani, S., Takada, H., Takahashi, I., et al., Infect. Immun., 52, 872 (1986).
Kotani, S., Takada, H., Tsujimoto, M., et al., Infect. Immun., 41, 758 (1983).
Kotani, S., Takada, H., Tsujimoto, M., et al., Infect. Immun., 49, 225–237 (1985).
Kreger, B. E., Craven, D. E. and McCabe, W. R., Am. J. Med. 68, 344–355 (1980).
Kumazawa, Y., Nakatsuka, M., Takimoto, H., et al., Infect. Immun., 56, 149 (1988).
Kumazawa, Y., Takimoto, H., Yamamoto, A., et al., FEBS Lett., 239, 117 (1988).
Kumazawa, Y., Matsuura, M., Nakatsuuru–Watanabe, Y., et al., Eur. J. Immunol., 14, 109 (1984).
Kumazawa, Y., Ikeda, S., Takimoto, H., et al., Eur. J. Immunol., 17, 663 (1987).
Kumazawa, Y., Matsuura, M., Homma, J. Y., et al., Eur. J. Immunol., 15, 199–201 (1985).
Kumazawa, Y., Matsuura, J., Homma, J. Y., et al., Eur. J. Immunol., 16, 1099–1103 (1986).
Kusawa, T., Soga, T., Shioya, E., et al., Chem. Parm. Bull., 38, 3366–3372 (1990).
Kusumoto, S., Yoshimura, H., Imoto, M., et al., Tetrahedron Lett., 26, 909 (1985).
Lemieux, U. R. and Ratcliffe, M. R., Can. J. Chem., 57, 1244 (1979).
Lerner, R. A., Benkovic, S. J. and Schultz, P. G., Science, 252, 659–667 (1991).
Littlefield, J. W., Expt'l. Cell Res., 41, 190 (1966).
Luderitz, O. C., Galanos, C. and Rietschel, E., Pharmacology of Bacterial Toxins, Dolmer, F. and Drews, J. (Eds.) 1986.
Luderitz, O., Westphal, O., Staub, A. M, and Nikaido, H., Microbial Toxins, 4, 145 (1971).
Maki, D. G., In Nosocomial Infection, Dixon, R. E. (Ed.) 183–196 (1981).
Martin, S, V., Woodard, S. S., Katsuki, Y., et al., J. Am. Chem. Soc., 103, 6237 (1981).
Matsuura, M., Kojima, Y., Homma, J. Y., et al., Bacterial Endotoxin Chemical, Biological and Clinical Aspects, Homma, Y, J., et al., 61 (Verlag Chemie) (1981).
Matsuura, M., Yamamoto, A., Kojima, Y., et al., J. Biochem., 98, 1229 (1985).
Matsuura, M., Kojima, Y., Homma, J., Y., et al., J. Biochem., 99, 1377 (1986).
Matsuura, M., Kojima, Y., Homma, J, Y., et al., FEBS Lett., 167, 226 (1984).
Matsuura, M., Kojima, Y., Homma, J. Y., et al., Eur. J. Biochem., 137, 639 (1983).
Maccafferty, J., Giffiths, A. D., Winter, G. and Chiswell, D. J., Nature, 348, 552–554 (1990).
Mcdermott, C. M., Cullor, J. S. and Fenwick, B. W., Infect. Immunol. 59, 478–485 (1991).
Menard, J. and Catt, K. J., Endocrinology, 90, 422–430 (1972).
Milstein, C. et al., Nature, 266, 550 (1977).
Munford, R. S. and Hall, C. L., Science, 234, 203 (1986).
Munford, R. S. and Hall, C. L., Infect. Immun., 48, 464–473 (1985).
Nagaoka, H. and Kishi, Y., Tetrahedron Lett., 37, 3873 (1981).
Nakatsuka et al., Int. J. Immunopharmacol., 11, 349–358 (1989).
Nakatsuka et al., Int. J. Immunopharmacol., 12, 599–603 (1990).
Nakatsuka et al., Int. J. Immunopharmacol., 13, 11–19 (1990).
Nakatsuka, M., Kumazawa, Y., Ikeda, S., et al., J. Clin. Lab. Immunol., 26, 43 (1988).
Napper, A. D., et al., Science, 237, 1041–1043 (1987).
Nichima, T., Soga, T. and Shiba, T., et al., Chem. Abstracts, 110, 1356486(1989).
Novotny, J., et al., Proc. Nat'l Acad. Sci. USA, 226 (1986).
Nowotny, A, Beneficial Effects of Endotoxins, Nowotny, A. (Ed). (Plenum Press) 1–55 (1983).
Page, M. I., (Ed), The Chemistry of Enzyme Action, Ch. 1 (Elsevier)(1984).
Pauling, L., Sci. Am., 36, 51 (1948).
Pert, C. B. et al., Proc. Nat'l. Acad. Sci, USA, 83, 9254–9258 (1986).
Pincus, M. R. et al., Biochem. Biophys. Res. Commun., 143(a), 248–251 (1987).
Pollack, et al., Science, 234, 1570–1573 (1986).
Powell, M. J. and Hansen, D. E., Protein Engineering, 3, 69–75 (1989).
Qureshi et al., Infect. and Immun. 59, 441–444 (1991).
Qureshi, N., Takayama, K., Heller, D. and Fenslelau, C., J. Biol. Chem., 258, 12947 (1983).
Raso et al., J. Am. Chem. Soc., 95, 1621–1628 (1973).
Schaff, M. D. et al., Cell, 8, 405 (1976).
Schuster, B. G. et al., J. Immunol. 122, 900–905 (1979).
Shenep, J. L., Barton R. P. and Mogan, K. A., J. Infect. Dis., 151, 1012–1018 (1985).
Shimizu, T., Akiyama, S., Masuzawa, T., et al., Chem. Pharm. Bull., 34, 5169 (1986).
Shimizu, T., Akiyama, S., Masuzawa, T., et al., Chem. Pharm. Bull., 33, 4621 (1985).
Shimizu, T., Akiyama, S., Masuzawa, T., et al., Infect. Immunity, 55, 2287 (1987).
Shokat, K., Leumann, C. J., Sugasawara, R. et al., Angew. Chem. Int. Ed. Engl., 27, 269–271 (1989).
Sidorczyk, Z., Zahringer, U. and Rietschel, E., Eur. J. Biochem., 137, 15 (1983).
Strain, S. M., Fesik, S. W. and Armitage, I. M., J. Biol. Chem., 258, 2906 (1983).
Szabo, P., Sarfati, S. R., Diolez, C. and Szabo, L., Carbohydrate Res., 111, c9–c12 (1983).
Takada, H., Kotani, S., Tanaka, S., et al., Eur. J. Biochem., 175, 573.
Takada, H., Kotani, S., Tsujimoto, M., et al., Infect. Immun., 48, 219–227 (1985).
Takayama, K., Qureshi, N., Ribi, E. and Cantrell, J. L., Rev. Infec. Dis., 6, 439 (1984).
Takayama, K., Qureshi, N., Mascagni, P., et al., J. Biol. Chem., 258, 14245 (1983).
Tanamoto, K., Zahringer, U., Mckenzie, G. R., et al., Infec. Immunity, 44, 421 (1984).
Teng, N. H., Kaplan, H. S., Herbert, J. M., et al., Proc. Natl. Acad. Sci. USA, 82, 1970 (1985).
Tramontano, et al., Pro. Nat'l Acad. Sci. USA, 83, 6736–6740 (1986).

Tramontano, et al., J. Cell. Biochem., Supp. 11c, Abtracts, 238 (1987).

Tramontano et al, Science, 234, 1566–1570 (1986).

Waage, A., Brandtzaeg, P., Halstensen, A., et al., J. Exp. Med., 169, 333–338 (1989).

Walker, B. D. et al., Proc. Nat'l. Acad. Sci. USA, 84, 8120 (1987).

Westphal, O., Luderitz, O., Eichenberger, E. and Keiderling, W. Z, Naturforsch, 76, 536 (1952).

Westphal, O., Luderitz, O., Eichenberger, E. and Neter, E., Chemistry and Biology of Monopolysaccharides, 187 (1958).

White, H. and Jencks, W. P., J. Biol. Chem., 252, 1688 and 1700 (1976).

Wilchek, M. and Banniger, S., Meth. Enzymol., 70, 151–159 (1980).

Yasuda, T., Kanegasaki, S., Tsumita, T., et al., Eur. J. Biochem., 140, 245–248 (1984).

Zeigler, E. J. et al., N. Engl. J. Med., 324, 429–436 (1991).

Immunogen-2M

Acid-4   Acid-3

PMB = P-methoxy benzyl

54

1. PTSA-MeOH
2. Ms-Cl
3. NaN₃
4. H2, Pd-C
5. HF-pyridine

Immunogen 2D-AL

Immunogen ID-AL

R=C₁₁H₂₃

79

88

R=C₁₁H₂₃
R'= 4-nitrobenzyl

89

LIPID-A ANALOGS: NEW MONOSACCHARIDE AND DISACCHARIDE INTERMEDIATES FOR ELICITING THERAPEUTIC ANTIBODIES AND FOR ANTITUMOR AND ANTIVIRAL ACTIVITIES

This application is a continuation of application Ser. No. 08/037,261, filed Mar. 6, 1993, now abandoned, which is a continuation-in-part of application Ser. No. 871,229, filed Apr. 17, 1992, now abandoned, which in turn is a continuation-in-part of application Ser. No. 861,362, filed Mar. 27, 1992, now abandoned, each of which are hereby incorporated herein by reference. This application is also a continuation-in-part of U.S. application Ser. No. 761,868, having an international filing date of May 4, 1989 under 35 U.S.C. §363, and a date of Sep. 3, 1991 under 35 U.S.C. §§102(e) and 371(c). This application is also a continuation-in-part of PCT/US89/01950 designating the U.S. and filed May 4, 1989. Said application Ser. No. 761,868 and said PCT/US89/01950 being hereby incorporated herein by reference. Reference is also made to U.S. application Ser. No. 07/700,210 having an international filing date of May 4, 1989 under 35 U.S.C. §363, and a date of Jun. 12, 1991 under 35 U.S.C. §§102(e) and 371(c), now abandoned, said application Ser. No. 07/700,210 being hereby incorporated herein by reference. Reference is further made to U.S. application Ser. No. 07/190,271, filed May 4, 1988, now abandoned, also incorporated herein by reference.

FIELD OF THE INVENTION

This invention relates to Lipid-A analogs and methods of using such analogs such as for eliciting catalytic antibodies for detoxification of LPS and Lipid-A, which bind to Lipid-A and LPS for the treatment of septic shock, for inducing protective immunity against the harmful effects of gram-negative bacterial infection, for protecting against viral infection, for treating and controlling tumor growth, and for binding to receptors in competition with Lipid-A. The invention also relates to Lipid-A analogs as transition state analogs for eliciting catalytic antibodies for the detoxification of LPS and Lipid-A, compositions which are useful for protective activity against gram-negative bacterial infection, as an antiviral composition, as an antitumor composition and for binding to receptors in competition with Lipid-A. The invention further relates to catalytic antibodies which cleave the ester bonds and glycosidic bond of Lipid-A for the detoxification of LPS and Lipid-A, and an antibody which binds to LPS, Lipid-A and the Lipid-A analogs and to methods of using such an antibody; for instance, in treating septicemia.

This invention further relates to a novel method for generating antibodies of both the IgG and the IgM isotype against Lipid-A and its analogs and amphipathic molecules of similar structures.

Various documents are cited parenthetically throughout the text of this disclosure, with full citation to these documents appearing as a list immediately preceding the claims. These documents pertain to the field of this invention; and, each of these documents is hereby incorporated herein by reference.

BACKGROUND OF THE INVENTION

Bacteremia is a severe infection of microorganisms in the bloodstream. The organisms cause a variety of symptoms including fever, shock, transient leukopenia and thrombocytopenia. Septic shock results when cardiac output cannot maintain the blood pressure due to a loss of intravascular volume. Septic shock can be caused by Gram-negative and Gram-positive bacteria, fungi, and although infrequently, by rickettsias or viruses. *Escherichia coli* account for a major portion of the cases of Gram-negative bacteremia.

The incidence of nosocomial bacteremia due to Gram-negative bacilli has been increasing since the 1950's despite the advent of antibiotics. It is now estimated to affect 260,000 to 300,000 patients per year in the United States with a mortality rate of 20 to 50% (1,2) even when treated under optimal situations. When the bacteremia is further complicated by renal or respiratory failure, the mortality approaches 90–100% (3).

Sepsis and septic shock may result from many causes, such as wound contamination in a traumatized patient, postoperative surgical complications, dissemination of a localized infection, or invasion of microorganisms through or around invasive instruments. Sepsis can be further complicated by immune suppression, as often occurs during critical illnesses. Most patients die from progressive multiorgan failure, which is thought to be due to the release of toxic substances from the infecting organisms (e.g., endotoxin), the release of secondary endogenous mediators, and altered metabolic status, resulting in progressive tissue ischemia.

Many of the symptoms and effects of Gram-negative bacteremia are consistent with the premise that endotoxin, or the lipopolysaccharide (LPS) component of the bacterial outer membrane, is the causative agent of the bacteria-induced shock. The Lipid-A portion of LPS is structurally conserved amongst the Enterobacteriaceae and is responsible for most of the biological effects attributed to endotoxin. Although the length, number, saturation, and position of the acyl and acyloxyacyl chains are heterogeneous in the Lipid-A structure, the basic structure is common to all the Lipid-A molecules. Lipid-A molecules from some organisms such as *E. coli* are not as variable. LPS stimulates various cell types to release mediators, hormones or other factors, in particular tumor necrosis factor (TNF), interleukin-1 and interleukin-6, which in turn act on other organs or target tissues (4). Current therapeutic intervention includes antibiotics and fluids to increase intravascular volume, though these treatments are often unsuccessful at halting the cascading effects triggered by LPS. Antibiotics may reduce the bacteremia, but may also increase the amount of LPS shed into the bloodstream (5). As secondary complications occur, the physician must use other therapies to compensate for or to save the affected target organs. Experimental treatments employing murine and human monoclonal antibodies specific for Lipid-A are yielding encouraging results (6, 7).

It has also been proposed to employ antibodies specific for the Lipid-A moiety of LPS as treatment for septicemia or septic shock. Such antibodies have been IgM antibodies which are relatively large molecules and do not easily penetrate tissues.

Most monoclonal antibodies generated against the Lipid-A region of LPS have been produced by immunizing with killed cells of R-mutant gram-negative bacteria, or with such cells coated with additional Lipid-A or analogs. This approach has the disadvantage that the immune system is presented with natural Lipid-A structures at the same time as it is presented with the analog so that it is not certain exactly what the eliciting antigen for a given Mab might have been. In order to generate novel antibodies against Lipid-A with improved therapeutic properties including catalytic activity, it is desired to specifically stimulate the immune system with defined analogs.

Liposomes have been used widely and successfully as the basis for immunogens and vaccines to generate antibody responses to otherwise poorly immunogenic proteins or to obviate the need for harmful adjuvants (8, 9). It has also long been known that liposomes incorporating Lipid-A could induce antibodies capable of reacting with purified Lipid-A (10). Recently liposomes incorporating Lipid-A have been used to raise antibodies against short synthetic peptides which react with the native protein from which the peptide sequence was derived (11).

Recently it has been shown that monoclonal antibody fragments can be isolated by methods other than the conventional process of fusing specific B-cells with myeloma cells to generate hybridomas which secrete MAbs. The new method involves the isolation of the gene fragments encoding antibody molecules by their amplification, by the polymerase chain reaction (PCR), and cloning followed by expression as functional antigen binding molecules on the surface of filamentous phage particles (12, 13), or into the periplasmic space of bacteria infected with recombinant lambda-phage (14). The starting point for the PCR amplification of antibody-encoding gene fragments can be any of the following: splenocytes isolated from a mouse or other animal immunized with an antigen, eg. a transition state analog; splenocytes isolated from an unimmunized animal; peripheral blood lymphocytes isolated from a human donor. Throughout this disclosure wherever reference is made to antibodies (or catalytic antibodies) or fragments thereof it is recognized that this applies both to antibodies derived by hybridoma technology and to antibodies isolated using the bacteriophage technologies outlined above. A fuller description of this technology is given in the copending application Ser. No. 07/841,648, filed Feb. 24, 1992, now abandoned, and incorporated herein by reference.

The manner in which catalytic antibodies carry out chemical reactions on substrates (or antigens) is essentially governed by the same theoretical principles that describe how enzymes carry out chemical reactions. For most chemical transformations to occur, substantial activation energy is required to overcome the energy barrier that exists between reactant and product. Enzymes catalyze chemical reactions by lowering the activation energy required to form the short-lived unstable chemical species found at the top of the energy barrier, known as the transition state (15, 16).

Four basic mechanisms are employed in enzymatic catalysis to lower the free energy of the rate limiting transition state, thereby accelerating the rate of a chemical reaction. Firstly, the active site of an enzyme is complementary in atomic and electronic structure to the transition state, such that the energy of the transition state is lower when bound to the enzyme than when free in solution. Secondly, general acid and base residues are often found optimally positioned for participation in catalysis within catalytic active sites causing the reaction to proceed via alternative and lower energy transition states. A third mechanism involves the formation of covalent enzyme-substrate intermediates. Fourth, model systems have shown that binding reactants in the proper orientation for reaction can increase the "effective concentration" of reactants by at least seven orders of magnitude (17).

Drawing upon this understanding of enzymatic catalysis, several antibodies with catalytic activity have been designed and isolated (18). Antibodies are elicited to compounds that resemble the transition state of a desired reaction (i.e., transition state analogs).

Several laboratories have studied the breakdown and detoxification of LPS and Lipid-A analogs (19, 20, 21, 22, 23, 24, 25, 26, 27, 28, 29, 30, 31, 32, 33). Their studies suggest that synthetic analogs of Lipid-A (*E. coli*) having one or more acyloxyacyl groups removed were less toxic than Lipid-A itself. The potential for detoxification of LPS is also demonstrated by the hydrolysis of the ester bonds of Lipid-A with the enzyme acyloxyacyl hydrolase, which removes the 3-hydroxytetradecanoyl chains of LPS, leaving hydroxyl groups (34, 35, 36, 37). Another study suggests that synthetic O-deacylated Lipid-A compounds are non-toxic (38, 39).

Based on these observations it is desired to develop transition state analogs of Lipid-A and LPS to elicit catalytic antibodies which can cleave the ester bonds of Lipid-A and LPS to detoxify the endotoxins. The target bonds for the catalytic antibodies are shown with arrows in FIG. 40 wherein the targets for ester bond hydrolysis are designated Immu-1, Immu-2, and Immu-3. It has also been shown that the synthetic monosaccharide analogs of Lipid-A and LPS are non-toxic (40). Based on this fact, it is also desired to design transition state analogs which will elicit catalytic antibodies which cleave the glycosidic bond of LPS and Lipid-A to the monosaccharide derivative (site Immu-4 in FIG. 40). It is desired to achieve this by eliciting catalytic antibodies to amidine transition state analogs of Lipid-A.

It is desired to employ catalytic antibodies to treat septicemia or septic shock. Catalytic antibodies are more efficacious than ordinary antibodies as a single molecule can inactivate many molecules of LPS. Catalytic antibodies can have better penetration of tissues as catalytic antibodies can be IgG-type antibodies or catalytically active fragments thereof (e.g. Fab, Fv, SCAb (single-chain antibodies) which are smaller in size). If these are conventional (non-catalytic) LPS binding antibodies of smaller size than IgM (e.g. IgG or fragments) they are unlikely to be effective in treatment or are less effective because they lack the effector functions associated with therapeutic action. On the contrary, the effector function of catalytic antibodies, namely the chemical detoxification of LPS, is mediated by the binding site such that any fragment which contains that site, however small, will be equally active. It is also desired to have new IgM-type antibodies which are also useful for treating septicemia or septic shock. Further, it is desired to be able to employ a cocktail of antibodies—of either various catalytic antibodies or of a mix of catalytic and binding antibodies (and of either IgG, IgM, antibody fragments, or a mix of IgG and IgM and antibody fragments)—to treat septicemia or septic shock. Thus, it is highly desired to obtain Lipid-A analogs which are capable of eliciting the desired catalytic and binding antibodies.

Further, therapeutic catalytic antibodies are desired for the treatment of sepsis and septic shock by means of cleavage of the glycosidic bond between the two monosaccharides for the detoxification of Lipid-A and LPS. In addition, antibodies generated against the analogs which bind to the Lipid-A moiety of LPS can have therapeutic efficacy in treatment of sepsis and are, therefore, also desired. Catalytic antibodies for reducing the toxicity of other compounds, e.g., glycosidic bond containing drugs or for activating compounds, e.g., glycosidic prodrugs, are also desired. It is also desired to be able to elicit such antibodies as an immunological response, for instance, to vaccinate against toxic substances. Thus, it is highly desired to obtain Lipid-A analogs which elicit these desired antibodies and which can be administered.

Lipid-A, which is responsible for endotoxic activity also exhibits beneficial antitumor (TNF inducing) and antiviral (IFN inducing) activities. Lipid-A analogs having decreased toxicity have been prepared and their biological activities studied (39, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91). Monophosphorylated Lipid-A analogs exhibited Limulus, mitogenic, PBA, TNF (tumor necrosis factor) —inducing and IFN (interferon)—inducing activities, as well as protective activity against gram-negative bacteria, antiviral activity and antitumor activity.

It is also desired to prepare Lipid-A analogs having decreased toxicity but equivalent or increased beneficial antitumor and antiviral activities. The above-referenced studies demonstrate that both monosaccharide derivatives of Lipid-A having acyl chains and monophosphoryl Lipid-A analogs are non-toxic but retain some of their beneficial activities. The activity of these molecules may be dependent upon the composition of the lipid chains (e.g., the presence and position of functional groups and individual lipid chains); but, Applicants do not wish to necessarily be bound by any one particular theory. For instance, the presence of both a free hydroxyl group (i.e., hydroxy tetradecanoic) on the lipid chain attached to the 3-hydroxy group and a lauroyloxy tetradecanoic acid group attached to the 2-amino group of the monosaccharide was shown to produce a compound having good TNF inducing activity but only moderate IFN inducing activity. In contrast, reversing the position of these two groups, i.e., a lauroyloxy tetradecanoic acid group attached to the 3-hydroxy group and a hydroxy tetradecanoic acid group attached to the 2-amino position resulted in good IFN inducing activity but only moderate TNF inducing activity. These observations show that the presence and position of functional groups in the hydrophobic lipid region of Lipid-A and LPS can play an important functional role in the expression of activity.

It is desired to design new and novel compounds for use as therapeutic agents. For instance, it is desired to design new compounds having a hydroxy functionality in the lipid region without changing the hydrophobicity by eliminating an acyl chain.

It is especially desired to synthesize analogs having the pentavalent phosphorus in place of carbonyl carbon at the ester bond, allowing both a hydroxyl group and a lipid chain at the same position. The structure-activity relationship noted above indicates that such compounds have unique, improved and desired biological activities.

It is desired to obtain Lipid-A analogs which exhibit the beneficial activities of Lipid-A or of previous Lipid-A analogs with reduced toxicity or even without toxicity. It is also desired to obtain Lipid-A analogs having conformational rigidity (for instance so that the analog's activities are closer to the activities of Lipid-A), as well as a means for introducing nucleophilic functionality, such as hydroxyl, without decreasing lipophilicity (for instance by a pentavalent phosphorous in the lipophilic region). It is further desired to have a Lipid-A analog which allows direct attachment of pentavalent phosphorous to a sugar backbone. More particularly, it is desired to have both ester and hydroxy moieties at either the Immu-1 or Immu-2 positions (FIG. 40) so that the resultant Lipid-A analog exhibits superior IFN and TNF inducing activities.

When one further considers the four positions labeled in the accompanying structure of Lipid-A, e.g., Immu-1, Immu-2, Immu-3 and Immu-4 (FIG. 40), these would be sites for cleavage of Lipid-A by a catalytic antibody so as to detoxify Lipid-A. However, heretofore, no such catalytic antibody or compounds to elicit such have been described. It is thus desired to provide compounds which mimic the transition state (transition state analogs) of hydrolytic reactions at these positions in Lipid-A so as to elicit superior catalytic antibodies which can detoxify Lipid-A, e.g., by cleavage of ester bonds and/or glycosidic bonds of Lipid-A or LPS.

SUMMARY OF THE INVENTION

The invention disclosed herein entails the production of catalytic antibodies which detoxify the endotoxin activity by hydrolyzing the LPS or Lipid-A to products which are inactive or have reduced toxicity. Clinical trials have demonstrated some success in treating sepsis with conventional antibodies of the IgM class, i.e. the pharmacokinetics for antibody therapy are favorable. Addition of catalytic degradation by the present invention offers the advantage of reduced doses with higher efficacy and the ability to use smaller antibody fragments which better penetrate the tissues and detoxify the LPS before it reaches the bloodstream.

The present invention provides a novel method of generating high titre IgG and IgM immune responses to Lipid-A, its analogs and other similarly amphipathic molecules. It employs liposomes as a vehicle and specific stimulatory peptides to enlist the involvement of T-Cells in the response. The generation of high titre IgM responses by this method means that such formulations are most effective as vaccines to induce protective immunity against the harmful effects of endotoxemia and gram-negative sepsis. The ability to generate a T-dependent immune response to Lipid-A and its analogs with the resulting high affinity, highly diversified IgG component greatly increases the ability to isolate catalytic monoclonal antibodies capable of detoxifying LPS which are therefore effective in treating endotoxemia and gram-negative sepsis.

A novel feature of this invention in using liposomes incorporating Lipid-A to raise antibodies is the use of a peptide sequence which is known to be the major T-Cell stimulatory region in Balb/c (H-$2^d$) mice immunized with Hen Egg Lysozyme (HEL) (92) in the liposome formulation to recruit T-cells into, and so dramatically increase, the immune response to Lipid-A and its analogs.

This invention encompasses the development of therapeutic catalytic antibodies for the treatment of Gram-negative bacteremia and septic shock. Four sites of the Lipid-A and LPS molecule are targeted for cleavage by the catalytic antibodies: 1) the ester bond of the acyloxyacyl chain which is linked to the 2'-N glucosamine position (designated Immu-1 in FIG. 40) (2) the ester bond of the acyloxyacyl chain of the 3'-O acyl group (designated Immu-2 in FIG. 40) (3) the ester bond of the O-acyl chain at the 3'-O position of the glucosamine (designated Immu-3 in FIG. 40); and, 4) the bond between beta 1-6 linked glucosamine residues (Immu-4 in FIG. 40).

The present invention provides Lipid-A analogs having a hydroxy functionality in the lipid region without changing the hydrophobicity (without eliminating an acyl chain) by substituting pentavalent phosphorus for tetravalent carbon at specific locations in the lipid region. The transition state analogs of the present invention contain hydroxy and ester functionalities at the same position and hence elicit superior antibodies.

It is therefore an object of the invention to provide Lipid-A analogs which elicit the desired therapeutic antibodies—either binding or catalytic antibodies, or both. It is a further object of this invention to provide novel Lipid-A analogs which exhibit the beneficial activities of Lipid-A or previous Lipid-A analogs, but have reduced or no toxicity. It is a further object of the invention to provide Lipid-A analogs having any or all of: conformational rigidity; means for introducing nucleophilic functionality, such as hydroxyl, without decreasing lipophilicity (e.g., pentavalent phosphorous in lipophilic region); and means for direct attachment of pentavalent phosphorous to a sugar backbone.

Thus, the present invention provides a compound of formula (I):

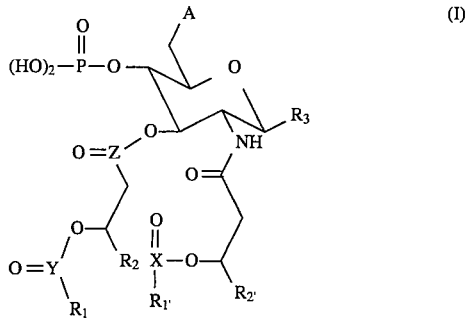

wherein:

each of $R_1$, $R_{1'}$, $R_2$ and $R_{2'}$, independent of each other is a substituted or unsubstituted, branched or linear $C_{1-12}$ alkyl, alkene or alkyne group, $R_3$ is OH, $OCH_3$, $CH_2COOH$ or

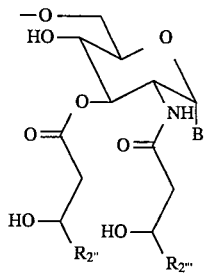

wherein each of $R_{2''}$ and $R_{2'''}$, independent of each other, is a substituted or unsubstituted, branched or linear $C_1$-$C_{12}$ alkyl, alkene or alkyne group, and:

A=$NH_2$, X=P(OH), Y=Z=C, B (if present)=$OCH_3$, or
A=OH, X=P(OH), Y=Z=C, B (if present)=$OCH_3$, or
A=$OCO(CH_2)_nNH_2$, X=P(OH), Y=Z=C, B (if present)=$OCH_3$, wherein n=1–10, or
A=OH, X=P(OH), Y=Z=C, B (if present)=$O(CH_2)_nCO_2H$, wherein n=1–10, or
A=OH, X=P(OH), Y=Z=C, B (if present)=$(CH_2)_nCO_2H$, where in n=1–10, or
A=$NH_2$, X=Z=C, Y=P(OH), B (if present)=$OCH_3$, or
A=OH, X=P(OH), Y=Z=C, B (if present)=$OCH_3$, or
A=$OCO(CH_2)_nNH_2$, X=Z=C, Y=P(OH), B (if present)=$OCH_3$, wherein n=1–10, or
A=OH, X=Z=C, Y=P(OH), B =$O(CH_2)_nCO_2H$, wherein n=1–10, or
A=OH, X=Z=C, Y=P(OH), B (if present)=$(CH_2)_nCO_2H$, wherein n=1–11, or
A=$NH_2$, X=Y=C, Z=P(OH), B (if present)=$OCH_3$, or
A=OH, X=Y=C, Z=P(OH), B (if present)=$OCH_3$, or
A=$OCO(CH_2)_nNH_2$, X=Y=C, Z=P(OH), B (if present)=$OCH_3$, wherein n=1–10, or
A=OH, X=Y=C, Z=P(OH), B (if present)=$O(CH_2)_nCO_2H$, wherein n=1–10, or
A=OH, X=Y=C, Z=P(OH), B (if present)=$(CH_2)_nCO_2H$ and n=1–11.

The substituents which may be on the branched or linear $C_{1-11}$ alkyl, alkene or alkyne groups of any or all of $R_1$, $R_{1'}$, $R_2$, $R_{2'}$, $R_{2''}$ and $R_{2'''}$ can be any substituents which permit antibodies to be elicited to the formula (I) compound and preferably which do not significantly reduce the therapeutic utilities of the formula (I) compound. These substituents can be one or more substituents selected from the group consisting of —OH, alkyl, chloro, fluoro, bromo, iodo, —$SO_3$, aryl, —SH,

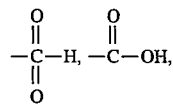

ester groups, ether groups, alkenyl, alkynyl —$N_2^+$, cyano, epoxide groups, heterocyclic groups, and —$N(R_4)_2$ wherein $R_4$ is H or a substituent listed above (so as to include substituted and unsubstituted amines).

The present invention also provides a method for eliciting catalytic antibodies to cleave the ester bonds or glycosidic bond of Lipid-A and LPS, and a method for eliciting antibodies comprising administering to an animal, as an immunogen, a compound of formula (I) or formula (II) as part of a composition designed to maximize the antibody response.

The present invention further provides a composition for protective activity against the effects of gram-negative bacterial infection comprising a suitable carrier and a compound of formula (I) or formula II). Likewise, the present invention includes a method for inducing protective activity against the effects of gram-negative bacterial infection in an animal in need of such protection comprising administering the composition.

Further, the invention provides an antitumor composition comprising a suitable carrier and a formula (I) or formula (II) compound; and, a method for treating or controlling tumor growth comprising administering the antitumor composition.

The invention also contemplates an antibody which binds to both Lipid-A and a compound of formula (I) or formula (II), as well as an antibody which binds to Lipid-A and a formula (I) or formula (II) compound, and has been made by a process comprising:

immunizing an animal with a composition
comprising the compound of formula I, removing
antibody-producing lymphocytes from said
animal, and
fusing the lymphocytes with myeloma cells and thereby producing hybridoma cells producing the antibody.

The invention also comprehends this process.

The invention further comprehends a method for producing an antibody which binds to Lipid A and a compound of formula (I) or (II) comprising immunizing an animal with a composition comprising the compound,
isolating spleen cells from the animal,
amplifying at least one gene fragment encoding all or part of both heavy and light chains of at least one antibody from said spleen cells, inserting said gene fragment in a recombinatoral fashion into a viral vector, producing a library of viable virus particles which express a protein derived from the gene fragment, and screening said library for binding and/or catalytic activity by expressed antigen binding protein of the gene fragment preferably with respect to Lipid A or the compound.

The invention also encompasses an antibody produced by this method, including a catalytic antibody.

In the foregoing antibody producing methods involving immunization of an animal, in preferred embodiments the immunizing comprises immunizing the animal with the compound complexed with a suitable immunogenic carrier, e.g., immunizing the animal with the compound, Lipid A, and a T-cell stimulatory peptide such as HEL[105-120].

In this disclosure an "antibody-encoding gene" includes fragments of such a gene which encode and express the antibody or a functional (by binding or catalytic activity) antibody fragments thereof.

The antibodies of the invention can be catalytic antibodies. These antibodies are useful for treating septicemia by administering them to a patient in need of such treatment; and thus, the invention includes a method for treating septicemia comprising administering a composition comprising such an antibody and a suitable carrier.

The invention also includes a method for binding to receptors in competition with Lipid-A comprising administering a composition comprising a suitable carrier and a formula (I) compound.

With respect to formula (I), in preferred embodiments $R_3$ is 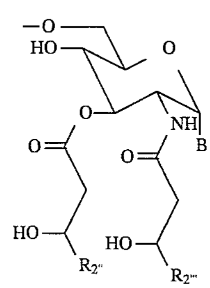 and each of $R_1$, $R_{1'}$, $R_2$, $R_{2'}$, $R_{2''}$ and $R_{2'''}$ is a $C_{12}$ linear alkyl group, such as $C_{12}H_{24}$, and:

Y=C, Z=C, X=P(OH), $B=OCH_3$ and A=OH; or

Y=C, Z=C, X=P(OH), $B=OCH_3$ and $A=NH_2$; or

Y=C, Z=C, X=P(OH), $B=OCH_3$ and $A=OCO(CH_2)_nNH_2$ wherein n=1–10 ; or,

Y=P(OH), Z=C, X=C, $B=OCH_3$ and A=OH; or,

Y=P(OH), X=C, Z=C, $B=OCH_3$ and $A=NH_2$; or,

Y=P(OH), X=C, Z=C, $B=OCH_3$, $A=OCO(CH_2)_nNH_2$ where in n=1–10; or,

Y=C, X=C, Z=P(OH), $B=OCH_3$ and A=OH; or,

Y=C, X=C, Z=P(OH), $B=OCH_3$ and $A=NH_2$; or,

Y=C, X=C, Z=P(OH), $B=OCH_3$ and $A=OCO(CH_2)_nNH_2$ wherein n=1–10.

The invention further relates to novel amidine compounds of formula (II) which are also transition state analogs and which are therefore useful in eliciting anti-bodies, especially catalytic antibodies, for binding to and cleavage of compounds containing glycosidic bonds. Like the formula (I) compounds, the amidine compounds and antibodies elicited thereto of the invention are useful for several applications. The antibodies elicited to the amidine compounds bind to Lipid-A and LPS; the catalytic antibodies elicited to the amidine compounds catalyze cleavage of glycosidic bonds (to render LPS and Lipid-A less or non toxic). The novel amidine compounds can be used as receptor antagonists of Lipid-A/LPS, as well as antitumor agents, antiviral agents, and as compounds which can provide protection against bacterial infection. The formula (II) compounds of the present invention have the structure:

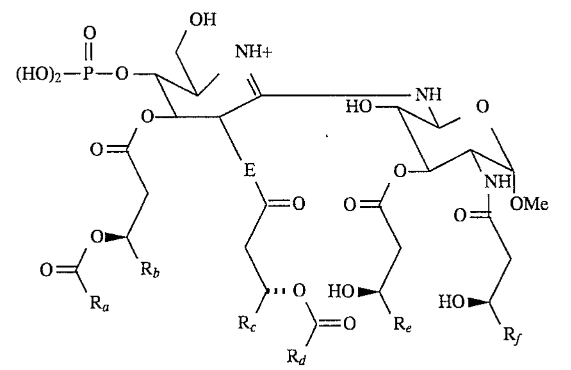

wherein each of $R_a$, $R_b$, $R_c$, $R_d$, $R_e$ and $R_f$, independent of each other is a substituted or unsubstituted, branched or linear $C_{1-11}$ alkyl, alkene or alkyne group; the substituents can be those for $R_1$, $R_{1'}$, $R_2$, $R_{2'}$, $R_{2'''}$ and $R_{2''}$ provided above, preferably each of $R_a$, $R_b$, $R_c$, $R_d$ and $R_f$ is a linear alkyl group, most preferably each is $C_{11}H_{23}$; and, E is NH or O.

The invention also comprehends pharmaceutically acceptable salts and pharmaceutically acceptable derivatives of formulae (I) and (II) compounds. Further, the invention encompasses the novel intermediates of formulae (I) and (II) compounds, as well as pharmaceutically acceptable salts and pharmaceutically acceptable derivatives thereof; and, the novel methods for preparing compounds of formulae (I) and (II), the intermediates thereof, and the pharmaceutically acceptable salts and derivatives thereof.

BRIEF DESCRIPTION OF DRAWINGS

The following Detailed Description will be better understood by reference to the accompanying Figures, incorporated herein by reference, wherein:

FIGS. 1–39 and 48–52 show reaction Schemes 1 to 10 (FIGS. 1–10), reaction Scheme 10a (FIG. 11), reaction Scheme 11 to 19 (FIGS. 12–20), reaction Scheme 19a (FIG. 21), reaction Schemes 20 to 37 (FIGS. 22–39), reaction Schemes 41 to 42 (FIGS. 48, 49), reaction Scheme 43a (FIG. 50), reaction Scheme 43b (FIG. 51) and reaction Scheme 44 (FIG. 52) for the synthesis of formula (I) compounds and intermediates thereof; these figures are discussed in the Detailed Description by reference to the particular "Scheme";

FIG. 40 shows the structure of Lipid-A with positions Immu-1, Immu-2, and Immu-3 and Immu-4 labelled; as the targets for catalytic action by a catalytic antibody for detoxification of Lipid-A and LPS;

FIG. 41 shows the structure of the amidine TS analog (79) of the present invention;

FIGS. 42–44 show reaction Schemes 38 to 40 for the synthesis of formula (II) compounds and intermediates thereof;

FIGS. 45–47 show reaction Schemes for the synthesis of formula (II) compounds and intermediates thereof; and FIG. 53 shows compounds of formula (I) of the invention.

DETAILED DESCRIPTION

The synthesis of compounds of formulae (I) and (II) can be according to the schemes which appear as Figures accompanying this description. The compounds of formulae (I) and (II) and of the amidine TS analogs can be used as Lipid-A and previous Lipid-A analogs are used in the literature.

It should be noted that, whereas some synthetic methods and compounds are specific as to a particular stereochemistry, this is not meant in any way to exclude methods and compounds of different stereochemistry or of a mixture of stereochemistries (or stereoisomers). The preferred embodiments of this invention entail methods and compounds having the same stereochemistry as naturally occurring Lipid-A and LPS.

Figure 40:
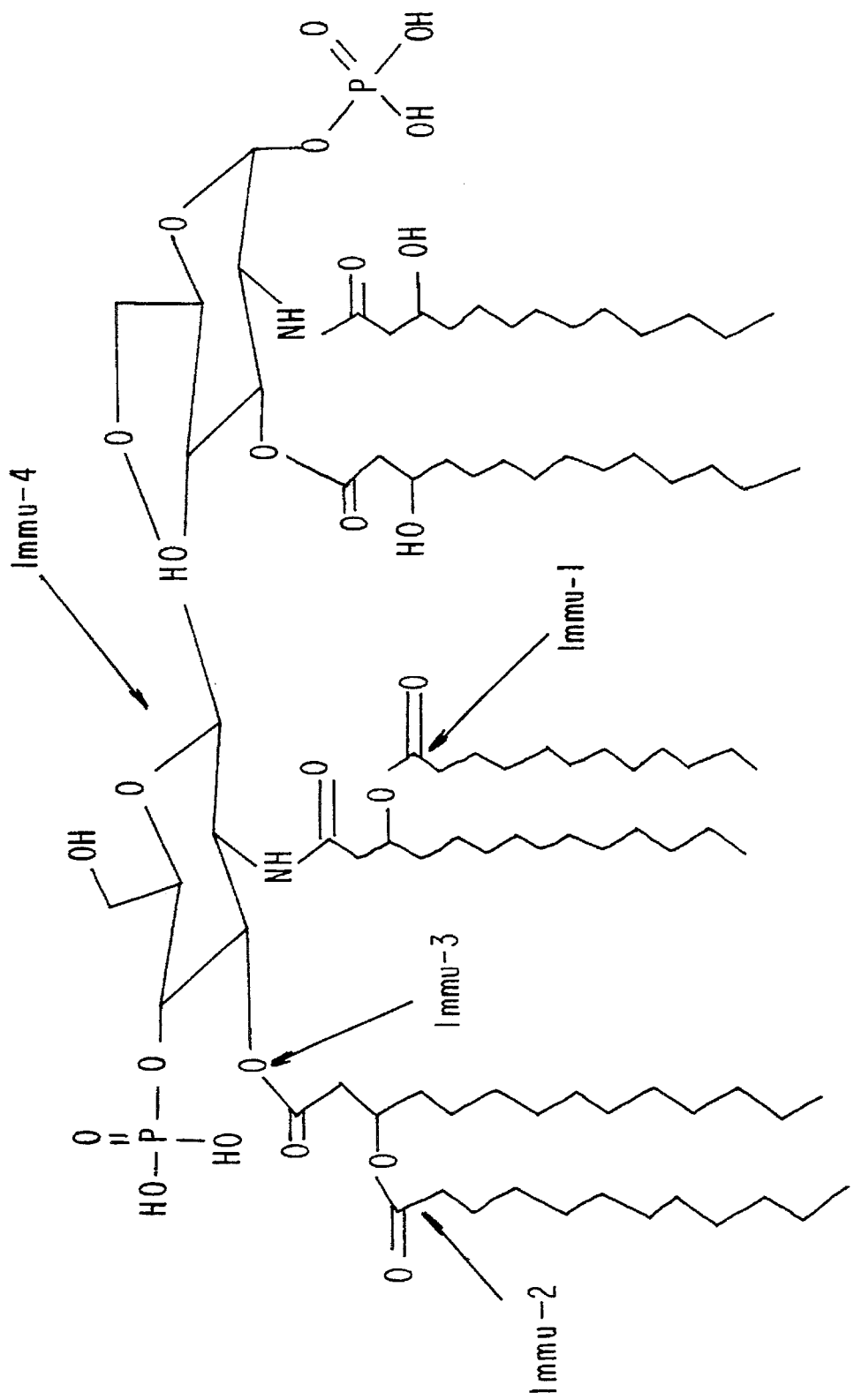

The compounds of formula (I) allow for both hydroxy and ester groups at the Immu-1 and Immu-2 positions of Lipid-A (FIG. 40) to provide compounds which exhibit superior IFN and TNF inducing activities. IFN activity is an antiviral activity; TNF activity is antitumor activity. Furthermore, the compounds of formulae (I) and (II) are transition state analogs of Lipid-A, and therefore are not only useful for eliciting antibodies, but are useful for eliciting catalytic antibodies. As to methods of eliciting catalytic antibodies, reference is made to Schochetman et al., U.S. Pat. No. 4,888,281, incorporated herein by reference. These antibodies have therapeutic uses (see also the applications referenced and incorporated herein above in the Cross-Reference to Related Applications). These therapeutic uses include reducing the toxicity of compounds such as the treatment of septicemia or septic shock which is caused by lipopolysaccharide or LPS. As to formula (I) compounds, three sites of the Lipid-A molecule are targeted by the catalytic antibodies elicited thereto: the ester bond of the acyloxyacyl chain which is linked to the 2'-N glucosamine position; the ester linked o-acyl chain at the 3'-O position of the glucosamine; and the bond between the beta 1–6 linked glucosamine residues. The catalytic antibodies elicited to formula (II) compounds target glycosidic bonds, including glycosidic bonds of Lipid-A. Monoclonal antibodies produced against the formulae (I) and (II) of the transition states for each of the hydrolysis reactions are screened for binding to and cleavage (catalytic activity) of Lipid-A (and LPS) to yield detoxified Lipid-A (and LPS) structures. The catalytic antibodies, alone or in combination, (for instance as a "cocktail") are expected to have therapeutic efficacy in several animal models of lethal bacteremia and septic shock and in treating human disease. Thus, the novel Lipid-A transition state analogs target one or more bonds of Lipid-A (see FIG. 40).

Other utilities include causing conditions such as the activation of prodrugs such as glycosidic prodrugs. Further, formulae (I) and (II) compounds are also useful to elicit antibodies as an immunological response; for instance, to vaccinate against toxic substances. Likewise, the formulae (I) and (II) compounds are useful for treating those in need of treatment for endotoxemia or for septicemia or septic shock because the formulae (I) and (II) compounds can compete for binding sites with LPS or Lipid-A (receptor antagonists), or stimulate an immune response thereto.

The compounds of formulae (I) and (II), or antibodies elicited thereto (to either or both of formula (I) and (II) are administered in typical doses to a patient, by the skilled artisan, physician or veterinarian, taking into consideration such typical factors as the condition being treated (e.g., viral, bacterial, tumor, LPS, etc.), and the age, weight, sex and general health of the patient.

In general, with reference to FIGS. 1–39, the synthesis and uses of compounds of formula (I) are as follows.

Figure 1:
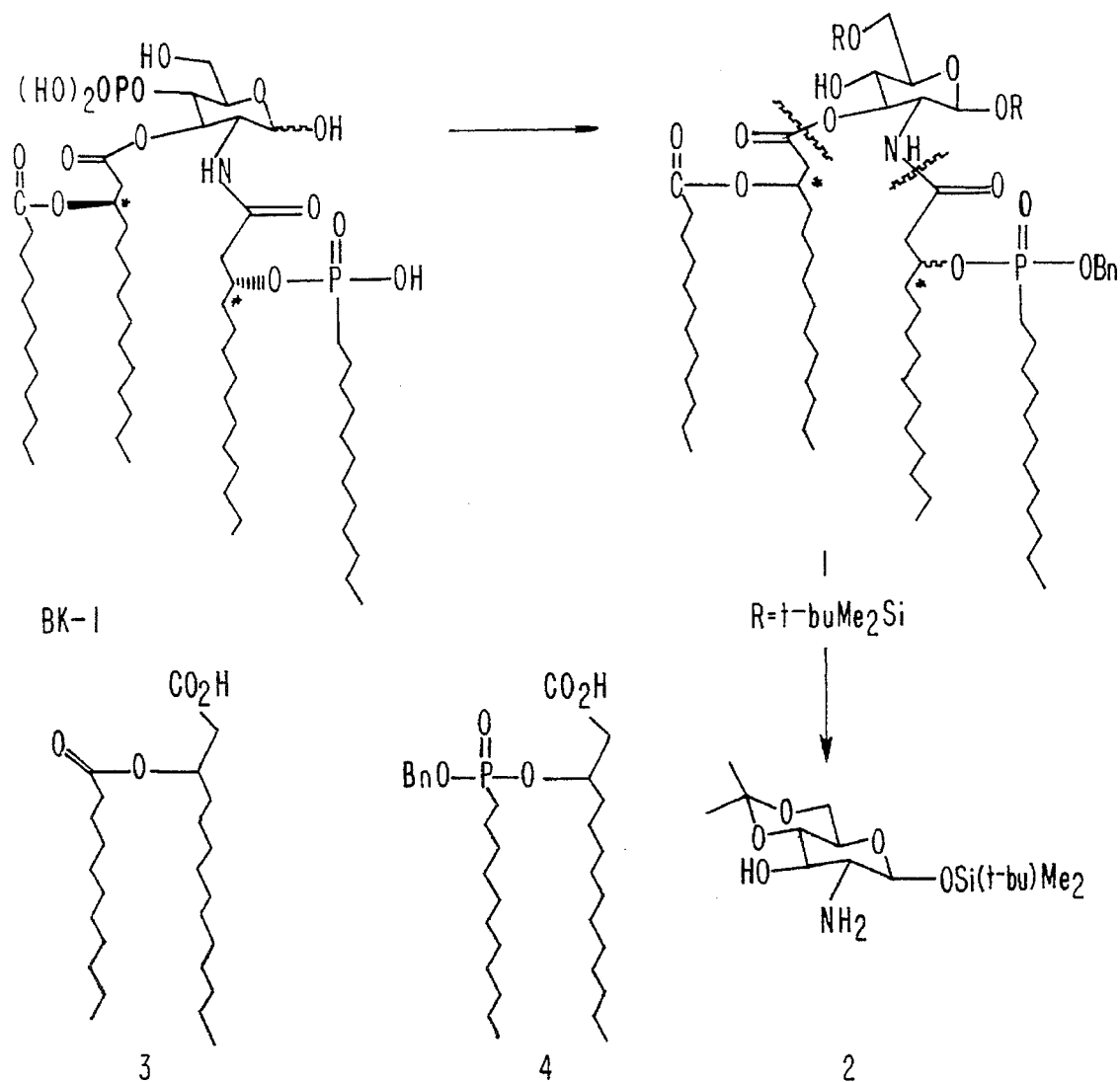
Figure 2:
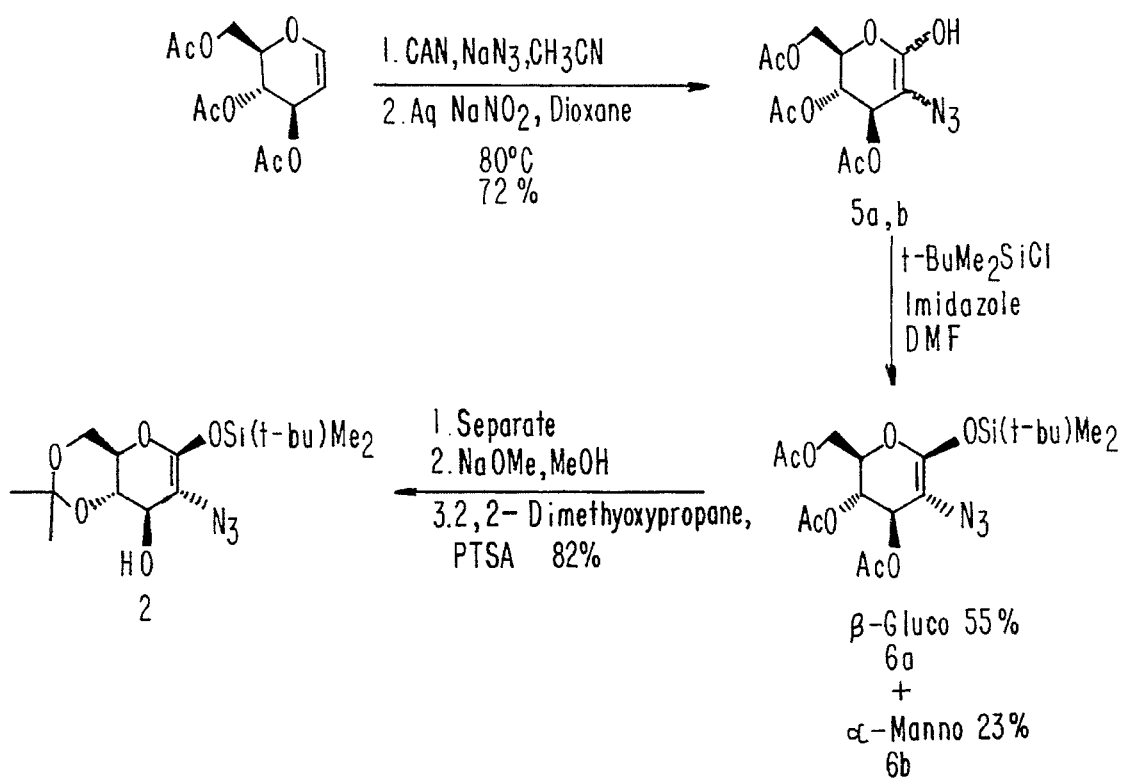

Synthesis of immunogen BK-1 is accomplished as shown in the retro-synthetic analysis (Scheme 1) (FIG. 1). Synthesis is achieved by first preparing the key intermediate 1, which is then transformed to BK-1 via appropriate chemical reactions. The intermediate in turn is synthesized starting from three key intermediates 2, 3 and 4. Accordingly compounds 2, 3 and 4 are prepared as follows.

Intermediate 2 is prepared starting from commercially available tri-O-acetyl-D-glucal. Azidonitration of tri-O-acetyl-D-glucal using ceric ammonium nitrate in acetonitrile followed by hydrolysis using aqueous sodium nitrate in dioxane affords the mixture of gluco and manno derivatives 5a and 5b (Scheme 2) (FIG. 2) (93). The mixture is subjected to a silylation reaction using t-butyldimethylsilyl chloride in DMF in the presence of imidazole to afford the mixture of β-gluco 6a and α-manno 6b derivatives in the ratio of 2.4:1. β-Gluco compound 6a is separated and treated with sodium methoxide in methanol to give the corresponding triol, which on treatment with 2,2-dimethoxypropane in methylene chloride in the presence of p-toluenesulphonic acid affords the azidosugar compound 2.

Figure 3:
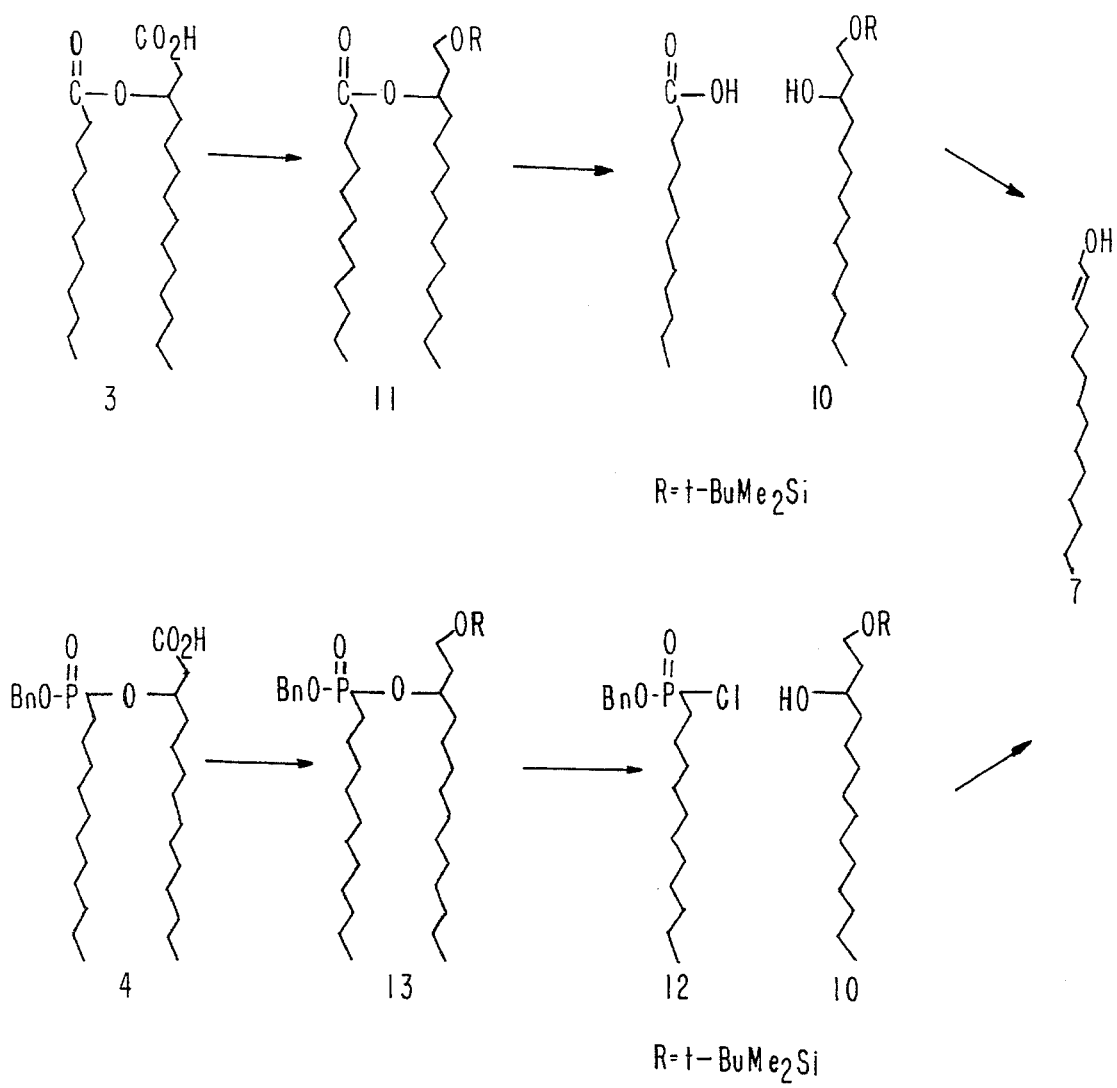

Other key intermediates, acid 3 and acid 4 are prepared by the following sequence of reactions. Both the intermediates 3 and 4 are prepared from the common intermediate 10, which is obtained from the allyl alcohol 7 (Scheme 3) (FIG. 3). The alkyl alcohol 7 can be substituted or unsubstituted, branched or linear.

Figure 4:
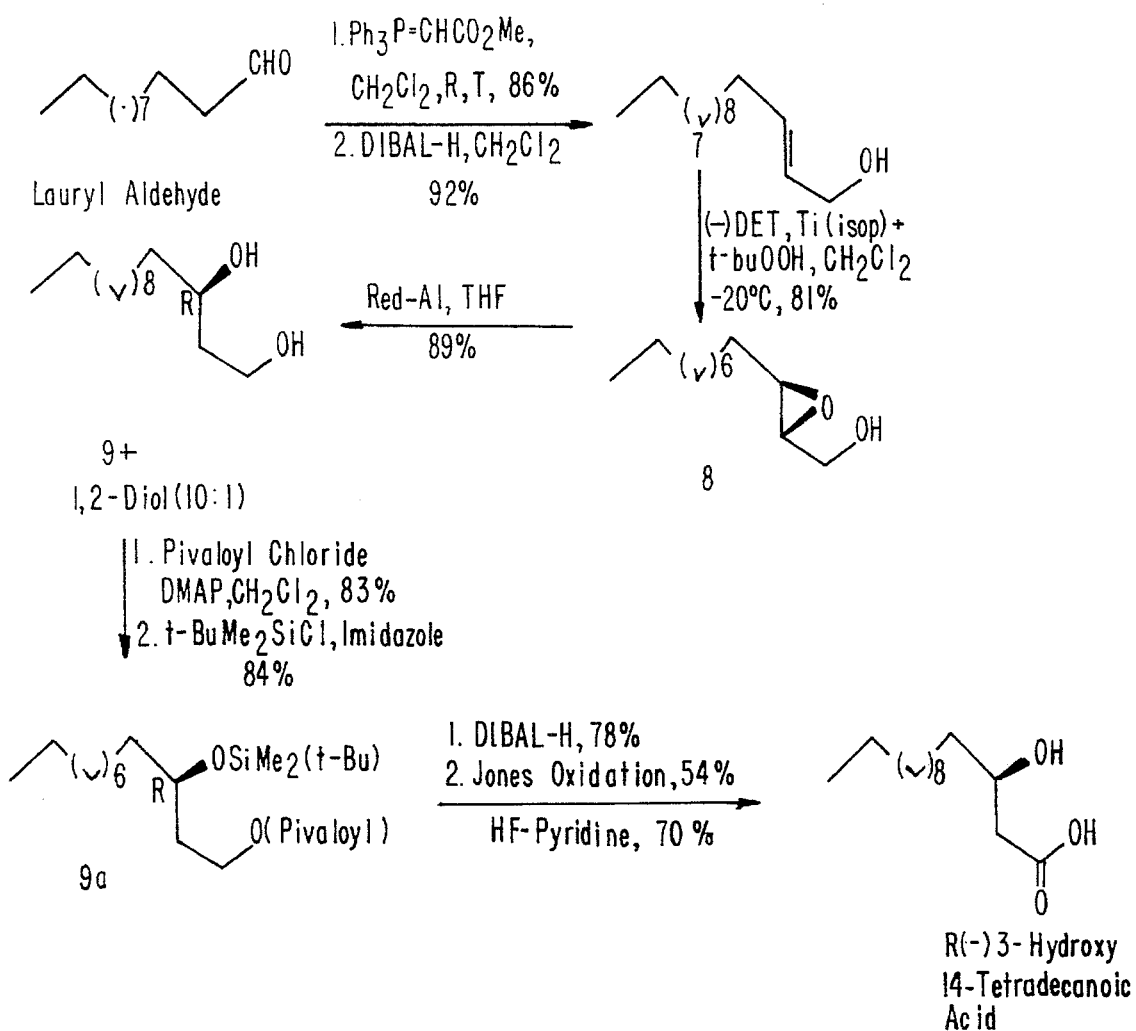

Synthesis of acid 3 is accomplished starting from dodecyl aldehyde (Scheme 4) (FIG. 4). Wittig reaction of the aldehyde with methyl (triphenylphosphoralenyledene) acetate in methylene chloride affords the corresponding E-α, β unsaturated ester (94), which on reduction with DIBAL-H in methylene chloride at −78° C. affords the allyl alcohol 7 (95). The allyl alcohol on enantioselective epoxidation (96, 97) using (−) diethyl tartrate, titanium tetraisopropoxide and t-butyl hydroperoxide in methylene chloride at −20° C. affords the epoxide 8. The epoxide is then reduced with Red-Al (98) to afford the 1,3 diol 9 along with 1,2 diol in the ratio of 10:1. The ratio of the regioisomers is determined by NMR of their acetate derivatives. The stereochemistry and optical purity of the 1,3 diol is determined by converting the diol to 3-hydroxytetradecanoic acid (Scheme 4) (FIG. 4) and is comparable with the literature reported values (99).

Figure 5:
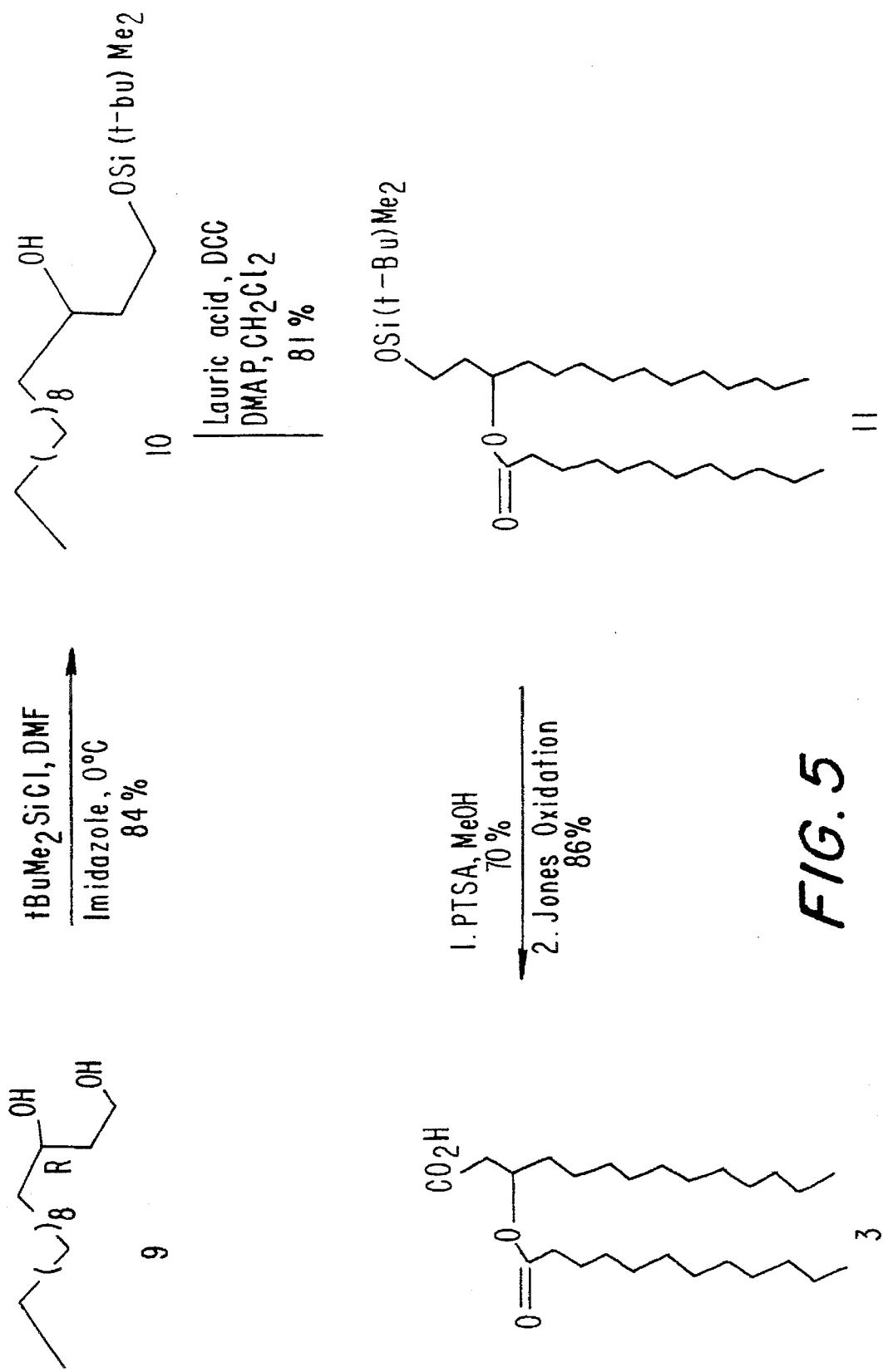

The diol 9 is a key intermediate for the preparation of both acids 3 and 4. The primary alcoholic functionality of the diol 9 is silylated selectively as the t-butyldimethylsilyl ether to afford the compound 10 (Scheme 5) (FIG. 5). Compound 10 is coupled with lauric acid in the presence of DCC and DMAP to afford the coupling compound 11. Desilylation of compound 11 is achieved by treating with PTSA in methanol at 0° C. to afford the corresponding primary alcoholic compound which after Jones oxidation affords the acid 3.

Figure 6:
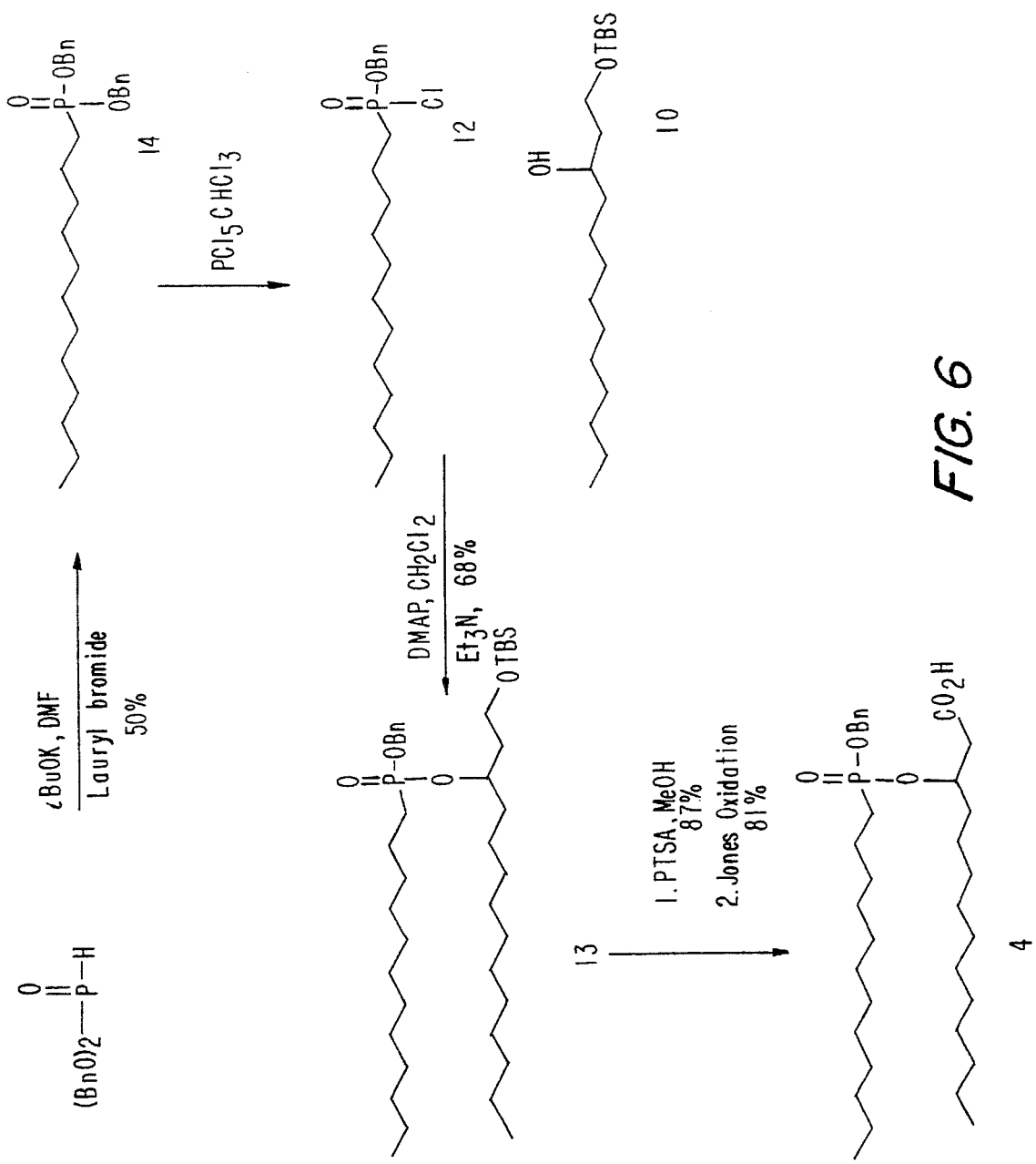

Preparation of the other acid 4, is achieved by the following sequence of reactions (Scheme 6) (FIG. 6). The phosphochloridate 12, a necessary component for the synthesis of acid 14, is prepared starting from dibenzyl phosphite. Dibenzyl phosphite is alkylated with lauryl bromide in dry DMF in the presence of potassium t-butoxide to afford the alkylated phosphate 14. The phosphate compound 14 is treated with phosphorus pentachloride in dry chloroform to afford the phosphochloridate 12. The phosphochloridate 12 is coupled with the hydroxy silyl compound 10 in methylene chloride in the presence of DMAP to give the corresponding coupled compound 13. The coupled compound 13 is then converted to the acid 4 by the same sequence of reactions used for the preparation of acid 3 from compound.

Figure 7:
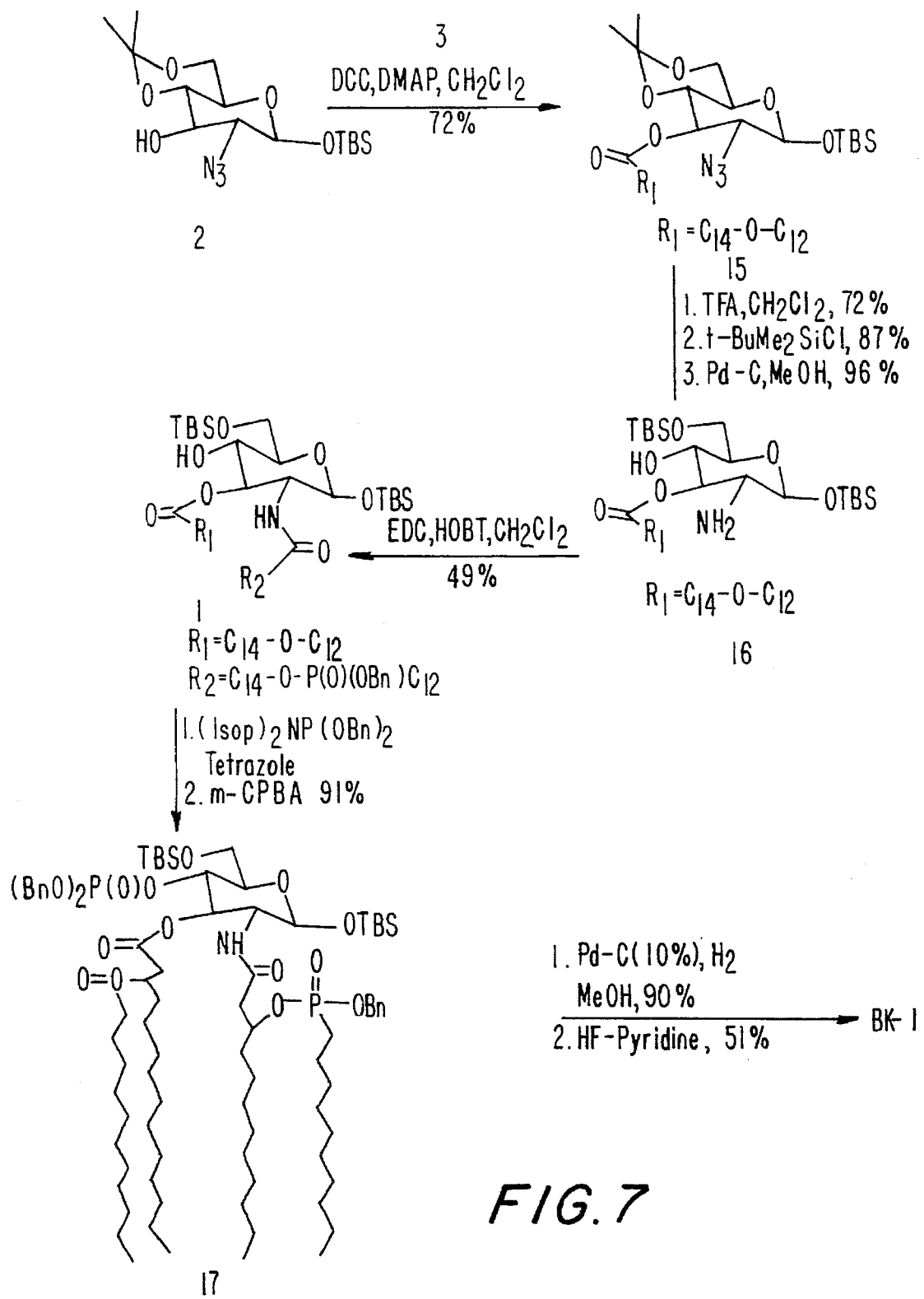

Having obtained the three intermediates, azido sugar 2, acid 3 and acid 4, BK-1 is prepared by the following sequence of reactions (Scheme 7) (FIG. 7). The azido compound 2 is coupled with acid 3 in methylene chloride in the presence of DCC and DMAP to afford the corresponding coupled compound 15. The acetonide of compound 15 is deprotected by using trifluoroacetic acid in methylene chloride to afford the corresponding diol, which is subjected to selective silylation with t-butyldimethyl silyl chloride to afford the monosilylated compound. The obtained monosilylated compound is then hydrogenated using Pd-C (10%) in methanol to afford the corresponding amino compound 16. The amino compound 16 is coupled with acid 4 in methylene chloride in the presence of EDC and HOBT to afford the compound 1. Compound 1 is phosphitylated at the 4 position with N,N-diisopropylamino dibenzyl phosphite in methylene chloride in the presence of tetrazole, followed by oxidation of the obtained phosphite with m-CPBA to afford the corresponding phosphate 17. Hydrogenation of the compound 17 using Pd-C (10%) in methanol, followed by desilylation using HF-pyridine, affords the immunogen BK-1.

Figure 8:
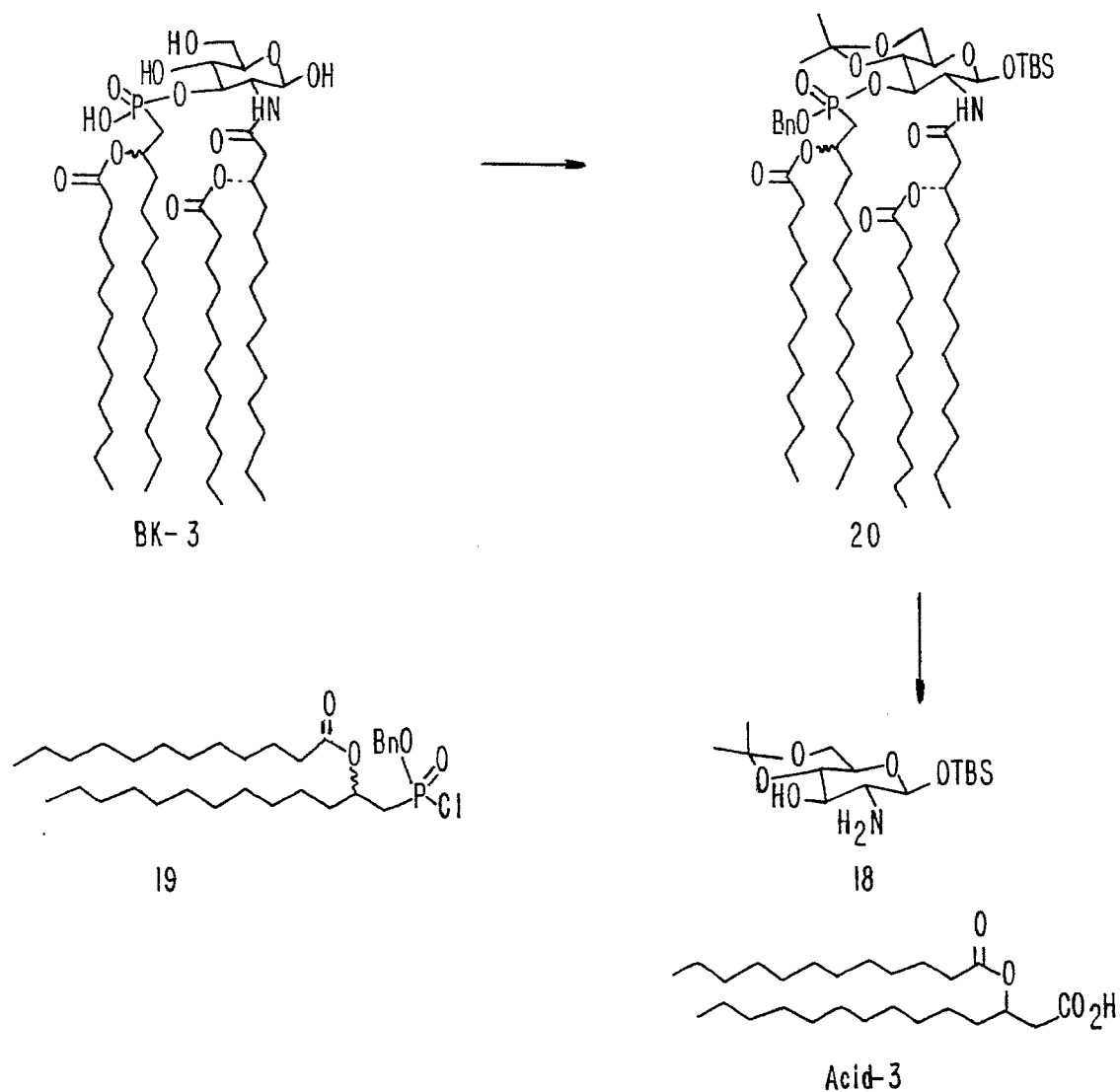

Synthesis of immunogen, BK-3 is accomplished as shown in Scheme 8 (FIG. 8). Accordingly a key intermediate 20 is prepared from three intermediates; acid 3, amino compound 8 and phosphochloridate 19.

Figure 9:
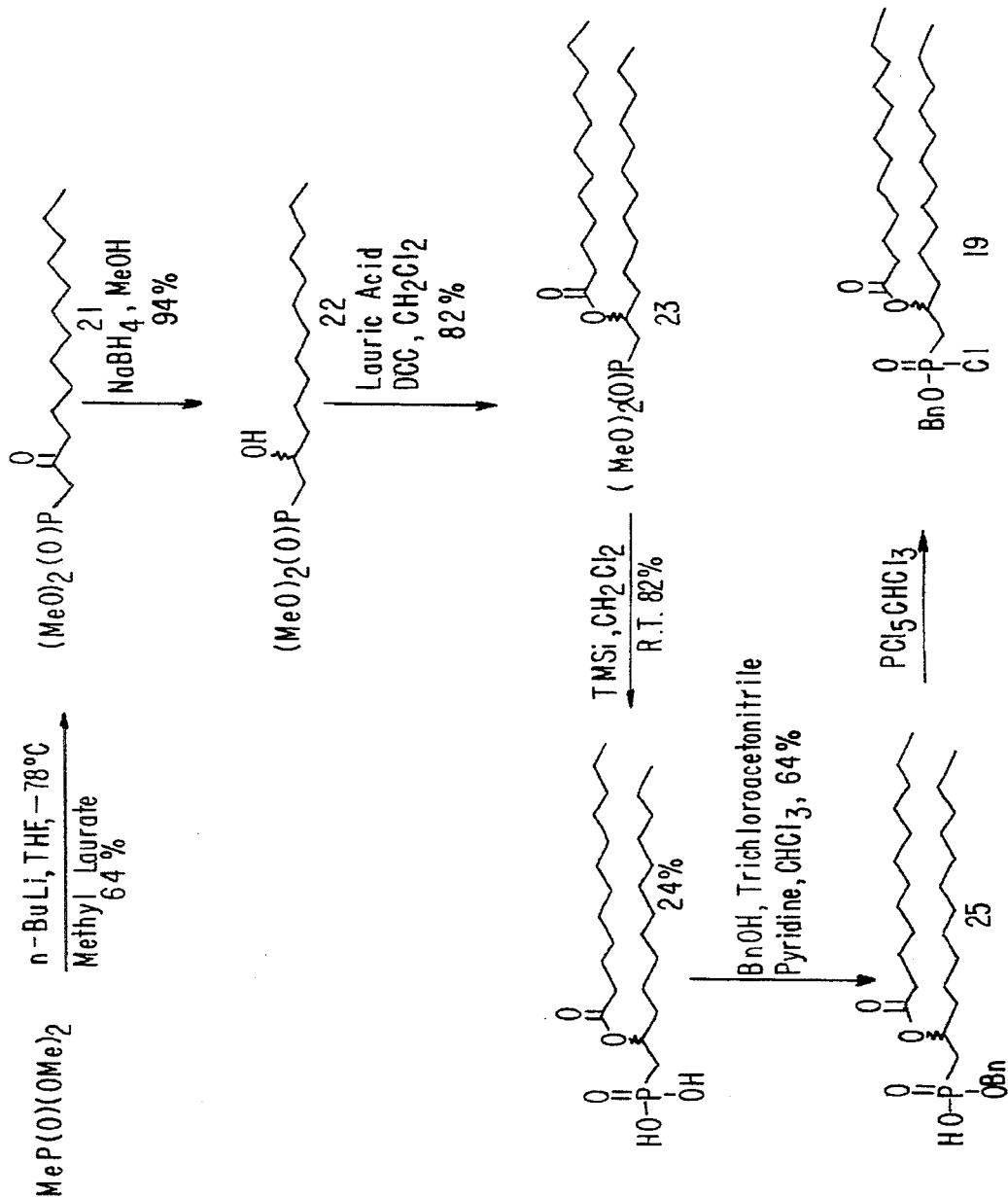

The intermediate phosphochloridate 19 is prepared starting from commercially available dimethyl methylphosphonate (Scheme 9) (FIG. 9). Dimethyl methylphosphonate is deprotonated using n-butyllithium at −78° C. and methyl laurate is added to afford the keto phosphonate 21. The keto phosphonate is reduced with sodium borohydride in methanol to give the corresponding hydroxy compound 22. Compound 22 is coupled with lauric acid in the presence of DCC to afford the corresponding ester 23. Demethylation of compound 23 with TMSI in dichloromethane affords the dihydroxy compound 24. Monobenzylation of compound 24 is achieved using benzyl alcohol and trichloroacetonitrile in pyridine and 25. chloroform to afford the monobenzylated compound 25 Compound 25, after treatment with phosphorus pentachloride in chloroform, affords the phosphochloridate 19.

Figure 10:
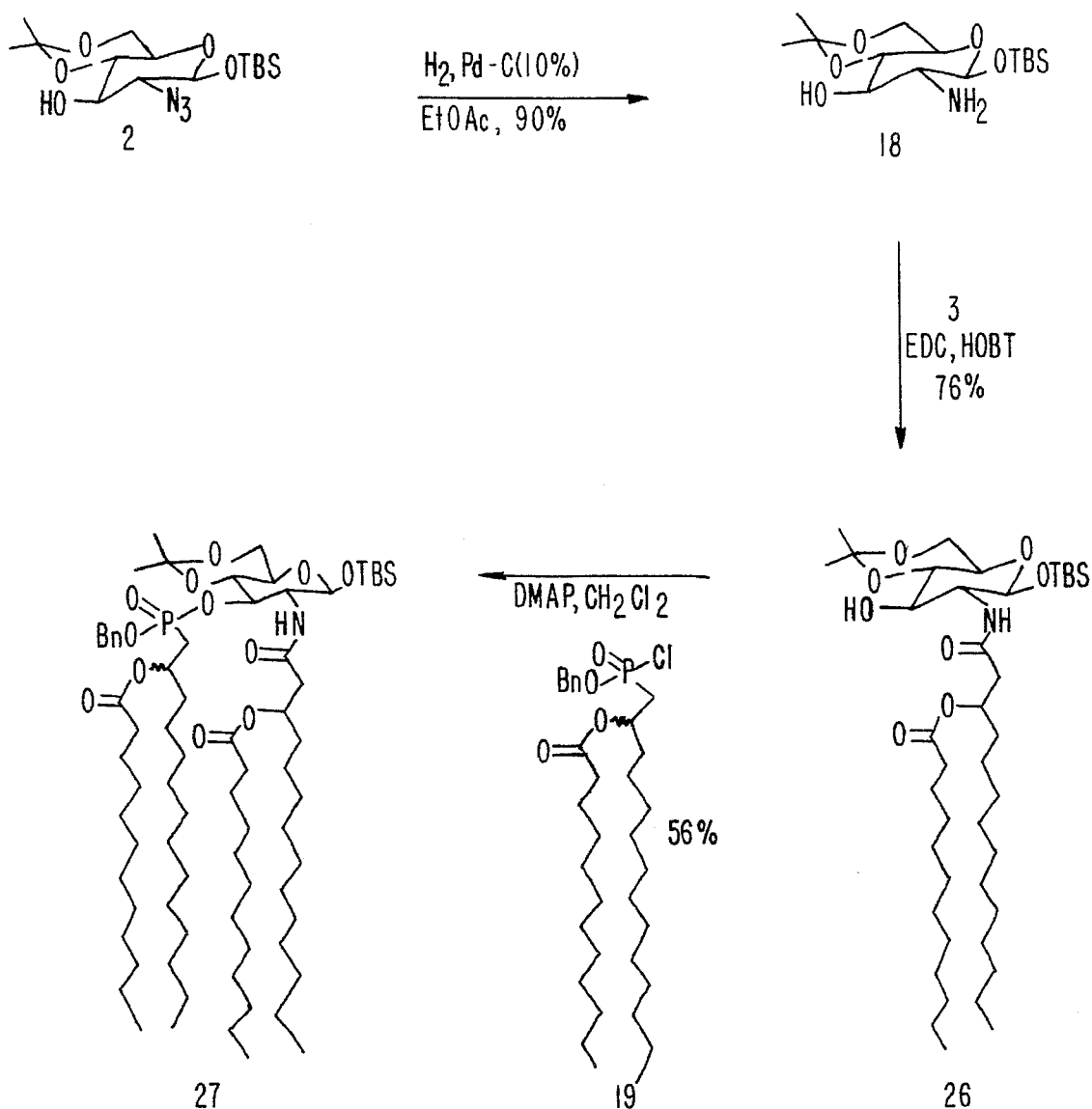
Figure 11:
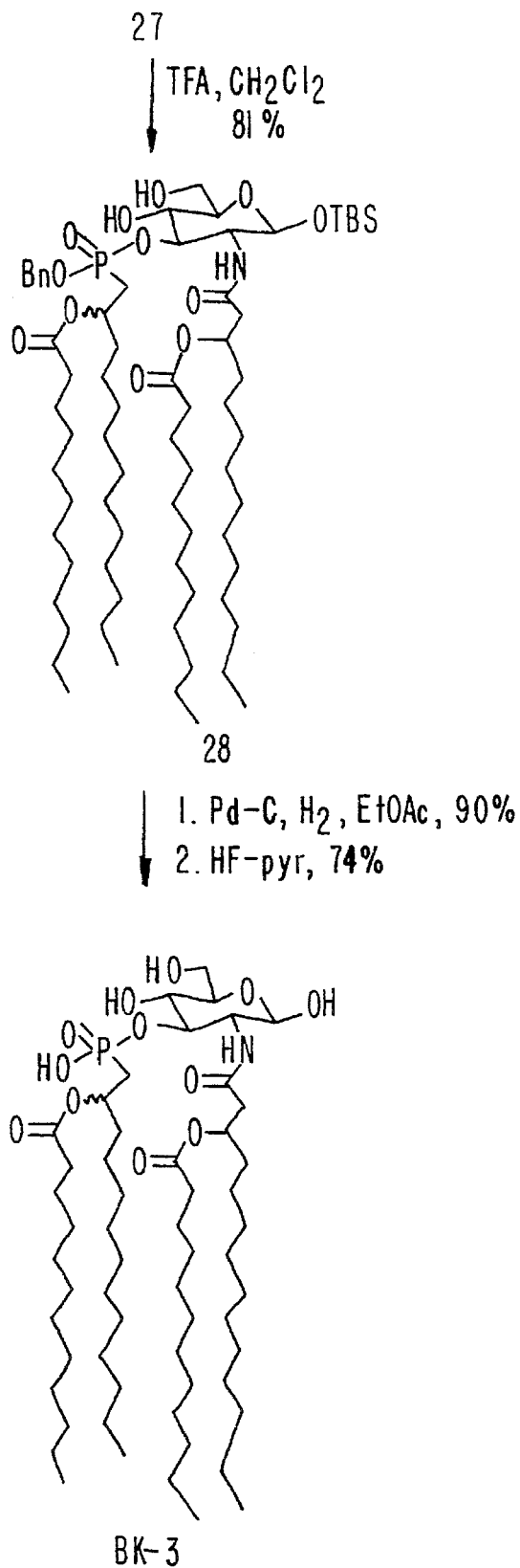

The immunogen BK-3 is then prepared by the following sequence of reactions. The amino sugar 18 (see discussion of BK-1 synthesis, above) is coupled with acid 3 (see discussion of BK-1 synthesis, above) under standard EDC reaction conditions to afford the acylated sugar 26 (Scheme 10) (FIG. 10). The hydroxy compound 26 is coupled with phosphochloridate 19 to afford the diacylated sugar 27. Deprotection of the acetonide of compound 27 is achieved using trifluoroacetic acid in dichloromethane to afford the corresponding diol 28 (Scheme 10a) (FIG. 11). Compound 28 is subjected to hydrogenolysis using Pd-C (10%) in ethyl acetate to give the corresponding debenzylated compound, which after desilylation using HF-pyridine affords the immunogen BK-3.

Figure 12:
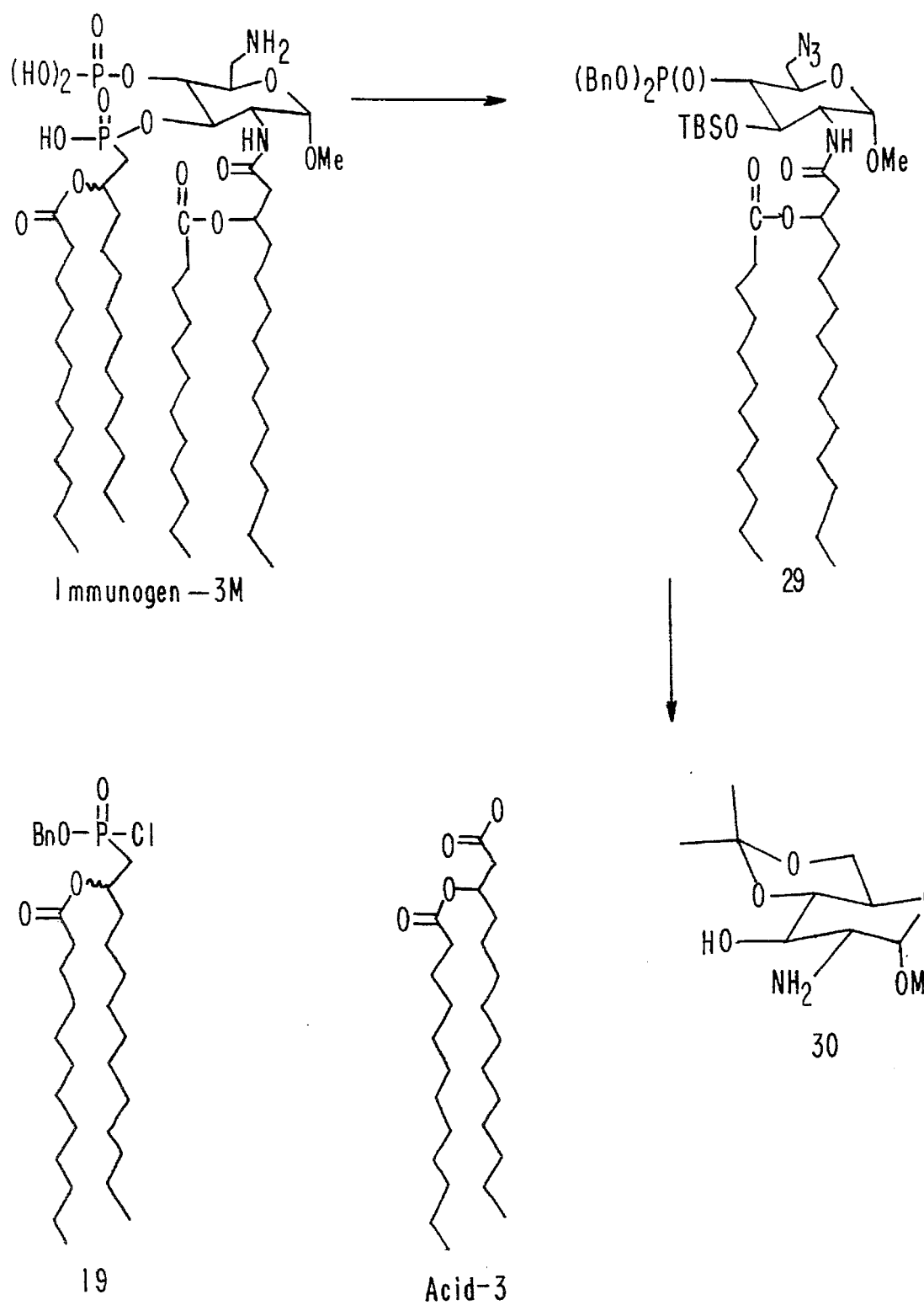

Synthesis of immunogen 3M is accomplished as shown in the retro-synthetic analysis (Scheme 11) (FIG. 12). Immunogen 3M is prepared by making use of the intermediate 29, phosphochloridate 19 and acid 3 via suitable chemical reactions to afford compound 29, which is subsequently converted to immunogen 3M.

Figure 13:
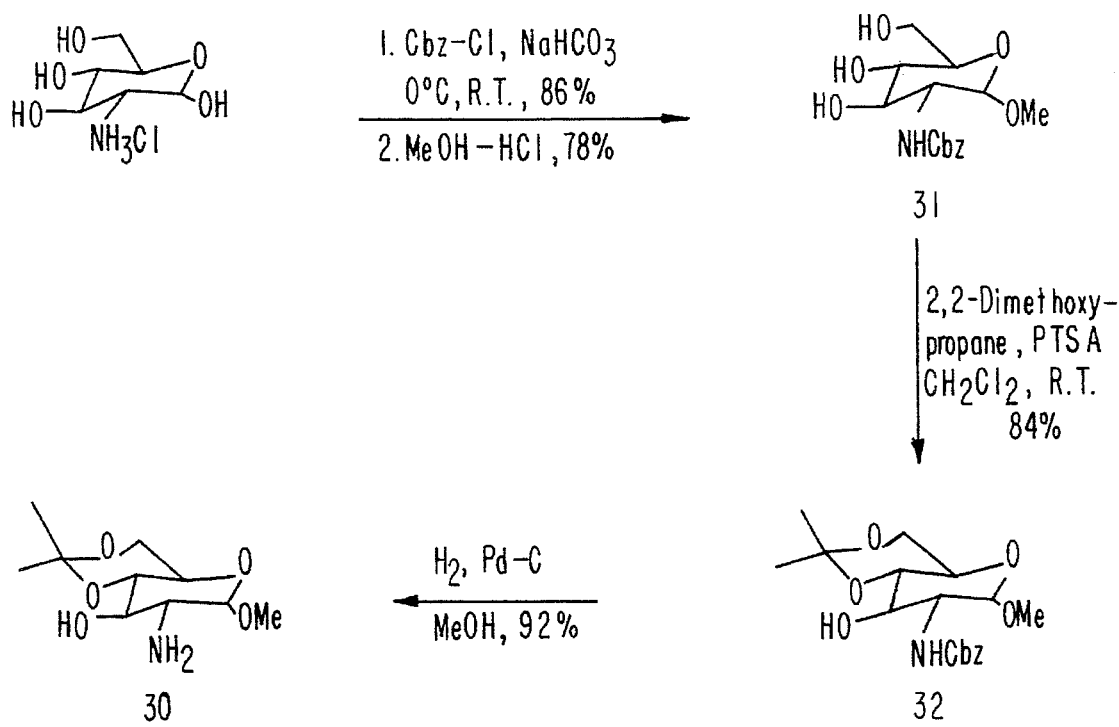

One of the intermediates for the synthesis of immunogen 3M, amino compound 30, is prepared starting from commercially available D-glucosamine hydrochloride (Scheme 12) (FIG. 13). Accordingly, glucosamine hydrochloride is treated with Cbz-Cl in aqueous sodium bicarbonate at room temperature to afford the amino-protected compound, which is then treated with methanolic HCl to afford compound 31. Compound 31 is then treated with 2,2-dimethoxypropane in dichloromethane in the presence of PTSA at room temperature to afford protected compound 32. Compound 32 is deprotected by hydrogenation using Pd-C (10%) in ethyl acetate to afford amino compound 30.

The other intermediates phosphochloridate 19 and acid 3 are prepared by following the same procedures used for BK-1 and BK-3.

Figure 14:
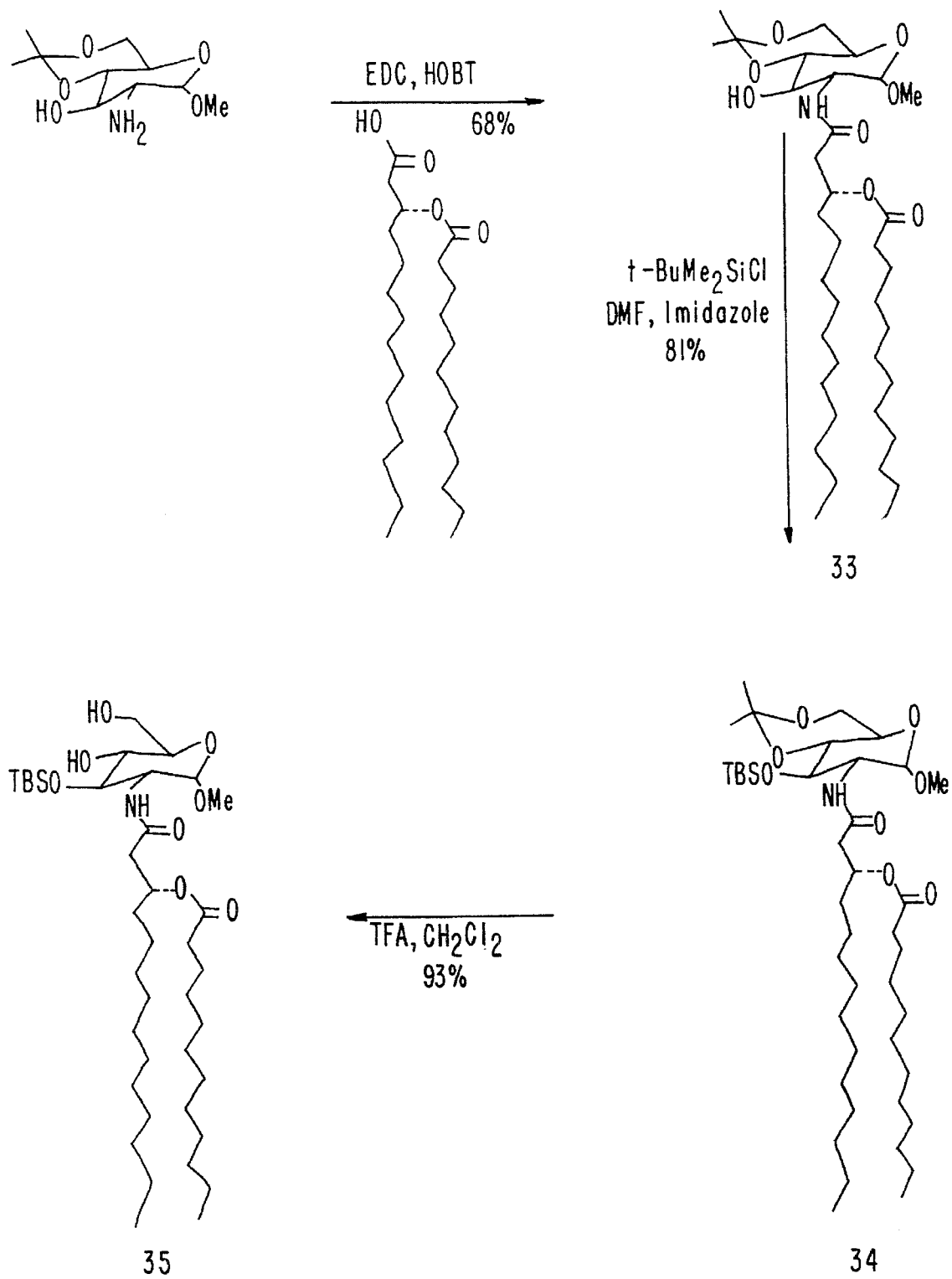
Figure 15:
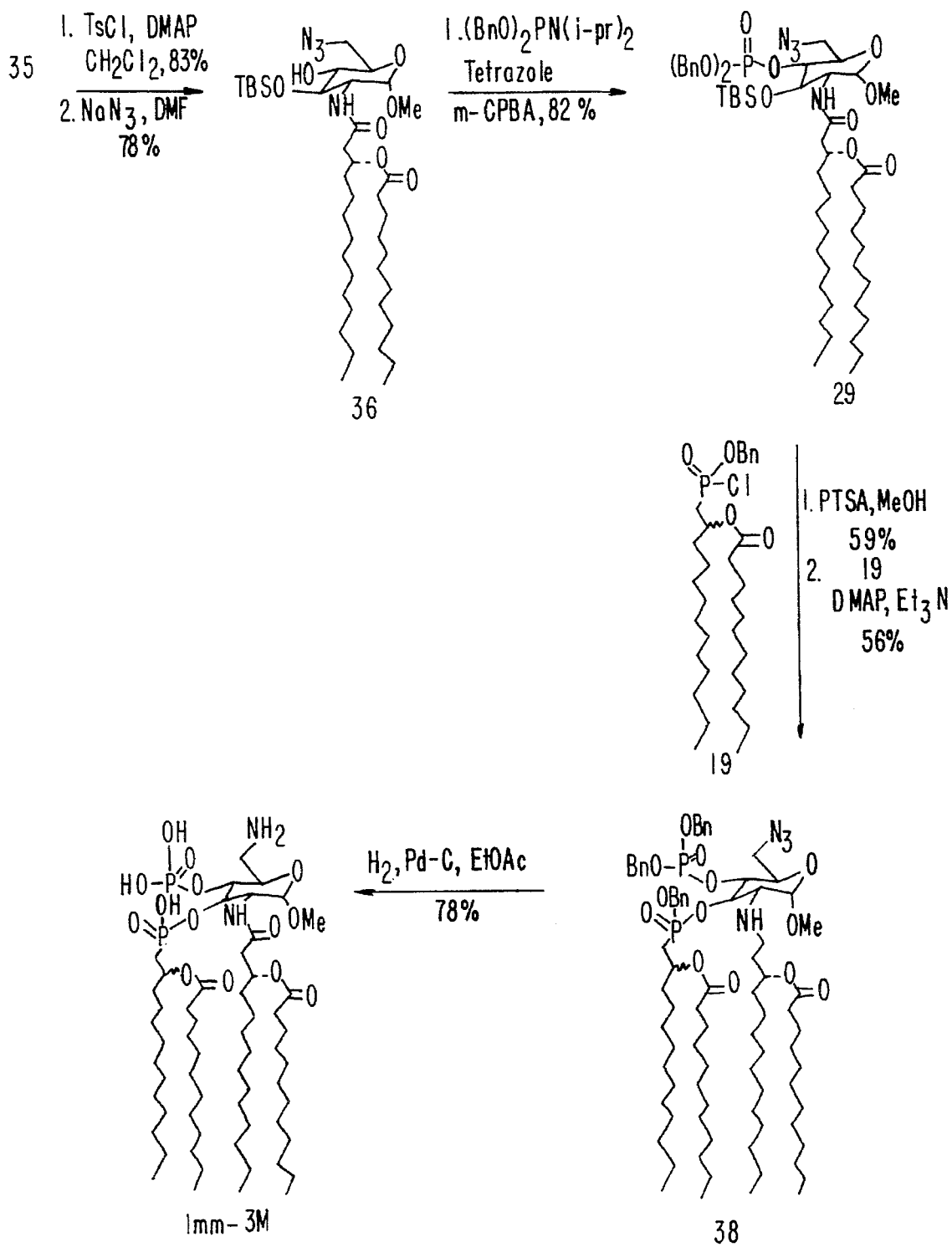

The amino compound 30 is converted to immunogen 3M via the following sequence of reactions (Scheme 13) (FIG. 14). Amino compound 30 is reacted with acid 3 in dichloromethane in the presence of EDC and HOBT to afford the acylated compound 33. Compound 33 is treated with t-butyldimethylsilyl chloride in DMF in the presence of imidazole to afford the silylated compound 34. The acetonide functionality of compound 34 is removed by treating compound 34 with trifluoroacetic acid in dichloromethane to give diol 35. The primary alcohol functionality of compound 35 is converted to the tosylate by treating it with tosyl chloride in the presence of DMAP, and the tosylate intermediate (Scheme 14) (FIG. 15) is reacted with sodium azide in DMF to afford the azido compound 36. Phosphorylation of compound 36 is accomplished by treatment with N,N-diisopropylamino di-benzyl phosphite in dichloromethane in the presence of tetrazole, followed by oxidation with m-CPBA to afford the corresponding phosphorylated compound 29. Desilylation of the phosphorylated compound 29 is achieved using PTSA in methanol and dichloromethane to give the corresponding hydroxy compound 37 (See structure in Scheme 15 (FIG. 16)). The hydroxy compound 37 is coupled with phosphochloridate 19 in dichloromethane in the presence of DMAP and triethylamine to afford the coupled compound 38. Compound 38 is deprotected by hydrogenolysis using Pd-C (10%) in ethyl acetate to afford immunogen 3M (Scheme 14) (FIG. 15).

Figure 16:
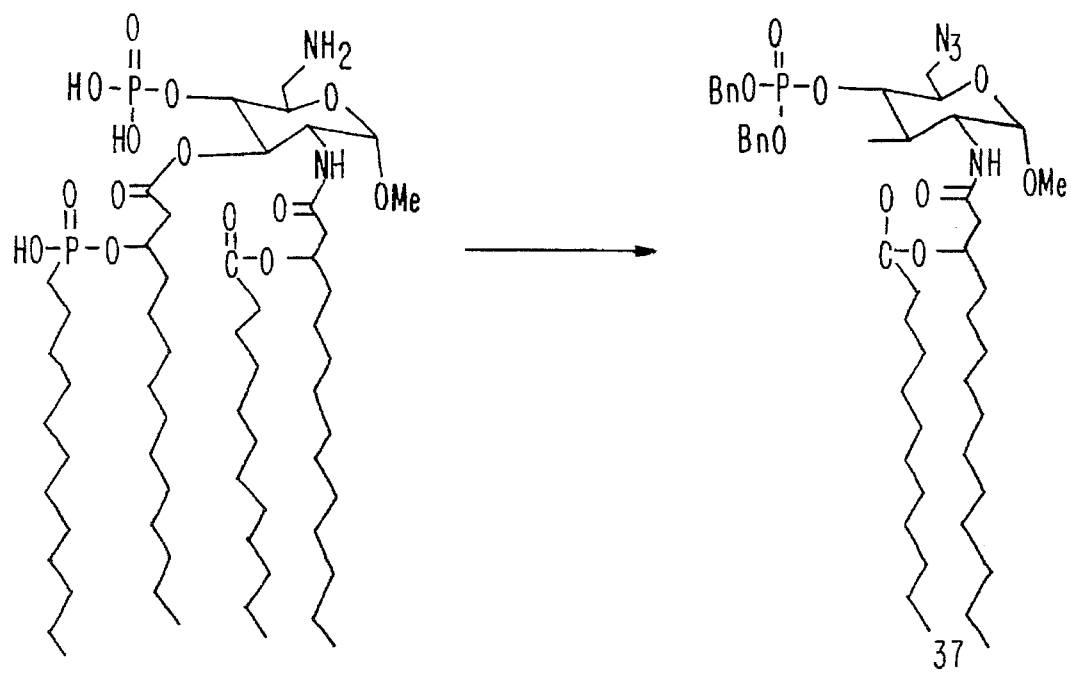
Figure 16:
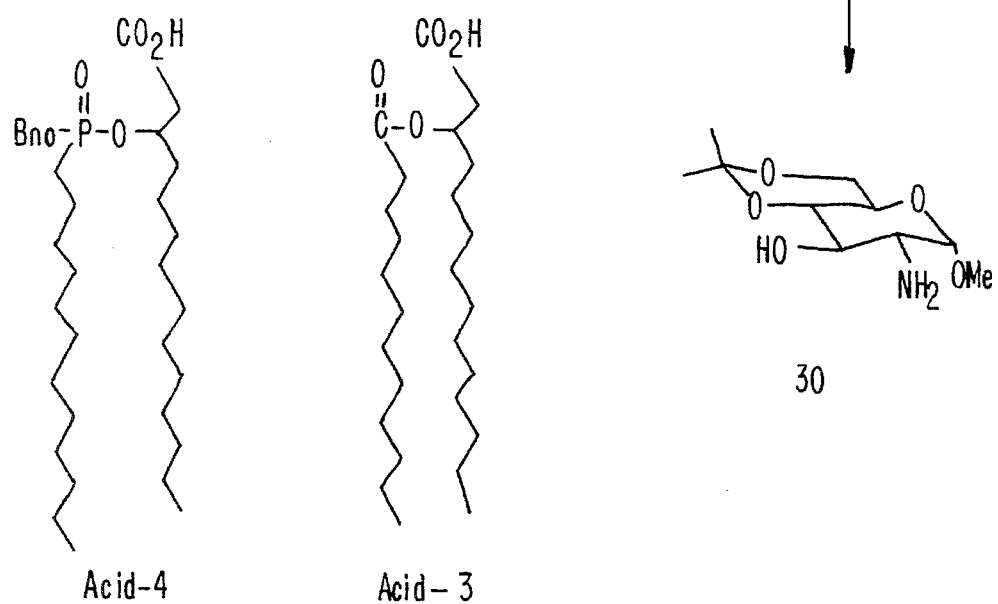
Figure 17:
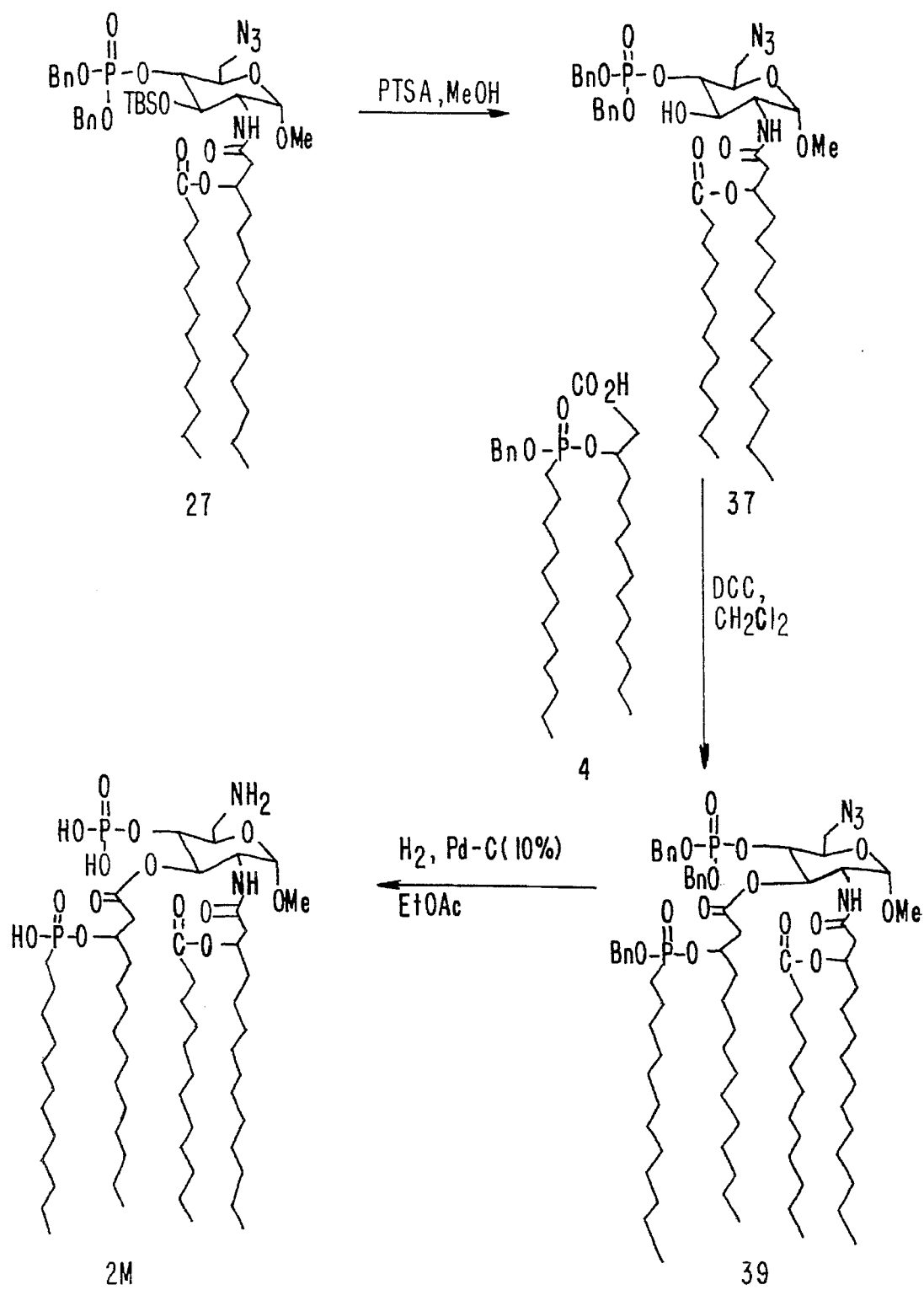
Figure 18:
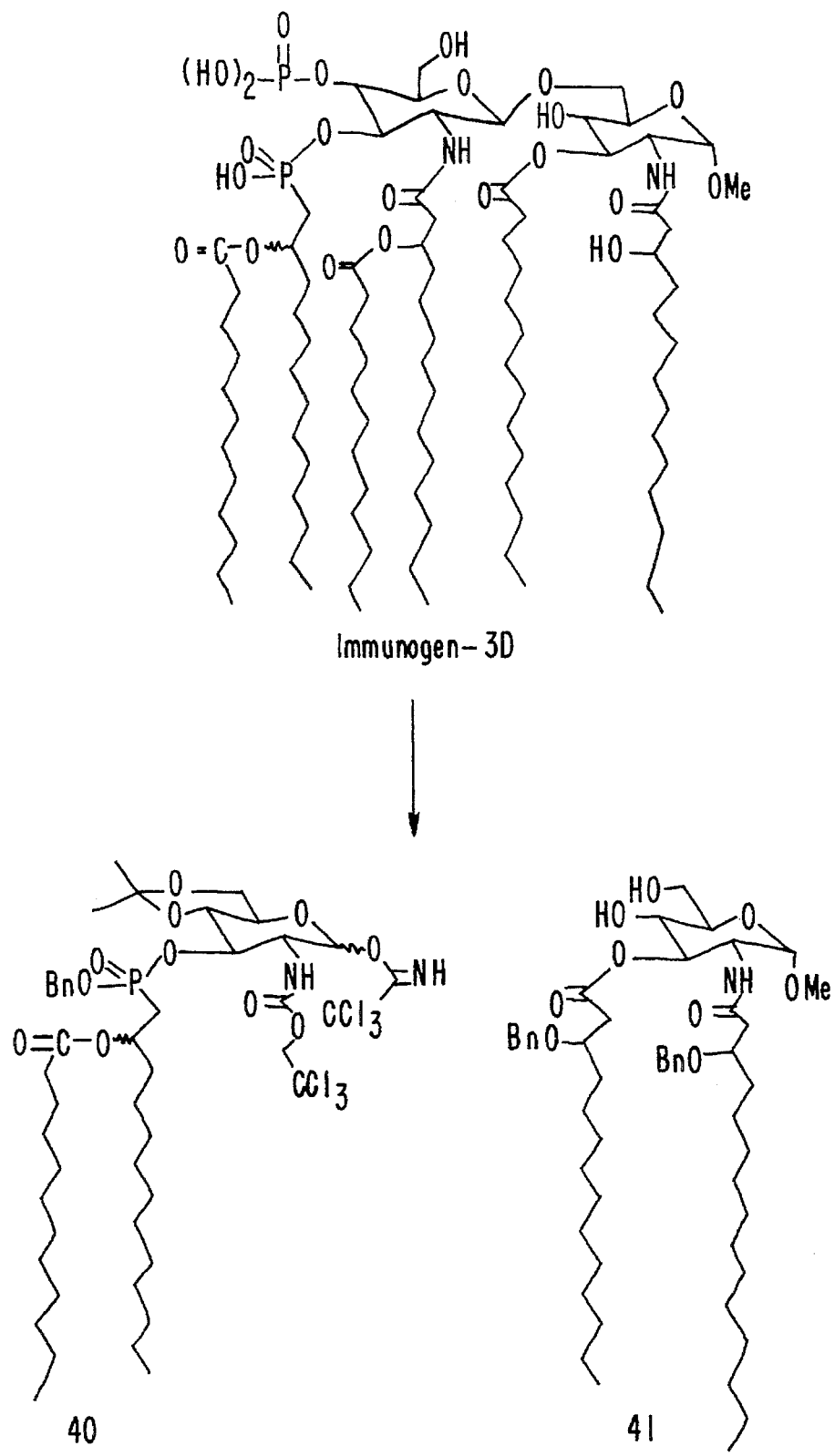

The synthesis of immunogen 2M is achieved as shown in Scheme 15 (FIG. 16). Intermediate 37 is prepared according to the procedure described above for immunogen 3M. In Scheme 16 (FIG. 17) compound 37 is coupled with acid 4 using DCC in dichloromethane to afford compound 39. Compound 39 after hydrogenation affords immunogen Synthesis of disaccharide immunogen 3D is accomplished as shown in Scheme 17 (FIG. 18). A key step involved in the synthesis of the disaccharide immunogen is the coupling reaction between the imidate 40 and diol 41 to afford the corresponding coupled compound and subsequent suitable chemical transformations to lead to immunogen-3D.

Figure 19:
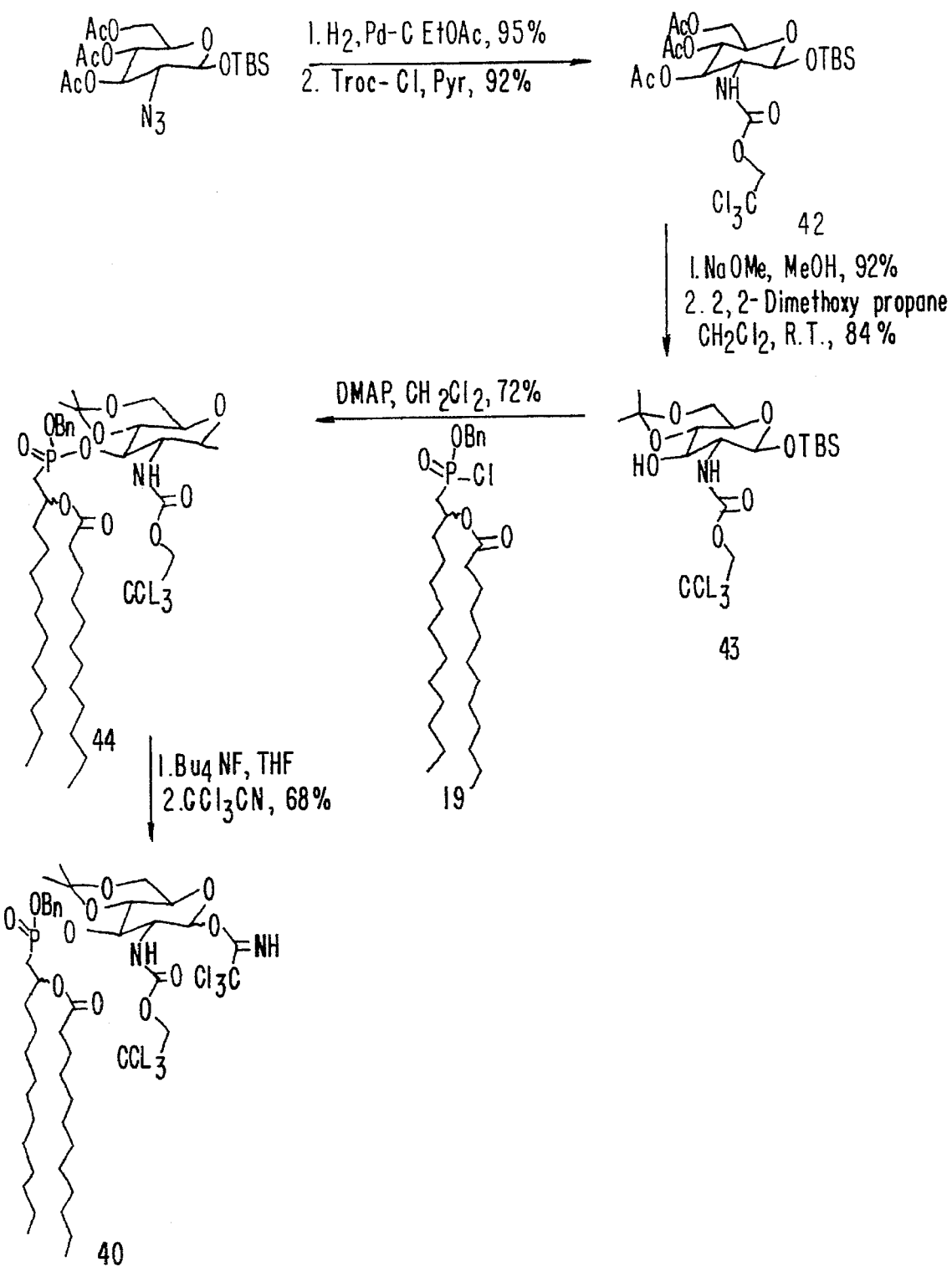
Figure 20:
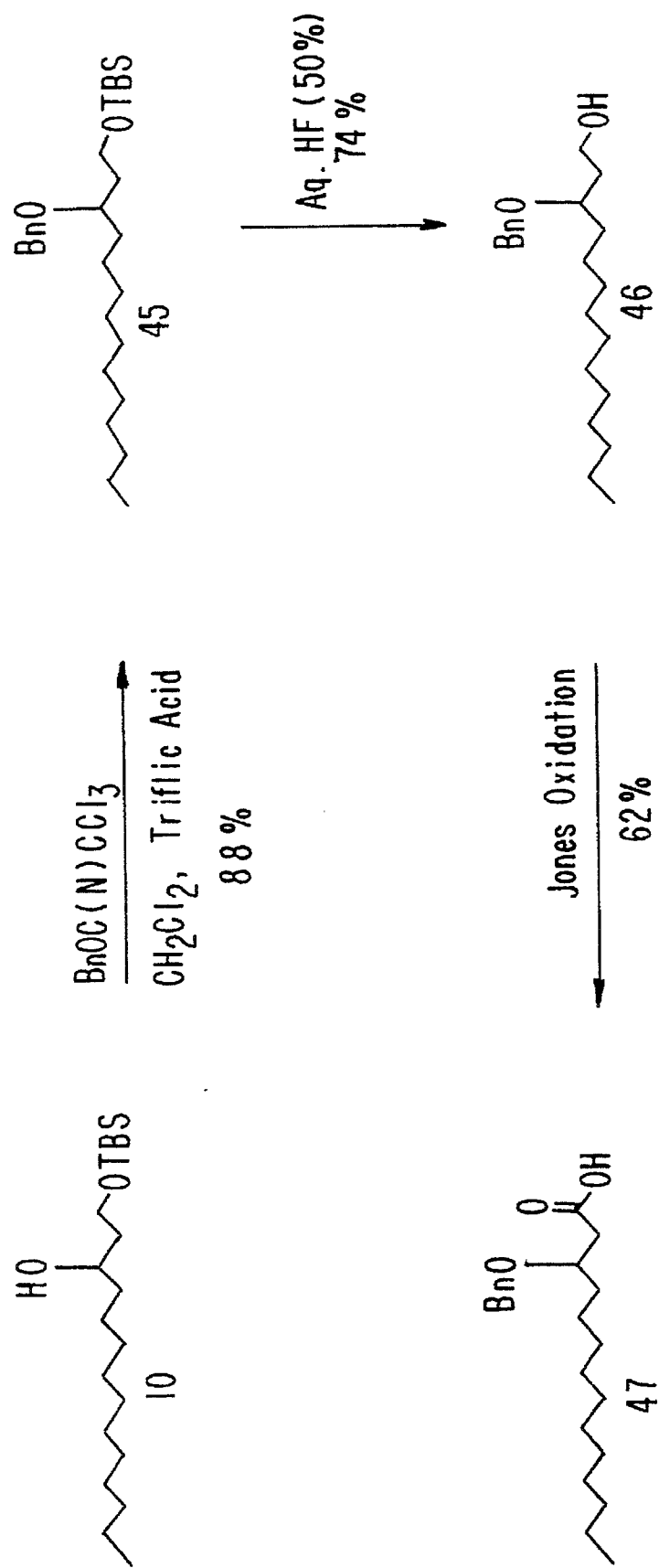

Accordingly, the synthesis of intermediate 40 is started from compound 6a (Schemes 18 and 19) (FIGS. 19 and 20). Compound 6a is prepared by the same procedure as described for the synthesis of BK-1. Compound 6a is hydrogenated using Pd-C as a catalyst in ethyl acetate to afford the corresponding amino compound, which after treatment with Troc-Cl in pyridine and dichloromethane, affords the trichloroethyl carbamate-protected compound 42. Compound 42 is treated with sodium methoxide in methanol to give the corresponding triol, which after treatment with 2,2-dimethoxypropane in dichloromethane in the presence of PTSA, affords the corresponding acetonide 43. Compound 43 is coupled with phosphochloridate 19 (the synthesis of phosphochloridate 19 is described above with respect to the synthesis of 3M) in the presence of DMAP in dichloromethane to afford the coupled compound 44. Then compound 44 is treated with tetrabutylammonium fluoride in THF and dichloromethane and subsequently with trichloroacetonitrile to afford a key intermediate, imidate 40, as an anomeric mixture.

Figure 21:
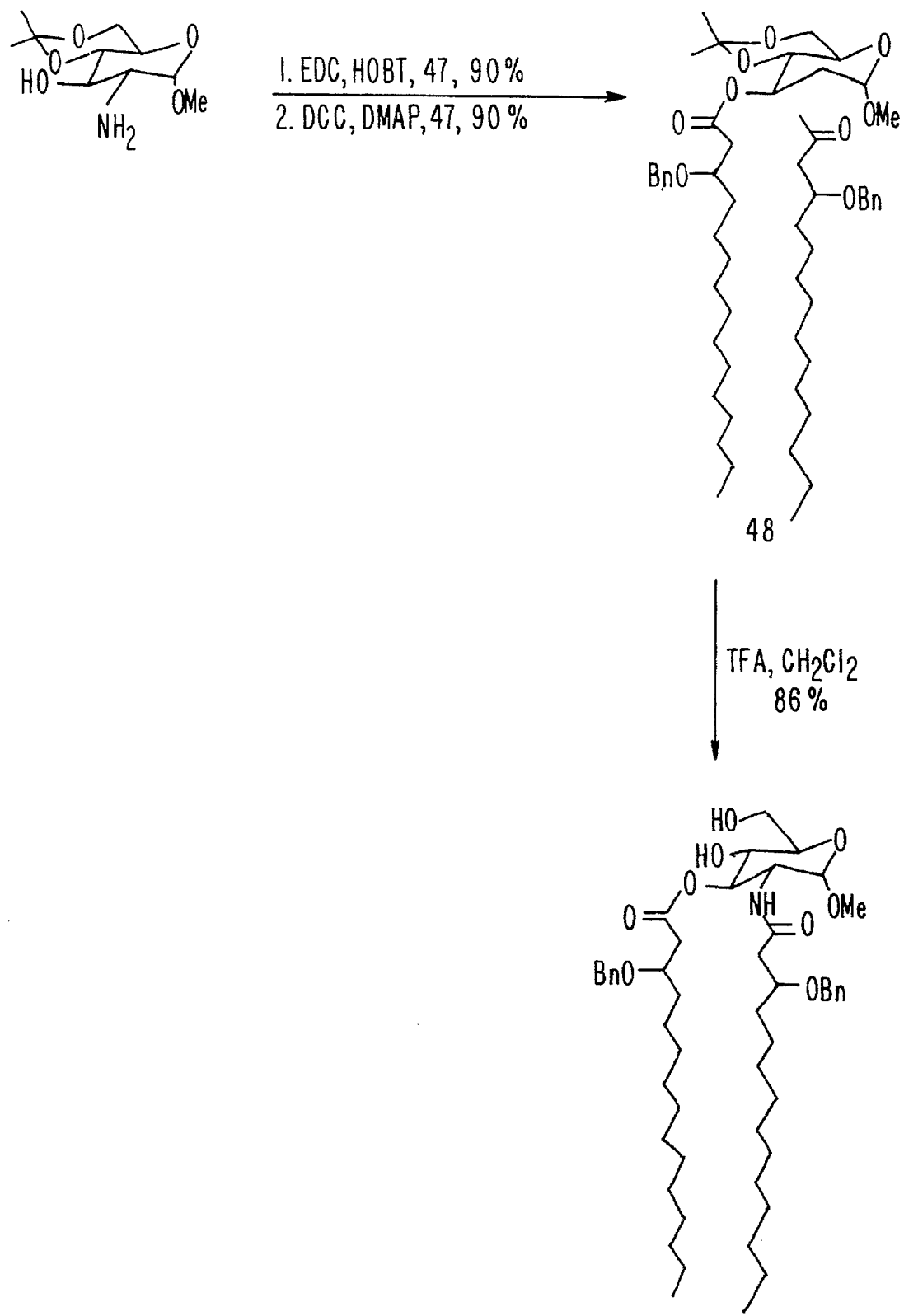

The other intermediate diol 41, is prepared by coupling compound 30 (the preparation of compound 30 is described with respect to the synthesis of 3M) and compound 47 and subsequent deprotection Scheme 19a (FIG. 21).

Compound 47 is prepared from compound 10 (the preparation of compound 10 is described with respect to the synthesis of BK-1). Compound 10 is first benzylated using benzyl 2,2,2-trichloro-acetimidate in dichloromethane in the presence of triflic acid to afford compound 45. Compound 45 is desilylated using PTSA in methanol and dichloromethane to afford the corresponding hydroxy compound 46. Compound 46 is subjected to Jones oxidation to afford compound 47. Compound 47 is coupled with compound 30 (Scheme 19a) (FIG. 21) to afford the coupled compound 48. Compound 48, after treatment with trifluoroacetic acid in dichloromethane, affords the diol compound 41.

Figure 22:
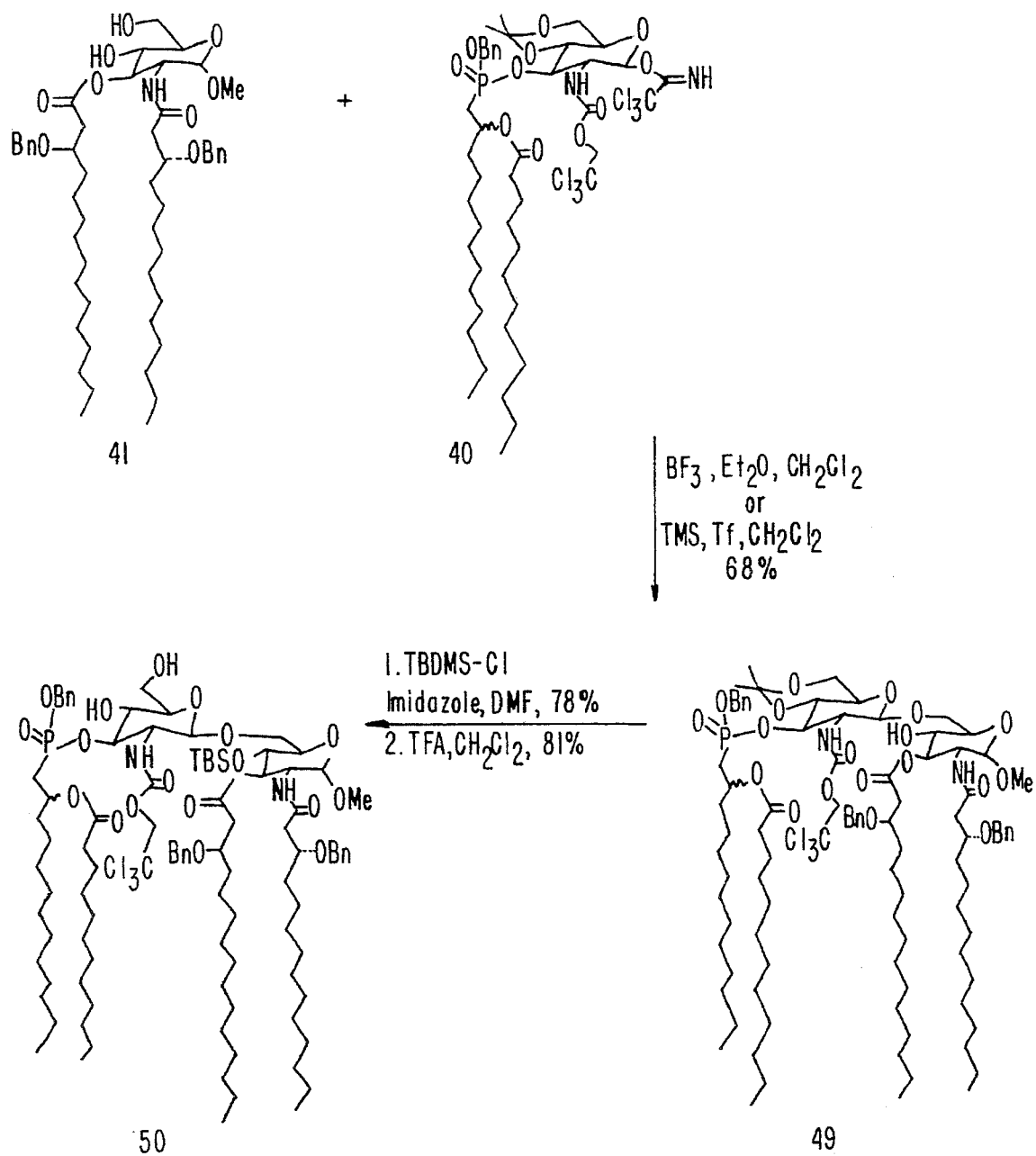
Figure 23:
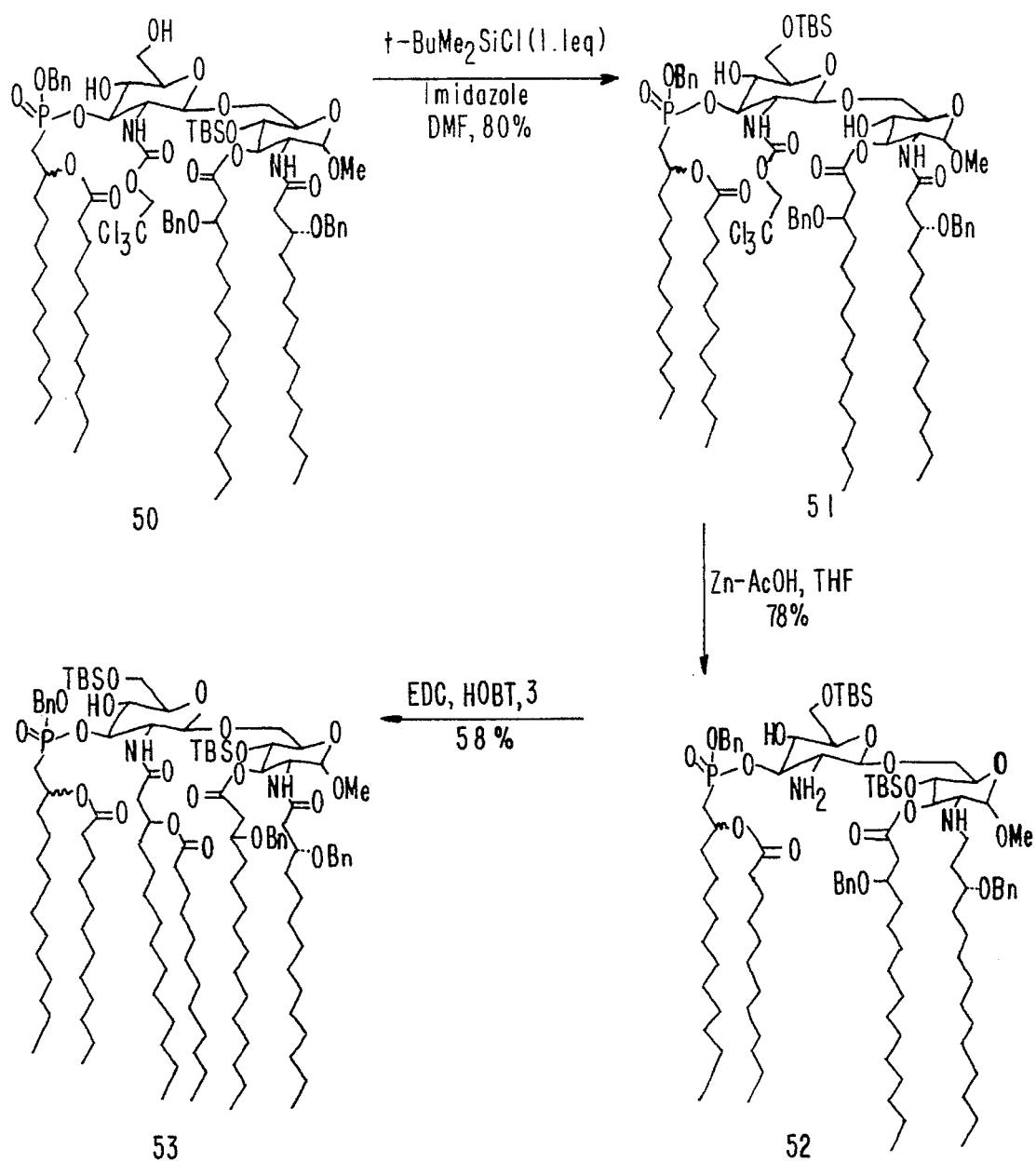

Having thus obtained the glycosyl donor 40 and the acceptor 41, the coupling reaction is performed using Lewis acids such as boron trifluoride etherate and/or TMS triflate. Treating compound 41 and compound 40 in dichloromethane with boron trifluoride etherate and/or TMS triflate affords the coupled compound 49 (Scheme 20) (FIG. 22). The coupled compound 49 is treated with t-butyldimethylsilyl chloride in DMF to afford the silylated compound. The acetonide functionality of the silylated compound is removed using trifluoroacetic acid in dichloromethane to afford the diol 50.

Figure 24:
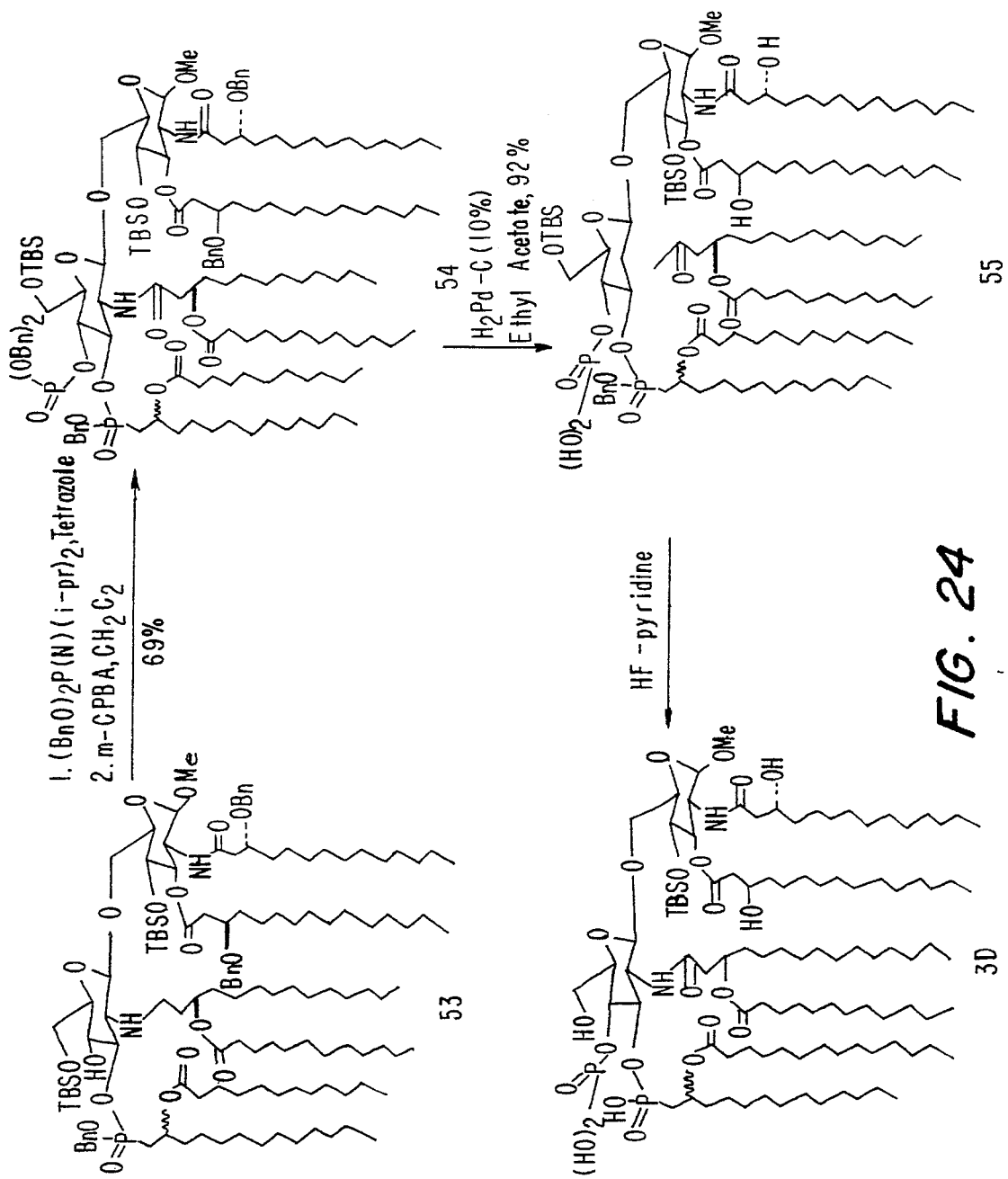

The primary alcohol functionality of the diol 50 is selectively protected as the t-butyldimethyl silyl ether using silylating reaction conditions (Scheme 21) (FIG. 23) to afford compound 51. Compound 51 is deprotected using zinc in acetic acid and THF to afford the diastereomeric mixture of amino compound 52. The amino compound 52 is coupled with acid 3 to afford the coupled compound 53. Phosphorylation of compound 53 at the 4'-position is accomplished by treating compound with N,N-diisopropylamino dibenzyl phosphite in dichloromethane in the presence of tetrazole to afford the corresponding phosphite, which after oxidation with m-CPBA affords the phosphorylated compound 54 (Scheme 22) (FIG. 24). Compound 54 is debenzylated by hydrogenation over Pd-C (10%) in ethyl acetate to afford compound 55. Compound 55 is treated with HF-pyridine to afford immunogen 3D.

Figure 25:
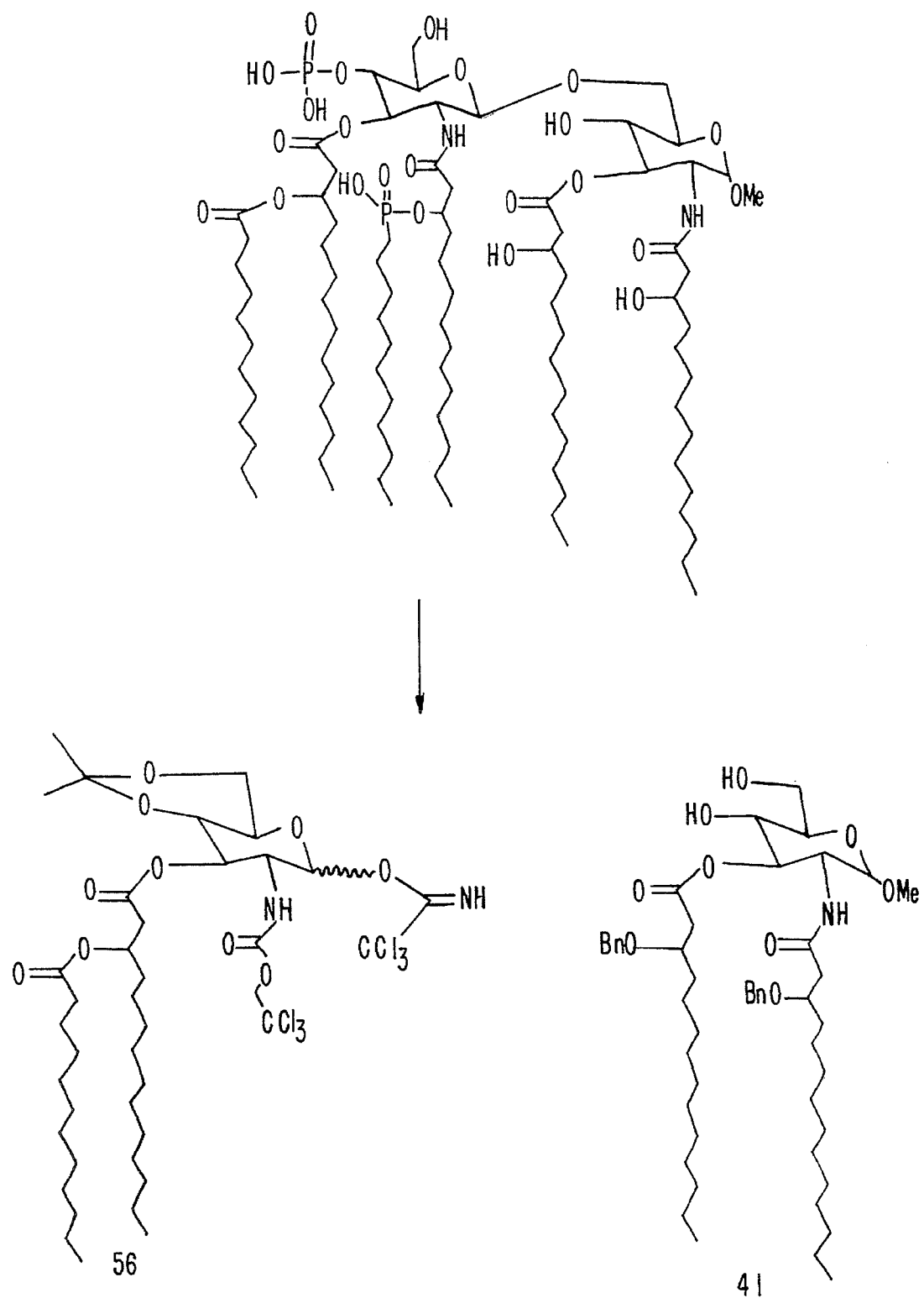

Synthesis of immunogen 1D is achieved starting from the intermediates 56 and compound 41 (Scheme 23) (FIG. 25).

Figure 26:
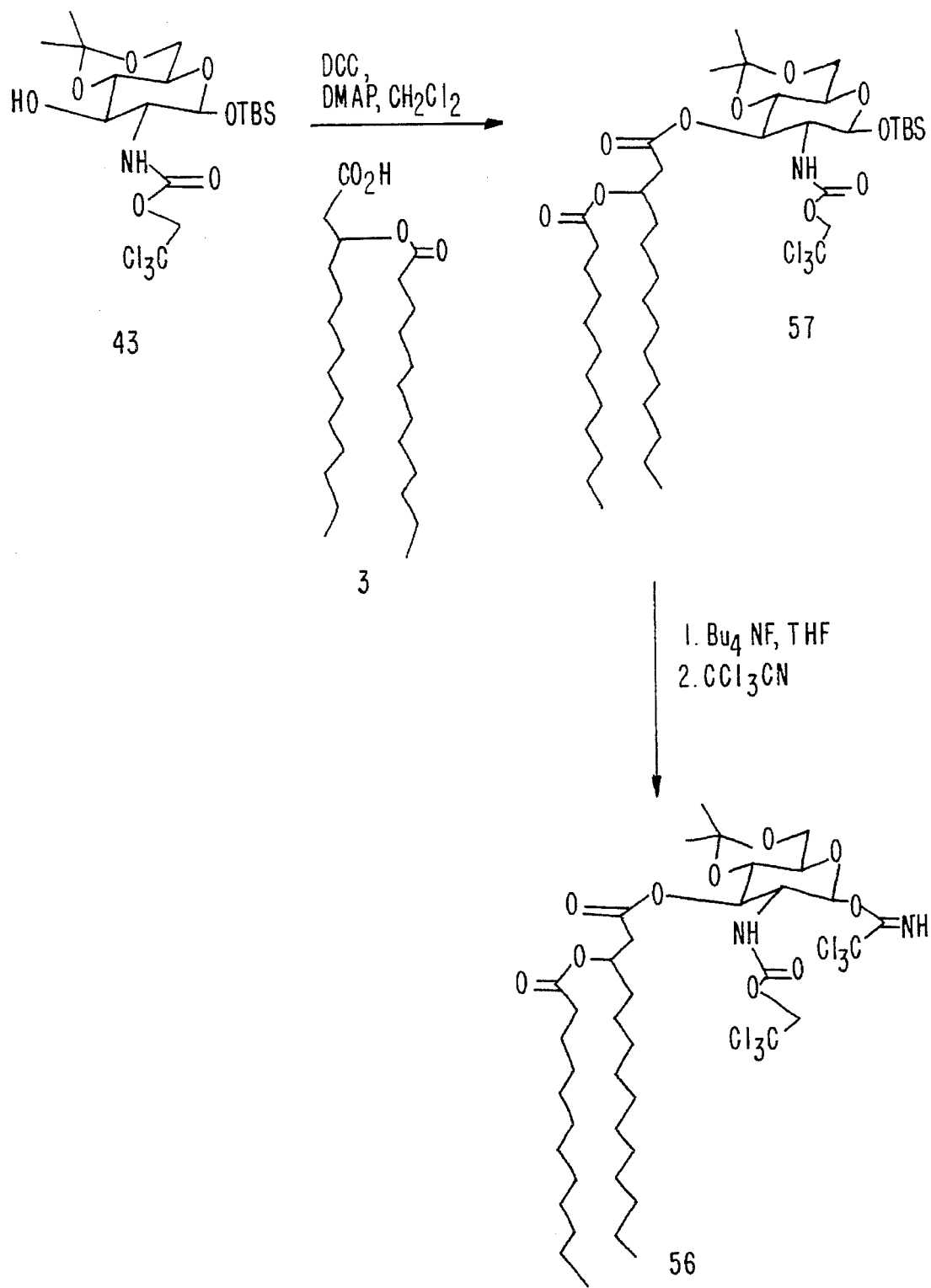
Figure 27:
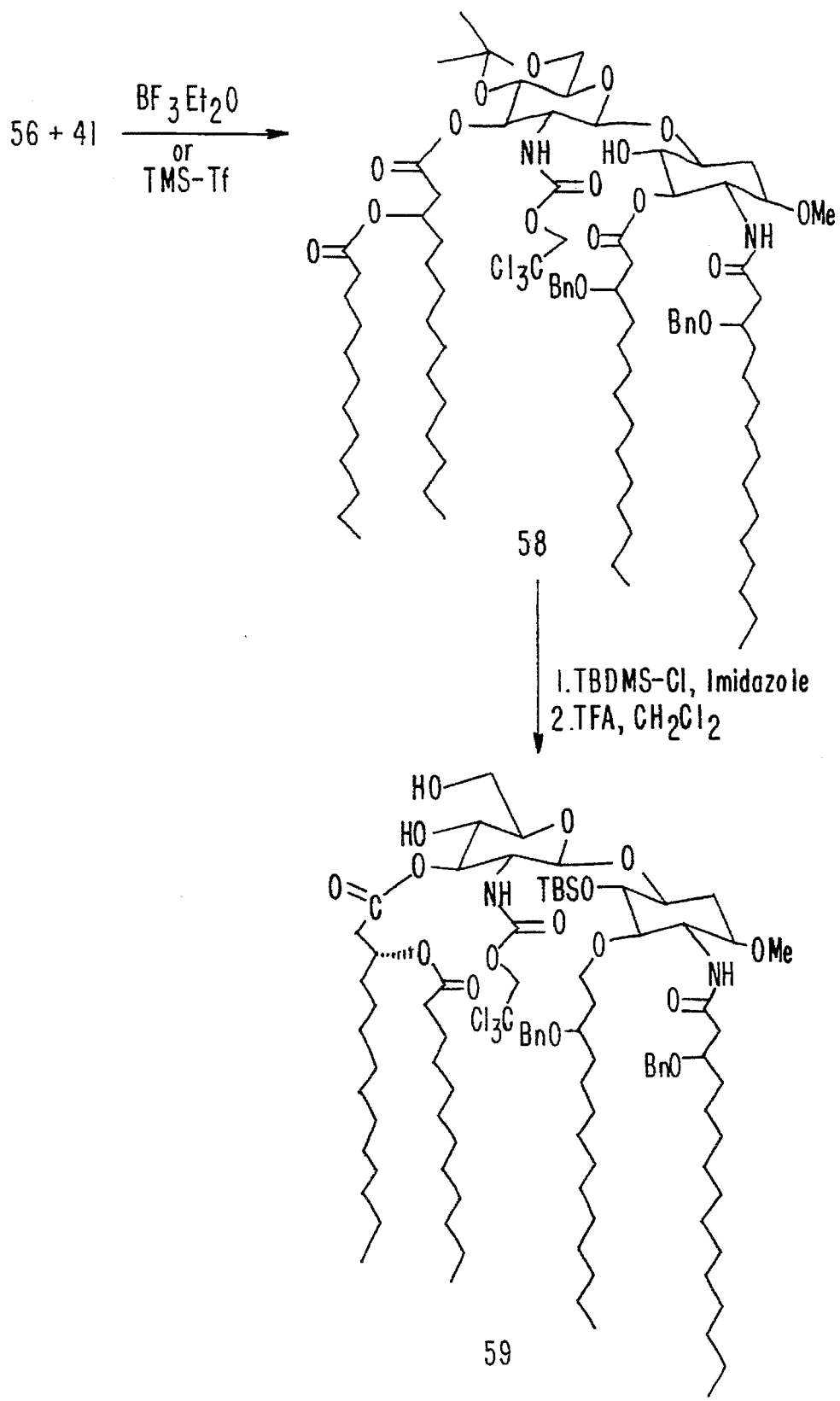
Figure 28:
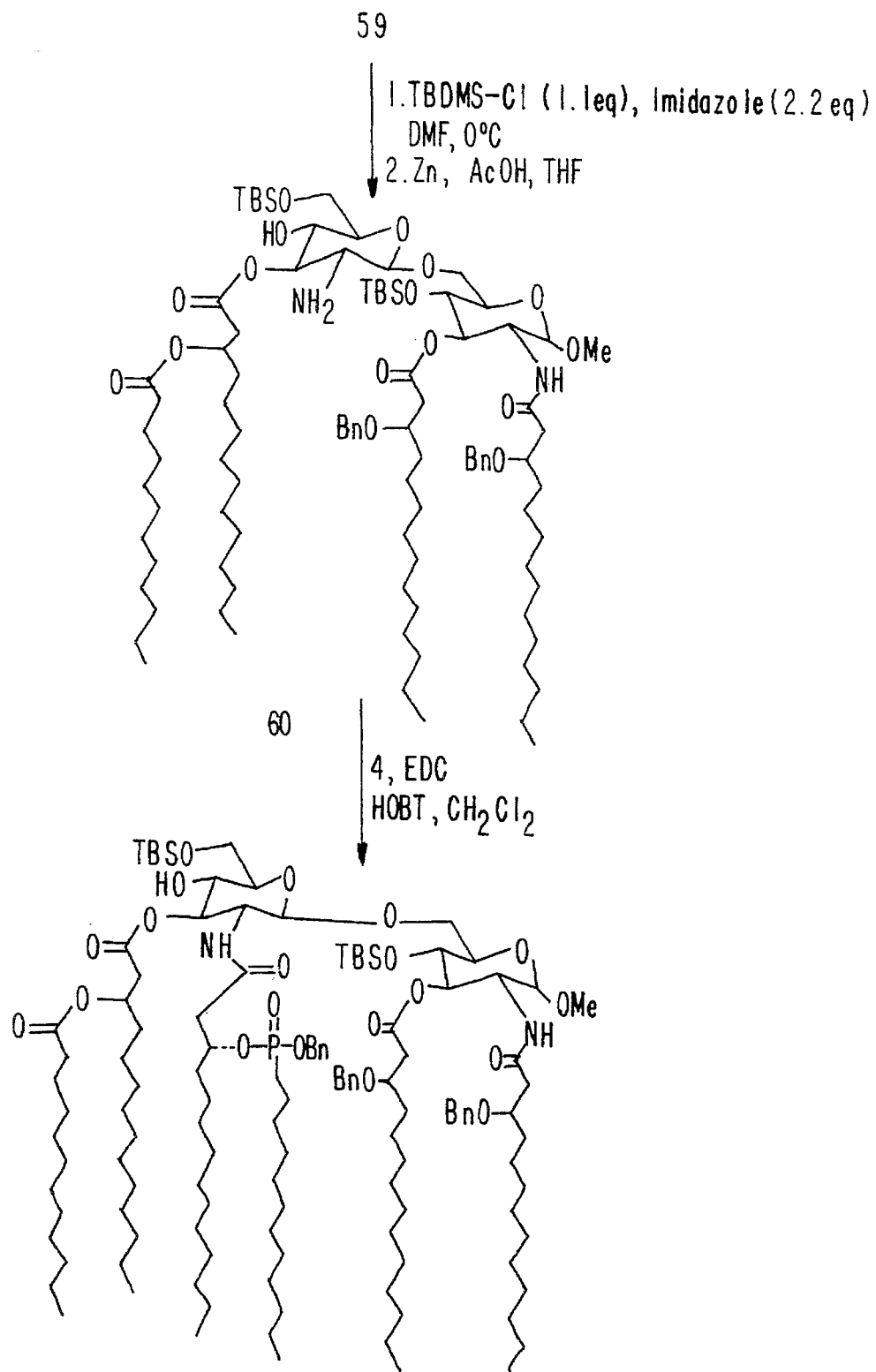

Preparation of intermediate 56 is accomplished by following the sequence of reactions outlined in Scheme 24 (FIG. 26). Accordingly, the compound 43 after coupling with acid 3 in dichloromethane in the presence of DCC and DMAP, affords the coupled product 57. Compound 57, after treatment with tetrabutylammonium fluoride in THF followed by addition of trichloroacetonitrile, affords an anomeric mixture of imidates 56.

The imidate compound 56 and diol compound 41 in dichloromethane in the presence of Lewis acid (either boron trifluoride etherate or TMS-triflate)(Scheme 25) (FIG. 27), affords the coupled compound 58. The hydroxyl functionality of compound 58 is protected as the t-butyldimethylsilyl ether using t-butyldimethylsilyl chloride in DMF in the presence of imidazole, and the resulting silylated compound, after treatment with trifluoroacetic acid, affords the corresponding diol compound 59. The primary hydroxyl functionality of the diol compound 59 is selectively protected as the TBDMS ether (Scheme 26) (FIG. 28) by using t-butyldimethylsilyl chloride (1.1 eq) in DMF in the presence of imidazole (2.2 eq) and the resulting compound after treatment with zinc in acetic acid and THF affords the amino compound 60. The amino compound 60 on coupling with acid 4 in dichloromethane in the presence of EDC and HOBT affords the coupled compound 6.

Figure 29:
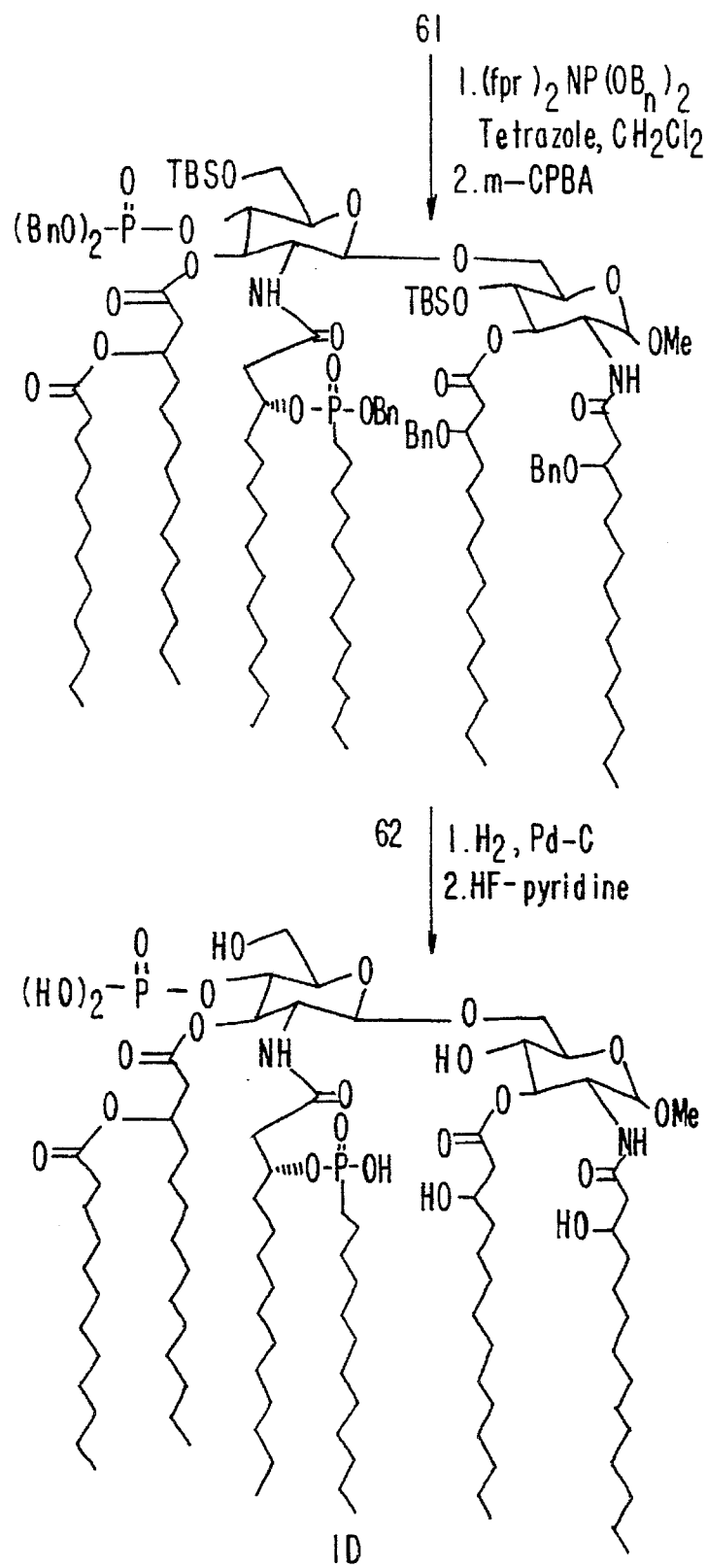

The C-4' hydroxyl position of compound 61 is phosphorylated using the same method as used for the synthesis of immunogen 3D. The phosphorylated compound 62 is converted to immunogen 1D by hydrogenation followed by desilylation using HF- pyridine (Scheme 27) (FIG. 29).

Figure 30:
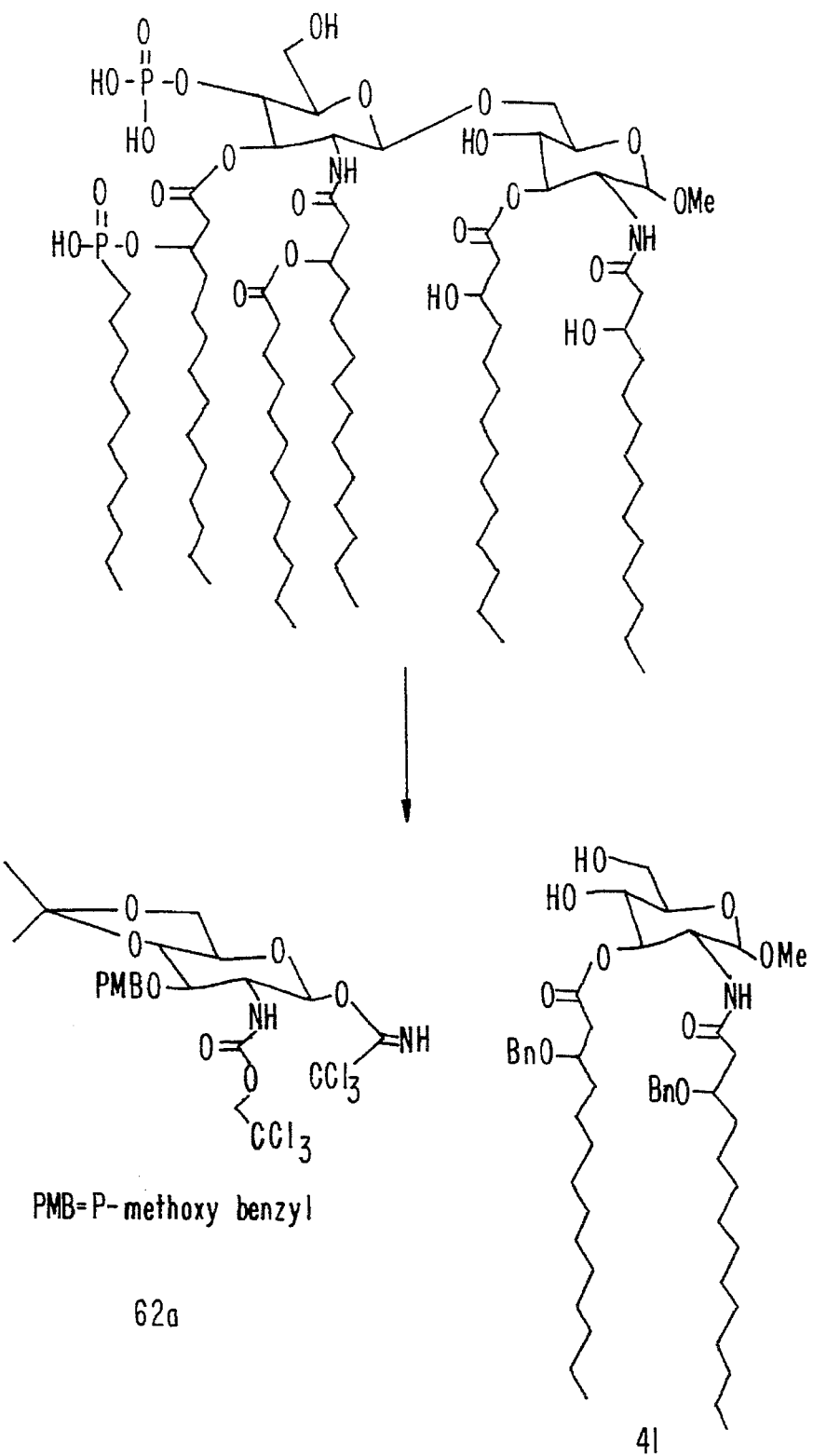

Synthesis of immunogen 2D is achieved by coupling the imidate 62a and compound 41 to afford the coupling compound, which on suitable chemical transformations affords the immunogen 2D (Scheme 28) (FIG. 30).

Figure 31:
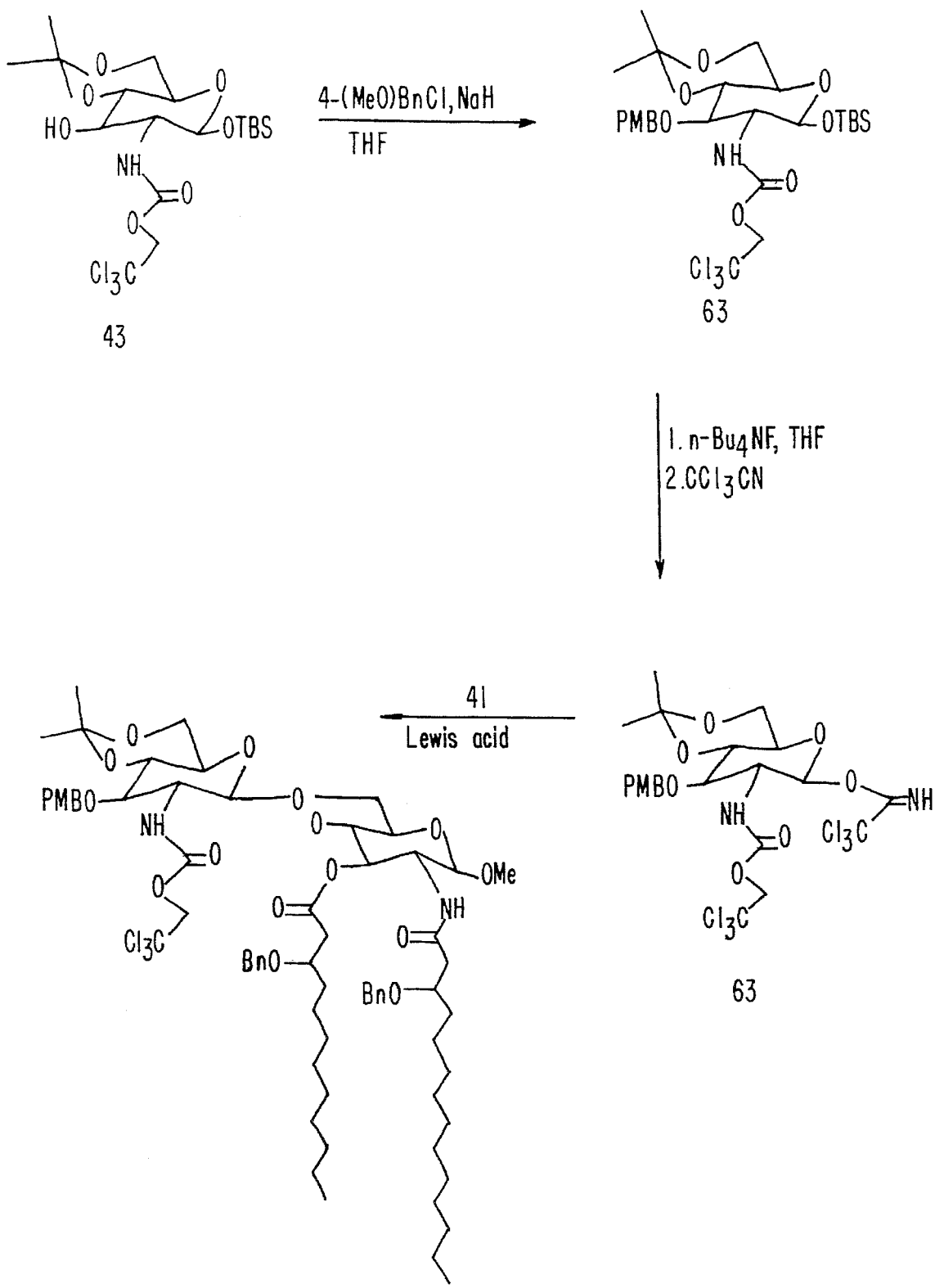
Figure 32:
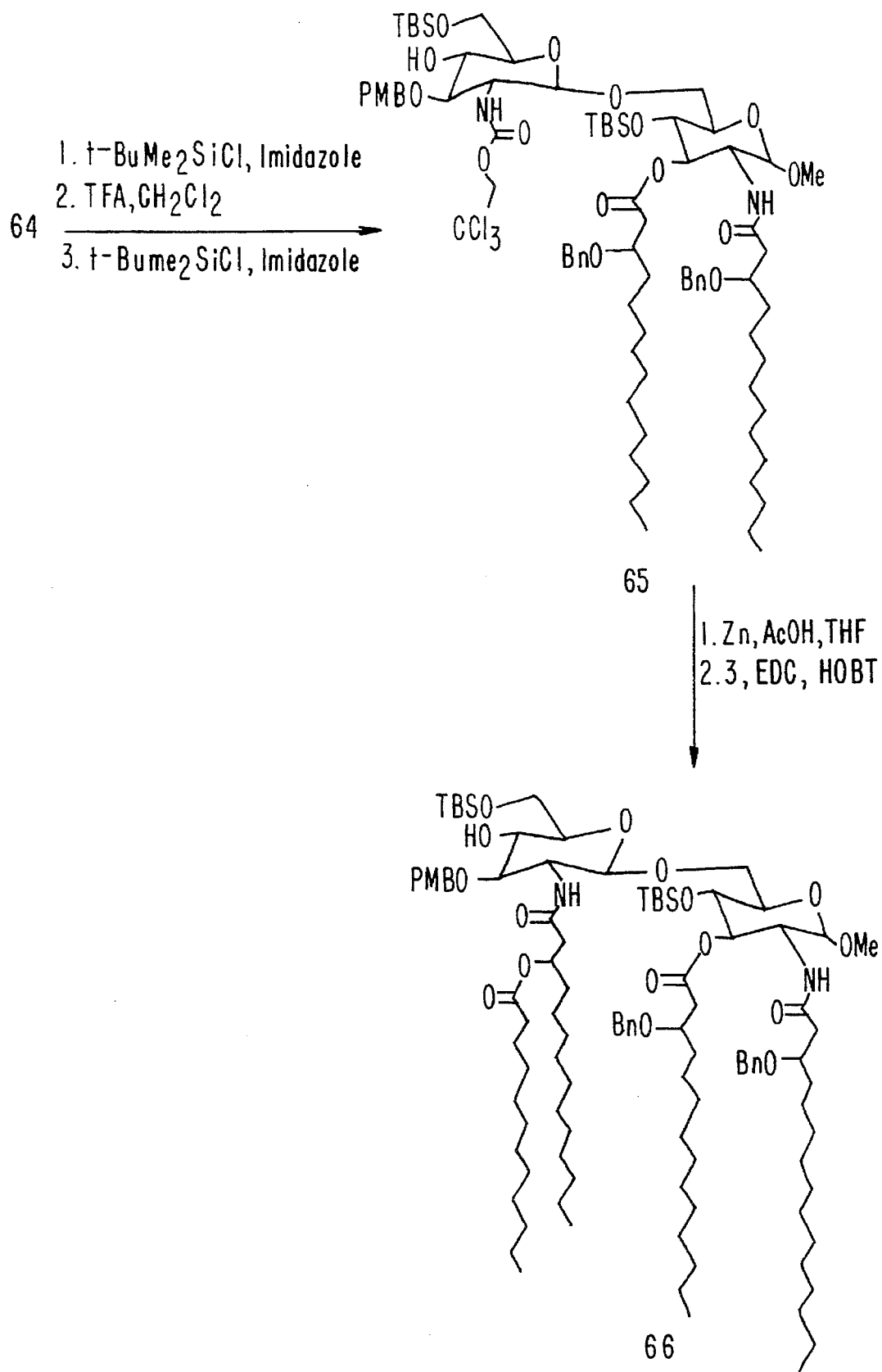

The hydroxy compound 43 is treated with 4-methoxybenzyl chloride in THF in the presence of sodium hydride to afford compound 63. Compound 63 after treatment with tetrabutyl-ammonium fluoride in THF followed by treatment with 62a trichloroacetonitrile, yields imidate 62a as an anomeric mixture (Scheme 29) (FIG. 31). The imidate is coupled with compound 41 in the presence of a Lewis acid (either boron trifluoride etherate or TMS-triflate) to afford the coupled compound 64. Compound 64 on treatment with t-butyldimethylsilyl chloride in DMF in the presence of imidazole, affords the corresponding silylated compound, which after treatment with trifluoroacetic acid, gives the diol (Scheme 30) (FIG. 32). The primary hydroxyl functionality of the diol compound is selectively protected as the t-butyldimethylsilyl ether by treatment with t-butyldimethylsilyl chloride (1.1 eq) in DMF in the presence of imidazole (2.2 eq) to afford the compound 65. Compound 65, after treatment with zinc in acetic acid and THF, gives the corresponding amino compound, which after treatment with acid 3 in dichloromethane in the presence of EDC and HOBT, affords the coupled compound 66.

Figure 33:
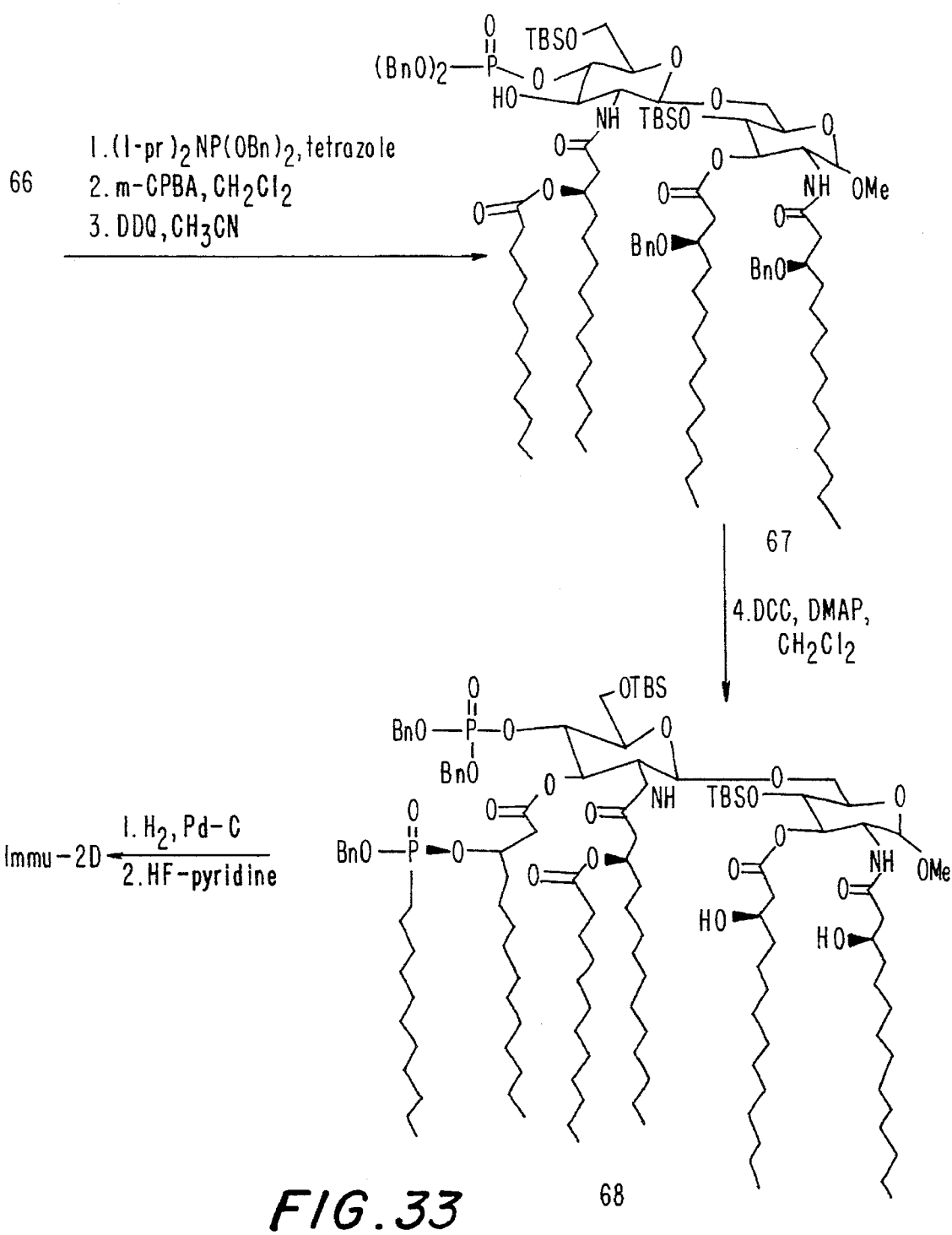

The C-4' hydroxyl of compound 66 is phosphorylated using the method utilized for the other immunogens to afford the corresponding phosphorylated compound, which after treatment with DDQ affords the corresponding deprotected compound 67 (Scheme 31) (FIG. 33). Compound 67, after treatment with acid 4 in dichloromethane in the presence of DCC and DMAP, affords the coupled compound 68. Compound 68 is converted to immunogen 2D by hydrogenation followed by desilylation (HF-pyridine).

Figure 34:
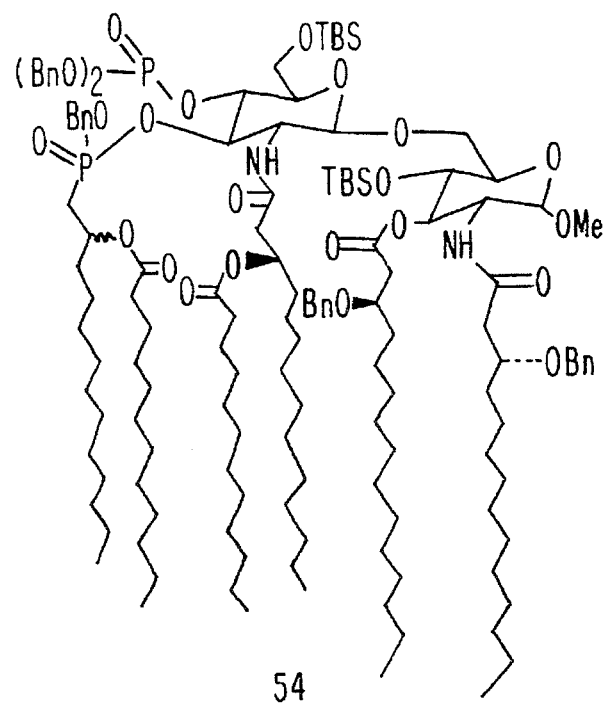
Figure 34:
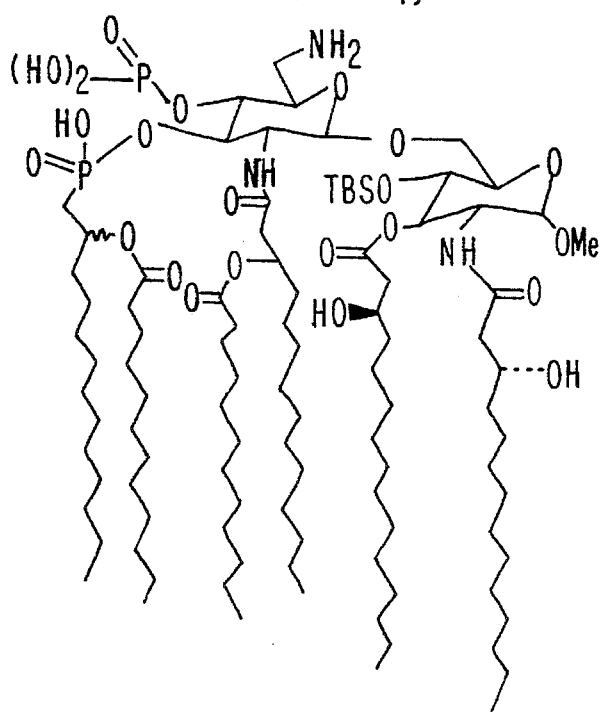
Figure 35:
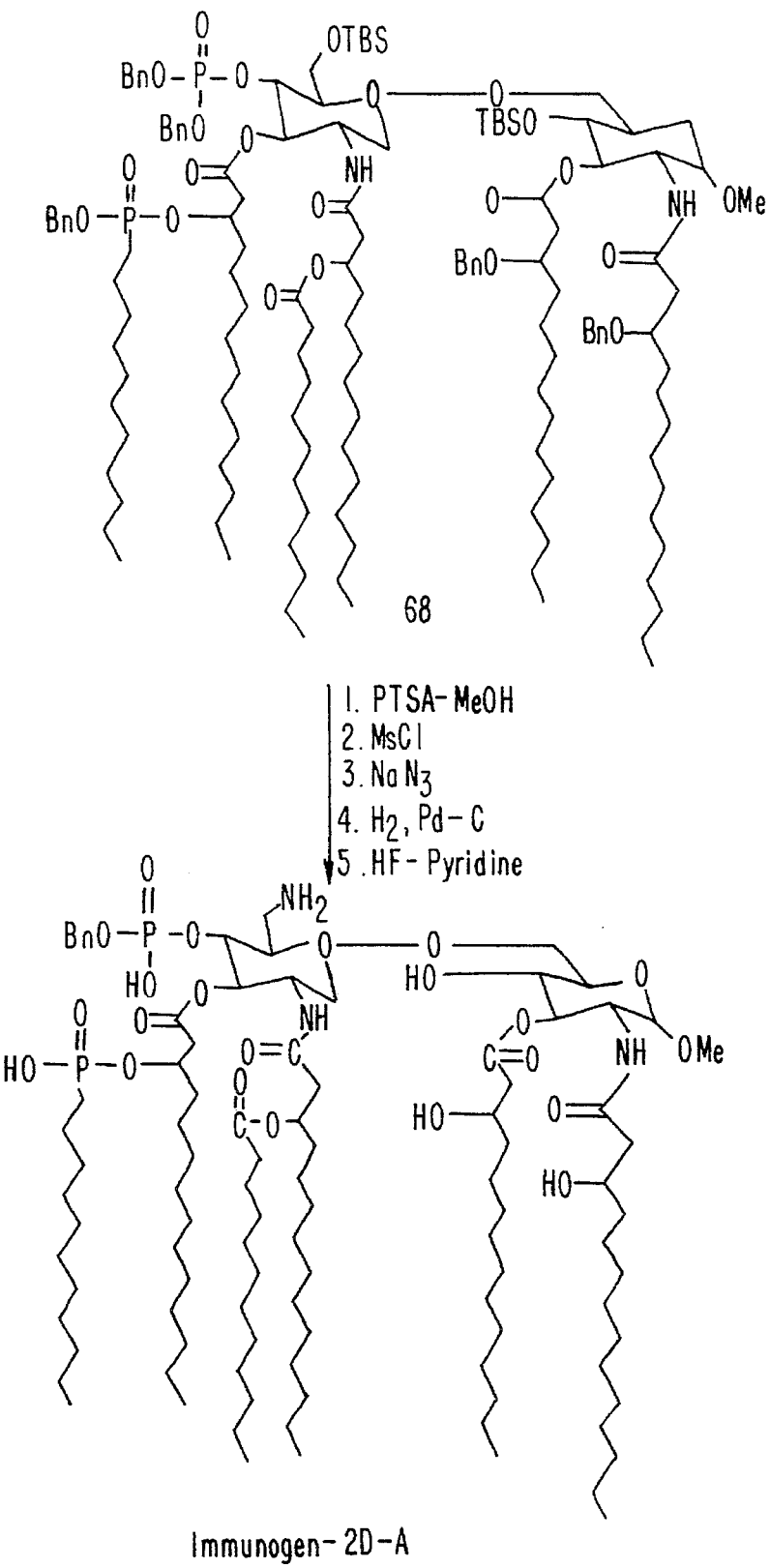
Figure 36:
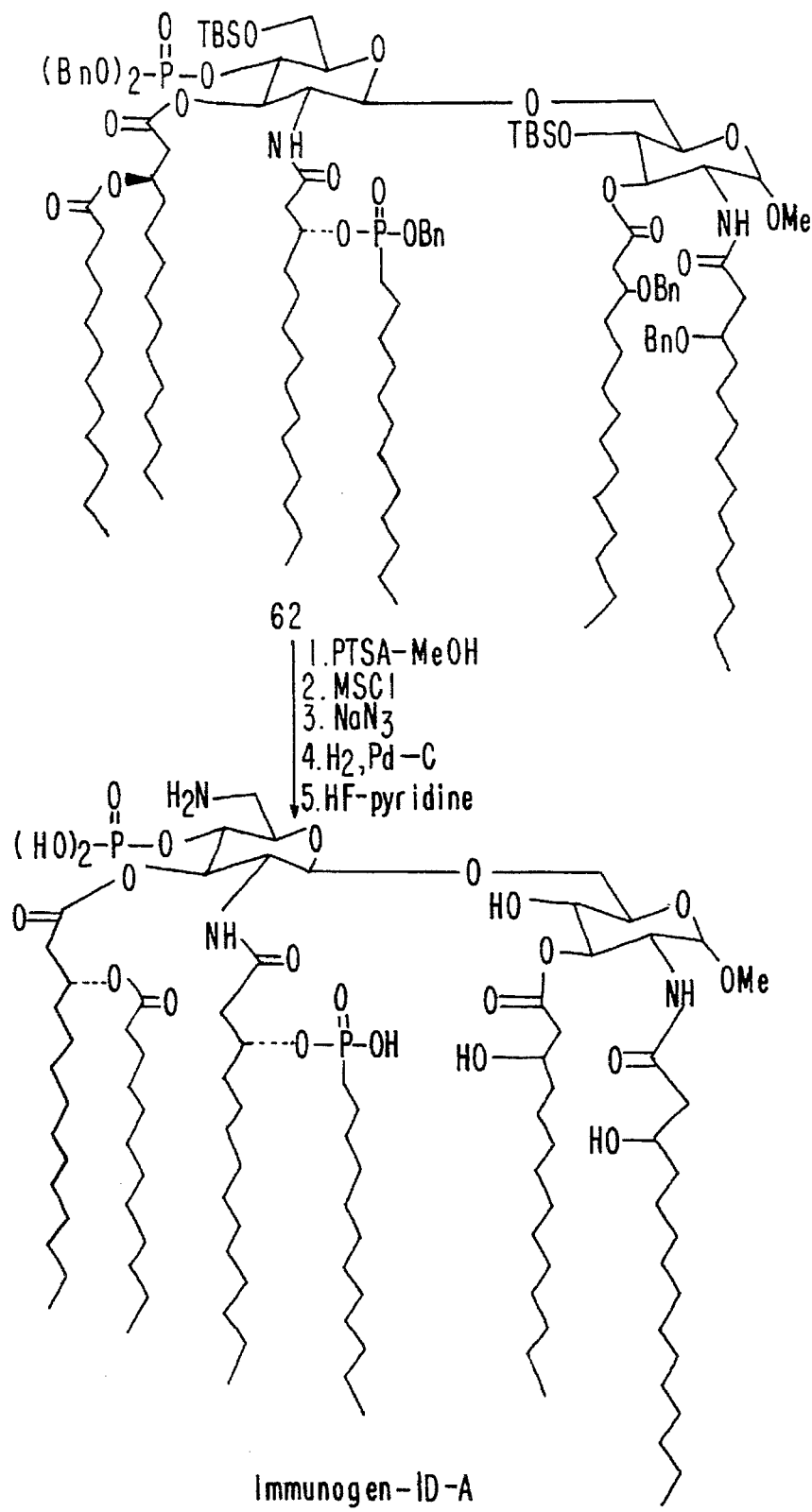

Synthesis of immunogen 3D-A is achieved starting from the intermediate 54 (Scheme 32) (FIG. 34). Accordingly, compound 54 on treatment with PTSA in methanol affords the corresponding hydroxy compound. The hydroxy compound on treatment with MsCl gives the mesylate, which on treatment with sodium azide gives the corresponding azide compound. The azido compound on hydrogenation with Pd-C in ethyl acetate and followed by treatment with HF-pyridine affords the immunogen 3D-A.

Synthesis of other immunogens 2D-A and D-A is also accomplished by the similar sequence of reactions starting from 68 (Scheme 33) (FIG. 35) and 62 (Scheme 34) (FIG. 36) respectively.

Figure 37:
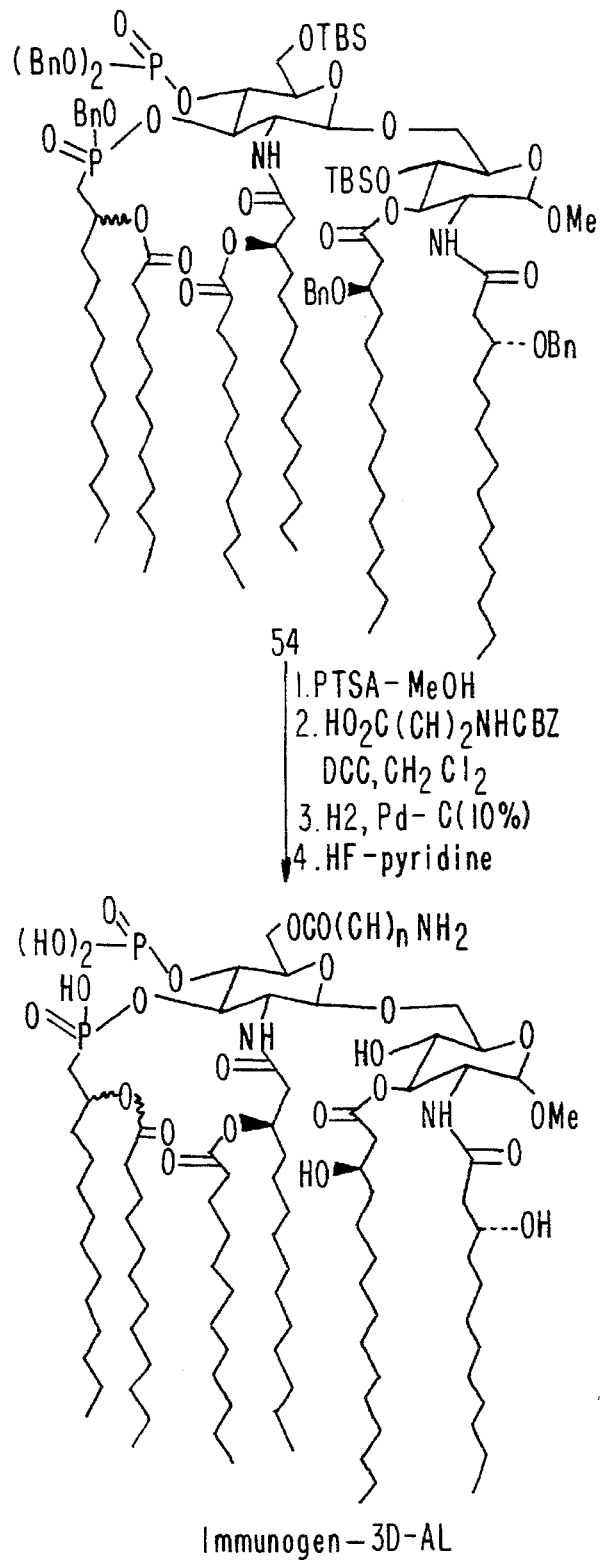
Figure 38:
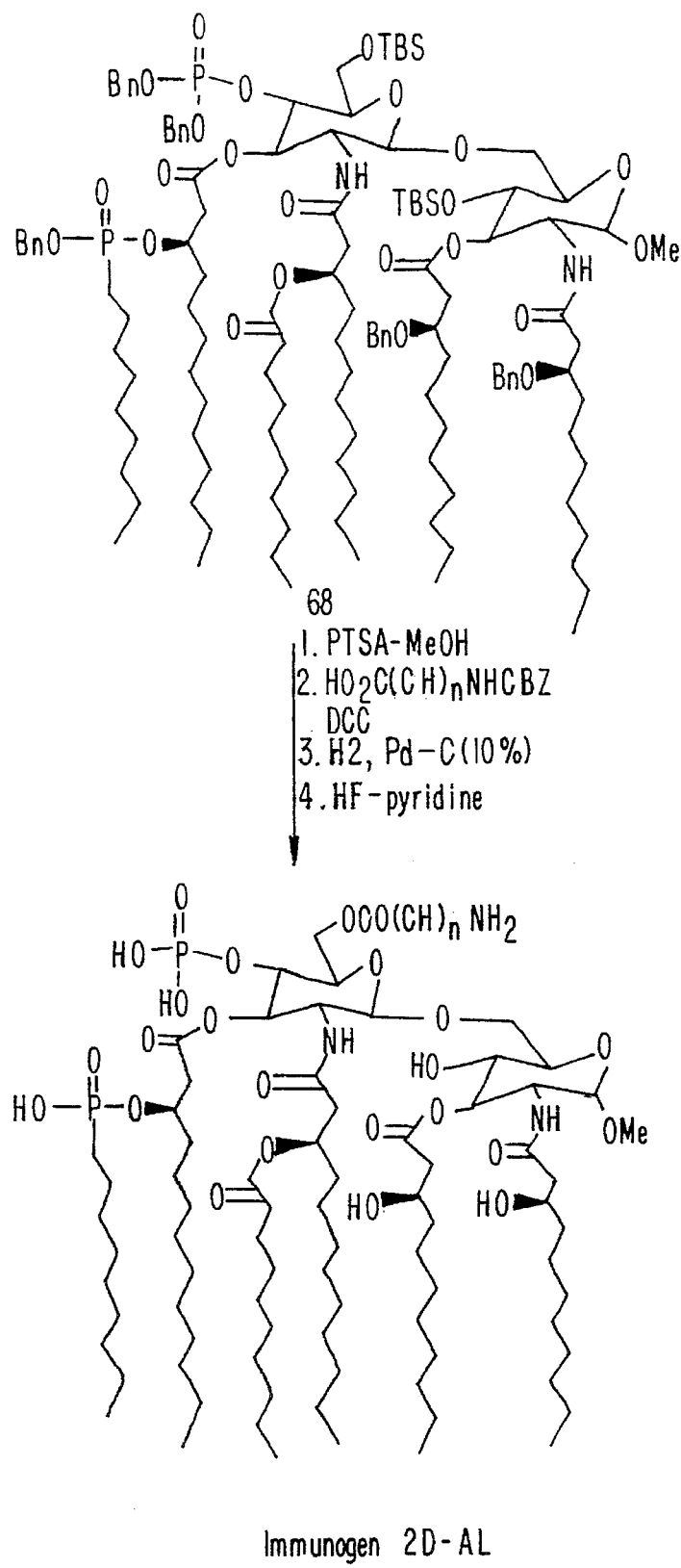
Figure 39:
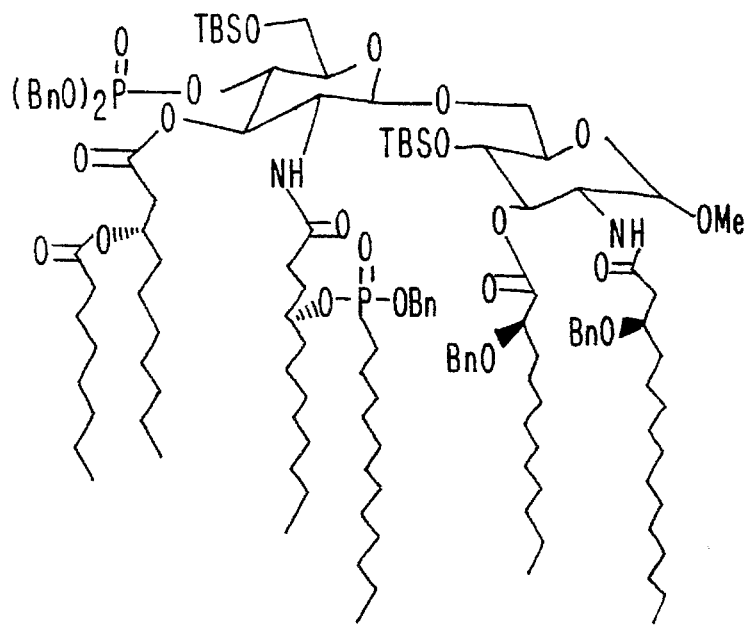
Figure 39:
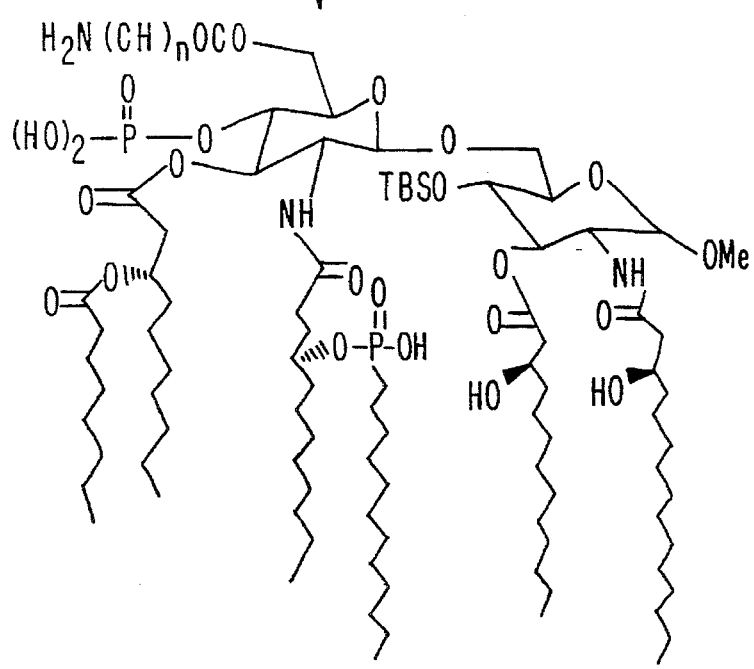

Synthesis of immunogen 3D-AL is achieved starting from the intermediate 54 (Scheme 35) (FIG. 37). Accordingly compound 54 on treatment with PTSA in methanol affords the corresponding hydroxy compound. The hydroxy compound on treatment with the amino protected acid in dichloromethane in the presence of DCC gives the corresponding coupled compound. The coupled compound after hydrogenation with Pd-C in ethyl acetate and followed by treatment with HF-pyridine affords the immunogen 3D-AL.

Synthesis of other immunogens 2D-AL and 1D-AL is accomplished starting from intermediates 68 (Scheme 36) (FIG. 38) and 62 (Scheme 37) (FIG. 39) respectively by the similar sequence of reaction adopted for 3D-AL from 54.

Figure 41:
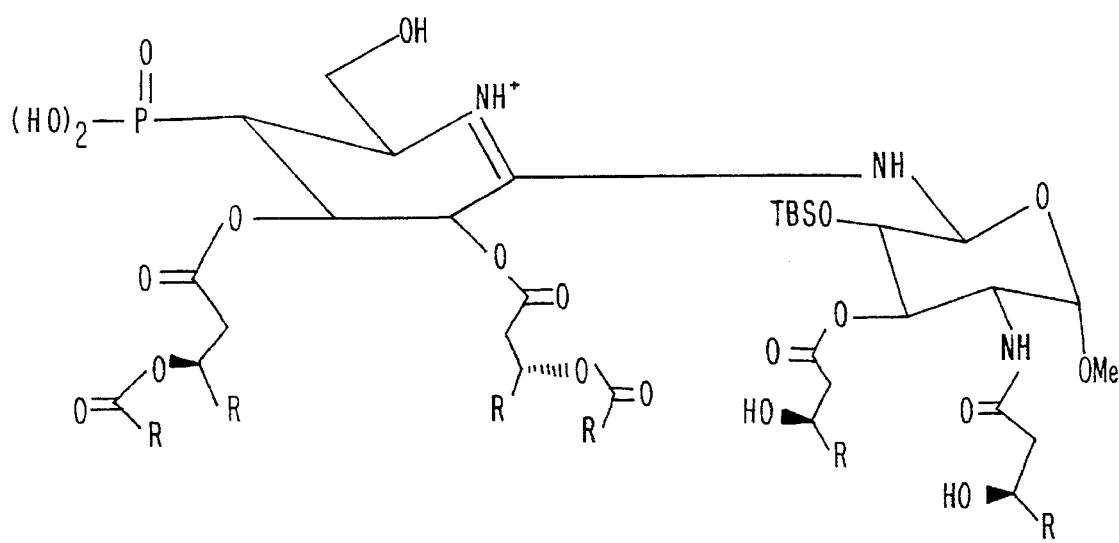

With reference to Schemes 38 to 45, (FIGS. 41–47) synthesis and uses of the formula (II), amidine TS analogs of Lipid-A of the present invention, particularly with respect to a preferred embodiment thereof, is as follows:

Synthesis of amidine TS analog 79 (FIG. 41) is performed as follows. In FIG. 41, compound 79 is shown as having $R=C_{11}H_{23}$; however, in formula (II), each of $R_a$, $R_b$, $R_c$, $R_d$ and $R_e$ independent of each other can be a branched or linear, substituted or unsubstituted $C_1$–$C_{11}$ alkyl, alkene or alkyne. From the herein described synthesis method for analog 79 the skilled artisan, without undue experimentation, can modify the procedure to obtain the compounds encompassed by the herein definition of formula (II). The synthesis of analog 79 is performed by first preparing two intermediate compounds 71 and 77 and coupling them by appropriate chemical reactions and then converting the coupled compound to the amidine compound.

Figure 42:
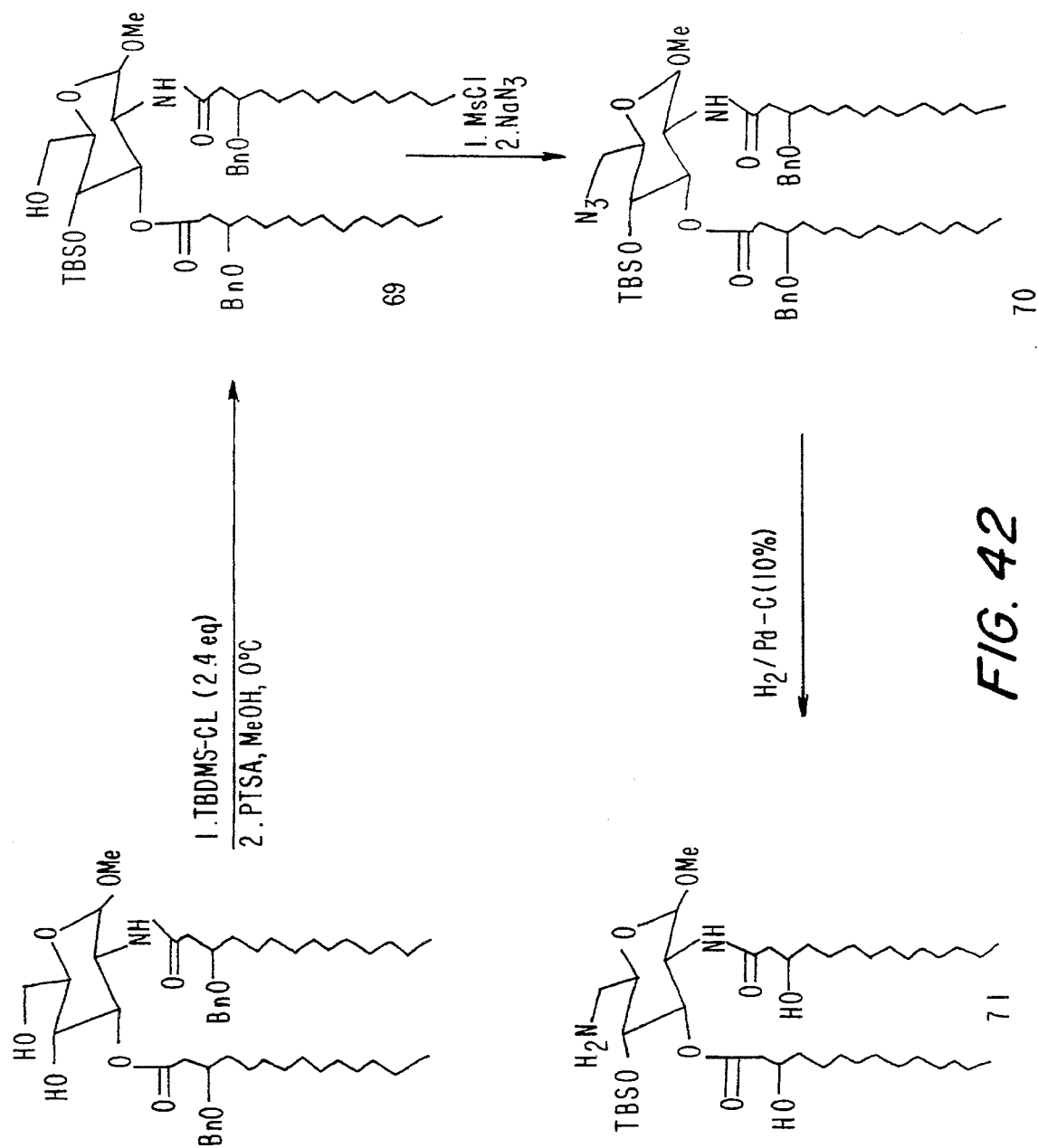

Synthesis of intermediate 71 (synthesis see immunogen 3D) is started from the diol compound 41 (FIG. 42). Compound 4 is treated with about 2.4 eq TBDMS-Cl in DMF in the presence of imidazole to afford the disilylated compound. The disilylated compound on treatment with a catalytic amount PTSA in methanol at 0° C. affords the primarysilyl cleaved compound 69. Hydroxy compound 69 is converted to mesylate by treatment with Ms-Cl, which on treatment with sodium azide affords the corresponding azide compound 70. Compound 70 on hydrogenation affords the amino compound 71.

Figure 43:
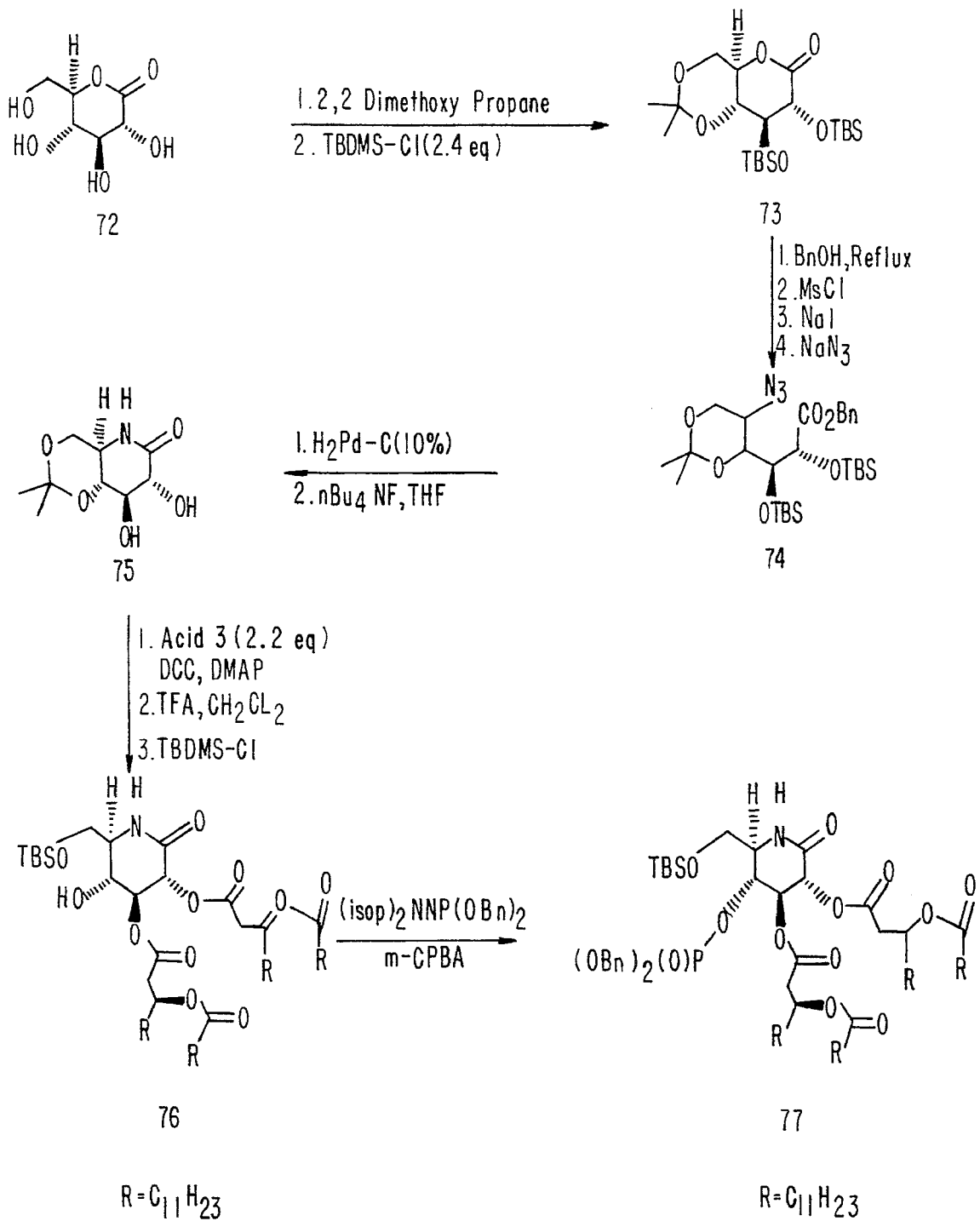
Figure 44:
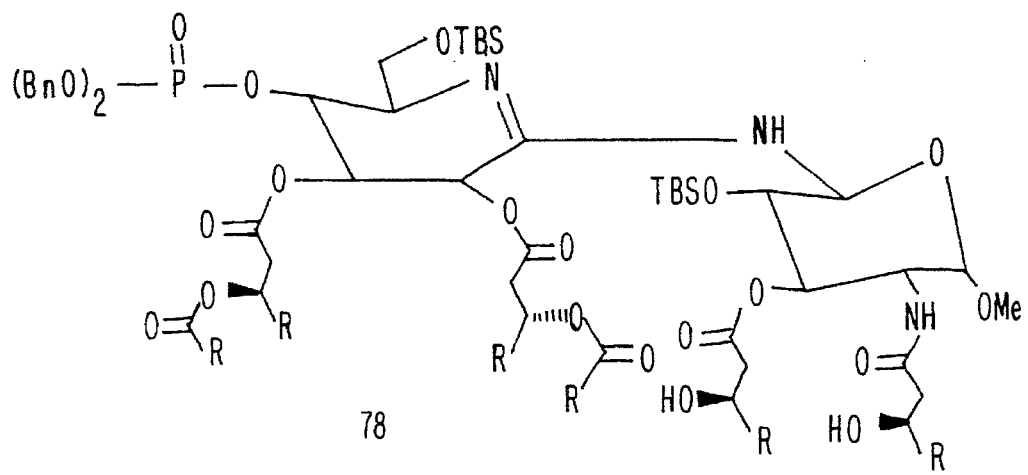
Figure 44:
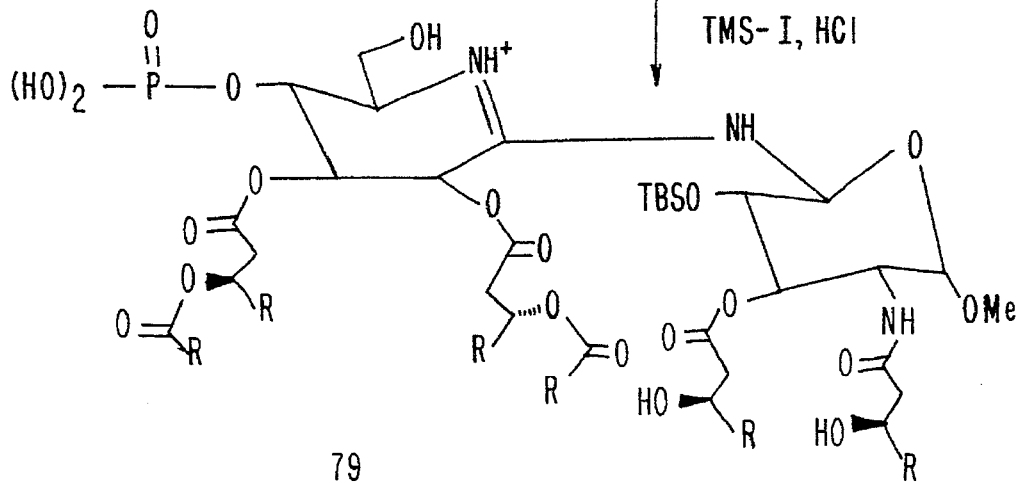

The other intermediate 77 is prepared from the commercially available lactone 72 (FIG. 43). Compound 72 on treatment with 2,2 dimethoxy propane affords the acetonide which, on treatment with about 2.4 eq TBDMS-Cl affords the compound 73. Compound 73, on treatment with benzyl alcohol at about reflux temperature, affords the hydroxy benzylester compound. The hydroxy ester compound on treatment with MS-Cl gives the mesylate compound, which on treatment with sodium iodide gives the corresponding iodo compound. The iodo compound on treatment with sodium azide affords the azido compound 74. Compound 74 on hydrogenation gives the lactam, which on treatment with tetrabutylammonium fluoride affords the hydroxy lactam 75. Compound 75 on treatment with about 2.2 eq acid 3 (synthesis of acid 3: see BK-1) in the presence of DCC and DMAP affords the coupled compound. The coupled compound, on treatment with trifluoroacetic acid affords the diol, which on reacting with about 1.1 eq TBDMS-Cl affords selectively the primary hydroxy protected compound 76. The phosphorylation at the 4-position is accomplished by treatment of compound 76 with N,N-diisopropylamino dibenzylphosphite in the presence of tetrazole. This results in forming the corresponding phosphite, which on oxidation with m-CPBA affords the corresponding phosphate compound 77 (FIG. 44). Compound 77, on treatment with Meerwein reagent followed by addition of compound 71 affords the coupled compound 78. Compound 78 is converted to compound 79 by hydrogenation followed by treatment with HF-pyridine. Alternatively, compound 78 is also converted to 79 by treatment with TMS-I followed by acidification.

Figure 45:
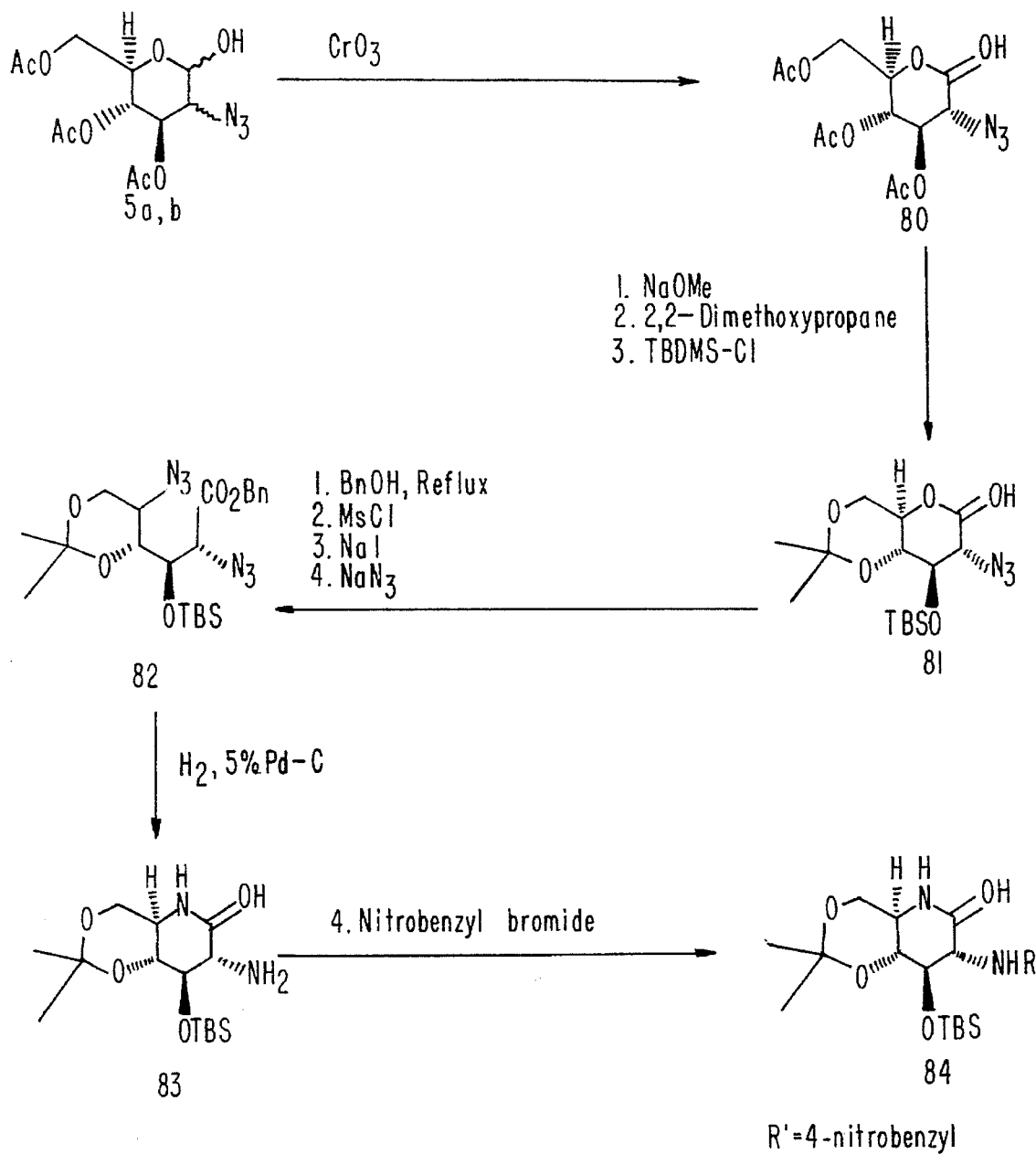
Figure 46:
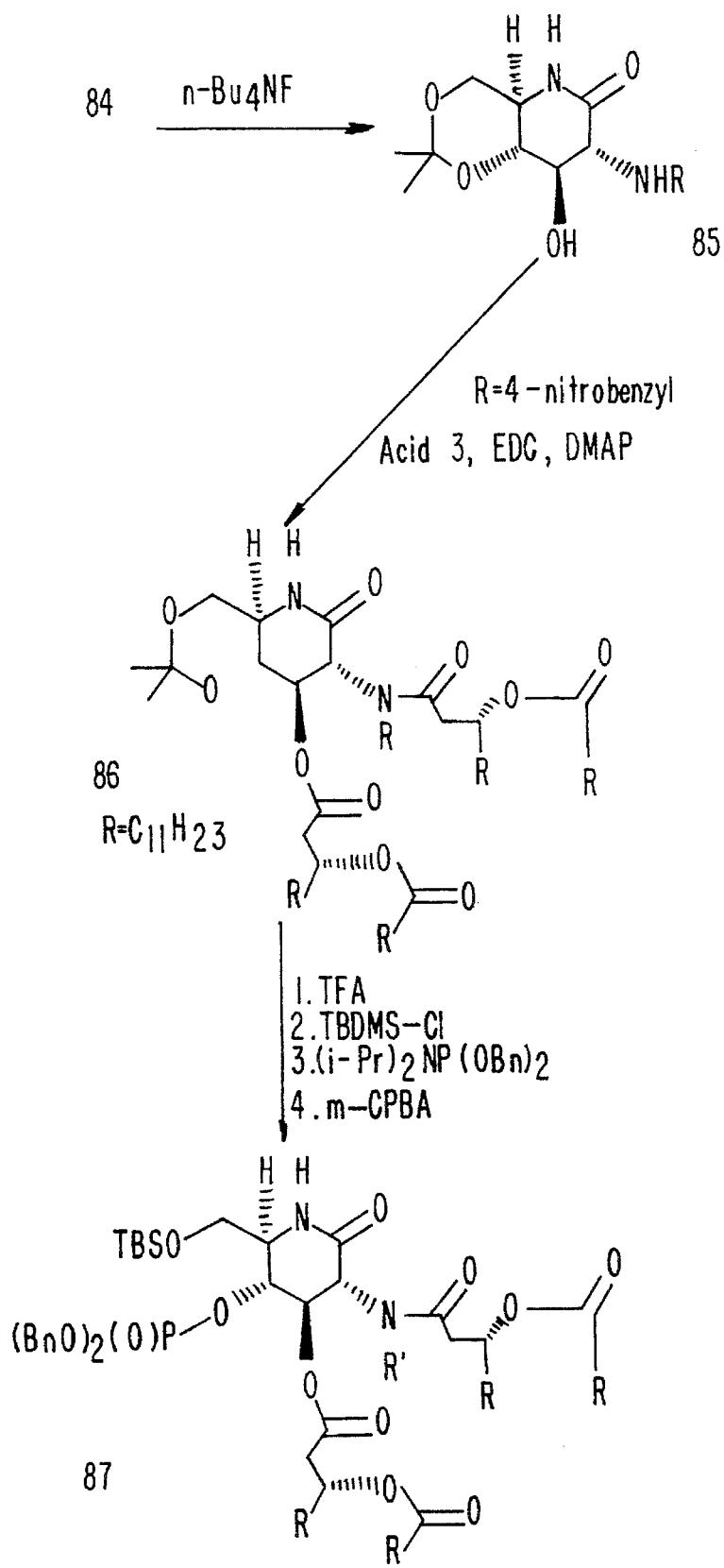
Figure 47:
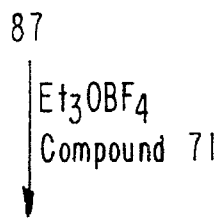
Figure 47:
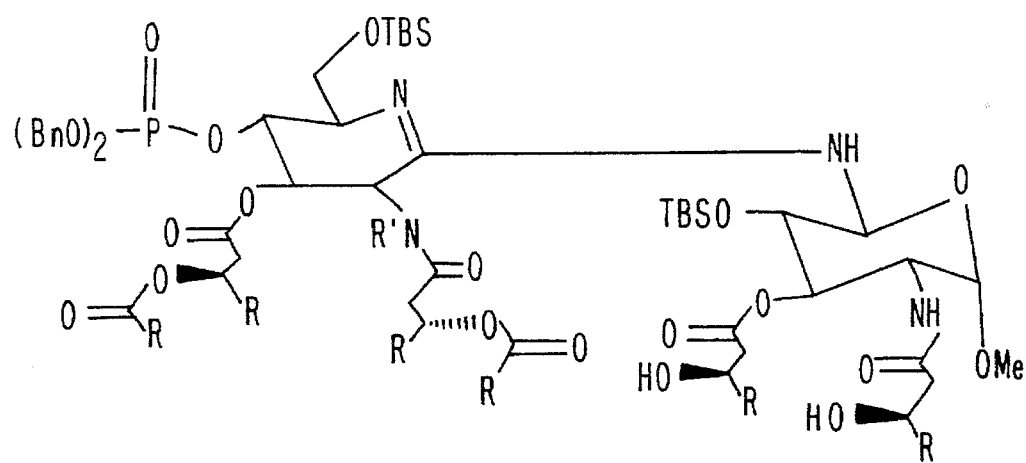
Figure 47:
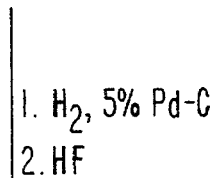
Figure 47:
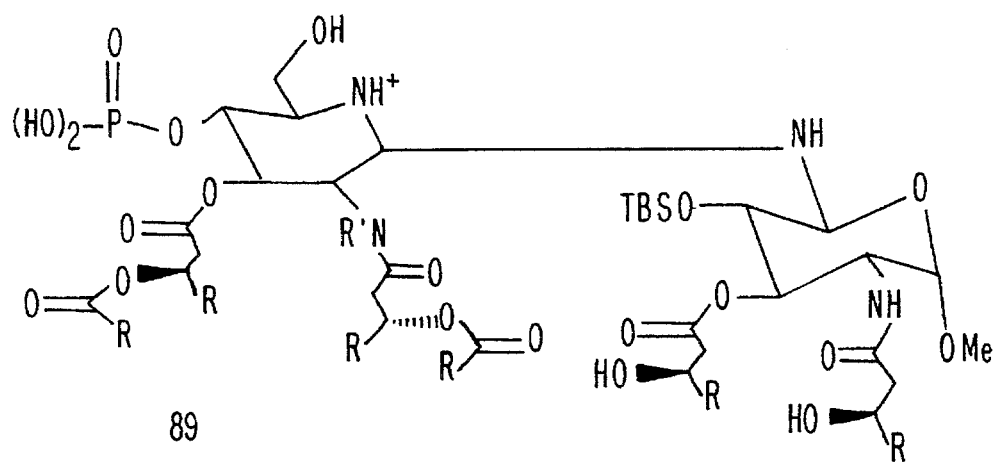

Amidine TS analog 89 is prepared from compound 71, the synthesis of which has been described above, and compound 87 (FIG. 47). Compound 87 is prepared in the following way. The mixture of compounds 5a and 5b (for the synthesis, see Scheme 2) is oxidized using Jones reagent to give compound 80 (FIG. 45). The hydroxyl protecting groups of compound 80 are replaced following standard chemical procedures to give lactone 81. The lactone ring of compound 81 is solvolyzed using benzyl alcohol to give an intermediate δ-hydroxy ester. Then, the hydroxyl group is substituted by an azido group using double inversion of chirality to obtain compound 82, which has the correct stereochemistry. Hydrogenation of compound 82 reveals an α, δ-diamino acid, which undergoes lactamization selectively to form the δ-lactam, compound 83. The amino group of compound 83 is protected with one 4-nitrobenzyl group to give compound 84. The silyl-protected hydroxyl group of compound 84 is deprotected to give compound 85 (FIG. 46), and then compound 85 is condensed with two equivalents of acid 3 (for the synthesis, see Scheme 5) to give compound 86. Hydrolysis of the isopropylidene protecting group of compound 86 produces a diol, the primary hydroxyl group of which is selectively reprotected with a TBDMS group. Phosphitylation of the secondary hydroxyl group and subsequent oxidation of the trialkylphosphite to the phosphate gives compound 87.

The coupling of compounds 87 and 71 to form compound 88 (see FIG. 47) is carried out using the same methodology as used for the preparation of compound 78 (FIG. 44). Subsequent deprotection of compound 88 gives the amidine TS analog, compound 89.

Preparation of substituted or alkene or alkyne compounds within the definition of formulae (I) and (II) is as provided above, except that the appropriate precursor compound is substituted or has the alkene or alkyne group on it.

In addition to being useful for eliciting antibodies (catalytic and binding), the compounds of formulae (I) and (II) are useful as antiviral, antitumor and antibacterial agents. At a dose of about 10 µg/kg in Japanese white rabbits, the formula (I) and (II) compounds do not show pyrogenic activity, whereas natural Lipid-A exhibits marked pyrogenicity at a dose of 0.001 µg/kg. While Lipid-A at a dose of 1 µg/mouse exhibits protective activity against gram-negative bacteria, at various doses including about 1–100, preferably about 1–10, and most preferably about 10 µg/mouse, formula (I) and (II) compounds exhibit protective activity against gram-negative bacteria (P. aeruginosa). In these tests the mice are inoculated and thereafter challenged. As to antiviral activity, mice are intravenously inoculated with various doses such as about 0.1–100, preferably about 1–10 µg of formula (I) or (II) and thereafter challenged with a suitable quantity, e.g., about $10^4$ pfu of vaccinia virus. The formulae (I) and (II) compounds perform similar to Lipid-A. With respect to antitumor activity, 1 or $2\times10^5$ Meth A fibrosarcoma cells, or about $10^5$ melanoma cells, or $10^6$ Pro b cells are administered into mice; Lipid-A or formula (I) or (II) compounds are administered at a dose of 250, 100 or 10 µg/mouse (e.g. Meth A fibrosarcoma) or up to 10 µg/kg body weight, either intravenously or intratumorly after transplantation or administration of the tumor cells. Tumor growth is retarded or prevented in mice receiving Lipid-A or formula (I) or (II) compounds. From these results, the skilled artisan can, without undue experimentation, determine the proper dosage for administering formulae (I) and (II) compounds and antibodies thereto to any suitable animal or human patient, taking into consideration such typical factors as the nature of the patient, the condition being treated, and the age, weight, sex and general health of the patient.

The formulae (I) and (II) compounds and antibodies thereto can be administered in any suitable form which is effective, for instance, orally, intravenously, subcutaneously, intradermally, intratumorally, and the like. The formulae (I) and (II) compounds and antibodies thereto can be administered in any suitable carrier or adjuvant, such as saline. These formulations can be coadministered with other treatments; for instance, formula (I) compounds and/or formula (II) compounds can be administered with other antineoplastic agents, or the antibodies can be administered with antibiotics. Furthermore, the antibodies to a formula (I) or formula (II) compound can be administered as a mixture with other antibodies, for instance to antibodies other formula (I) compounds, to other formula (II) compounds and/or with antibodies to other Lipid-A analogs and/or with antibodies to Lipid-A, i.e., the antibodies of the present invention can be administered as a "cocktail". This cocktail can include both IgG and IgM antibodies as well as both binding and catalytic antibodies. And, by "antibodies" the invention includes either binding or catalytically active fragments of antibodies.

In addition, the invention contemplates that the formula (I) and (II) compounds and antibodies thereto can be dispensed in concentrated form or lyophilized form for dilution by the ultimate user. These preparations can be in kit form. The kit form can also include suitable instructions for administration in accordance with this invention.

The following non-limiting Examples are given by way of illustration only and are not to be considered a limitation of this invention, many apparent variations of which are possible without departing from the spirit or scope thereof.

EXAMPLES

With respect to the Examples, the following are general remarks:

Melting points were recorded on Haake Buchler melting point apparatus, with electric coil heating were uncorrected. E. Merck precoated silica gel with F 254 (0.25 mm thickness), thin-lay chromatography (TLC) plates were used for monitoring the reactions. E. Merck silica gel 60 (70–230) mesh) was used for column chromatography. Organic layers were dried with anhydrous $MgSO_4$. Infrared (IR) absorption spectra were recorded on a Perkin-elmer (1710) spectrophotometer as neat unless otherwise mentioned. Proton nuclear magnetic resonance ($^1H$ NMR) spectra and Carbon nuclear magnetic resonance ($^{13}C$ NMR) were measured on General Electric QE-300 (300Mhz) spectrometer with $CDCl_3$ as a solvent unless otherwise mentioned, using tetramethylsilane as internal standard.

In this disclosure and in particular in the following Examples, the following abbreviations (as defined) are used:

AHB Acid Hydrolysed Bacteria
Cbz-Cl: Benzylchloroformate
CFA Complete Freund's Adjuvant
DCC: 1,3 Dicyclohexylcarbodiimide
DET: Diethyl tartrate
DIPT: Diisopropyl tartrate
DMAP: 4-Dimethylaminopyridine
DMF: N,N-Dimethylformamide
EDC: 1-Ethyl 3 (3 dimethylaminopropyl) carbodimide
ELISA Enzyme-Labelled ImmunoSorbant Assay
HCl: Hydrochloric acid
HEL Hen Egg-white Lysozyme
HEL[105–120] A peptide having an amino acid sequence corresponding to positions 105–120 of HEL preferably with an additional C-terminal cysteine residue, or a homologous peptide, or a peptide having an amino acid sequence which has substantial homology with positions 105–120 of HEL (preferably with the additional C-terminal cysteine residue) and preferably the peptide is a synthetic peptide
HOBT: 1-Hydroxybenzotriozole
IFA Incomplete Freund's Adjuvant
IFN Interferon (alpha, beta or gamma)
IL-1 Interleukin-1
IL-6 Interleukin-6
$LD_{50}$ The dose of a toxic moiety sufficient to kill 50% of animals to which it is administered
LPS Lipopolysaccharide
m-CPBA: 3-Chloroperoxybenzoic acid
MAb Monoclonal Antibody
PBS Phosphate Buffered Saline (10 mM Na phosphate, 0.15M NaCl, pH 7.2)
PPBE Proteose Peptone Beef Extract (Bacterial culture medium)
PTSA: p-Toluenesulfonic acid
SCAb Single Chain Antibody
SRBC Sheep Red Blood Cells
TBDMS-Cl: ter-Butyldimethylsilyl chloride
TFA: Trifluoroacetic acid
THF: Tetrahydrofuran
TMS-I: Trimethylsilyl iodide
TMS-Tf: Trimethylsilylmethyl trifluoromethanesulfonic acid
TNF Tumor Necrosis Factor alpha
Troc-Cl: 2,2,2-Trichloroethyl chloroformate Example 1

Preparation of 2-Azido-2-deoxy-3,4,6-tri-O-acetyl β-D-glucopyranose (5a) and 2-azido-2-deoxy-3,4,6tri-O-acetyl α-D-mannopyranose (5b)

To a stirred solution of tri-O-acetyl-D-glucal (27.24 g, 0.1 m) in dry acetonitrile (600 ml) at −25° C., was added a mixture of sodium azide (7.2 g, 0.11 mol) and ceric ammonium nitrate (219.20 g, 0.4 mol) and the suspension was stirred at −25° C. for 16 h (TLC analysis showed the completion of the reaction). Then the cold ether (500 mL) and water (200 mL) were added to the reaction mixture and was separated the organic layer, dried ($MgSO_4$), filtered and concentrated to give the oily compound (Rf 0.72, silica, ethyl acetate:petroleum ether 1:1, 29 g, 77%). The crude compound obtained from the above procedure was subjected to the next reaction without purification. A mixture of the above compound (29 g, 77 mmol) in dioxane (500 mL), and an aqueous solution of sodium nitrite (27.6 g, 0.4 mol in 200 mL of water) was heated at 80° C. for 8 h. Then the organic layer was separated and the aqueous layer was extracted with ethyl acetate (300 mL). The combined organic layers were dried (MgSO$_4$) and concentrated to give a pale yellow oil as an inseparable mixture of gluco and manno pyranoses 5a and 5b (24 g, 94%).

Example 2

Preparation of
t-Butyldimethylsilyl-2-azido-2-deoxy-3,4,6
tri-O-acetyl b-D-glucopyranose (6a) and
t-butyldimethylsilyl-2-azido-2-deoxy 3,4,6
tri-O-acetyl α-D- Mannopyranose (6b)

To a solution of the hydroxy compounds (obtained above as a mixture, 23 g, 9 mmol) in N,N-dimethylformamide at 0° C., was sequentially added imidazole (11.26 g, 166 mmol, 2.4 eq) and t-butyldimethylsilyl chloride (12.5 g, 83 mmol 1.2 eq), and the mixture was stirred for 4 h. After the completion of the reaction (TLC) the mixture was diluted with ethyl acetate (300 mL) and washed with water (3×150 mL). The organic layer was dried and concentrated to give a mixture of two compounds which were separated by flash chromatography (silica) using 8% ethyl acetate in petroleum ether as eluent to afford 6a and 6b. Compound-6a (Rf 0.60, silica, ethyl acetate:petroleum ether, 1:4, 16.8 g. 55%) was found to be β-gluco derivative $^1$H NMR (CDCl$_3$): 4.915 (m, 2H), 4.604 (d, J=7.8 Hz, 1H, C-1), 4.110 (m, 2H), 3.633 (m, 1H), 3.366 (t, 1H), 2.020 (s, 3H, OAc), 2.006 (s, 3H, OAc), 1.958 (s, 3H, OAc), 0.881 (s, 9H, t-bu) and 0.08 (s, 6H, Me$_2$Si).

$^{13}$C NMR: 170.324, 169.778, 169.487, 97.002, 72.128, 71.757, 68.788, 65.788, 65.914, 62.251, 25.443, 20.556, 20.459, 17.857, –4.557, –5.319. IR: 3484, 2958, 2859, 2114, 1752, 1659, 1435, 1240, 1107, 1007, 940, 843, 785 and 676.

The slower moving compound 6b (Rf 0.51, silica, ethyl acetate:petroleum ether, 1:4, 7 g, 23%) was found to be the manno derivative.

$^1$H NMR (CDCl$_3$): 5.12 (t, 1H), 4.96 (m, 2H), 4.0–4.19 (m, 3H), 3.61 (m, 1H), 2.06 (s, 3H, OAc), 2.02 (s, 3H, OAc), 1.94 (s, 3H, OAc), 0.91 (s, 9H, t-bu), 0.15 (s, 3H, MeSi) and 0.1 (s, 3H, MeSi).

Example 3

Preparation of
t-Butyldimethylsilyl-2-azido-2-deoxy-3-hydroxy-
4,6-O-isopropyledene-β-D-glucopyranose (2)

A mixture Of compound 6a (19 g, 42 mmol), sodium methoxide (3 ml, 1M) in methanol (120 mL) was stirred at room temperature for 2 h. After completion of the reaction (TLC), methanol was removed in vacuo and the resulting material was filtered through a small pad of silica gel using ethyl acetate as eluent to afford the corresponding triol as an oil (Rf 0.21, silica, petroleum ether:ethyl acetate, 1:1, 12.7 g, 95%).

$^1$H NMR (CDCl$_3$): 4.60 (d, J=7.2 Hz, 1H, anomeric), 3,841 (m, 2H), 3.60 (t, 1H), 3.32 (m, 3H), 0.91 (s, 9H, t-bu), 0.1 (s, 6H, Me$_2$ Si).

$^{13}$C NMR: 97,167, 75.362, 74.351, 70,027, 68,314, 61,751, 25,564, 17,920, –4,311, and –5,232.

IR: 3369, 2956, 2860, 2114, 1566, 1464, 1364, 1218, 1173, 1079, 957, 843, 760 and 691.

The triol compound obtained above (12 g, 37 mmol), was treated with 2,2-dimethoxy propane (7.70 g, 74 mmol) in methylene chloride (150 mL) in the presence of p-toluenesulfonic acid (0.3 g) and the mixture was stirred at room temperature for 4 h. Then the reaction mixture was diluted with methylene chloride (200 mL), and washed with water (200 mL), sodium bicarbonate solution (5%, 100 mL) and water (150 mL). The organic layer was separated, dried, and concentrated to give a thick mass, which after flash chromatography afforded compound 2 as an oil (Rf 0.32, silica, ethyl acetate:petroleum ether 1:4, 11.4 g, 86%).

$^1$H NMR (CDCl$_3$): 4,601 (d, J=7.5 Hz, 1H, anomeric), 3.84 (m, 2H), 3.589 (t, 9.3 Hz, 1H), 3.470 (t, J=9.3 Hz, 1H), 3.30 (m, 1H), 3.0 (bs, 1H, exchanged with D$_2$O), 2.232 (m, 2H), 1.58 (s, 3H, other CH$_3$), 1.46 (s, 3H, CH$_3$ of isopropylidene), 0.94 (s, 9H, t-bu), 0.12 (s, 3H, CH$_3$), 0.1 (s, 3H, CH$_3$).

$^{13}$C NMR: 99.930, 97.503, 73.497, 72.072, 69.151, 67.930, 61.909, 28.952, 25.519, 19.049, –4.397, –5.238.

IR: 3453, 2932, 2114, 1643, 1382, 1279, 1040, 866, and 680.

Example 4

Preparation of (E)-2 Tetradodec-ene-1-ol (7)

A mixture of dodecanal (18.4 g, 100 mmol), methyl (triphenylphosphoralenyledene) acetate (40.3 g, 120 mmol), in chloroform (400 mL), was stirred at room temperature for 4 h. After completion of the reaction (TLC), the solvent was removed and the resulting material was dissolved in ether (100 mL). The precipitated triphenylphosphine oxide was removed by filtration. The filtrate was concentrated in vacuo and subjected to the flash chromatography to afford a mixture of the E and Z isomers of α, β-unsaturated esters as an oil (Rf 0.62, silica, ethyl acetate:hexane 1:7, 20 g, 86%).

$^1$H NMR (CDCl$_3$): 6.98 (m, 1H, olefinic), 5.82 (d, J=7.2 Hz, olefinic), 3.76 (s, 3H, OCH$_3$), 2.1 (m, 2H, allylic methylene), 1.20 (bs, 18H, 9×CH$_2$) and 0.86 (t, 3H, terminal CH$_3$).

To a solution of the above obtained ester compound (18 g, 75 mmol) in methylene chloride (250 mL), at −78° C., was added a solution of DIBAL-H (160 mL, 1M), and the reaction mixture was stirred at that temperature for 1 h. After completion of the reaction (TLC), the excess DIBAL-H was quenched with methanol (15 mL) and transferred to a conical flask containing ethyl acetate (750 mL) and rochelle salt solution (200 mL) and stirred until two clear phases separated (approximately 1 h). Then the organic layer was separated, dried, and concentrated to give a colorless oil, which was purified by flash chromatography to afford the allyl alcohol 7 as a colorless oil (Rf 0.25, silica, ethyl acetate:hexane, 1:4, 14.5 g, 92%).

$^1$H NMR (CDCl$_3$): 5.60 (m, 2H, olefinic), 4.06 (d, 2H), 2.02 (m, 2H, allylic CH$_2$), 1.20 (bs, 18H, 9×CH$_2$) and 0.9 (t, 3H, CH$_3$).

Example 5

Preparation of (2S, 3R)-2,3-
Epoxy tetradecan-1-ol (8)

To a solution of methylene chloride (150 mL) containing powdered activated molecular sieves (4 A, 8 g) and titaniumtetra-isopropoxide (1.41 g, 5 mmol, 10% by weight), at −20° C. sequentially added (−) diethyl tartrate (1.23 g, 6 mmol, 12%), allyl alcohol 7 (10.50 g, 50 mmol) in methylene chloride (50 mL) and t-butyl hydroperoxide in methylene chloride (15 ml, 5.19M, 1.5 eq) with 5 min between each addition. The mixture was stirred for 2 h at that temperature and allowed to stand at −20° C. overnight (at which time reaction was completed, TLC). The molecular sieves were removed by filtration and the filtrate was treated with a saturated solution of sodium sulfate (5 ml) for 2 h. The precipitated inorganic salts were removed by filtration through celite, the solvent was removed, and the product was purified by flash chromatography to afford the epoxide 8 as a colorless solid (Rf 0.54, silica, ethyl acetate:hexane 1:5, 9.10 g, 81%). m.p=85°–86° C.

$^1$M NMR (CDCl$_3$): 3.92 (m, 1H, diastereotopic proton of C-1), 2.98 (m, 2H), 3.60 (m, 1H), 1.61 (q, 2H), 1.20 (bs, 18H, 9×CH$_2$) and 0.9 (t, 3H, CH$_3$).

$^{13}$C NMR: 63.211, 60.124, 57.397, 33.232, 32.899, 30.983, 30.863, 30.720, 30.662, 27.262, 23.995, 15.394.

IR: 3573, 2918, 2848, 1584, 1549, 1480, 1430, 1377, 1252, 1154.

Example 6

Preparation of (R)-3-Hydroxy tetradecan-1-ol (9)

To a solution of epoxide 8 (9.00 g, 40 mmol) in tetrahydrofuran (80 mL) at −20° C. was added a solution of Red-Al (40 mL, 3M) and the reaction temperature was slowly raised to 0° C. and subsequently to room temperature and stirred for 12 h. After completion of the reaction (TLC), the excess of Red-Al was quenched with methanol (10 mL) and poured in to a conical flask containing ethyl acetate (400 mL) and rochelle salt solution (100 mL) and stirred for 2 h until clear separation of two layers occurred. The organic layer was separated, dried and concentrated to give the diol 9 as a colorless solid (8.1 g, 89%). m.p. 59°–60° C.

$^1$H NMR: 3.783 (m, 3H), 1.652 (m, 2H), 1.236 (m, 20H), 0.855 (t, J=6.6 Hz, 3H).

$^{13}$C NMR: 73.033, 62.528, 39.697, 39.122, 33.268, 31.019, 30.709, 26.978, 24.024 and 15.429.

IR: 3310, 2917, 2849, 1565, 1431, 1108, 1029, 980, 860 and 721.

The diol was characterized as its acetate derivative. The acetate was prepared by the standard procedure using acetic anhydride, DMAP in methylene chloride.

$^1$H NMR (CDCl$_3$): 4.98 (m, 1H, C-3), 4.04 (t, 2H, C-1), 2.04 (S 6H, 2×OAc), 1.84 (4H), 1.30 (bs, 18H, 9×CH$_2$), 0.9 (t, 3H, CH$_3$).

Example 7

Preparation of Compound 9a

To a solution of diol 9 (920 mg, 4 mmol) and DMAP (610 mg, 5 mmol) in dichloromethane (20 mL) at 0° C., a solution of pivoloyl chloride (600 mg, 5 mmol) in dichloromethane (1 mL) was added and the mixture was stirred at 0° C. for 2 h. After completion of the reaction excess chloride was neutralized with methanol and solvents were removed in vacuo to afford an oil, which after purification by flash chromatography afforded the pivoloyl protected compound as an oil (Rf 0.62, silica, 8% ethyl acetate in hexane, 1.04 g, 83%).

$^1$H NMR: 4.12 (m, 2H), 3.46 (m, 1H), 1.56 (m, 4H), 1.24 (bs, 18H), 1.16 (s, 8H), 0.86 (t, 3H).

To the above-obtained compound (520 mg, 1.65 mmol) in DMF (8 mL) was sequentially added imidazole (272 mg, 4 mmol) and t-butyldimethylsilyl chloride (308 mg, 2 mmol) and the mixture was stirred at room temperature for 4 h. After completion of the reaction, mixture was diluted with ethyl acetate (10 mL) and washed with water (3×5 mL). The organic phase was separated, dried, concentrated to afford an oil, which after purification by flash chromatography afforded compound 9a as an oil (Rf 0.61, 5% ethyl acetate in hexane, 0.592 g, 84%).

$^1$H NMR: 4.16 (m, 2H), 3.46 (m, 1H), 1.64 (m, 4H), 1.26 (bs, 18H), 1.16 (s, 9H), 0.842 (m, 12H), 0.03 (s, 6H).

Example 8

Preparation of R (−) 3-Hydroxy 14-tetradecanoic acid

To a solution of compound 9a (690 mg, 1.6 mmol) in dichloromethane (8 mL) at −78° C., a solution of DIBAL-H (2.5 mL, 4 mmol, 1.6M in toluene) was added under an argon atmosphere and mixture was stirred at that temperature for 1h. After completion of the reaction, excess DIBAL-H was neutralized with methanol (2 mL) and mixture was transferred to a conical flask containing ethyl acetate (30 mL) and saturated solution of rochelle's salt (10 mL) and stirred for 1 h. The organic phase was separated, dried, concentrated and purification by flash chromatography afforded the hydroxy compound as thick oil (Rf 0.24, 8% ethyl acetate in hexane, 430 mg, 78%).

H$^1$ NMR: 3.48 (m, 3H), 1.58 (m, 4H), 1.26 (bs, 18H), 0.86 (m, 12H), 0.03 (s, 6H).

The above-obtained alcohol (0.342 mmol) was dissolved in acetone (10 mL) and cooled to 0° C. and added Jones reagent until orange color persisted. After completion of the reaction, solvent was removed in vacuo, the resulting material was dissolved in ethyl acetate (10 mL) and washed with water (3×5 mL), separated the organic phase, dry, concentrate and purified by flash chromatography to afford the corresponding acid as an oil (Rf 0.18, 10% ethyl acetate in hexane, 195 mg, 54%).

$^1$H: NMR 10.02 (bs, 1H), 3.48 (s, 1H), 2.24 (m, 2H), 1.64 (m, 2H), 1.24 (bs, 18H), 0.84 (m, 12H), 0.03 (s, 6H).

The above-obtained silyl acid (180 mg, 0.5 mmol) was dissolved in THF (2 mL) in a plastic container and cooled to −20° C. and HF-pyridine (1 mL) was added and the mixture was stirred for 1 h. After completion of the reaction excess acid was neutralized with sodium bicarbonate solution (5%, 2 mL) and extracted with dichloromethane (5 mL). The organic phase was separated, dried, concentrated and purified by flash chromatography to afford the hydroxy acid as colorless solid (Rf 0.16, 30% ethyl acetate in hexane, 85 mg, 70%). m.p. 74° C. (a)$_D$ $^{21}$ (−) 16.44 (C 0.46, CHCl$_3$) Literature (76), m.p. 73° C., (a)$^{25}_D$ (−) 16.20 (C 2, CHCl$_3$).

$^1$H NMR: 10.12 (s, 1H), 3.46 (m, 1H), 2.36 (m, 2H), 1.26 (bs, 20H), 0.846 (t, 3H).

Example 9

Preparation of (R)-1-t-Butyldimethylsilyloxy-3-hydroxytetradecane (10)

To a solution of diol compound 9 (2.28 g, 10 mmol) in N,N-dimethyl formamide (50 mL) at 0° C. was added sequentially imidazole (1.63 g, 24 mmol), and t-butyldimethylsilyl chloride (1.65 g, 11 mmol), and the reaction mixture was stirred for 2 h. After completion of the reaction (TLC). The mixture was diluted with ethyl acetate (200 mL), washed with water (2×50 mL), dried and concentrated to give a colorless oil, which after purification by flash chromatography, afforded the pure monosilyl compound 10 as an oil (Rf 0.71, silica, ethyl acetate and hexane, 1:10, 2.80 g, 84%).

The alcohol was characterized as its acetate derivative.

$^1$H NMR (CDCl$_3$): 5.0 (q, 1H, C-3) 3.62 (t, 2H, C-1), 1.80 (q, 2H), 1.56 (m, 2H), 0.92 (m, 12H, CH$_3$ and t bu), 0.1 (s, 6H, Me$_2$Si).

Example 10

Preparation of (R)-1-t-Butyldimethylsiloxy-3-dodecanoyloxy tetradecane (11)

A mixture of compound 10 (1.02 g, 3 mmol) and lauric acid (720 mg, 3.6 mmol), DCC (680 mg, 3.3 mmol) and DMAP (400 mg, 3.3 mmol) in methylene chloride (12 mL) was stirred at room temperature for 4 h. After completion of the reaction the insoluble material was removed by filtration, the solvent was removed, and the product was isolated by flash chromatography to afford coupling compound 11 as an oil (Rf 0.64, silica, ethyl acetate:hexane 1:9, 1.26 g, 81%).

$^1$H NMR (CDCl$_3$): 4.96 (q, 1H), 3.75 (t, J=6.6 Hz, 2H), 2.228 (t, J=7.5 Hz, 2H), 1.691 (m, 4H), 1.512 (m, 2H), 1.228 (bs, 36H), 0.91 (m, 15H), 0.002 (s, 6H, methyls of silyl).

$^{13}$C. NMR: 174.469, 72.660, 72.623, 60.903, 38.585, 35.936, 35.738, 33.261, 30.970, 30.917, 30.828, 30.686, 30.532, 27.244, 27.184, 27.059, 26.534, 26.463, 24.008, 19.511, 15.392.

IR: 2926, 1738, 1585, 1494, 1415, 1255, 1176, 1097, 940, 837, 723.

Example 11

Preparation of (R)-3-Dodecanoyloxy tetradecanoic acid (3)

To a solution of compound 11 (2.63 g, 5 mmol) in methanol and methylene chloride (20 mL, 1:1 mixture) at 0° C., was added PTSA (200 mg) and the resulting mixture was stirred at 0° C. for 2 h. After completion of the reaction, acid was neutralized with triethylamine (1 mL) and the solvents were removed in vacuo and the product was purified by flash chromatography to give the corresponding alcohol as an oil. (Rf 0.24, silica, ethyl acetate:hexane, 1:1, 1.44 g, 70%).

$^1$H NMR: 4.984 (m, 1H), 3.501 (m, 2H), 2.775 (bs, 1H, OH), 2.329 (t, J=7.2 Hz, 2H), 1.571 (m, 6H), 1.226 (bs, 36H), 0.864 (t, J=6.6 Hz, 6H).

$^{13}$C NMR: 175.488, 72.550, 69.959, 59.824, 38.913, 38.864, 37.732, 35.997, 35.891, 35.676, 33.251, 30.963, 30.875, 30.682, 30.613, 30.513, 26.979, 26.780, 26.462, 26.324, 24.012, 15.408.

IR: 3535, 2924, 1739, 1692, 1565, 1494, 1427, 1379, 1171, 1059, 936.

The alcohol obtained-above (1.49 g, 3.61 mmol) was dissolved in acetone (40 mL), and Jones reagent was added slowly until the orange color persisted. After completion of the reaction, the solvent was removed in vacuo and the resulting material was dissolved in ethyl acetate (50 mL) and washed with water (3×30 mL) until organic phase was almost colorless. The organic layer was separated, dried, and concentrated to give an oil, which was purified by flash chromatography to afford acid 3 as a colorless solid (1.32 g, 86%).

$^1$H NMR: 9.86 (bs, 1H, OH of COOH), 5.186 (m, 2H), 2.579 (t, J=6.6 Hz, 6H), 2.44 (t, J=7.5 Hz, 2H), 1.592 (bs, 4H), 1.231 (bs, 36 H), 0.847 (t, J=6.6 Hz, 6H, terminal methyl).

$^{13}$C NMR: 177.659, 174.650, 71.390, 40.277, 35.774, 35.292, 33.247, 30.969, 30.880, 30.636, 30.617, 30.445, 26.326, 24.010, 15.383.

IR: 3573, 2921, 2675, 1746, 1713, 1675, 1549, 1513, 1466, 1379, 1283, 1206, 1164, 1114, 1070, 1012, 935, 723.

Example 12

Preparation of Dibenzyl dodecanephosphonate (14)

To a solution of potassium t-butoxide (6.16 g, 55 mmol), in dry DMF (50 mL), under an argon atmosphere was added dropwise via syringe a solution of dibenzyl phosphite (13.1 g, 50 mmol) in dry DMF (5 mL), and the reaction mixture was stirred at room temperature for 20 min. Then a solution of lauryl bromide (18.6 g, 75 mmol) in dry THF (15 mL), was added dropwise under argon atmosphere, and the mixture was stirred at room temperature for an additional 1 h. After completion of the reaction, the mixture was neutralized with dilute HCl (40 mL) and extracted with ethyl acetate (200 mL), the organic phase was dried, concentrated, and purified by flash chromatography to afford the pure dibenzyl phosphate 14 as a colorless oil (Rf 0.46, silica, ethyl acetate and hexane, 1:2, 10.5 g, 50%).

$^1$H NMR (CDCl$_3$): 7.36 (m, 10H, aromatic) 5.02 (m, 4H benzylic) 1.52 (m, 2H), 1.24 (bs, 18H), 0.9 (t, 3H).

Example 13

Preparation of Phosphochloridate (12)

A mixture of compound 14 (6 g, 14 mmol) and phosphorus pentachloride (2.9 g, 14 mmol), in chloroform (40 mL), was heated at 60° C. for 2 h. After completion of the reaction (progress of the reaction was monitored by NMR) solvent was removed in vacuo to afford the phosphochloridate 12 as an oil.

$^1$H NMR (CDCl$_3$): 7.36 (m, 5H, aromatic) 5.24 (m, 2H, benzylic), 1.26 (bs, 18H), 0.92 (t, 3H).

Example 14

Preparation of Compound 13

A mixture of hydroxy compound 10 (1.05 g, 3 mmol) and phosphochloridate compound 12 (1.42 g, 4 mmol), was stirred in methylene chloride (12 mL) in the presence of DMAP (0.41 g, 3.3 mmol) and triethylamine (2 mL) for 3 h. After completion of the reaction, methanol (1 mL) was added, the solvent was removed in vacuo and the product was purified by flash chromatography (Rf 0.46, silica, ethyl acetate and hexane 1:9, 1.36 g, 68%).

$^1$H NMR (CDCl$_3$): 7.42 (m, 5H, aromatic), 5.02 (m, 2H, benzylic) 4.58 (m, 1H), 3.76 (m, 2H), 1.82 (m, 6H), 1.28 (bs, 36H), 0.92 (m, 9H), 0.12 (s, 3H) and 0.1 (s, 3H).

Example 15

Preparation of Acid 4

A mixture of compound 13 (800 mg, 1.2 mmol), and PTSA (60 mg) in methanol and methylene chloride (6 mL, 1:1 mixture) was stirred at 0° C. for 1 h. After completion of the reaction the acid was neutralized with triethylamine (2 mL), the solvents were removed, and the mixture was subjected to flash chromatography to afford the corresponding hydroxy compound as an oil (Rf 0.24, silica, ethyl acetate and hexane, 1:4, 580 mg, 87%).

$^1$H NMR: 7.36 (m, 5H, aromatic), 5.124 (m, 2H, benzylic), 4.612 (m 1H), 3.728 (m, 2H), 3.052 (bs, OH), 1.642 (m, 4H), 1.264 (bs, 40H) 0.846 (t, 6H).

The above alcohol compound (550 mg, 1 mmol) was dissolved in acetone (10 mL) and cooled to 0° C., and Jones reagent was added until a red color persisted and the mixture was stirred at that temperature for 1 h. After completion of the reaction the acetone was removed, and the resulting material was dissolved in ethyl acetate (10 mL) and washed with water (3×5 mL) until the organic layer became almost colorless. The organic layer was dried and concentrated to give acid 4 as an oil (520 mg, 81%).

$^1$H NMR: 7.36 (m, 5H, aromatic), 5.124 (m, 2H), 4,746 (m, 1H), 2.562 (m, 2H), 1,462 (m, 4H), 1.264 (bs, 40H), and 0.861 (t, 6H).

Example 16

Preparation of Compound 15

A mixture of compound 2 (1.79 g, 5 mmol), acid 3 (2.13 g, 5 mmol), DCC (1.24 g, 6 mmol) and DMAP (0.74 g, 6 mmol) in methylene chloride (20 mL) was stirred at room temperature overnight. The insoluble material was removed by filtration, the solvent was removed, and the product was purified by flash chromatography to afford the coupled compound 15 as an oil (Rf 0.24, silica, ethyl acetate and hexane 1:19, 2.76 g, 72%).

$^1$H NMR (CDCl$_3$): 5.26 (m, 1H), 4.98 (t, 1H), 4.70 (d, J=8. 6 Hz, 1H, anomeric), 3.80 (m, 3H), 3.32 (m, 2H), 2.72 (AB quartet, 2H), 2.32 (t, 2H), 1.68 (m, 2H), 1.42 (s, 3H, isopropylidene Me), 1.30 (s, 3H, isopropylidene Me), 1.26 (bs, 36H), 0.92 (m, 15H), 0.2 (2×s, 6H).

Example 17

Preparation of Amino Compound 16

A mixture of compound 15 (2.37 g, 3.1 mmol) and trifluoroacetic acid (8 mL) in methylene chloride (20 mL) was stirred at room temperature. After completion of the reaction the acid was neutralized with triethylamine (10 mL), and the solvents were removed to give a thick oil. The product was purified by flash chromatography to afford the diol as an oil (Rf 0.36, silica, ethyl acetate and hexane, 1:6, 1.62 g, 72%).

$^1$H NMR (CDCl$_3$): 5.20 (m, 1H), 4.80 (t, 1H), 4.70 (d, 1H, anomeric), 3.82 (AB quartet, 2H), 3.60 (t, 1H), 3.41 (m, 1H), 3.30 (dd, 1H), 3.08 (m, 1H), 2.60 (d, 2H), 2.32 (t, 2H), 1.60 (m, 2H), 1.28 (bs, 36H), 0.94 (s, 8H), 0.90 (t, 2H) and 0.1 (s, 6H).

The primary alcohol functionality of the diol obtained above (1.53 g, 2.1 mmol) was protected as t-butyldimethylsilyl ether following the same procedure used for the preparation of ether 8 to give the primary silyl ether (Rf 0.34 silica, ethyl acetate and hexane, 1:19, 1.54 g, 87%).

$^1$H NMR: 5.20 (m, 1H), 4.82 (t, 1H), 4.61 (d, 1H, anomeric), 3.84 (d, 2H), 3.60 (t, 1H), 3.40 (m, 1H), 3.30 (dd, 1H), 2.61 (d, 2H), 2.30 (t, 2H), 1.60 (m, 2H), 1.26 (bs, 36H), 0.92 (m, 24H), 0.14 (2×s, 6H) 0.1 (s, 6H)

The monosilylated compound obtained above (1.49 g, 1.77 mmol), was hydrogenated over Pd-C., (10%, 200 mg) in methanol (10 mL) to afford the corresponding amino compound 16 as an oil (Rf 0.24, silica, ethyl acetate:hexane, 1:9, 1.38 g, 96%).

$^1$H NMR (benzene-d$_6$): 5.40 (m, 1H), 5.14 (t, 1H), 4.51 (d, 1H, anomeric), 3.82 (m, 2H), 3.72 (t, 1H), 3.30 (m, 1H), 2.91 (m, 3H, after exchange with D$_2$O integration decreases, amino), 2.60 (d, 2H), 2.20 (m, 2H), 1.62 (m, 2H), 1.24 (bs, 36H), 0.92 (m, 24H), 0.2 (2×s, 6H) 0.0 (s, 6H).

Example 18

Preparation of Compound 1

To a solution of acid 4 (526 mg, 1 mol) in methylene chloride (5 mL), was added EDC (200 mg, 1 mmol) and the reaction mixture was stirred for 10 min. Then the amino compound 16 (815 mg, 1 mmol), and 1-hydroxy benzotriazole (130 mg, 1 mmol) were added and the resulting mixture was stirred under argon atmosphere for 4 h. After completion of the reaction the mixture was diluted with ether (10 mL) and washed with water (2×5 mL) dried, concentrated and chromatographed to give the coupled compound 1 as an oil (Rf 0.71, silica, methylene chloride:ether, 3:1, 640 mg, 49%).

$^1$H NMR: 7.40 (m, 5H, aromatic), 6.32 (d, 1H, NH), 4.60–5.23 (m, 5H), 3.82 (m, 2H), 3.40 (m, 2H), 3.36 (m, 2H), 3.30 (m, 1H), 2.52 (m, 2H), 2.24 (t, 2H), 1.62 (m, 2H), 1.24 (bs, 36H), 0.91 (m, 24H) and 0.06 (bs, 12H).

Example 19

Preparation of Compound 17

A mixture of compound 1 (400 mg, 0.302 mmol), N,N-diisopropylamino dibenzyl phosphite (164 mg, 0.5 mmol), and tetrazole (55 mg, 0.75 mmol) in methylene chloride (2 mL) was stirred at room temperature for 30 min. After completion of the reaction (TLC), the mixture was cooled to −20° C. and m-CPBA (140 mg, 0.85 mmol) was added and the reaction mixture was stirred for 30 min. After completion of the oxidation the mixture was diluted with ether (10 mL) and washed with water (5 mL), and then again washed with sodium bicarbonate solution (5%, 5 mL). The organic layer was dried, concentrated, and purified by flash chromatography to afford the phosphorylated compound 17 as an oil (Rf 0.36, silica, ethyl acetate and hexane, 1:3, 435 mg, 91%).

$^1$H NMR: 7.340 (m, 15H, aromatic), 5.012 (m, 6H), 4.742 (m, 2H), 4.395 (m, 1H), 3.676 (m, 2H), 3.264 (m, 2H), 2.421 (m, 8H), 1.521 (m, 8H), 1.246 (bs, 72H), 0.862 (m, 30H, and 0.08 (m, 12H).

Example 20

Preparation of Immunogen BK-1

A suspension of compound 17 (220 mg, 0.014 mmol) in methanol (1 mL) was subjected to hydrogenation using Pd-C (10%, 20 mg). After completion of the reaction, catalyst was removed by filtration and the solvent was then removed to afford the debenzylated compound (Rf 0.36, silica, 30% methanol in ethyl acetate, 65 mg, 90%).

$^1$H NMR: 5.102 (m, 2H), 4.642 (m, 2H), 3.962 (m, 2H), 3.24 (m, 2H), 2.42 (m, 8H), 1.521 (m, 8H), 1.241 (bs, 72H), 0.824 (m, 30H) and 0.08 (m, 12H).

The compound obtained above (131 mg, 0.01 mmol) was treated with HF-pyridine (0.5 mL), in THF (1 mL), in a plastic container at 0° C. for 30 min. After completion of the reaction, the mixture was diluted with ethyl acetate (5 mL) and stirred with sodium bicarbonate (5%, 2 mL) solution for 20 min. The organic layer was separated and the aqueous solution was washed with chloroform (5 mL), organic phases were dried and the solvents were removed in vacuo to give an oil. The oil was dissolved in a chloroform-methanol mixture (1:1, 10 mL) and insoluble particles were filtered. The filtrate was dried and concentrated to give a thick oil and the residue was redissolved in water and lyophilized to give BK-1 (Rf 0.21, silica, 50% methanol in chloroform, 55 mg, 51%).

$^1$H NMR: 5.112 (m, 2H), 4.462 (m, 2H), 3.621 (m, 4H), 2.221 (m, 8H), 1.562 (m, 8H), 1.221 (bs, 72H), and 0.824 (t, 12H).

Example 21

Preparation of Compound 18

A suspension of azido compound 2 (3.59 g, 10 mmol) and Pd-C (10%, 0.35 g) in ethyl acetate (40 mL) was stirred under hydrogen atmosphere. After completion of the reaction (TLC) the mixture was filtered through a pad of celite to remove catalyst and the solvent was removed in vacuo to give a thick oil. The oil was purified by flash chromatography to afford compound 18 as a colorless solid (Rf 0.26, silica, ethyl acetate, 3.0 g, 90%). m.p. 154°–155° C.

$^1$H NMR: 4,463 (d, J=7.8 Hz, 1H, C-1), 3,785 (m, 2H), 3,538 (t, J=9.3 Hz, 1H), 3,415 (t, J=9.3 Hz, 1H), 3,229 (m, 1H), 2,682 (m, 1H), 1,463 (s, 3H), 1,385 (s, 3H), 0.869 (s, 8H, t-butyl), 0,082 (s, 6H, SiMe$_2$).

$^{13}$C NMR: 99.655, 99.313, 74.049, 73.104, 67.557, 62.130, 59.904, 29.080, 25.682, 19.149, −4.088, −5.190.

IR: 3573, 3391, 2931, 2249, 1666, 1512, 1464, 1383, 1266, 1181, 1141.

Example 22

Preparation of Compound 26

To a solution of amino compound 18 (2.85 g, 8.55 mmol) and acid 3 (3.83 g, 9 mmol) in dichloromethane (18 mL) under an Ar atmosphere, was added sequentially EDC (1.91 g, 10 mmol) and HOBT (1.30 gms, 10 mmol), and the resulting reaction mixture was stirred at room temperature for 4 h. After completion of the reaction the solvent was removed in vacuo and the product was isolated as an oil after flash chromatography (Rf 0.34, silica, ethyl acetate:hexane 3:7, 4.81 g, 76%).

$^1$H NMR: 6. 249 (d, J=6.9 Hz, 1H, NH), 5.133 (m, 1H, CHOCO), 4,875 (d, J=8.1 Hz, 1H, C-1), 3.833 (m, 3H), 3,615 (t, J=9 Hz, 1H), 3.415 (m, 1H), 3.280 (m, 1H), 2,439 (m, 2H), 2.263 (t, J=7.2Hz, 2H), 1.513 (s, 3H, acetonide methyl) 1.427 (s, 3H, acetonide methyl), 1,247 (bs, 34H), 0.876 (m, 15H, t-butyl and terminal methyls) and 0.08 (s, 6H, SiMe$_2$).

$^{13}$C NMR: 174.242, 171.041, 99.719, 95.891, 74.284, 71.657, 71.406, 67.280, 62.036, 60.810, 42.508, 34.534, 34.478, 31.880, 29.594, 29.513, 29.482, 29.262, 29.167, 29.036, 25.608, 25.259, 24.271, 22.642, 19.035, 17.836, 14.080, −4.135, −5.196.

IR: 3298, 2928, 1733, 1654, 1465, 1306, 1257, 1098, 941, 842, 784, 673.

Example 23

Preparation of Keto Phosphonate 21

To a cooled solution (−78° C.) of dimethyl methylphosphonate (6.20 g, 50 mmol) in dry THF (250 mL) was added under Ar atmosphere a solution of n-butyllithium (1.6M, 30 mL, 52.8 mmol) through a syringe and the mixture was stirred at that temperature for 1 h. Then a solution of methyl laurate (12.8 g, 60 mmol) in THF (30 mL) was added and the reaction mixture was stirred further for 1 h at −78° C. and then at 0° C. for 30 min. After completion of the reaction, the base was neutralized with ammonium chloride solution (10%, 100 mL) and the organic layer was separated, dried, and concentrated to give an oil. The product, keto phosphonate 21, was purified by flash chromatography to afford a colorless solid (Rf 0.46, ethyl acetate, 9.8 gms. 64%). m.p. 43°–44° C.

$^1$H NMR: 3.757 (s, 3H, OMe), 3,720 (s, 3H, OMe), 3,038 (d, J=22.5 Hz, 2H, CH$_2$), 2.559 (t, J=7.2 Hz, 2H), 0.826 (t, J=6.6 Hz, 3H, side-chain terminal methyl).

$^{13}$C NMR: 203.012, 54.122, 54.043, 45.291, 43.231, 41.534, 33.070, 30.777, 30.634, 30.503, 30.562, 30.114, 24.567, 23.849, 15.252.

IR: 2967, 1704, 1588, 1474, 1378, 1237, 1193, 1105, 1057, 895, 826, 794.

Example 24

Preparation of Hydroxy Phosphonate 22

To a solution of keto phosphonate 21 (6.12 g, 20 mmol), in methanol (100 mL) cooled to 0° C. was added sodium borohydride (0.95 g, 25 mmol) in four portions, and the mixture was stirred at 0° C. for 1 h. After completion of the reaction, the excess hydride reagent was quenched with water (2 mL) and the solvent was removed in vacuo to afford the crude hydroxy phosphonate. The product was purified by flash chromatography to afford the hydroxy phosphonate 22 as a colorless solid (Rf 0.21, silica, ethyl acetate, 5.80 g, 94%). m.p. 72°–73° C.

$^1$H NMR: 4.02 (m, 1H, CHOH), 3.7325 (d, J=9.9 Hz, 6H, P OCH$_3$), 3,410 (bs, 1H, OH), 1.976 (m, 2H, CH$_2$), 1,352 (m, 4H, 2×CH$_2$), 1.206 (bs, 16H), 0.826 (t, J=6.6 Hz, 3H, terminal methyl).

$^{13}$C NMR: 90.241, 67.796, 67.711, 40.124, 39.538, 34.855, 33.211, 33.026, 30.944, 30.919, 30.885, 30.787, 30.636, 26.721, 23.972. 15.381.

IR: 3338, 2956, 2743, 1741, 1471, 1266, 1129, 1030, 988, 854, 727, 572.

Example 25

Preparation of Compound 23

To a solution of hydroxy phosphonate 22 (5.54 g, 18 mmol) and lauric acid (4.0 g, 20 mmol) in dichloromethane (40 mL), was added sequentially DCC (4.12 g, 20 mmol) and DMAP (2.44 g, 20 mmol) and the contents were stirred at room temperature for 4 h under argon atmosphere. After completion of the reaction (4 h, TLC), the insoluble material was removed by filtration and the filtrate was concentrated to give the crude ester 23, which after flash chromatography, afforded the ester 23 as a colorless solid (Rf 0.64, ethyl acetate, 7.23 g, 82%). m.p. 74°–75° C.

$^1$H NMR: 5.186 (m, 1H, CHCOO), 3.732 (d, J=6.9 Hz, 6H, P OCH$_3$), 2.346 (t, J=7.2 Hz, 2H), 2.102 (m, 2H), 1.614 (m, 4H, 2×CH$_2$), 1.240 (bs, 32H), 0,826 (t, J=6.2Hz, 6H).

$^{13}$C NMR: 174.005, 69.761, 53.545, 54.460, 36.221, 36.111, 35.587, 33.099, 32.151, 30.804, 30.670, 30.526, 30.430, 30.336, 30.290, 26.257, 26.079, 23.850, 15.222.

IR: 2926, 2855, 1739, 1494, 1251, 1183, 1035, 844, 756, 666.

Example 26

Preparation of Diacid 24

Under an Ar atmosphere, to a solution of compound 23 (6.86 gms, 14 mmol) in dichloromethane (25 mL) cooled by an ice bath was added trimethylsilyl iodide (7 mL), and the mixture was stirred at room temperature for 1 h. After completion of the reaction, the mixture was diluted with dichloromethane (20 mL) and stirred with sodium thiosulfate solution (10%, 20 mL) for 10 min. Then the organic layer was separated and concentrated to give the crude diacid 24. The crude material was dissolved in THF (50 mL) dilute HCl (5%, 20 mL) and the solution was stirred for 1 h. To the solution was added dichloromethane (100 mL), and the organic layer was separated, dried, and concentrated to give compound 24 as a colorless solid (5.30 g, 82%). m.p. 78°–79° C.

$^1$H NMR 4R: 5.186 (m, 1H, CHOH), 2.324 (t, J=7.2Hz, 2H), 2.084 (m, 2H), 1.632 (m, 4H), 1.286 (bs, 34 H), 0.826 (t, J=6.6 Hz, 6H).

$^{13}$C NMR: 175.488, 70.250, 36.755, 36.610, 35.875, 33.299, 31.058, 31.058, 31.037, 30.947, 30.738, 30.582, 26.392, 26.227, 24.049, 15.436.

IR: 2954, 1740, 1687, 1471, 1277, 1170, 1090, 998, 900, 855, 720, 610, 570.

Example 27

Preparation of Compound 25

A mixture of compound 24 (4.62 g, 10 mmol), benzyl alcohol (3.24 g, 30 mmol), trichloroacetonitrile (5 mL), pyridine (10 mL) and chloroform (20 mL) was heated at 50° C. overnight. After completion of the reaction, the solvents were removed in vacuo and the resulting material was dissolved in THF (40 mL) and stirred with HCl (5%, 20 mL) for 1 h. Then the organic layer was separated, concentrated, and the product was purified by flash chromatography to afford the monobenzylated compound 25 as a brown thick oil (3.64 g, 64%).

$^1$H NMR: 11.56 (bs, 1H, OH), 7.363 (m, 5H, aromatic), 5.197 (m, 1H), 5.062 (d, 2H), 2.112 (m, 4H), 1.652 (m, 4H), 1.264 (bs, 36 H), 0.896 (t, 3H).

$^{13}$C NMR: 174.442, 137.520, 137.615, 129.845, 129.172. 129.367, 69.930, 67.947, 36.553, 36.430, 35.770, 33.581, 33.302, 31.024, 30.966, 30.738, 30.693, 30.548, 26.393, 6.244, 24.065, 15.476.

IR: 3359, 3063, 2957, 2873, 1869, 1717, 1636, 1499, 1382, 072. 997.

Example 28

Preparation of phosphochloridate 19

A solution of compound 25 (1,707 g, 3 mmol) and phosphorus pentachloride (0.615 g, 3 mmol) in dry chloroform (10 mL) was stirred at room temperature in an Ar atmosphere for 3 h. After completion of the reaction (3 h, NMR) the solvent was removed and the resulting product phosphochloridate was used in the next reaction without the need for further purification.

$^1$H NMR: 7.340 (m, 5H, aromatic), 5.124 (m, 3H, benzylic & CHCOO), 2.241 (m, 4H), 1.42 (m, 4H), 1.24 (bs, 34H), 0.864 (t, 6H, terminal methyls).

Example 29

Preparation of Compound 27

To a solution of compound 26 (1.48 g, 2 mmol), DMAP (0.244 g, 2 mmol) and triethylamine (4 mL) in dichloromethane (8 mL) under an Argon atmosphere was added a solution of phosphochloridate 19 (1.76 gms, 3 mmol, crude) in dichloromethane (5 mL) through a syringe over a period of 10 min and the resulting reaction mixture was stirred at room temperature for a further 1 h. After completion of the reaction, the solvents were removed in vacuo and the product was purified by flash chromatography to afford compound 27 as an oil (Rf 0.36, silica, ethyl acetate:hexane 1:5, 1.5 g, 56%).

$^1$H NMR: 7.340 (m, 5H, aromatic), 6.589 (m, 1H, NH), 5.033 (m, 4H, benzylic and 2×CHCOO), 4.665 (m, 1H, C-1), 4.371 (m, 1H), 3.774 (m, 3H), 3.349 (m, 1H), 2.231 (m, 8H), 1.592 (m, 8H), 1.521 (s, 3H, acetonide methyl), 1.367 (s, 3H, acetonide methyl), 1.258 (bs, 68H), 0.874 (m, 21H, t-butyl and side-chain terminal methyls), 0.08 (s, 3H, SiMe), 0.07 (s, 3H, SiMe).

$^{13}$C NMR: 174.678, 172.091, 169.665, 128.516, 127.875, 99.558, 97.067, 72.538, 70.366, 68.523, 66.840, 61.811, 56.701, 42.021, 34.448, 31.835, 29.884, 29.002, 25.569, 25.196, 22.642, 19.109, 17.192, 14.054, −4,300 and −5,416.

IR: 3289, 2993, 1744, 1661, 1464, 1306, 1252, 1199, 1098, 942, 842, 732, 698, 525.

Example 30

Preparation of Compound 28

To a solution of compound 27 (0.51 g, 0.4 mmol) in dichloromethane (5 mL) cooled to 0° C. was added trifluoroacetic acid (3 mL) and the resulting reaction mixture was stirred at 0° C. for 1 h. After completion of the reaction, the acid was neutralized with triethylamine (4 mL), and the solvents were removed in vacuo to afford the crude diol 28 as an oil, which after purification by flash chromatography afforded the pure diol 28 as an oil (Rf 0.16, ethyl acetate:hexane, 1:4, 0.30 g, 81%).

$^1$H NMR: 7.346 (m, 5H, aromatic), 6.211 (m, 1H, NH), 5.116 (m, 4H), 4.842 (d, J=7.2Hz, 1H, C-1), 4.420 (m, 1H), 3.642 (m, 5H), 2.228 (m, 8H), 1.33 (m, 8H), 1.261 (bs, 68H), 0.824 (m, 21H, terminal methyls and t-butyl), 0.08 (s, 3H, SiMe), 0.074 (s, 3H, SiMe).

$^{13}$C NMR: 173.799, 173.287, 169.818, 128.634, 128.347, 95.666, 74.927, 70.810, 68.884, 62.879, 34.524, 34.405, 31.892, 29.775, 29.682, 29.397, 29.332, 29.129, 25.607, 24.974, 24.939, 24.868, 24.848, 22.658, 17.822, 14.083, −4.002, −5.014.

IR: 3286, 2955, 2362, 1736, 1656, 1500, 1416, 1379, 1229, 1081, 939, 784.

Example 31

Preparation of BK-3

A suspension of compound 28 (123 mg, 0.1 mmol) and Pd-C (10%, 12 mg) in ethyl acetate (2 mL) was stirred under a hydrogen atmosphere. After completion of the reaction the catalyst was removed by filtration and removal of the solvent afforded the debenzylated compound as an oil (103 mg, 90%).

$^1$H NMR: 6.208 (m, 1H, NH), 5.012 (m, 1H), 4.782 (m, 2H), 3.742 (m, 3H), 3.124 (m, 2H), 2.228 (m, 8H), 1.32 (m, 8H), 1.261 (bs, 68H), 0.824 (m, 21H), 0.80 (s, 6H).

The above-obtained compound (100 mg, 0.087 mmol) was dissolved in THF (2 mL) in a plastic container cooled to 0° C. and HF-pyridine (0.2 mL) was added. After completion of the reaction (30 min) the mixture was diluted with dichloromethane (5 mL), and stirred with sodium bicarbonate solution (5%, 2 mL). The organic layer was separated, dried, and concentrated to give BK-3 as an oil. The oil was dissolved in water (5 mL) and lyophilized to give BK-3 as a thick oil. (65 mg, 74%).

$^1$H NMR: 6.021 (m, 1H, NH), 5.034 (m, 1H), 4.420 (m, 2H), 3.342 (m, 5H), 2.228 (m, 8H), 1.30 (m, 8H), 1.24 (m, 68H), 0.832 (t, 12H).

Example 32

Preparation of Compound 31

To a solution of glucosamine hydrochloride (21.55 g, 100 mmol) in aqueous sodium bicarbonate (14.4 g, 300 mmol, 400 mL water) cooled to 0° C. was added dropwise Cbz-Cl (18.75 g, 110 mmol) and the reaction mixture was stirred at 0° C. for 2 h and then at room temperature overnight. The precipitated compound was filtered, washed with cold acetone (40 mL) and dried to give the amino protected compound as a colorless solid (26.90 g, 86%).

The above-obtained amino-protected compound (25 g, 79.8 mmol) was dissolved in methanolic hydrogen chloride solution (2% v/w, 350 ml), and the mixture was heated at reflux for 4 h. After completion of the reaction, the solvent was removed in vacuo to afford compound 31 as a colorless solid (Rf 0.24, Silica, 10% methanol in dichloromethane, 20.30 g, 78%).

Example 33

Preparation of Compound 32

A solution of compound 31 (22 g, 67.2 mmol), PTSA (0.5 g) in acetone (200 mL), dichloromethane (300 mL), and 2,2-dimethoxypropane (28 g, 4 eq) was stirred at room temperature for 4 h. After completion of the reaction, the acid was neutralized with triethylamine (5 mL) and washed with water (50 mL), dried, and concentrated to give a slurry, which after flash chromatography, afforded compound 39 as a colorless solid (Rf 0.52, ethyl acetate:hexane 2:3, 20.71 g, 84%). m.p. 64°–65° C.

$^1$H NMR: 7.313 (m, 5H, aromatic), 5.362 (d, J=8Hz, 1H, NH), 5.093 (m, 2H, benzylic), 4.683 (d, J=3 Hz, 1H, C-1), 3.709 (m, 6H), 3.308 (s, 3H, OCH$_3$), 2.432 (bs, 1H, OH) 1.483 (s, 3H, acetonide methyl), 1.414 (s, 3H, acetonide methyl).

$^{13}$C NMR: 158.159, 137.547, 129.879, 129.714, 129.546, 101.202, 100.075, 75.902, 71.398, 68.531, 64.723, 63.658, 56.570, 30.435, 20.461.

IR: 3422, 3382, 2995, 1708, 1531, 1374, 1268, 1163, 1022, 991, 895, 752.

Example 34

Preparation of Amino Compound 30

A suspension of compound 32 (19 g, 51.7 mmol) and Pd-C (10%, 1 g), in ethyl acetate (200 mL) was stirred under an atmosphere of hydrogen. After completion of the reaction, the catalyst was removed by filtration through a pad of celite and removal of the solvent afforded amino compound 30 as a colorless solid (Rf 0.46, silica, ethyl acetate, 11.3 g. 92%). m.p. 152°–153° C.

$^1$H NMR: 4.637 (d, J=3.6 Hz, 1H, C-1), 3.714 (m, 2H), 3.483 (m, 3H), 2.700 (m, 1H), 2.342 (bs, 2H, NH$_2$), 1.481 (s, 3H), 1.398 (s, 3H).

$^{13}$C NMR: 102. 532, 100. 963, 75. 960, 73. 320, 64. 811, 63. 823, 58.070, 58.030, 56.601, 30.512, 20.522.

IR: 3454, 2938, 1580, 1466, 1383, 1273, 1201, 1122, 1041, 994, 898, 752, 738.

Example 35

Preparation of Compound 33

To a solution of amino compound 30 (4.66 g, 20 mmol) and acid 3 (8.52 g, 20 mmol) in dichloromethane (100 mL) was added sequentially EDC (4.18 g, 22 mmol) and HOBT (2.86 g, 22 mmol) and the mixture was stirred at room temperature under an argon atmosphere for 2 h. After completion of the reaction, the mixture was transferred to a separation funnel, washed with water (25 mL), dried, and concentrated to give an oil. The product was purified by flash chromatography to afford compound 33 as an oil (Rf 0.41, silica, ethyl acetate:hexane, 9.58 g, 68%). 1H NMR: 6.134 (d, J=9 Hz, 1H, NH), 5.159 (m, 1H, CHOCO), 4.634 (d, J=3.8 Hz, 1H, C-1), 4.134 (m, 1H), 3.766 (m, 5H), 3.352 (s, 3H, OCH$_3$), 3.193 (bs, 1H, OH), 2.483 (d, J=6 Hz, 2H), 2.290 (t, J=7.2 Hz, 2H), 1.605 (m, 4H), 1.524 (s, 3H), 1.431 (s, 3H, CH$_3$ of acetonide), 1.246 (bs, 34H), 0.875 (t, J=6.6 Hz, 3H, terminal CH$_3$)

$^{13}$C NMR: 174.960, 172.237, 101.191, 100.162, 75.913, 72.549, 72.176, 64.671, 63.618, 56.441, 55.535, 43.149, 35.884, 35.451, 33.237, 30.954, 30.863, 30.837, 30.668, 30.515, 26.633, 26.318, 24.004, 20.423, 15.425.

IR: 3418, 3354, 2994, 1734, 1652, 1467, 1339, 1267, 1197, 1131, 1074, 994, 896, 735.

Example 36

Preparation of Compound 34

To a solution of compound 33 (7.16 g, 11.17 mmol) in DMF (40 mL) was added sequentially imidazole (1.76 g, 26 mmol) and t-butyldimethylsilyl chloride (1.95 g, 13 mmol) and the mixture was stirred at room temperature under an argon atmosphere for 6 h. After completion of the reaction, the mixture was transferred to a separatory funnel, diluted with ethyl acetate (150 mL), and washed with water (2×100 mL). The organic layer was separated, dried, and concentrated to give an oil. The product was isolated after flash chromatography to afford the silylated compound 34 as an oil (Rf 0.62, silica, ethyl acetate:hexane, 6.83 g, 81%).

1H NMR: 5.726 (d, J=9.6 Hz, 1H, NH), 5.124 (m, 1H, OCHCO), 4.615 (d, J=3.6 Hz, 1H, C-1), 4.190 (m, 1H), 3,827–3.537 (m, 5H), 3.31 (s, 3H, OCH₃), 2,462 (m, 2H, CH₂CO), 2.287 (t, J=7.2 Hz, 2H, CH₂CO), 1.612 (m, 4H), 1.522 (s, 3H), 1,432 (s, 3H), 1.321 (bs, 34H), 0,894 (m, 15H, t-butyl and side-chain terminal CH₃), 0.042 (s, 6H, SiMe₂)

¹³C NMR: 174,419, 170.738, 100.637, 100,736, 76.157, 73.000, 72.947, 72.888, 72.280, 64.977, 63.768, 56.360, 55,388, 43.169, 35.860, 35.765, 33.229, 30.935, 30.865, 30.810, 30.654, 30.616, 30.501, 30.382, 27.112, 27.064, 27.031, 26.473, 26.323, 23.992, 20.271, 19.482, 15.408.

IR: 2995, 1724, 1667, 1516, 1382, 1267, 1164, 1083, 1005, 910, 838, 780, 734

Example 37

Preparation of Compound 35

To a solution of acetonide compound 34 (4.53 g, 6 mmol) in dichloromethane (10 mL) at 0° C. was added trifluoroacetic acid (5 mL) and the mixture was stirred at 0° C. for 2 h. After completion of the reaction the acid was neutralized with triethylamine (6 mL) and the mixture was washed with water (10 mL). The organic layer was separated, dried, and concentrated to give the crude diol, which after purification by flash chromatography afforded the diol 35 as an oil (Rf 0.36 silica, ethyl acetate:hexane, 1:1, 3.98 g, 93%).

¹H NMR: 5.724 (d, J=9.6 Hz, 1H; NH), 5.124 (m, 1H, OCHCO), 4.612 (d, J=3.6 Hz, 1H, C-1), 3.724–3.401 (m, 5H), 3.32 (s, 3H, OCH₃), 2.416 (t, J=7.6 Hz, 2H), 2.232 (t, J=7.6 Hz, 2H), 1.618 (m, 4H), 1.321 (bs, 34H), 0.894 (m, 12H, t-butyl and side chain terminal CH₃), 0.042 (s, 3H, SiMe), 0.038 (s, 3H, SiMe).

¹³ C NMR: 174.519, 171.030, 100.153, 74.732, 73.220, 72.992, 72.611, 63.675, 56.391, 54.923, 43.272. 35.873, 35.790, 33.231, 30.941, 30.872. 30.820, 30.686, 30.652, 30.517, 27.107, 26.107, 26.476, 26.339, 23.992, 19.420, 15.393, –2.602, –3.060.

IR: 3567, 3434, 3300, 2922, 1719, 1654, 1466, 1254, 1190, 1055, 861, 756, 736.

Example 38

Preparation of Compound 36

To a solution of compound 35 (2.14 g, 3 mmol) and DMAP (0.488 g. 4 mmol) in dichloromethane (10 mL), a solution of tosyl chloride (0.686 g, 3.6 mol) in dichloromethane (3 mL) was added at 0° C. slowly through a syringe under an argon atmosphere and the mixture was stirred at 0° C. for 4 h. After completion of the reaction, the excess tosyl chloride was reacted with methanol (1 mL), and the mixture was transferred to a separatory funnel, washed with water (10 mL), dried and concentrated to give an oil. The monotosylated compound was purified by flash chromatography to afford an oil (Rf 0.34, silica, ethyl acetate:hexane, 1:4, 2.16 g, 83%).

¹H NMR: 7.814 (d, J=8.1 Hz, 2H, aromatic), 7.363 (d, J=8.1 Hz, 2H, aromatic), 5.674 (d, J=9.3 Hz, 1H, NH), 5.088 (m, 1H, CHOCO), 4.517 (d, J=3.6 Hz, 1H, C-1), 4.058 (m, 3H), 3.665 (m, 3H), 3.279 (s, 3H, OCH₃), 2.458 (s, 3H, CH₃), 2.276 (m, 4H), 1.638 (m, 4H), 1.267 (bs, 34H), 0.864 (m, 12H, t-butyl & terminal side chain methyl), 0.042 (s, 3H, SiMe), 0.038 (s, 3H, SiMe).

¹³C NMR: 174.402, 170.848, 146.180, 134.360, 131.103, 129.283, 100.006, 74.633, 72.905, 72.465, 70.911, 70.515, 56.472. 54.594, 43.192, 35.829, 35.774, 33.205, 30.902, 30.838, 30.790, 30.624, 30.602, 30.482, 27.058, 26.440, 26.310, 23.964, 22.897, 19.371, 15.376, –2.688, –3.092.

IR: 3524, 3359, 2914, 2535, 2063, 1992, 1780, 1717, 1652, 1541, 1348, 1292, 1174, 1098, 1065, 1004, 978, 862, 835.

The above-obtained monotosylate compound (1.73 g, 2 mmol) was dissolved in DMF (10 mmol) and heated at 60° C. in the presence of sodium azide (0.39 g, 6 mmol) for 6 h. After completion of the reaction, the mixture was transferred to a separatory funnel, diluted with ethyl acetate (20 mL) and washed with water (10 mL) and the organic layer was separated, dried, and concentrated to give an oil, which after purification by flash chromatography, afforded azide 36 as an oil (Rf 0.58, silica, ethyl acetate:hexane, 1:4, 1.15 g, 78%).

¹H NMR: 5.701 (d, J=9.6 Hz, 1H, NH), 5.093 (m, 1H, CHOCO), 4.619 (d, J=3.6 Hz, 1H, C-1), 4.138 (m, 1H), 3.63 (m, 5H), 3.372 (s, 3H, OCH₃), 2.417 (m, 2H), 2.285 (t, J=7.6 Hz, 2H), 1.620 (m, 4H), 1.264 (bs, 34H), 0.874 (m, 15H, t-butyl and terminal side chain methyl), 0.056 (s, 3H, SiMe), 0.052 (s, 3H, SiMe).

¹³C NMR: 174.470, 170.885, 100.118, 90.241, 74.834, 73.804, 72.969, 73.804, 72.969, 72.263, 56.535, 54.634, 52.959, 43.280, 35.853, 35.791, 33.219, 30.926, 30.855, 30.803, 30.643, 30.618, 30.501, 27.055, 26.457, 26.327, 23.980, 19.971, 15.396, –2.672. –2.993.

IR: 3567, 3434, 2920, 2852, 2252, 2100, 1718, 1654, 1466, 1259, 1125, 1063, 910, 839, 735.

Example 39

Preparation of phosphorylated Compound 29 phosphorylation of compound 36 was accomplished by the same procedure used to convert compound 1 to compound 17 (Example 19), to afford the corresponding phosphorylated compound 29 as an oil (Rf 0.54, silica, ethyl acetate:hexane, 1:4, 82%).

¹H NMR: 7.343 (m, 10H, aromatic), 5.653 (d, J=9.6 Hz, 1H, NH), 5.07 (m, 5H, 2×CH₂O and CHCOO), 4.608 (d, J=3.6 Hz, 1H, C-1), 4.112 (m, 2H), 3.802 (m, 2H), 3.553 (m, 2H), 3.367 (s, 3H, OCH₃), 2.419 (m, 2H), 2.287 (t, J=6.6 Hz, 2H), 1.630 (m, 4H), 1.261 (bs, 34H), 0.892 (t, J=6.2Hz, 6H, side chain terminal CH₃), 0.841 (s, 8H, t-butyl), 0.084 (s, 3H, SiMe), 0.064 (s, 3H, SiMe).

¹³C NMR: 174.465, 171.200, 136.394, 131.437, 130,980, 130.183, 130.103, 129.991, 129.961, 129.933, 129.795, 99.365, 73.067, 72.449, 71.497, 71.047, 66.439, 56.749, 54.7521, 52.616, 43.341, 35.827, 35.880, 33.257, 30.959, 30.889, 30.841, 30.534, 27.150, 26.483, 26.355, 24.030, 19.163, 15.163, 15.447, –2.523, –2.701.

IR: 2927, 2101, 1728, 1679, 1529, 1464, 1380, 1257, 1135, 1016, 924, 858, 780, 698, 675, 647.

Example 40

Preparation of Compound 37

The above-obtained phosphorylated compound 29 (1.1 g, 1.1 mmol) was dissolved in methanol (3 mL) and dichloromethane (3 mL) cooled to 0° C. and stirred with a catalytic amount of PTSA (100 mg) for 2 h. After completion of the reaction, the acid was neutralized with triethylamine (1 mL)

and the solvents were removed in vacuo to afford the crude hydroxy compound as an oil, which after purification by flash chromatography afforded the hydroxy compound 37 as an oil (Rf 0.46, silica, ethyl acetate:hexane, 1:1, 0.53 g, 59%).

$^1$H NMR: 7.343 (m, 10H, aromatic), 6.281 (d, J=8.4 Hz, 1H, NH), 5.067 (m, 5H, 2×OCH$_2$Ph, and CHOCO), 4.717 (d, J=3.6 Hz, 1H, C-1), 4.185 (m, 2H), 3.851 (m, 2H), 3.361 (s, 3H, OCH$_3$), 3.300 (m, 2H), 2.493 (m, 2H), 2.281 (t, J=7.2 Hz, 2H), 1.608 (m, 4H), 1.247 (bs, 34H), 0.877 (t, J=6.6 Hz, 6H, side chain terminal methyl)C $^{13}$C NMR: 174.723, 171.801, 136.977, 136.889, 136.821, 130.046, 129.970, 129.897, 129.694, 129.464, 129.299, 99.374, 79.880, 79.249, 72.526, 72.363, 71.508, 71.431, 71.257, 71.187, 70.726, 70. 627, 69.910, 56.748, 54.912, 52.338, 42.953, 38.520, 35.869, 35.124, 33.246, 30.958, 30.875, 30.844, 30.705, 30.669, 30.533, 27.178, 26.614, 26.331, 24.015, 15.441.

IR: 3419, 3348, 2921, 2100, 1719, 1654, 1641, 1457, 1380, 1283, 1214, 1152, 1121, 998, 887, 698, 597, 486.

Example 41

Preparation of Coupled Compound 38

The coupling reaction of the above-obtained hydroxy compound 37 (0.42 g, 0.48 mmol) and phosphochloridate 19 (0.380 g, 0.672 mmol) was achieved by using the same procedure described for the preparation of compound 27 from compound 26 (Example 29) to afford compound 38 (Rf 0.42 silica, ethyl acetate, hexane, 1:4, 0.37 g, 56%).

$^1$H NMR: 7.347 (m, 15H, aromatic), 7.013 (m, 1H, NH), 4.997 (m, 8H, 3×OCH$_2$Ph and 2×CHOCO), 4.710 (d, J=3.6 Hz, C-1), 4.569 (m, 2H), 4.235 (m, 1H), 4.039 (m, 1H), 3.794 (m, 1H), 3.486 (m, 1H), 3.352 (s, 3H, OCH$_3$), 2.262 (m, 8H), 1.535 (m, 8H), 1.26 (bs, 68H), 0.870 (t, 12H).

Example 42

Preparation of Immunogen 3M

A suspension of the above obtained coupled compound 38 (0.24 g, 0.17 mmol) in methanol (4 mL), was hydrogenated using Pd-C (10%, 30 mg) for 4 h. After completion of the reaction, the catalyst was removed by filtration through a small pad of celite and the solvents were removed in vacuo to afford an oil. The oil was dissolved in chloroform (5 mL) and acidified with acetic acid (0.5 mL) and filtered through a small pad of celite to remove any solid particles. The solvents were removed in vacuo to give a thick oil. The oil was dissolved in acetonitrile (1 mL), and water (3 mL), sonicated (the mixture was still turbid) and lyophilized to give immunogen 3M as a colorless solid (140 mg, 78%).

$^1$H NMR: 5.206 (m, 2H, CHOCO), 4.682 (m, 2H), 4.242 (m, 5H), 3.801 (m, 1H), 3.401 (s, 3H, OCH$_3$), 2.842 (m, 2H), 2.400 (m, 6H), 1.807 (m, 8H), 1.26 (m, 68H), 0.892 (t, 12H, side chain terminal methyls).

Example 43

Preparation of Compound 39

To a solution of compound 37 (1 eq), and acid 4 (1.2 eq) in dichlororomethane is added DCC (1.2 eq) and the resulting reaction mixture is stirred for 4 h. After completion of the reaction, by filtration the salts are separated. Removal of the solvent and flash chromatography affords compound 39.

Example 44

Preparation of Immunogen 2M

Hydrogenation of compound 39 by a suspension of compound 39 and Pd-C (10%) in ethyl acetate, affords the immunogen 2M.

Example 45

Preparation of Compound 42

A suspension of compound 6a (4.45 g, 10 mmol) and Pd-C (10%, 0.5 g) in ethyl acetate (50 mL) was stirred under an atmosphere of hydrogen overnight. The progress of the reaction was monitored by TLC and showed the disappearance of the starting material and the formation of a new, more polar, compound. The catalyst was removed by filtration and the solvent was removed in vacuo to afford an oil, which, after flash chromatography, afforded the amine as a colorless crystalline solid (Rf 0.16, ethyl acetate:hexane 1:3, 3.98 g, 95%). m.p. 63°–64° C.

$^1$H NMR: 4.869 (m, 2H, CHOAc), 4.41 (d, J=7.8 Hz, 1H, anomeric), 4.075 (m, 2H, CH$_2$OAc), 3.610 (m, 1H), 2.74 (m, 1H), 1.96 (s, 6H, two acetates), 1.92 (s, 3H, acetate), 1.36 (bs, 2H, NH$_2$), 0.824 (s, 8H, t-butyl), 0.0 (s, 6H, Si (CH$_3$)$_2$)

$^{13}$C NMR: 171.837, 171.767, 171.022, 100.343, 90.241, 76.622, 76.459, 63.964, 58.986, 73.197, 70.629, 70.46 26.989, 22.040, 21.939, 19.275, −2.914, −3.877

IR: 2954, 2862, 2777, 2743, 2482, 2127, 2127, 1939, 1771, 1717, 1594, 1473, 1386, 1331, 1282, 1145, 1017, 973.

To a solution of the amino compound (2.72 g, 6.5 mmol) in dichloromethane (20 mL) and pyridine (12 mL) under an Ar atmosphere was added dropwise through a syringe a solution of trichloroethyl chloroformate (1.60 g, 7.6 mmol) in dichloromethane (3 mL), and the mixture was stirred for 3 h. After completion of the reaction (TLC), the mixture was transferred to a separatory funnel, diluted with dichloromethane (40 mL), and washed successively with water (10 mL), sodium bicarbonate (5%, 10 mL) and water (10 mL). The organic layer was separated, dried, and concentrated to give the crude product, which after purification by flash chromatography, afforded the carbamate 42 as a colorless solid (Rf 0.51, silica, ethyl acetate:hexane, 1:3, 3.55 g, 92%) m.p. 170°–171° C.

$^1$H NMR: 5.541 (d, J=9.3 Hz, 1H, NH), 5.227 (t, J=9.9 Hz, 1H, C-3), 4.980 (t, J=9.6 Hz, 1H, C-4), 4.776 (d, J=8.1Hz, 1H, C-1), 4.652 (AB, 2H, CH$_2$ of Troc), 4.146 (m, 2H, C-6), 3.675 (m, 2H, C-2 and C-5), 2.033 (s, 3H, Acetate), 2.012 (s, 6H, two acetates), 0.839 (s, 8H, t-bu), 0.05 (s, 3H, SiMe), 0.03 (S, 3H, SiMe).

$^{13}$C NMR: 172.175, 171.951, 170.830, 155.488, 97.508, 75.921, 73.460, 73.092, 70.654, 63.927, 59.472. 32.982, 26.860, 23.950, 21.943, 21.975, 22.004, 19,242, 15.429, 2.962, −3.934.

IR (KBr): 3291, 3171, 3087, 2959, 2932, 2531, 1752, 1747, 1708, 1473, 1464, 1435, 1370, 1230, 1191, 1141, 1108, 980, 957, 887.

Example 46

Preparation of Compound 43

A solution of compound 42 (3.56 g, 6 mmol) in methanol (25 mL) and sodium methoxide in methanol (1M, 0.2 mL) was stirred at room temperature for 1 h. After completion of the reaction, the base was neutralized with acetic acid (1 mL) and the solvents were removed in vacuo. The crude product was purified by flash chromatography to afford the corresponding trihydroxy compound as a colorless crystalline solid (Rf 0.45, silica, ethyl acetate, 2.42 g, 92%). m.p. 136°–137° C.

$^1$H NMR (CD$_3$OD): 4.657 (m, 2H, CH$_2$ of Troc), 4.595 (d, J=7.2 Hz, 1H, C-1), 3.790 (m, 2H), 3.349 (m, 4H), 0.840 (s, 8H, t-butyl), 0.031 (s, 3H, SiMe), 0.020 (s, 3H, SiMe).

$^{13}$C NMR (CD$_3$OD): 156.828, 97.823, 79.208, 79.107, 77.464, 75.930, 75.430, 72.144, 62.897, 61.030, 26.483, 26.442, 18.954, −3.605, −4.721.

IR (KBr): 3365, 2957, 2887, 2805, 2712, 2045, 1718, 1545, 1362, 1255, 1175, 1083, 949, 785.

A solution of the above-obtained trihydroxy compound (2.33 g, 5 mmol), dichloromethane (20 mL), PTSA (200 mg), and 2,2-dimethoxy propane (1.56 g, 15 mmol) was stirred under an argon atmosphere for 4 h. After completion of the reaction (TLC), the acid was neutralized with triethylamine (1 mL) and the mixture was transferred to a separatory funnel. The mixture was diluted with dichloromethane (40 mL) and washed with water (10 mL). The organic layer was separated, dried (MgSO$_4$), and the product was purified by flash chromatography to afford compound 43 as an oil. (Rf 0.46, silica, ethyl acetate:hexane, 1:4, 2.12 g, 84%). m.p. =90°–91° C.

$^1$H NMR: 5.711 (d, J=7.2 Hz, 1H, NHCO), 4.824 (d, J=6.9 Hz, 1H, C-1), 4.715, (AB, 2H, CH$_2$ of Troc), 3.874 (m, 2H), 3.771 (t, J=10.2Hz, 1H), 3.578 (t, J=9.2Hz, 1H), 3.496 (bs, 1H, OH), 3.22 (m, 2H), 1.496 (s, 3H, CH$_3$ of acetonide), 1.415 (s, 3H, CH$_3$ of acetonide), 0.861 (s, 8H, t- bu), 0.086 (s, 3H, SiCH$_3$) 0.069 (s, 3H, SiCH$_3$).

$^{13}$C NMR: 155.904, 110.996, 101.176, 97.499, 96.654, 76.134, 75.670, 72.318, 68.507, 63.400, 62.285, 30.435, 26.958, 20.520, 19.255, -2.870, -3.874.

IR (KBr): 3094, 2996, 2193, 1987, 1718, 1560, 1474, 1382, 1288, 1200, 1166, 1095, 986, 842, 735.

Example 47

Preparation of Compound 44

Under an Ar atmosphere, to a solution of compound 43 (2.02 g, 4 mmol) in dichloromethane (20 mL) containing DMAP (0.488 g, 4 mmol) and triethylamine (1.10 g), was added (through a syringe), over a period of 15 min, a solution of phosphochloridate 9 (2.70 g, 5 mmol) in dichloromethane (5 mL). After completion of the reaction (TLC), the contents were transferred to a separatory funnel and washed with water (10 mL). The organic layer was separated, dried and concentrated to give an oil. The product was purified by flash chromatography to afford compound 44 as an oily compound (Rf 0.61 silica, ethyl acetate:hexane 1:3, 2.90 g. 72%).

$^1$H NMR (CDCl$_3$): 7.299 (m, 5H, aromatic), 6.979 (t, 1H, NH), 5.190 (1H, CHCO), 5.00 (m, 2H, OCH$_2$Ph), 4.775 (m, 1H, C-1, anomeric), 4.605 (m, 1H), 4.431 (AB, CH$_2$ of Troc), 3.916–3.796 (m, 4H), 3.513 (m, 1H), 2.165 (m, 4H, CH$_2$CO,and CH$_2$-P), 1.548 (s, 3H, CH$_3$ acetonide), 1.423 (s, 3H, CH$_3$ of acetonide), 1.26 (m, 28H, CH$_2$), 0.860 (m, 15H, side chain terminal CH$_3$ and t-bu Si), 0.003 (s, 6H, SiMe).

$^{13}$C NMR: 174.00, 155.943, 137.255, 129.898, 129.137, 100.932, 98.674, 96.467, 76.050, 74.144, 69. 842, 67.722, 67.409, 63.252, 60.571, 35.675, 30.984, 26.878, 24.040, 20.498, 20.436, 19.161, 15.469, −2.863, −3.778.

IR: 2926, 1718, 1671, 1520, 1430, 1354, 1214, 1156, 1021, 908, 864, 740.

Example 48

Preparation of Imidate 40

A solution of compound 44 (1.61 g, 1.6 mmol) in dichloromethane (3 mL) was stirred with tetrabutylammonium fluoride (1M solution in THF, 2.6 ml) for 4 h. After completion of the reaction (TLC) trichloroacetonitrile (3 mL) was added and the solution stirred for additional 4 h. After the intermediate hydroxy compound was nearly consumed (TLC), the solvents were removed in vacuo and the residue was purified by flash chromatography to afford the imidate as an anomeric mixture.

α-Imidate (Rf, 0.52, silica, ethylacetate: hexane 1:3, 0.583 g, 34%)

$^1$H NMR: 8.746 (s, 1H, NH of imidate), 7.289 (m, 5H, aromatic), 6.489 (d, J=3.9 Hz, 1H, C-1), 6.234 (d, J=7.8 Hz, 1H, NH of Troc), 5.064 (m, 3H, OCH$_2$Ph and CHOCO), 4. 571 (m, 3H, CH$_2$ of Troc and 1H), 4.173 (m, 1H), 3.835 (m, 4H), 2.199 (m, 4H), 1.422 (s, 3H, Methyl of acetonide), 1.391 (s, 3H, methyl of acetonide), 1.26 (bs, 34H), 0.824 (t, 6H).

β-Imidate (Rf 0.49, silica, ethyl acetate:hexane, 1:3, 0.59 g, 34%).

$^1$H NMR: 8.721 (s, 1H, NH of imidate), 7.361 (m, 5H, aromatic), 6.501 (t, 1H, NH), 6.392 (d, J=7.2 Hz, 1H, C1), 5.018 (m, 3H, OCH2Ph and CHOCO), 4.512 (m, 3H), 4.186 (m, 1H), 3.993 (m, 4H), 2.241 (m, 4H), 1.462 (s, 3H, methyl of acetonide), 1.392 (s, 3H, methyls of acetonide), 1.201 (bs, 34H), 0.910 (t, 6H).

Example 49

Preparation of (R)-3- Benzyloxy-1-tert-butyldimethylsiloxytetradecane (45 )

Trifluoromethanesulphonic acid (0.14 mL, 1.6 mmol) was added to a mixture of alcohol 10 (6.9 g, 20 mmol) and benzyl trichloroacetimidate (12.3 g, 49 mmol) in a 1:1 mixture of dichloromethane and cyclohexane (320 mL) at room temperature. After completion of the reaction (5 h) a saturated solution of sodium bicarbonate (50 mL) was added and the phases were separated. The aqueous phase was extracted with ethyl acetate (2×50 mL) and the organic phases were washed with brine (50 mL), dried (MgSO$_4$), and concentrated in vacuo. The product was purified by flash chromatography to afford compound 45 as an oil (Rf 0.18, silica, 2% ethyl acetate in hexane, 7.7 g, 88%).

$^1$H NMR: 7.49-7.23 (m, 5H, aromatic), 4.60 (AB, 2H, benzylic), 3.85–3.70 (m, 2H), 3.67–3.55 (m, 1H), 1.90 1.77 (m, 2H), 1.67–1.55 (m, 2H), 1.45–1.35 (m, 18H), 0.97 (m, 12H), 0.11 (s, 6H).

$^{13}$C NMR: 139.25, 128.19, 127.64, 127.26, 76.25, 71.02, 59.89, 37.52, 34.21, 31.89, 29.78, 29.60, 29.30, 25.94, 25.27, 22.63, 18.23, 14.00, −5.33.

IR (Neat): 3089, 3066, 3031, 2927, 2855, 1497, 1464, 1388, 1361, 1255, 1224, 1097, 1029, 1006, 939, 836, 776, 733, 697, 682, 666.

Example 50

Preparation of (R)-3-Benzyloxy-1-tetradecanol (46)

A solution of aqueous HF (50%, 12 mL) was added to a mixture of compound 45 (6.3 g, 14.5 mmol) in acetonitrile (120 mL) and the mixture was stirred for 30 min. After completion of the reaction, the acid was neutralized with saturated sodium bicarbonate solution and extracted with ethyl acetate (3×150 mL) and the organic phase was separated, dried, concentrated, and the product was purified by flash chromatography to afford compound 46 as colorless oil (Rf 0.42, 25% ethyl acetate in hexane, 3.4 g, 74%).

$^1$H NMR: 7.43–7.25 (m, 5H), 4.60 (AB, 25H), 3.90–3.73 (m, 2H), 3.70–3.63 (m, 1H), 1.92–1.47 (m, 4H), 1.42–1.23 (m, 18H), 0.93 (t, 3H).

$^{13}$C NMR: 138.44, 128.42, 127.81, 127.67, 78.55, 70.92, 60.74, 35.92, 33.44, 31.91, 29.81, 29.60, 29.34, 25.13, 22.67, 14.10.

Example 51

Preparation of (R)-3-Benzyloxytetradecanoic acid (47)

Jones reagent was added in portions to a mixture of alcohol 46 (3.23 g, 10.1 mmol) in acetone (50 mL) at 0° C. until the alcohol was consumed. The mixture was partitioned between 0.1M HCl (100 mL) and ethyl acetate (400 mL), and the organic phases were washed with brine (100 mL), dried, and concentrated in vacuo. The product was purified by flash chromatography to give compound 47 as an oil (Rf 0.38, silica, 25% ethyl acetate in hexane, 2.09 g, 62%).

$^1$H NMR: 7.42–7.26 (m, 5H), 4.61 (bs, 2H), 3.91 (q, 1H), 2.63 (ddd, 2H), 1.76–1.51 (m, 2H), 1.46–1.24 (m, 20H), 0.93 (t, 3H).

$^{13}$C NMR: 177.29, 138.16, 128.36, 127.83, 127.67, 75.74, 71.54, 39.56, 34.18, 31.91, 29.63, 29.57, 25.12, 22.69, 14.11.

IR (neat): 3400–2400 (broad), 3065, 3032, 2926, 2855, 1713, 1497, 1377, 1353, 1295, 1240, 1207, 1097, 1070, 1029, 939.

Example 52

Preparation of Compound 48

A solution of amino compound 30 (2.35 g, 10 mmol), compound 47 (3.34 g, 10 mmol), EDC (1.91 g, 10 mmol), and HOBT (1.35 g, 10 mmol) in dry dichloromethane (30 mL) was stirred at room temperature under an argon atmosphere for 4 h. After completion of the reaction the solvents were removed in vacuo, and the resulting material was purified by flash chromatography to afford the coupled compound as an oil (Rf 0.31, silica, ethyl acetate:hexane, 1:1, 4.93 g, 90%).

$^1$H NMR: 7.321 (m, 5H, aromatic), 4.512 (m, 3H, benzylic and C-1), 3.814 (m, 7H), 3.194 (s, 3H, OCH$_3$), 2.421 (m, 2H), 1.546 (s, 3H, methyl of acetonide), 1.486 (s, 3H, methyl of acetonide), 1.214 (bs, 20H), 0.894 (t, 3H, terminal side chain methyl).

To the above-obtained compound (4.40 g, 8 mmol) and compound 47 (3.34 g, 10 mmol) in dichloromethane (30 mL) sequentially added was DCC (2.06 g, 10 mmol) and DMAP (1.22 g, 10 mmol) and the mixture was stirred at room temperature under an argon atmosphere for 4 h. After completion of the reaction, the insoluble material was removed by filtration and the solvent was evaporated in vacuo to afford an oil. The crude product was purified by flash chromatography to afford compound 48 as an oil (Rf 0.60, silica, ethyl acetate:hexane 3:7, 6.25 g, 90%).

$^1$H NMR: 7.362 (m, 10H, aromatic), 6.312 (d, J=7.6 Hz, 1H, NH), 5.200 (t, J=7.6 Hz, 1H, CHCOO), 4.562 (m, 6H), 3.812 (m, 6H), 3.189 (s, 3H, OCH$_3$), 2.741-2.346 (m, 4H), 1.456 (s, 3H, acetonide methyl), 1.312 (s, acetonide methyl), 1.216 (bs, 40H), 0.816 (t, J=6.3 Hz, 6H).

Example 53

Preparation of Compound 41

A cooled solution of compound 48 (4.30 g, 5 mmol) in dichloromethane (20 mL), and trifluoroacetic acid (6 mL) was stirred at 0° C. for 2 h. After completion of the reaction the acid was neutralized with triethylamine (6 mL), the solvent was evaporated, and the residue was purified by flash chromatography to afford the diol compound 48 as an oil (Rf 0.24, silica, ethyl acetate:hexane, 1:1, 3.55 g, 86%).

$^1$H NMR: 7.360 (m, 10H, aromatic), 6.346 (d, J=7.2 Hz, 1H, NH), 5.226 (m, 1H), 4.612 (d, J=3 Hz, 1H, C-1), 4.502 (m, 4H), 3.724 (m, 5H), 3.191 (s, 3H, OCH$_3$), 2.464 (m, 4H), 1.264 (bs, 40H), 0.826 (t, J=6.6 Hz, 6H).

$^{13}$C NMR: 172.449, 172.077, 138.329, 137.902, 128.810, 128.313, 127.551, 127.395, 98.050, 97.975, 71.274, 70.412, 69.926, 69.544, 62.426, 54.911, 51.941, 50.813, 41.275, 33.951, 31.873, 29.598, 29.309, 25.407, 25.306, 21.643, 13.911, 13.778.

IR: 3324, 2952, 1728, 1674, 1499, 1168, 965, 834.

Example 54

Preparation of Compound 49

Under an Ar atmosphere, to a cooled solution (−78° C.) of imidate 40 (either e or B, 0.685 g, 0.63 mmol) and compound 41 (0.570 g, 0.689 mmol) in dichloromethane (5 mL) was added (through a syringe) a solution of boron trifluoride etherate (0.1 mL) in dichloromethane (1 mL). The reaction mixture was stirred at −78° C. for 2 h and then at −20° C. for 12 h. After completion of the reaction, triethylamine (0.3 mL), was added, the mixture was transferred to a separatory funnel, diluted with dichloromethane (5 mL), and washed with sodium bicarbonate (5%, 5 mL). The organic layer was separated, dried, and concentrated to give an oil, which was subjected to flash chromatography to afford compound 49 as an oil (Rf 0.54, silica, ethyl acetate:hexane 1:1, 0.75 g, 68%). 1H NMR: 7,332 (m, 15H, aromatic), 6,521 (bs, 1H, NH of Troc), 6.224 (d, J=6.6 Hz, 1H, NH), 5.082 (m, 4H), 4,556 (m, 7H), 3.874 (m, 12H), 3.242 (s, 3H, OCH$_3$), 2,462 (m, 8H), 1.542 (s, 3H, methyl of acetonide), 1,464 (s, 3H, methyls of acetonide), 1.246 (bs, 80 H), 0.846 (t, 12H, terminal methyls).

$^{13}$C NMR: 174,485, 174,414, 173.967, 172.385, 156,138, 156,171, 139,830, 139,729, 137.065, 136,946, 129,925, 129,701, 129.653, 129.187, 128,894, 109,246, 105,421, 100.724, 96.246, 78.610, 72.889, 72.354, 70,246, 67,424, 63.246, 43.246, 41.208, 35,481, 33.290, 31,012, 30,729, 30.513, 26,585, 26,501, 26.240, 24.061, 21,142, 15,492.

IR: 3276, 2996, 1735, 1670, 1499, 1379, 1178, 1095, 941, 821.

Example 55

Preparation of Compound 50

A solution of compound 49 (0.84 g, 0.48 mmol), imidazole (0.068 g, 1 mmol) and t-butyldimethylsilyl chloride (0.135 g, 0.9 mmol) in dry DMF (3 mL) was stirred at 50° C. for 12 h. After completion of the reaction, the mixture was diluted with ethyl acetate (10 mL) and washed with water (5 mL). The organic layer was separated, dried and concentrated to give an oil. The oil was purified to give the silyl compound as an oil (Rf 0.42, silica, ethyl acetate:hexane 1:3, 0.69 g, 78%).

$^1$M NMR: 7,312 (m, 5H, aromatic), 6.541 (bs, 1H, NH of troc), 6.194 (d, J=6.3 Hz, 1H, NH), 5.014 (m, 4H), 4.524 (m, 7H), 4.184 (m, 2H), 3,746 (m, 12H), 3,186 (s, 3H, OCH$_3$), 2.462 (m, 8H), 1.542 (s, 3H, methyl of acetonide), 1,462 (s, 3H, methyls of acetonide), 1.246 (bs, 80H), 0.884 (t, 12H, terminal side chain methyls), 0.812 (s, 8H, t-butyl), 0.04 (s, 3H, SiMe), 0.032 (s, 3H, SiMe).

The above-obtained silyl compound (1.05 gm, 0.57 mmol) was dissolved in dichloromethane (5 mL) and cooled to 0° C. and trifluoroacetic acid (1.5 mL) was added. The resulting solution was stirred at that temperature for 3 h. After completion of the reaction (TLC) the acid was neutralized with triethylamine (2 mL), and the solvents were removed in vacuo. The diol compound 50 was purified by flash chromatography (Rf 0.42, silica, ethyl acetate:hexane 1:1, 0.84 g, 81%).

$^1$H NMR: 7.294 (m, 15H, aromatic), 6.192 (d, J=6.3 Hz, 1H, NH), 5.120 (m, 4H), 4.542 (m, 7H), 4.169 (m, 2H), 3.642 (m, 12H), 3.184 (s, 3H, OCH$_3$), 2.824–2.246 (m, 8H), 1.246 (bs, 80H), 0.892 (t, 12H), 0.812 (s, 8H, t-butyl), 0.040 (s, 3H, SiMe), 0.036 (s, 3H, SiMe).

Example 56

Preparation of Compound 51

To diol 50 (0.82 g, 0.45 mmol) in DMF (4 mL) at 0° C., was added sequentially imidazole (0.068 g, 0.1 mmol) and t-butyldimethylsilyl chloride (75 mg, 0.5 mmol) and the resulting solution was stirred at that temperature for 2 h. After completion of the reaction, the mixture was diluted with ethyl acetate (10 mL), and washed with water (2×5 mL). The organic layer was separated, dried, and concentrated to give an oil, which after purification by flash chromatography, afforded compound 51 as an oil (Rf 0.41, ethyl acetate:hexane, 1:3, 0.69 g, 80%).

$^1$H NMR: 7.310 (m, 15H, aromatic), 6.146 (d, J=6.3 Hz, 1H, NH), 5.146 (m, 4H), 4.746 (m, 7H), 4,184 (m, 2H), 3.746 (m, 12H), 3,178 (s, 3H, OCH$_3$), 2.476 (m, 8H), 1.246 (bs, 80H), 0.876 (m, 30H), 0.040 (m, 12H).

Example 57

Preparation of Compound 52

A suspension of compound 51 (240 mg, 0.12 mmol) in aqueous THF (20%, 2 mL) and zinc dust (300 mg) was stirred at room temperature. Then acetic acid (0.5 mL) was added to the reaction and the mixture was stirred at room temperature for 4 h. After completion of the reaction (TLC., silica, ethyl-acetate:hexane, 1:1), the inorganic salts were removed by filtration and washed with chloroform (10 mL). The organic layer was neutralized with triethylamine (1 mL), diluted with ethyl acetate (5 mL), washed with water (5 mL), dried, concentrated, and purified by flash chromatography to afford amino compound 52 (diastereomers were separated).

Product A (Rf 0.40, silica, ethyl acetate:hexane 1:1, 100 mg, 48%):

$^1$H NMR: 7,324 (m, 15H, aromatic), 6.246 (d, J=6.3 Hz, 1H, NH), 5,124 (m, 4H), 4.674 (m, 7H), 4.14–3.64 (m, 12H), 3.124 (s, 3H, OCH$_3$), 2.468–2.124 (m, 8H), 1.246 (bs, 80H), 0,892 (m, 20H), 0.04 (m, 6H).

Product B (Rf 0.14, silica, ethyl acetate:hexane 1:1, 64 mg, 30%):

$^1$H NMR: 7. 294 (m, 5H, aromatic), 6.204 (d, J=6.3 Hz, 1H, NH), 5.184 (m, 4H), 4.584 (m, 5H), 4.241 (m, 3H), 3,786 (m, 11H), 3.126 (s, 3H, OCH$_3$), 2.942 (m, 1H), 2.642–2.242 (m, 8H), 1.296 (bs, 80H), 0.896 (m, 30H), 0.04 (m, 12H).

Example 58

Preparation of Compound 53.

A solution of amino compound 52 (340 mg, 0.195 mmol, product A from Example 57), acid 3 (90 mg, 0.211 mmol), EDC (45 mg, 0.2 mmol), and HOBT (27 mg, 0.2 mmol) in dichloromethane (2 mL) was stirred at room temperature for overnight. After completion of the reaction, the solvent was removed in vacuo and purification by flash chromatography afforded compound 53 as an oil (diaster-omeric mixture was separated).

Product 53a (Rf 0.62 silica, ethyl acetate: hexane, 2: 3, 105 mg, 25 %):

$^1$H NMR: 7.346 (m, 15H, aromatic), 6.196 (m, 2H, NH), 5,196 (m, 5H), 4.562 (m, 5H), 4.21–3.624 (m, 12H), 1.296 (bs, 120H), 0.918 (m, 36H), 0.04 (m, 12H).

Product 53b (Rf 0.41, silica, ethyl acetate: hexane, 2: 3, 140 mg, 33%):

$^1$H NMR: 7.304 (m, 15H, aromatic), 6.346 (m, 1H, NH), 6.192 (m, 1H, NH), 5.210 (m, 5H), 4.612 (m, 5H), 4.201–3.562 (m, 14H), 3.192 (s, 3H, OCH$_3$), 2.746–2.196 (m, 12H), 1.286 (bs, 120H), 0.942 (m, 36H), 0.04 (m, 2H).

Example 59

Preparation Of Compound 54

To a solution of compound 53 (72 mg, 0.033 mmol) and N,N-diisopropylamino dibenzyl phosphite (17 mg, 1.5 eq) in dichloromethane (1.0 mL) was added tetrazole (1.4 mg, 2 eq) and the mixture was stirred at room temperature for 2 h. After the alcohol was consumed (TLC), the reaction mixture was cooled to 0° C. m-CPBA (2 eq) was added, and the mixture was stirred for 1 h. After completion of the reaction, the mixture was diluted with dichloromethane (5 mL) and washed with sodium bicarbonate (10%, 5 mL). The organic layer was separated, dried, and concentrated to give an oil, which was purified by flash chromatography to afford compound 54 as an oil (Rf 0.28, silica, ethyl acetate:hexane, 3:7, 55 mg, 69%).

$^1$H NMR: 7.346 (m, 25H, aromatic), 6.246 (m, 2H, NH), 5.146 (m, 8H), 4.521 (m, 5H), 4.124–3.426 (m, 14H), 3,102 (s, 3H, OCH$_3$), 2.746–2.194 (m, 12H), 1.286 (bs, 120H), 0.942 (m, 36H), 0.036 (m, 12H).

Example 60

Preparation of Compound 55

A suspension of compound 54 (39 mg, 0.016 mmol) and Pd-C (10%, 6 mg) in ethyl acetate was stirred under a hydrogen atmosphere at room temperature for 3 h. After completion of the reaction, the catalyst was removed by filtration, and the solvent was evaporated to afford compound 55 as an oil (28 mg, 92%).

$^1$H NMR (CDCl$_3$+TFA- d) : 5.246 (m, 3H), 4.624 (m, 4H), 3,942 (m, 11H), 2.412 (m, 12H), 1.294 (bs, 12H), 0.896 (m, 30H).

Example 61

Preparation Of Immunogen 3D

To a solution of compound 55 (24 mg, 0.012 mmol) in THF (1 mL) cooled to −20° C. was added HF-pyridine (0.2 mL) and the mixture was stirred under argon atmosphere for 1 h at −20° C. and then at 0° C. for 1 h. After completion of the reaction, the reaction mixture was diluted with chloroform (5 mL), and stirred with sodium bicarbonate (5%, 1 mL). The organic layer was separated, the aqueous layer was extracted with chloroform, and the combined organic phases were dried and concentrated to give immunogen 3D as an oil. The compound was dissolved in acetonitrile (2 mL) and water (6 mL) and sonicated to give an almost homogeneous solution, which after lyophilization, afforded the immunogen 3D as a colorless powder (18 mg, 86%).

Example 62

Preparation of Compound 57

A solution of hydroxy compound 43 (1 eq), acid 3 (1.1 eq), DCC (1.1 eq) and DMAP (1.1 eq) in dichloromethane (0.2M) is stirred at room temperature for 4 h. After completion of the reaction, the insoluble material is filtered off, and removal of the solvent and flash chromatography affords compound 57.

Example 63

Preparation Compounds 58 through Immunogen 1D

Preparation of all these compounds is accomplished by following similar procedures to those set forth above to prepare compounds 49 through immunogen 3D (Example 54 to 61), in particular:

Preparation Compound 56: To a solution of compound 57 in THF and dichloromethane (1:1, 0.2M) under an Ar atmosphere, a solution of tetrabutylammonium fluoride (1 eq) is added and the resulting mixture is stirred at room temperature until the starting material (compound 57) disappears, then trichloroacetonitrile (4 eq) is added and the stirring is continued for additional 4 hr. After completion of the reaction solvents, are removed in vacuo and flash chromatography affords the compound 56 as an anomeric mixture.

Preparation Of Compound 58: To a solution of imidate compound 56 (1 eq) and compound 41 (1.2 eq) in dichloromethane (0.2M) at −78° C. under an Ar atmosphere a solution of borontrifluoride etherate (catalytic amount) in dichloromethane is added and the resulting mixture is stirred initially at −78° C., then at −20° C. for 12 hr. After completion of the reaction (TLC), the mixture is neutralized with triethylamine, and solvents are removed in vacuo and flash chromatography affords compound Preparation of Compound 59: To a solution of compound 58 (1 eq) in dry DMF (0.2M) at room temperature sequentially added are: imidazole (2.4 eq) and ter- butyldimethylsilyl chloride (1.2 eq); and the resulting mixture is stirred at that temperature under an Ar atmosphere until the starting material disappears (TLC). After completion of the reaction the mixture is transferred into separatory funnel and diluted with ethyl acetate and washed with water. The organic phase is separated, dried and concentrated, and flash chromatography affords the silylated compound. To the silyl compound (1 eq) in dichloromethane (0.2M) a solution of trifluoroacetic acid (2 eq) is added and the resulting mixture is stirred at 0° C. until the starting material disappears (TLC). After completion of the reaction acid is neutralized with triethylamine at 0° C. and solvents are removed in vacuo and flash chromatography affords the compound 59.

Preparation of Compound 60: To a solution of compound 59 (1 eq) in dry DMF (0.2M) is added sequentially imidazole (2.4 eq) and ter butyldimethylsilyl chloride (1.2 eq) at 0 ° C. and the resulting mixture is stirred at that temperature until starting material disappears. After completion of the reaction the mixture is transferred into a separatory funnel, diluted with ethyl acetate and washed with water; the organic phase is separated, dried and solvents are removed in vacuo and flash chromatography affords the monosilylated compound. A suspension of the silylated (1 eq) compound in THF (0.2M), acetic acid and zinc powder is stirred at room temperature until starting material disappears. After completion of the reaction, the inorganic salts are filtered off and the solvents are removed in vacuo. Purification by flash chromatography affords the compound 60.

Preparation of Compound 61: A solution of compound 60 (1 eq), acid 4 (1.2 eq) EDC (1.2 eq) and HOBT (1.2 eq) is stirred in dichloromethane (0.2M) under an Ar atmosphere until the starting material disappears. After completion of the reaction, the solution is transferred into a separating funnel and washed with water. The organic phase is separated, dried and concentrated, and flash chromatography affords the compound 61.

Preparation of Compound 62: A solution of compound 61 (1 eq), N,N- diisopropylamino dibenzylphosphite (1.2 eq) in dichloromethane (0.2M) is stirred under an Ar atmosphere in the presence of tetrazole. After completion of the reaction (TLC), the mixture is cooled to 0° C. and m-CPBA (1.4 eq) is added and the mixture is stirred further until the starting material has disappeared (TLC). After completion of the reaction solvents are removed in vacuo and the product 62 is purified by flash chromatography.

Preparation Of Immunogen 1D: A suspension of compound 62 (1 eq) in ethyl acetate in the presence of Pd-C (10%) is hydrogenated by using a hydrogen balloon. After completion of the reaction, catalyst is filtered through a pad of celite and removal of the solvent affords the hydrogenated compound. The hydrogenated compound (1 eq) is dissolved in THF in a plastic container, cooled to 0° C. and HF-pyridine is added. The resulting mixture is stirred at 0° C. for 0.5 hr. After completion of the reaction sodium bicarbonate solution (10%) is added and the organic layer is separated, dried and concentrated to affords immunogen 1D.

Example 64

Preparation of Compound

To a cooled solution of compound 43 (1 eq) in dry THF, sodium hydride (60% suspension in mineral oil, 1.1 eq) is added and the resulting suspension is stirred under an argon atmosphere for 1 h. Then 4-methoxybenzyl chloride (1.4 eq) is added to the reaction mixture and the stirring continued for 2 h. After completion of the reaction (TLC), the excess base is neutralized with ammonium chloride solution, and the organic layer is separated, dried, concentrated, and purified by flash chromatography to afford compound 63.

Example 65

Preparation of Imidate Compound

To a solution of compound 63 (1 eq) in dichloromethane, tetrabutylammonium fluoride (1M in THF, 1.1 eq) is added and the reaction mixture is stirred under an argon atmosphere until the starting material (Compound 63) disappears (TLC). Then trichloroacetonitrile (3 eq) is added to the reaction mixture and stirring is continued for an additional 4 h. After completion of the reaction, the solvents are removed and flash chromatography affords the imidates as an anomeric mixture.

Example 66

Preparation of Compound 64

To a cooled solution (−20° C.) of imidate compound 62a (1 eq) and diol compound 41 (1 eq) in dichloromethane is added a catalytic amount of a Lewis acid (boron trifluoride etherate or TMS-Triflate) and the mixture is stirred under an argon atmosphere at that temperature overnight. After completion of the reaction, the acid is neutralized with ammonium chloride solution, the organic layer is separated, dried, concentrated, and purified by flash chromatography to afford the coupled compound 64.

Example 67

Preparation of Compound

To a solution of compound 64 (1 eq) in dry DMF (0.2M) is added sequentially imidazole (2.4 eq) and t-butyldimethylsilyl chloride (1.2 eq) and the mixture is stirred at room temperature under argon for 6 h. After completion of the reaction, the reaction mixture is diluted with chloroform and washed with water and the organic phase is separated, dried, concentrated and purified by flash chromatography to afford the silylated compound.

Trifluoroacetic acid is added to a solution of the silylated compound in dichloromethane at 0° C. and the mixture is stirred for 2 h. After completion of the reaction, the acid is neutralized with triethylamine, the solvents are removed and the diol is purified by flash chromatography.

To a cold solution (0° C.) of the diol (1 eq) in dry DMF under an argon atmosphere is added sequentially imidazole (2.2 eq) and t-butyldimethylsilyl chloride (1.1 eq), and the mixture is stirred at that temperature for 2 h. After completion of the reaction, the mixture is diluted with dichloromethane and washed with water, the organic layer is separated, dried, concentrated and purified by flash chromatography to afford the compound 65.

Example 68

Preparation of Compound 66

Zinc powder is added to a solution of compound 65 (1 eq) in THF and acetic acid, and the mixture is stirred until the starting material (compound 65) disappears (TLC). After completion of the reaction, the salts are removed by filtration, the filtrate is neutralized with triethylamine and the solvent is removed. The amino compound is purified by flash chromatography. To a solution of the amino compound (1 eq) and acid 3 (1.1 eq) in dichloromethane is added sequentially EDC (1.1 eq) and HOBT (1.1 eq) and the mixture is stirred overnight. After completion of the reaction, the mixture is diluted with dichloromethane, and washed with water, and the organic layer is separated, dried, concentrated, and the product 66 is purified by flash chromatography.

Example 69

Preparation of Compound 67

A mixture of compound 66 (1 eq), N,N-diisopropylamino dibenzyl phosphite (1.2 eq) and tetrazole (1.4 eq) in dichloromethane is stirred for 2 h under an argon atmosphere. After completion of the phosphitylation reaction (TLC), the mixture is cooled to 0° C. and m-CPBA (1.3 eq) is added and stirring is continued for an additional 1 h. After completion of the oxidation reaction, the mixture is diluted with dichloromethane, and washed with sodium bicarbonate solution (5%). The organic layer is separated, dried, and concentrated, and the product is purified by flash chromatography.

To a solution of the phosphorylated compound (1 eq) in acetonitrile, is added DDQ (1.5 eq) and the mixture is stirred for 1 h. After completion of the reaction, an aqueous workup followed by flash chromatography affords the compound 67.

Example 70

Preparation of Compound 68

To a solution of compound 67 (1 eq) and acid 4 (1.2 eq) in dichloromethane is added sequentially DCC (1.2 eq) and DMAP (1.2 eq) and the mixture is stirred for 6 h. After completion of the reaction, the insoluble material is filtered off, the filtrate is concentrated, and the product, compound 68, is purified by flash chromatography.

Example 71

Preparation of Immunogen 2D

Conversion of compound 68 to immunogen 2D is accomplished by conditions similar to those set forth above for the conversion of compound 62 to immunogen 1D.

In particular, a suspension of compound 68 (1 eq) in ethyl acetate is hydrogenated by using a hydrogen balloon in the presence of Pd-C (10%). After completion of the reaction catalyst is filtered through a pad of celite and removal of the solvent affords the hydrogenated compound. The hydrogenated compound (1 eq) is dissolved in dry THF (0.2M) in a plastic container and HF-pyridine is added and the mixture is stirred under an Ar atmosphere at 0° C. After completion of the reaction a solution of sodium bicarbonate (10%) is added and with stirring. The organic layer is separated and dried, and removal of the solvent affords Immunogen 2D.

Example 72

Preparation of Immunogens 3D-A, 2D-A and 1D-A

A solution of compound 54 in methanol and a catalytic amount of PTSA is stirred at 0° C. until the starting material disappears (TLC). After completion of the reaction, acid is neutralized with triethylamine and removal of the solvents and purification by flash chromatography affords the hydroxy compound.

To a solution of the above hydroxy compound (1 eq) and triethylamine (2 eq) in dichloromethane, methanesulphonic chloride is added at 0° C. and the mixture is stirred in an argon atmosphere for 1 h. After completion of the reaction, solvents are removed in vacuo and the mesylate reaction product is used in the next reaction without the need for further purification.

A solution of the mesylate compound (reaction product above) (1 eq) and sodium azide (3 eq) in dry DMF is heated at 50° C. in an argon atmosphere for 4 h. After completion of the reaction the mixture is diluted with dichloromethane and washed with water, the organic phase is separated, dried, concentrated, and purified by flash chromatography to afford the azide.

A suspension of the azide and Pd-C (10%) in ethyl acetate is stirred under an hydrogen atmosphere for 4 h. After completion of the reaction, the catalyst is filtered, and removal of the solvent affords the corresponding amino compound, which on treatment with HF-pyridine, affords immunogen 3D-A.

Preparation of Immunogens 1D-A: A solution of compound 62 in methanol and a catalytic amount of PTSA is stirred at 0° C. until the starting material disappears (TLC). After completion of the reaction, acid is neutralized with triethylamine and removal the solvents and purification by flash chromatography affords the hydroxy compound. To a solution of the hydroxy compound (1 eq) and triethylamine (2 eq) in dichloromethane, a solution of methanesulphonic chloride is added at 0° C. and the mixture is stirred in an argon atmosphere for 1 h. After completion of the reaction, solvents are removed in vacuo and the mesylate compound used for next reaction without purification. A solution of the mesylate compound (1 eq) and sodium azide (3 eq) in dry DMF is heated at 50° C. in an argon atmosphere for 4 h. After completion of the reaction the mixture is diluted with dichloromethane and washed with water. The organic phase is separated, dried and concentrated, and the azide is purified by flash chromatography. A suspension of the azide and Pd-C (10%) in ethyl acetate is stirred under a hydrogen atmosphere for 4 h. After completion of the reaction the catalyst is filtered and removal of the solvent affords the corresponding amino compound, which on treatment with HF-pyridine affords the immunogen 1D-A.

Preparation of Immunogens 2D-A: A solution of compound 68 in methanol and a catalytic amount of PTSA is stirred at 0° C. until the starting material disappears (TLC). After completion of the reaction, acid is neutralized with triethylamine and removal the solvents and purification by flash chromatography affords the hydroxy compound. To a solution of the hydroxy compound (1 eq) and triethylamine (2 eq) in dichloromethane, a solution of methanesulphonic chloride is added at 0° C. and the mixture is stirred in an argon atmosphere for 1 h. After completion of the reaction, solvents are removed in vacuo and the mesylate compound is used for next reaction without purification. A solution of mesylate compound (1 eq) and sodium azide (3 eq) in dry DMF is heated at 50° C. in argon atmosphere for 4 h. After completion of the reaction the mixture is diluted with dichloromethane and washed with water. The organic phase is separated, dried and concentrated and the azide is purified by flash chromatography. A suspension of the azide and Pd-C (10%) in ethyl acetate is stirred under a hydrogen atmosphere for 4 h. After completion of the reaction the catalyst is filtered and removal of the solvent affords the corresponding amino compound, which on treatment with HF-pyridine affords the immunogen 2D-A.

Example 73

Preparation of Immunogens 3D-AL, 2D-AL, and 1D-AL

To a solution of compound 54 in methanol and a catalytic amount of PTSA at 0° C. is stirred until starting material (compound 54) disappears (TLC). After completion of the reaction, acid is neutralized with triethylamine and removal of the solvents and flash chromatography affords the corresponding hydroxy compound.

To a solution of the above hydroxy compound (1 eq) and CBZ-protected amino acid (1.2 eq) in dichloromethane is added sequentially DCC (1.2 eq) and DMAP (1.2 eq); and the mixture is stirred in an argon atmosphere for 4 h. After completion of the reaction, insoluble salts are removed by filtration. The filtrate is concentrated in vacuo and purification of the product by flash chromatography affords the coupled compound.

A suspension of the above coupled compound and Pd-C (10%) in ethyl acetate is stirred under an Ar atmosphere 4 h. After completion of the reaction the catalyst is filtered and removal of the solvent affords the amino compound, which on treatment with HF-pyridine, affords immunogen 3D-AL Preparation of Immunogens 2D-AL: A solution of compound 68 in methanol and a catalytic amount of PTSA at 0° C. is stirred until the starting material disappears (TLC). After completion of the reaction, acid is neutralized with triethylamine and removal of the solvents and flash chromatography affords the corresponding hydroxy compound. To a solution of the hydroxy compound (1 eq) and CBZ protected amino acid (1.2 eq) in dichloromethane is added sequentially DCC (1.2 eq) and DMAP (1.2 eq) and the mixture is stirred in argon atmosphere for 4 h. After completion of the reaction, insoluble salts are removed by filtration. The filtrate is concentrated in vacuo and purification of the product by flash chromatography affords the coupled compound. A suspension of the coupled compound and Pd-C (10%) in ethyl acetate is stirred under an Ar atmosphere 4 h. After completion of the reaction the catalyst is filtered and removal of the solvent affords the amino compound, which on treatment with HF-pyridine affords the immunogen 2D-AL.

Preparation of Immunogens 1D-AL: A solution of compound 62 in methanol and catalytic amount of PTSA at 0° C. is stirred until the starting material disappears (TLC). After completion of the reaction, acid is neutralized with triethylamine and removal of the solvents and flash chromatography affords the corresponding hydroxy compound. To a solution of the hydroxy compound (1 eq) and CBZ protected amino acid (1.2 eq) in dichloromethane is added sequentially DCC (1.2 eq) and DMAP (1.2 eq) and the mixture is stirred in argon atmosphere for 4 h. After completion of the reaction, insoluble salts are removed by filtration. The filtrate is concentrated in vacuo and purification of the product by flash chromatography affords the coupled compound. A suspension of the coupled compound and Pd-C (10%) in ethyl acetate is stirred under an Ar atmosphere 4 h. After completion of the reaction the catalyst is filtered and removal of the solvent affords the amino compound, which on treatment with HF-pyridine affords the immunogen 1D-AL.

Example 74

Immunization with Lipid-A Analogs for the Generation of Monoclonal Antibodies

BK-1

Sheep Red Blood Cells (SRBC) were coated with BK-1 as follows (100):

i) Formaldehyde fixed, lyophilized SRBC (Sigma Chemicals) were resuspended in sterile PBS to give a 10% v/v suspension. 0.5 ml of this suspension was washed three times with 10 ml PBS by centrifugation and finally resuspended to 0.5 ml. BK-1 was dissolved in 0.05% triethylamine by sonication to a concentration of 1 mg/ml. This solution was then neutralized by the addition of 1/10 volume of 1M Tris buffer pH 7. 150 µl of this solution was diluted to 3 ml with PBS to give a concentration of 50 µg/ml and this was added to the washed SRBC to give a total volume of 3.5 ml. This mixture was incubated overnight on a rotary mixer at room temperature. The coated SRBC were then pelleted by centrifugation and washed twice with 4 ml of PBS, finally being resuspended to 1.5 ml in PBS to give a 3.3% suspension.

ii) Mice were immunized with these BK-1-coated SRBC., in the absence of adjuvant, multiple times. Following the later bleeds serum was obtained from individual mice by bleeding from the retro-orbital sinus and BK-1-specific IgM and IgG antibody was measured separately in these sera by ELISA assays. Mice immunized in this way produced only IgM responses. Those individuals giving the highest titer anti-BK-1 responses were selected and hybridomas secreting monoclonal antibodies were generated from their splenocytes by conventional cell fusion techniques.

BK-3

Acid hydrolysed bacteria (AHB) coated with BK-3 were prepared as follows (101):

i) *E. coli* strain HB101 were grown to late log phase by inoculating 100 ml volumes of PPBE medium with 0.5 ml of stationary phase overnight cultures in the same medium. Cultures were grown at 37° C. with rotary mixing at 250 rpm. for approximately 5 hrs until reaching an $O.D._{540}$ of 0.85. Cells were harvested by centrifugation, washed in 1% acetic acid and harvested again by centrifugation. A total of 500 ml of culture yielded 0.92 g wet weight of bacteria. These cells were resuspended in 45 ml of 1% acetic acid, hydrolysed for 2 hrs in a boiling water bath at 100° C. then kept at 4° C. overnight. The cells were washed twice in 1% acetic acid, once in water, once in acetone then dried under vacuum, yielding 130 mg of acid hydrolysed bacteria. These were resuspended in water, aliquotted into 10 mg fractions, dried under vacuum and stored at −20° C. until used.

ii) 2 mg of AHB were suspended in 4 ml water in a 50 ml round bottomed flask. 80 µl of a vigorously sonicated 2.5 mg/ml solution (200 g) of BK-3 in 0.05% triethylamine was added. The mixture was dried on a rotary evaporator, resuspended in 2 ml water by sonication and dried again. These antigen coated AHB were stored dry at 4° C. until used for immunization. Coated AHB were resuspended in 0.9% NaCl to give a concentration of 1 mg/ml AHB (100 µg/ml BK-3) and mixed with an equal volume of Complete or Incomplete Freund's Adjuvant for injection. Mice were immunized with 100 µl of this suspension either intraperitoneally or subcutaneously, the first immunization used CFA and subsequent immunizations used IFA.

iii) Mice were immunized as above, multiple times. Following the later bleeds serum was obtained from individual mice by bleeding from the retro-orbital sinus and BK-3-specific IgM and IgG antibody was measured separately in these sera by ELISA assays. Mice which showed the highest titer anti-BK3 IgG responses were selected and hybridomas secreting monoclonal antibodies were generated from their splenocytes by conventional cell fusion techniques.

Immunogen 3D

Immunogen 3D was incorporated into liposomes as follows:

i) A stock solution of lipids for the formation of liposomes was prepared by mixing 10 mM solutions of dimyristoyl phosphatidyl choline, dicetyl phosphate and cholesterol (all from Sigma Chemicals) in the ratio 1.0:0.11:0.75. This stock was aliquotted into 1.0 ml volumes and dried under argon and stored at −20° C. until used.

ii) 500 µg of immunogen 3D dissolved in $CHCl_3$ was dried into a 50 ml round bottomed flask on a rotary evaporator. One aliquot of the lipid stock was dissolved in 1 ml of $CHCl_3$:MeOH (9:1) and added to the dried immunogen 3D. The dissolved lipids were thoroughly mixed then dried together on a rotary evaporator under argon until all solvent had been removed and then for an additional 15 mins. The flask was then placed in a high vacuum dessicator for 2 hrs. 1.0 ml of swelling solution, approximately 0.9% NaCl, was added to the dry lipid film with 0.5 g of glass beads and mixed vigorously by swirling and vortexing. Liposomes were allowed to swell at room temperature overnight. The nominal concentration of immunogen 3D in these liposome preparations was therefor 500 µg/ml (≈0.25 mM), and the concentration of the other lipids was 10 mM.

iii) Optimal conditions for immunization of mice with these liposomes were found in preliminary experiments to be the injection of 0.1 ml (50 g immunogen 3D) in the absence of adjuvant. Mice were therefor immunized in this way on day 0, day 21 and day 35 then bled from the retro-orbital sinus on day 42 for the determination of the immunogen 3D response by ELISA.

iv) In a modification of this basic protocol, liposomes were synthesized which incorporated a synthetic peptide known to be a dominant T-cell stimulatory epitope in Balb/c mice. This peptide comprises residues 105–120 of Hen Egg Lysozyme (HEL) and was incorporated into liposomes by dissolving it to a concentration of 25 µg/ml in the swelling solution. This preparation was used to immunize mice according to the schedule described above. These mice had been primed 10 days before the first injection of liposomes with 10 µg of HEL in CFA.

Example 75

Monoclonal Antibodies Generated Against Lipid-A Analogs

BK-1

A total of 14MAbs which bound specifically to Lipid-A in ELISA were generated from two fusions performed with splenocytes from C57BL/6 mice immunized with BK-1/ SRBC. All of these MAbs were of the IgM/kappa isotype. Inhibition ELISAs were performed to determine the relative affinities of these MAbs for Lipid-A analogs (analogs used were: monophosphoryl Lipid-A, MPL; ReLPS from salmonella minnesota strain R595; BK-1 and BK-3). The MAbs fell into four specificity groups based on their relative affinities for these ligands:

| I  | MPL = ReLPS > BK1 >> BK3 |
| II | MPL = ReLPS = BK1 >> BK3 |

| | |
|---|---|
| III | MPL = BK1 > ReLPS >> BK3 |
| IV | MPL = ReLPS >> BK1 ≈ BK3 |

Similar inhibition ELISAs with different LPS chemotypes showed that all of the MAbs reacted with ReLPS, some reacted with low affinity with ReLPS but none of them had any affinity for fully O-glycosylated *E. coli* S-LPS. Five of these MAbs (4 from group II and 1 from group I) were purified from ascites fluid and tested for their ability to release fatty acyl chains from $^3$H-Lipid-A and $^3$H-ReLPS substrates. None were catalytically active. However, each of these MAbs is useful for binding to LPS and for treating septicemia or septic shock. This also demonstrates that formula (I) compounds can compete for binding sites with Lipid-A and LPS and are thus useful for treatment in this manner.

BK-3

Five fusions were performed and a total of 24 MAbs selected which showed specific binding to Lipid-A and to BK-3 as measured by inhibition ELISAs. Of these MAbs 23 were IgM/kappa and one was IgG/kappa. Twenty three MAbs demonstrated a higher affinity for Lipid-A than for BK-3, whilst two had a higher affinity for BK-3 than for Lipid-A. Eleven of these MAbs were tested for their ability to release fatty acyl chains from $^3$H-Lipid-A and $^3$H-ReLPS substrates; none were catalytically active. However, each of these MAbs is useful for binding LPS and for treating septicemia or septic shock. This also demonstrates that formula (I) compounds can compete for binding sites with Lipid-A and LPS and are thus useful for treatment in this manner.

Immunogen 3D

Fusions are performed as set forth above with respect to BK-1 and BK-3. Both IgM and IgG MAbs are generated. The MAbs have high affinity for both immunogen 3D and Lipid-A; none are catalytically active; but all are useful for binding to LPS and are thus useful for treating septicemia or septic shock. This also demonstrates that formula (I) compounds can compete for binding sites with Lipid-A and LPS and are thus useful for treatment in this manner.

Example 76

Catalytic Antibodies

The procedures of Examples 74 and 75 are performed and the anti-BK-1, anti-BK-3 and anti-immunogen 3D MAbs are tested for their ability to release fatty acyl chains from $^3$H-Lipid-A and $^3$H-ReLPS; these MAbs release the fatty acyl chains and are thus catalytic antibodies. These catalytic antibodies are useful for treating septicemia or toxic shock, either alone, or in admixture with each other or in admixture with MAbs of Example 75 (as a cocktail), as further described below.

MAbs of any isotype, but preferably IgG, generated against transition state analogs (formula (I) compounds) as described above are screened for their ability to hydrolyse ester bonds, resulting in the liberation of fatty acyl chains from $^3$H-labelled ReLPS according to the method described in Munford and Hall (36).

Those MAbs which are catalytically active in this assay (or smaller fragments derived from them, either by protein chemical techniques or by the expression in any system of the genes encoding the anti-bodies or fragments of those genes encoding parts of the antibodies, which include the antigen combining site) (herein termed ABZYMEs™) are then tested for their ability to react in purified form with LPS in such a way as to neutralize its in vitro and in vivo bioactivities which are well known to those skilled in the art, including but not limited to: Reactivity in, or immunoprotection from, challenge in the Dermal Schwartzman Reaction; pyrogenicity; leukopenia; complement activation; cytokine (TNF, IL-1, IL-6) induction; priming of neutrophils for oxygen radical release; and induction of procoagulant activity in cultured epithelial cells. The catalytic MAbs or fragments thereof of the invention suitably react in purified form with LPS in such a way as to neutralize its in vitro and in vivo bioactivities.

Catalytic MAbs are also be tested for their ability to reduce the toxicity of LPS preparations towards both galactosamine sensitized and unsensitized mice in assays which are well known to those skilled in the art: Galactosamine primed mice (62) are injected with increasing doses of LPS treated with individual catalytic antibodies and untreated LPS and the $LD_{50}$ in such mice is determined after a period of three days. The catalytic Mabs or fragments thereof of the present invention reduce the toxicity of LPS preparations.

The ability of the catalytic MAbs to afford protection against lethal gram-negative bacteremia is assessed in the standard mouse toxicity assay (102). Briefly, female CF1 mice of 6 to 8 months of age are injected with live cultures of *E. coli* diluted to give a graded response. The prophylactic protection afforded by the catalytic antibodies is determined by injection of the mice with the MAbs 18 hrs prior to infection. The $LD_{50}$ of mice treated in this way is determined after a period of three days. In order to test for the efficacy of the antibodies in treating bacteremia, the MAbs which are effective in the above experiment are administered following bacterial infection. The catalytic Mabs or fragments thereof of the present invention afford protection against gram-negative bacteremia.

Following these pre-clinical animal studies, then there is testing of the MAbs for therapeutic action in humans. Two major studies on the treatment of gram-negative sepsis with MAbs as an adjunct to conventional therapy including antibiotic treatment and intensive supporting care have been carried out (6,7); these studies define the criteria for enrolling a suitable patient population and the preferred protocols for the administration of antibody based therapeutics in this disease. These protocols are followed in studies using catalytic MAbs or fragments derived therefrom of the present invention ("ABZYME™").

Initial dose escalation safety and toxicity studies are carried out, according to methods well known in the art, to establish the maximum tolerable dose of selected "ABZYMEs™". Efficacy testing then involves the administration of the "ABZYME™" via intravenous, intramuscular or intraperitoneal route to patients suspected of having or being susceptible to a gram-negative bacterial infection. The "ABZYME™" is administered in a physiologically acceptable solution such as phosphate buffered saline, which can be supplemented with an excipient such as dextran or human serum albumin, at a dose determined by the body weight of the host. This dose is preferably in the range of about 0.1 mg/kg to about 40 mg/kg and usually in the range of about 1.0 mg/kg to about 10 mg/kg of host body weight, not to exceed the maximum tolerable dose determined as described above. Treatment is repeated at intervals as necessary until the recovery of the patient from infection is effected. The catalytic Mabs or fragments thereof of the present invention are effective.

Example 77

Preparation of Compound 69

To a solution of diol compound 41 (1 eq) in dry DMF (0.2M), under an Ar atmosphere the following are sequentially added: imidazole (4.8 eq) and t-butyldimethylsilyl chloride (2.4 eq); and the mixture is stirred at room temperature until the starting material (compound 41) disappears. After completion of the reaction, the mixture is diluted with ethyl acetate (0.1 M) and washed with water. The organic phase is separated and dried and removal of the solvent and flash chromatography affords the corresponding disilylated compound.

The above-obtained compound (1 eq) is dissolved in methanol (0.2M) cooled to 0° C. and PTSA (catalytic amount) is added. The resulting mixture is stirred at that temperature until the starting material disappears (TLC). After completion of the reaction acid is quenched with triethylamine, and removal of the solvent and flash chromatography affords compound 69.

Example 78

Preparation Of Compound 70

To a solution of compound 69 (1 eq) in dry dichloromethane (0.2M) containing triethylamine (3 eq) at 0° C. under an Ar atmosphere is added MsCl (1.2 eq) dropwise through a syringe. The mixture is stirred at that temperature until the hydroxy compound disappears. After completion of the reaction, a solution of ammonium chloride (10%) is added and the organic phases are separated, dried and concentrated. Removal of the solvent and flash chromatography affords the corresponding mesylate compound.

A mixture of the above-obtained mesylate compound (1 eq) and sodium azide (3 eq) in dry DMF (0.2 M) is heated at 50° C. under an Ar atmosphere until the starting material disappears. After completion of the reaction, the mixture is diluted with ethyl acetate (0.1M) and washed with water. The organic phase is separated, dried and concentrated and flash chromatography affords the azido compound 70.

Example 79

Preparation Of Compound

A suspension of compound 70 (1 eq) in ethyl acetate (0.2M) in the presence of catalyst (Pd-C., 10%) is hydrogenated by using a hydrogen balloon. After completion of the reaction (TLC) the catalyst is filtered through a pad of celite and removal of the solvent affords the amino compound 71.

Example 80

Preparation of Compound 73

A solution of commercially available lactone 72 (1 eq) and 2.2 dimethoxy propane, in dry DMF (0.1M) in the presence of PTSA (catalytic amount) is stirred at room temperature under an Ar atmosphere. After completion of the reaction (TLC) the solvent is removed in vacuo and fresh dry DMF (0.2M) is added followed by sequential addition of imidazole (4.8 eq) and t-butyldimethylsilyl chloride (2.4 eq). The mixture is stirred under an Ar atmosphere until the starting material disappears. After completion of the reaction, the mixture is diluted with ethyl acetate (0.1M), washed with water; and the organic phase is separated, dried and concentrated, and flash chromatography affords the compound 73.

Example 81

Preparation of Compound 74

A solution of compound 73 (1 eq) in benzyl alcohol (10 eq) is heated at reflux, until the starting material disappears. After completion of the reaction benzyl alcohol is removed in vacuo and the resulting mixture on flash chromatography affords the hydroxy ester compound.

To a solution of the above-obtained hydroxy ester compound (1 eq) in dry dichloromethane (0.2M) in the presence of triethylamine (3 eq), Ms-Cl (1.2 eq) is added through a syringe under an Ar atmosphere and the mixture is stirred at room temperature. After completion of the reaction (TLC), a solution of ammonium chloride (10%) is added and the organic layer is separated, dried and concentrated, and flash chromatography affords the corresponding mesylate compound.

A solution of the mesylate compound (1 eq), sodium iodide (2 eq) in dry acetone (0.2M) is heated at 50° C. under an Ar atmosphere. After completion of the reaction (TLC), removal of the solvent and flash chromatography affords the iodo compound.

A solution of the above-obtained iodo compound (1 eq) and sodium azide (3 eq) in dry DMF (0.2M) is heated at 50° C. under an Ar atmosphere. After completion of the reaction (TLC) the solution is diluted with ethyl acetate (0.1M), and washed with water. The organic phase is separated, dried, and concentrated, and flash chromatography affords the azido compound 74.

Example 82

Preparation of Compound 75

A suspension of compound 74 (1 eq) in ethyl acetate (0.2M) in the presence of catalyst (Pd-C., 10%) is stirred under a hydrogen atmosphere. After completion of the reaction the catalyst is filtered and removal of the solvent affords the silyl lactam.

To a solution of silyl lactam (1 eq) in dry THF (0.2M), a solution of n-tetrabutylammonium fluoride (1M solution in THF, 2.4 eq) is added through a syringe under an Ar atmosphere. After completion of the reaction, the solution is diluted with ethyl acetate and washed with a minimum amount of water. The organic phase is separated, dried and concentrated, and flash chromatography affords the compound 75.

Example 83

Preparation of Compound 76

A solution of compound 75 (1 eq), DCC (2.4 eq), DMAP (2.4 eq) and acid 3 (2.4 eq) in dry dichloromethane (0.2M) is stirred under Ar atmosphere at room temperature. After completion of the reaction insoluble particles are separated by filtration and removal of the solvent and flash chromatography affords the coupling compound.

The above-obtained compound (1 eq) is stirred in a solution of dichloromethane (0.2M) and trifluoroacetic acid (3 eq) at room temperature under an Ar atmosphere. After completion of the reaction, the excess acid is neutralized with triethylamine, the solvents are then removed in vacuo, and flash chromatography affords the diol compound.

To a solution of the above-obtained diol (1 eq) in dry DMF (0.2M) at 0° C. under an Ar atmosphere sequentially added are: imidazole (2.2 eq) and t-butyldimethylsilyl chloride (1.1 eq); and the mixture is stirred at that temperature until the starting material disappears. After completion of the reaction, the mixture is diluted with ethyl acetate, washed with water, dried and concentrated and flash chromatography affords the compound 76.

Example 84

Preparation of Compound 77

A solution of compound 76 (1 eq), N,N diisopropylamino dibenzylphosphite, tetrazole in dry dichloromethane (0.2M) is stirred under an Ar atmosphere at room temperature. After completion of the reaction the mixture is cooled to 0° C. and m-CPBA (1.2 eq) is added and the mixture is stirred until completion of the reaction. After completion of the reaction, the solvent is removed and flash chromatography affords the compound 77.

Example 85

Preparation Of Compound 78

To a solution of compound 77 (1 eq) in dry dichloromethane (0.2M), a solution of triethyloxonium tetrafluoroborate (1 eq, 1M solution in dichloromethane, Meerwein reagent) is added and the mixture is stirred for 1 h under an Ar atmosphere at 0° C. Then a solution of amino compound 71 (1.2 eq) in dichloromethane (0.2M) is added and the mixture is stirred until the completion of the reaction. After completion of the reaction the solvent is removed and flash chromatography affords the compound 78.

Example 86

Preparation of Compound 79

Method-A: A suspension of compound 78 (1 eq) in ethyl acetate (0.2M) is stirred under a hydrogen atmosphere in the presence of catalyst (Pd-C., 10%). After completion of the reaction the catalyst is filtered and the solvent is removed to afford the hydrogenated compound. A solution of the hydrogenated compound (1 eq) in THF (0.1M) in a plastic container is stirred with HF-pyridine at 0° C. After completion of the reaction, the solution is neutralized with sodium bicarbonate. The organic phase is separated and removal of the solvent affords compound 79.

Method-B: A solution of compound 78 (1 eq), trimethylsilyl iodide (2 eq) in dry dichloromethane (0.2M) is stirred at 0° C. under an Ar atmosphere. After completion of the reaction, the solution is neutralized with dilute HCl (5%) and stirred for 1 h. The organic phase is separated and removal of the solvent affords the compound 79.

Example 87

Pyrogenicity of Formula (I) and (II) Compounds

Japanese white rabbits are administered 1 and 10 µg/kg of BK-1, BK-3 and immunogen 3D, and compound 79 as well as 0.001 µg/kg Lipid-A. The formula (I) and (II) compounds do not show pyrogenicity whereas Lipid-A does. This demonstrates that the formula (I) and (II) compounds are less toxic than Lipid-A and that the immunopharmaocological activities, e.g., B cell and macrophage activation, Ifn, TNF inducing activities, are separate from toxic activities such as pyrogenicity, lethality and Schwartzman reactivity.

Example 88

Nonspecific Protection against Bacterial Infection

The ability of compounds BK-1, BK-3, immunogen 3D and compound 79 to enhance the nonspecific resistance to bacterial infection is measured in the *Pseudomonas aeruginosa* model described by Nakatsuka et al. (103). Briefly, the compounds of the invention are injected at various doses (1–10 µg/mouse) ip. into ICR mice one day prior to ip. infection with graded doses of viable *P. aeruginosa* organisms (of a clinically isolated strain such as 5E81-1), between $10^7$ and $2 \times 10^8$ CFU/mouse. A number of mice survive for seven days following infection and this is recorded as the final result, control treated mice (*P. aeruginosa* without prior administration of inventive compound) die within about three days following infection. The compounds of the present invention enhance the nonspecific resistance to bacterial infection.

Example 89

Protection from Vital Challenge

The ability of compounds BK-1, BK-3, immunogen 3D and compound 79 of the present invention to enhance the nonspecific resistance to viral infection is measured in the vaccinia virus model described by Ikeda et al. (73). Briefly, groups of 10–20 four week old female ddY mice are injected iv. with the compounds of the present invention one day before iv. infection with $10^4$ pfu of vaccinia virus. Seven days following vital challenge, vaccinia virus lesions on the tails of the mice are counted following visualization by staining with 1% fluorescein-0.5% methylene blue. The anti-viral potency is measured as the reduction in the number of lesions in treated mice relative to untreated controls. Mice treated with the compounds of the present invention exhibit a reduction in the number of lesions relative to untreated control mice; thus, the compounds of the present invention exhibit antiviral activity.

Example 90

Antitumor Agents

The antitumor action of the compounds BK-1, BK-3, immunogen 3D and compound 79 is investigated in the animal models well known to those skilled in the art, for example:

The B16 murine melanoma metastasis model, described by Nakatsuka et al. (104). Briefly, the compounds of the present invention are injected iv. into mice in various doses (0.1–10 µg/mouse) and with varying frequency and timing of administration, prior to the iv. inoculation with $10^5$ B16 melanoma cells. The number of melanoma metastases on the surface of the lungs of mice are counted with the aid of a dissecting microscope at day 21 following transplantation of the tumor cells. Efficacy of the compounds of the present invention is manifested as a reduction in the number of metastases in mice treated with compounds of the present invention.

The rat colon carcinoma model described by Jeannin et al. (105). Briefly, BDIX rats are inoculated with $10^6$ Pro b cells ip. Fourteen days later treatment with the compounds of the present invention is initiated: compounds are injected at various doses, up to 10 mg/kg body weight, and according to various schedules, up to 5 injections made twice a week. The extent of the disease is monitored six weeks after tumor transplantation by inspection of the size and number of tumor nodules in the abdominal cavity of sacrificed rats. Rats treated with compounds of the present invention exhibit less and smaller tumor nodules than control rats.

The Meth A fibrosarcoma model as described by Nakatsuka et al. (78). $10^5$ or $2\times10^5$ Meth A cells are injected intradermally into the flank of 7 week old Balb/c mice. The compounds of the present invention are injected, at doses of 100 µg/mouse, either intravenously or directly into the growing tumor mass, on days 7 and 9 following tumor transplantation. The size of the tumors are measured with calipers at intervals of 2–4 days. After four weeks mice are sacrificed and the tumors excised and weighed. The number of mice in which the tumors have resolved is also scored. Mice treated with compounds of the present invention exhibit smaller tumors or tumors which have resolved. Thus, the compounds of the present invention are useful as anti-tumor agents.

Example 91

Receptor Antagonists of Lipid-A/LPS

The ability of compounds BK-1, BK-3, immunogen 3D and compound 79 to compete for receptor binding and so block the endotoxic effects of Lipid-A or LPS are evaluated in the mouse model described by Quereshi et al. (106) Briefly, groups of Balb/c mice 8–12 weeks of age are injected with the compound(s) in PBS or PBS alone as control, followed 60 mins later by 1 µg of ReLPS. After a further 60 mins animals are exsanguinated and serum levels of TNF measured using the L929 fibroblast toxicity assay described by Flick and Gifford (107). The compounds of the present invention significantly reduce the levels of TNF production in this assay and are further tested for their ability to inhibit TNF production by human monocytes in culture as described by Golenbock et al. (108); the compounds of the present invention inhibit TNF production in human monocytes.

Example 92

Antibodies to Formula (II) Compounds

Using the procedures set forth in Examples 74, 75 and 76, binding and catalytic antibodies are elicited against compound 79. These antibodies are useful like those elicited against BK-1, BK-3, and immunogen 3D.

Example 93

Immunization with Liposomes Incorporating T-Cell Stimulatory Peptides

Mice which were primed with HEL and immunized with Immunogen 3D("Imm-3D") and Lipid-A incorporated separately into liposomes along with the peptide HEL[105–120] (synthetic, with additional C-terminal cysteine residue) according to the schedule outlined in Example 74 gave enhanced IgG antibody responses to the eliciting antigen. This was best shown in an experiment with Lipid-A: Four groups of five Balb/c mice each were immunized with 50 µg of Lipid-A incorporated in liposomes. Half of the mice were primed with HEL 10 days before the first immunization, half of the mice received liposomes which incorporated the peptide HEL[105–120] (synthetic, with additional C-terminal cysteine residue). Seven days after the final immunization, serum samples were taken and the titres of IgG and IgM anti-Lipid-A antibodies determined separately by ELISA. The results are given in the Table I, below:

TABLE I

| GROUP | HEL PRIMED | PEPTIDE IN LIPOSOMES | IgM TITRE | IgG TITRE |
|---|---|---|---|---|
| A | + | + | 1:60,000 | 1:10,000 |
| B | + | − | 1:6,000 | 1:150 |
| C | − | + | 1:10,000 | 1:1,000 |
| D | − | − | 1:15,000 | 1:100 |

These data show that the generation of a high-titre IgG response is dependent upon both HEL priming and the inclusion of the peptide in the liposome preparations. The tenfold enhanced IgG titre of group C over groups B and D is presumably due to the fact that the earlier doses of peptide in the liposomes prime specific T-Cells for the later immunizations, resulting in T-Cell help and the resulting switch from IgM to IgG isotype antibodies.

The combination of HEL priming and peptide incorporation into the liposomes (group A) also increases the IgM titre by 4–10 fold over groups B–D. This titre of 1:60,000 against Lipid-A is the highest we have seen from any of the protocols tried, including prolonged immunization regimes using killed bacterial cells coated with large amounts of Lipid-A. This shows that formulations of this type are most effective for use as a vaccine to induce an IgM response capable of protecting animals from the harmful effects of endotoxemia or gram-negative sepsis.

In a simultaneous experiment mice were immunized with Imm-3D in liposomes plus HEL[105–120] (synthetic, with additional C-terminal cysteine residue) following priming with HEL. The results are given in Table II below:

TABLE II

| ISOTYPE | TITRE ON IMM-3D | TITRE ON LIPID-A |
|---|---|---|
| IgM | 1:3,000 | 1:3,000 |
| IgG | 1:10,000 | 1:1,500 |

This immunization has therefore resulted in a higher titre IgG response than IgM response to Imm-3D. In addition there is a degree of antigen specificity in the IgG antibodies raised against Imm-3D; the titre on Lipid-A is six-fold lower than on the homologous antigen. The IgM response, on the other hand, is more cross-reactive, producing the same titre on Lipid-A and Imm-3D.

Example 94

Monoclonal Antibody Fragments Isolated from a Bacteriophage Expression Library which Bind to BK3

Mice were immunized with BK3-coated *E. coli* HB101 cells as described in Example 74. Splenocytes from two of these mice were used for the preparation of mRNA by standard methods. cDNA was synthesized from this mRNA using primers based in the CH1 domains of IgG, IgM and the Cκ domain. PCR amplification of this initial cDNA was then performed using standard methodologies, known to those skilled in the art, and sets of primers as described in U.S. application Ser. No. 07/841,648, filed Feb. 24, 1992 now abandoned and previously incorporated herein by reference (reference is also made to PCT patent publication WO92/01047, published Jan. 23, 1992. entitled "Methods for Producing Members of Specific Binding Pairs", as well as to PCT publications WO91/17271 and WO91/19818; and all of these PCT publications are hereby incorporated herein by reference). Two fd-phage expression libraries were generated, one from cDNA synthesized from the IgM specific primer and the other from cDNA synthesized from the IgG specific primer. These libraries contained $1.2 \times 10^6$ and $2.8 \times 10^6$ independent clones respectively. Phage particles expressing antibody fragments capable of binding to BK3 were selected by a "panning" procedure on a solid surface coated with BK3. 35 mm diameter petri dishes were coated with BK3 by evaporating a solution containing 15 µg of the compound in $CHCl_3$/MeOH (3:1 ratio) to dryness. The dishes were incubated with a 3% solution of dried milk in PBS for 1 hr to block non-specific binding then phage from the libraries incubated in them for 2–3 hrs at room temperature. After washing with PBS/0.1% Tween 20 and PBS, specific phage were eluted with 100 mM triethylamine in water and used to infect E coli TG1 cells. The resultant expanded phage population was further selected by repeating this procedure a total of three times. Phage particles isolated from the third round of panning were expanded again in TG1 cells and then plated out and single clones picked and used to infect individual cultures of bacteria. Supernatants from these cultures were analyzed for binding to BK3 coated plastic wells in a standard ELISA, well known to those skilled in the art (100 µl of phage supernatant was reacted with the antigen coated wells, binding was detected with sheep anti-fd serum). Ten clones from a total of 156 which were analyzed from the IgM library demonstrated strong binding to BK3 in this assay; four out of 240 analyzed from the IgG library did likewise. Thus, antibodies from these clones are useful for treating septicemia. Ten of these binders were further characterized.

The genetic diversity of the clones isolated in this way was investigated. The insert encoding the antibody chains was amplified by PCR and the product digested with the restriction enzyme BstN1, which cuts frequently in antibody gene sequences, and the resulting fragments analyzed on a 4% agarose gel. This analysis revealed that ten distinctly different antibody molecules had been selected from the library. Subsequent sequence analysis revealed the usage of three different Vκ genes, with one employed by 8 antibodies and two others by one antibody each. At least four different VH genes were used by the antibodies. The antibodies expressed by this method show binding and catalytic activity and are thus useful in treating septicemia. Screening for catalytic activity can be as described in U.S. application Ser. No. 07/841,648, filed Feb. 24, 1992.

Alternatively, splenocytes or peripheral blood lymphocytes from unimmunized animals or humans can be used as the source of immunoglobulin mRNA and libraries constructed as above.

Example 95

Preparation of Compound 80

Compound 5a,b (10 mmol) is dissolved in 50 mL of acetone and cooled to 0° C. Jones reagent is added until a red color persists, and the mixture is stirred at that temperature for 1 h. After completion of the reaction the acetone is evaporated in vacuo, and the residue is dissolved in ethyl acetate (100 mL) and washed with water (3×50 mL) until the organic layer becomes almost colorless. The organic layer is dried over anhydrous $MgSO_4$ and concentrated in vacuo. Purification by flash chromatography gives compound 80 as an oil.

Example 96

Preparation of Compound 81

1M Sodium methoxide in methanol (0.8 ml) is added to a mixture of compound 80 (10 mmol) and 30 mL of methanol, and the mixture is stirred at room temperature for 2 h. After completion of the reaction, the volatile components are evaporated in vacuo and the residue is filtered through a small pad of silica gel using ethyl acetate as eluent to afford the triol as an oil.

PTSA (0.1 g) is added to a mixture of the above triol (10 mmol), 2.2-dimethoxypropane (25 mmol), and 50 mL of methylene chloride, and the mixture is stirred at room temperature for 4 h. Then the reaction mixture is diluted with methylene chloride (70 mL) and washed with water (70 mL), 5% sodium bicarbonate (30 mL) and water (50 mL). The organic phase is dried over anhydrous $MgSO_4$ and concentrated in vacuo. Purification by flash chromatography gives the acetonide as an oil.

A mixture of the above acetonide (10 mmol), imidazole (22 mmol), and TBDMS-Cl (11 mmol) in 10 mL of DMF cooled to 0° C. is stirred until the starting material is consumed. The mixture is diluted with ethyl acetate (150 mL), washed with water (2×50 mL) and brine (50 mL), dried over anhydrous $MgSO_4$, and concentrated in vacuo. Purification by flash chromatography gives compound 81 as a colorless oil.

Example 97

Preparation of Compound 82

A solution of compound 81 (5 mmol) in benzyl alcohol (50 mmol) is heated at reflux until the starting material is consumed. After completion of the reaction, the excess benzyl alcohol is removed in vacuo. Purification by flash chromatography gives the hydroxy ester.

Triethylamine (5.5 mmol) is added to a mixture of methanesulfonyl chloride (5.5 mmol) and the above hydroxy ester (5.0 mmol) in 50 mL of THF cooled to 0° C. After the starting material is consumed, the mixture is partitioned between water (75 mL) and ethyl acetate (3×50 mL), and the organic phases are washed with brine (50 mL), dried over anhydrous $MgSO_4$, and concentrated in vacuo. Purification by flash chromatography gives the methanesulfonate as a colorless solid.

A mixture of the above methanesulfonate (5 mmol) and sodium iodide (10 mmol) in acetone (25 mL) is heated at reflux. After the starting material is consumed, the solvent is removed in vacuo, and purification by flash chromatography gives the product as a yellow oil.

A mixture of the above iodide (5 mmol) and sodium azide (15 mmol) in 10 mL of DMF is heated at 50° C. After completion of the reaction, the mixture is partitioned between water (75 mL) and ethyl acetate (3×50 mL), and the organic phases are washed with brine (50 mL), dried over anhydrous $MgSO_4$, and concentrated in vacuo. Purification by flash chromatography gives compound 82 as a colorless solid.

Example 98

Preparation of Compound 83

A suspension of compound 82 (5 mmol) and 5% Pd—C (0.5 mmol) in 25 mL of methanol is stirred under a hydrogen atmosphere. After the starting material is consumed, the catalyst is removed by filtration, and evaporation of the solvent in vacuo gives compound 83.

Example 99

Preparation of Compound 84

4-Nitrobenzaldehyde (5 mmol) is added to a solution of compound 83 (5 mmol) and triethylamine (5 mmol) in 25 mL of methylene chloride cooled to 0° C. After the starting material is consumed, the solvent is evaporated in vacuo, and the residue is partitioned between saturated sodium bicarbonate (30 mL) and ether (4×80 mL), the organic phases are dried over anhydrous potassium carbonate, and the solvent is evaporated in vacuo. Purification by flash chromatography gives compound 84 as an oil.

Example 100

Preparation of Compound 85

Tetra-n-butylammonium fluoride (1M solution in THF, 12 mmol) is added to a solution of compound 84 (5 mmol) in 35 mL of THF at room temperature. After the starting material is consumed, the mixture is washed with saturated sodium bicarbonate (2×10 mL), the aqueous phases are extracted with ether (2×20 mL), and the combined organic phases are dried over anhydrous potassium carbonate and concentrated in vacuo. Purification by flash chromatography gives compound 85 as an oil.

Example 101

Preparation of Compound 86

A solution of compound 85 (1 mmol), EDC (2.2 mmol), DMAP (2.2 mmol) and compound 3 (2.2 mol) in 20 mL of methylene chloride is stirred at room temperature until the starting materials are consumed. The mixture is poured into water (60 mL) and extracted with ethyl acetate (3×60 mL), and the organic phases are washed with brine (50 mL), dried over anhydrous MgSO$_4$, and concentrated in vacuo. Purification by flash chromatography gives compound 86 as a colorless oil.

Example 102

Preparation of Compound 87

Trifluoroacetic acid (3 mL) is added to a mixture of compound 86 (1 mmol) and 3 mL of methylene chloride cooled to 0° C. After 30 min, the acid is neutralized by the slow addition of triethylamamine while maintaining the temperature at 0° C. Then the mixture is poured carefully into saturated sodium bicarbonate (50 mL) and extracted with ethyl acetate (4×60 mL), and the organic phases are washed with brine (50 mL), dried over anhydrous MgSO$_4$, and concentrated in vacuo. Purification by flash chromatography gives the diol as a colorless oil.

A mixture of the above diol (1 mmol), imidazole (2.2 mmol), and TBDMS-Cl (1.1 mmol) in 2 mL of DMF cooled to 0° C. is stirred until the starting material is consumed. The mixture is diluted with ethyl acetate (40 mL), washed with water (2×10 mL) and brine (10 mL), dried over anhydrous MgSO$_4$, and concentrated in vacuo. Purification by flash chromatography gives the silyl ether as a colorless oil.

A solution of the above secondary alcohol (1 mmol), N,N-diisopropylamino dibenzylphosphite (2 mmol), and tetrazole (2 mmol) in 10 mL of methylene chloride is stirred under an argon atmosphere at room temperature. After the starting material is consumed, the mixture is cooled to 0° C. and m-CPBA (2 mmol) is added. After 2 h, the solvent is evaporated in vacuo. Purification by flash chromatography affords compound 87 as a colorless oil.

Example 103

Preparation of Compound 88

A 1M solution of triethyloxonium tetrafluoroborate in methylene chloride (1 mmol) is added to a solution of compound 87 (1 mmol) in 9 mL of methylene chloride cooled to 0° C. After 1 h, a solution of compound 71 (1.2 mmol) in 4 mL of methylene chloride is added. After completion of the reaction, the solvent is evaporated in vacuo, and purification by flash chromatography affords compound 88.

Example 104

Preparation of Compound 89

A suspension of compound 88 (0.1 mmol) and 5% Pd-C (10 weight percent) in 5 mL of ethyl acetate is stirred under a hydrogen atmosphere. After completion of the reaction, the catalyst is removed by filtration, the solvent is evaporated in vacuo, and the residue is taken up in 4.75 mL of acetonitrile in a plastic container. 48% Aqueous hydrofluoric acid (0.25 mL) is then added to the resulting mixture. After 1 h, the volatile components are evaporated in vacuo to give compound 89 as a solid.

Example 105

Figure 48:
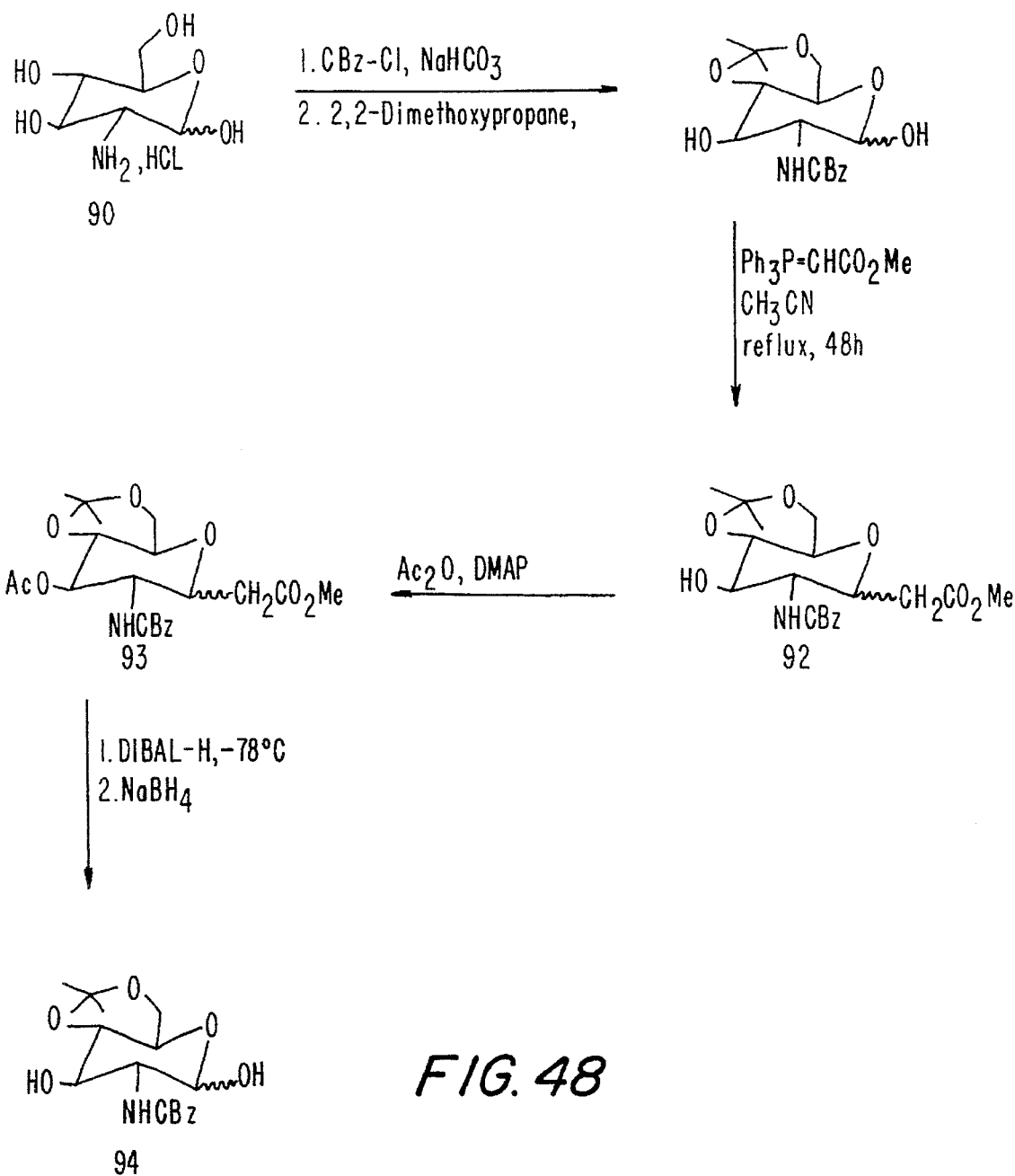

Synthesis of Compound 94 (Reaction Scheme 41; FIG. 48)

Compound 94 was synthesized starting with D-glucosamine hydrochloride 90; amino protection using benzyl chloroformate and sodium bicarbonate followed by acetonation using 2.2-dimethoxypropane and para-toluenesulfonic acid catalyst gave the protected glucosamine 91. Reaction of the aldo form of compound 91 with carbomethoxymethyltriphenylphosphorane in acetonitrile at reflux for 48 hours gave the C-glycoside 92 contaminated with triphenylphosphine oxide after purification by flash chromatography. The Wittig reaction proceeded with a selectivity of 3.5:1 favoring the α isomer. In order to obtain a better separation from the phosphine oxide and to separate the α and β isomers, the hydroxyl of compound 92 was acetylated and gave compound 93. Purification by flash chromatography using 30% ethyl acetate/hexane separated the phosphine oxide contaminant. Separation of the α and β isomers was achieved by flash chromatography using 2% methanol/methylene chloride. Reduction of compound 93 using 4 equivalents of DIBAL-H in methylene chloride at −78° C. resulted in complete deacetylation, as expected, but resulted in only partial reduction of the methyl ester; a mixture of the aldehyde and the alcohol resulted. The reduction was completed: the mixture was treated with sodium borohydride in methanol for 10 minutes which gave diol 94.

Example 106

Figure 49:
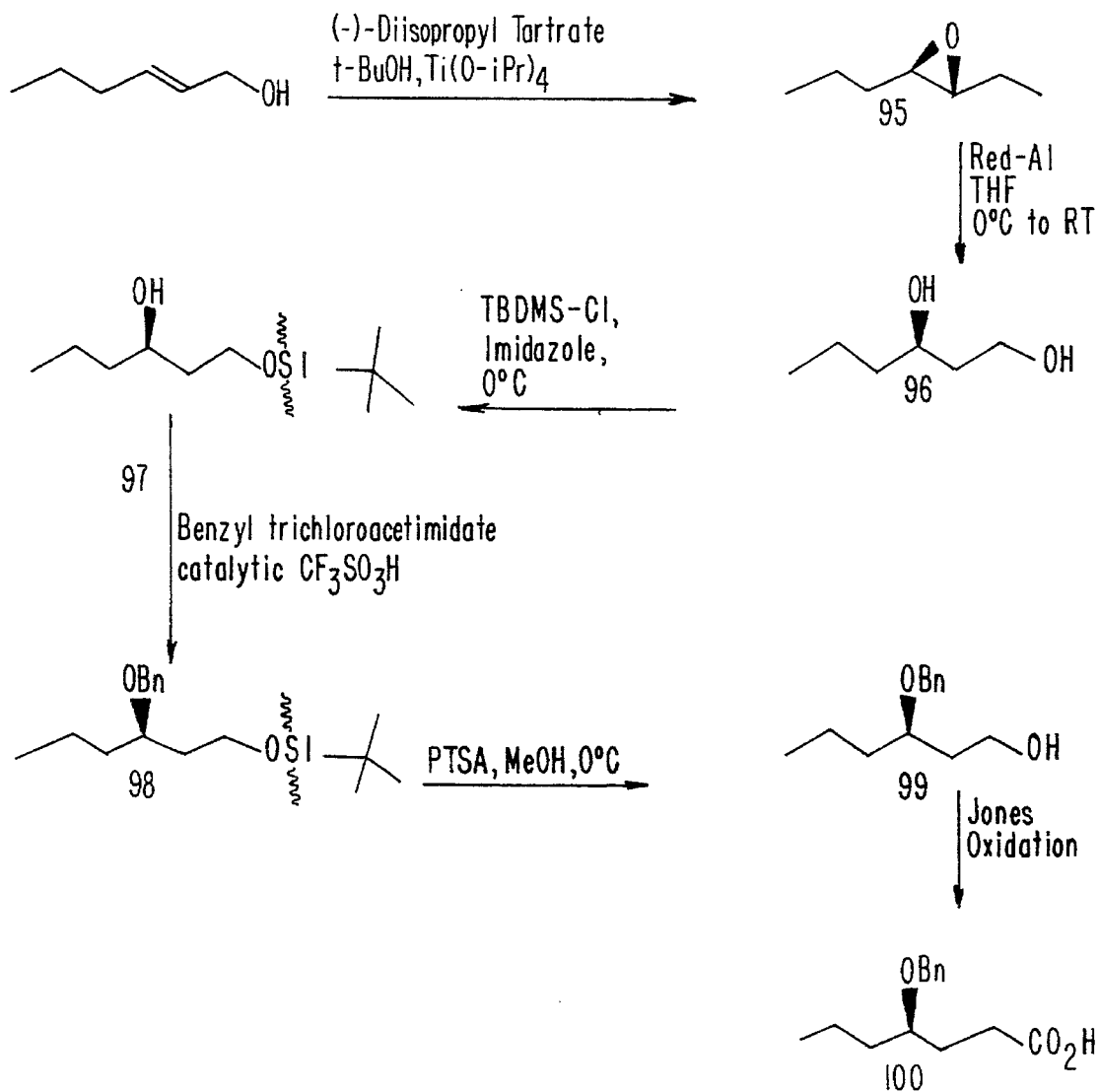

Synthesis of Compound 100 (Reaction Scheme 42; FIG. 49)

(R)-3-Benzyloxyhexanoic acid, compound 100, was synthesized starting from trans-2-hexen-1-ol. A Sharpless asymmetric epoxidation with (−)-diisopropyl tartrate was utilized to introduce the chiral center of epoxide 95. Red-Al reduction of the epoxide gave (R)-1,3-hexanediol, compound 96, selectively in good yield. The primary hydroxyl of diol 96 was selectively silylated under standard conditions to give alcohol 97. The remaining hydroxyl was benzylated using benzyl trichloroacetimidate and catalytic trifluoromethanesulfonic acid which gave compound 98. The primary hydroxyl was deprotected using acidic methanol which gave alcohol 99, which was oxidized to the acid 100 using Jones reagent.

Example 107

Figure 50:
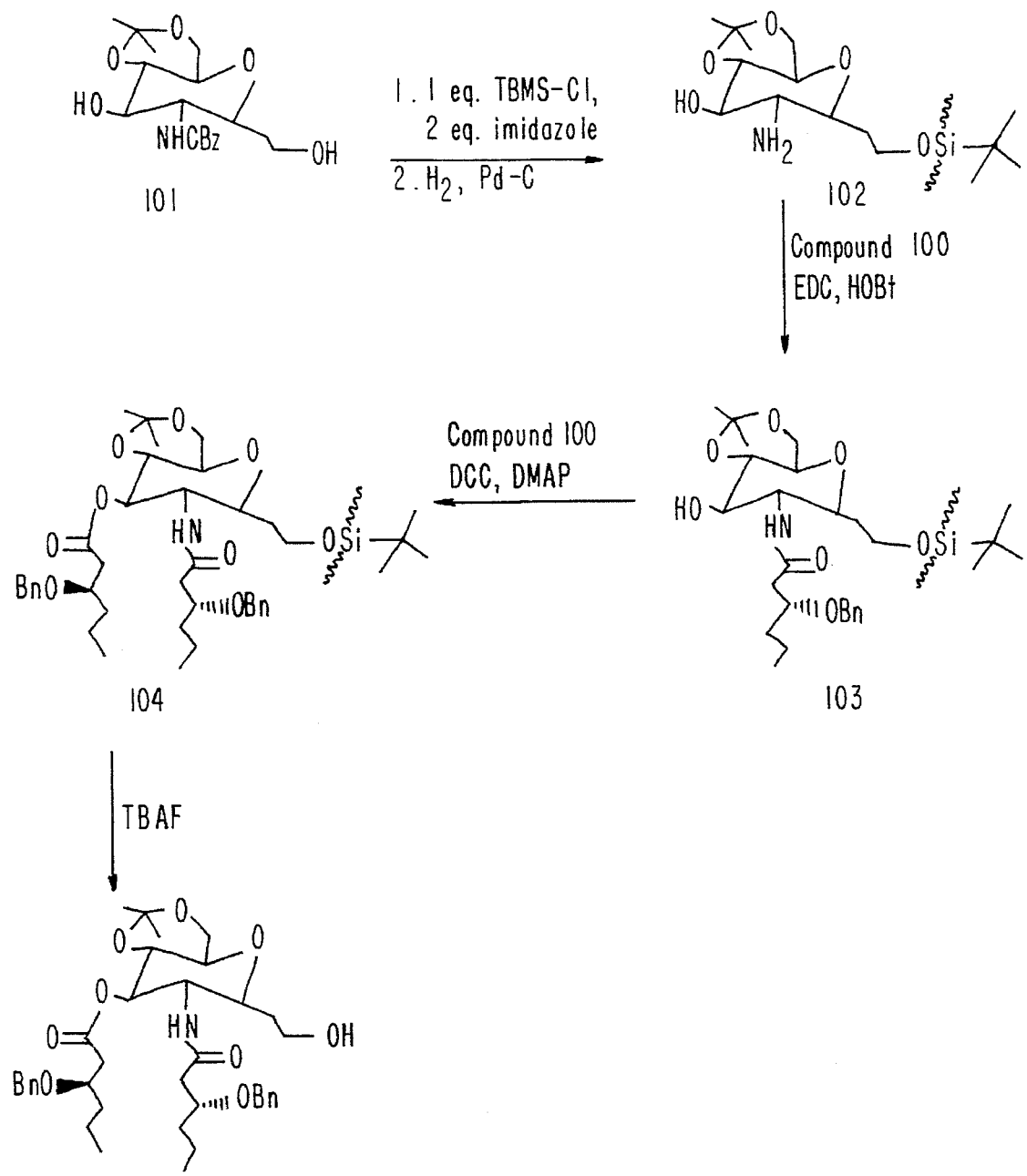
Figure 51:
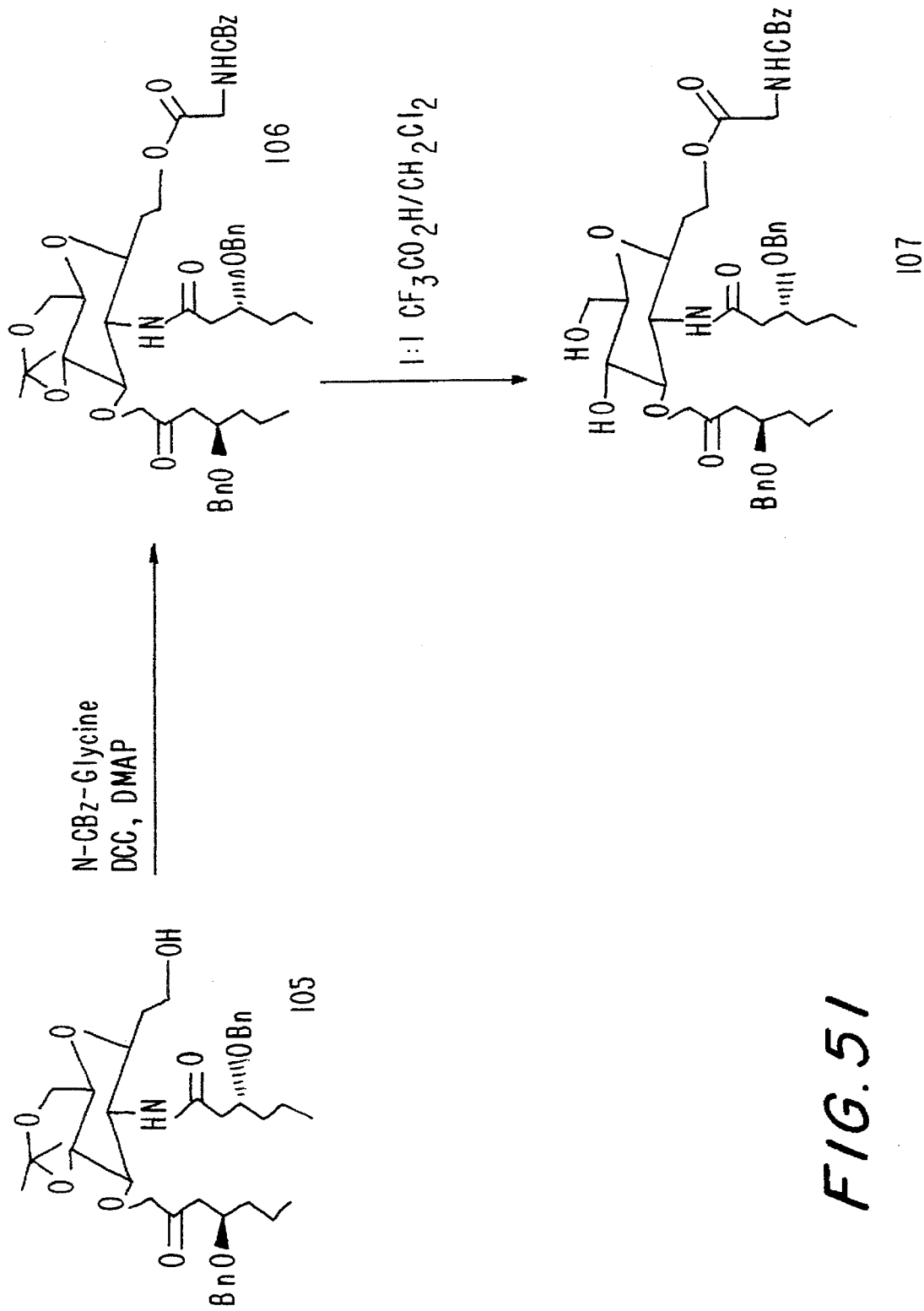

Preparation of Compound 107 (Reaction Schemes 43a, 43b; FIGS. 50,51)

The primary alcohol functionality of the diol 101 was selectively protected as the t-butyldimethyl silyl ether and the CBZ group was removed by catalytic hydrogenation which afforded the amino compound 102. Subsequent condensation of 102 with acid 100 using EDC yielded compound 103. Further acylation of 103 using acid 100. EDC and DMAP gave the fully protected compound 104. Removal of the silyl group was performed using tetrabutylammonium fluoride in THF which afforded the hydroxy compound 105. Acylation of 105 with N-CBZ-Glycine using DCC and DMAP gave compound 106. The diol 107 was prepared by the acid hydrolysis of 106 with trifluoroacetic acid.

Example 108

Figure 52:
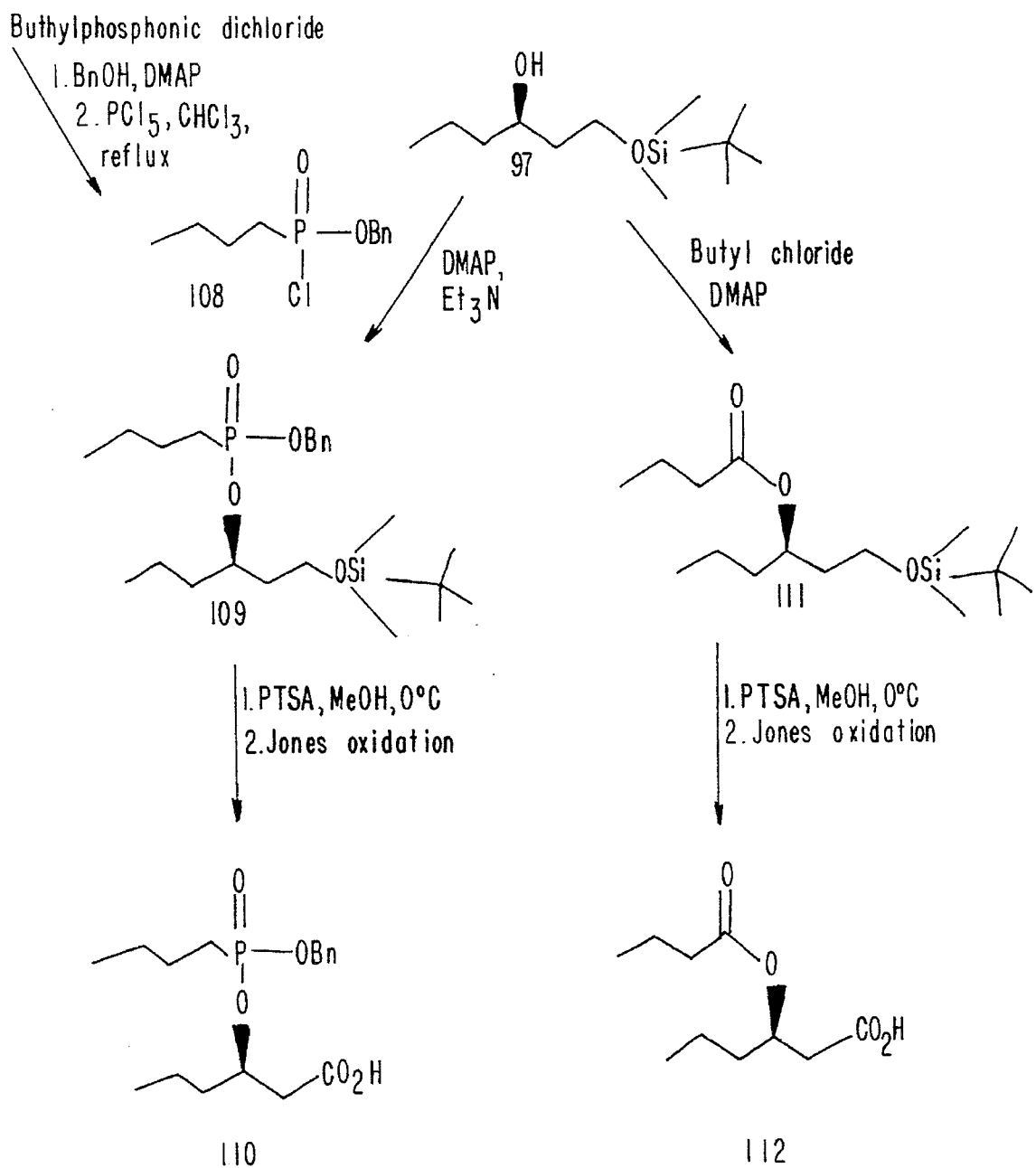

Preparation of Compounds 110 and 112 (Reaction Scheme 44; FIG. 52

The syntheses of acids 110 and 112 originated from the same chiral intermediate, alcohol 97. Butylphosphonic dichloride was reacted with DMAP and excess benzyl alcohol. The resultant dibenzyl ester was reacted with 1.1 equivalents of phosphorus pentachloride in chloroform at reflux which gave monochloridate 108. Compound 108 was reacted with alcohol 97 and base which gave compound 109. Compound 109 was desilylated using acidic methanol at 0° C. and the resultant alcohol was oxidized to the acid 110 using Jones reagent. In a similar manner, alcohol 97 was acylated using butyryl chloride and DMAP which gave compound 111. Careful acidic methanolysis of the TBDMS ether at 0° C. was carried out in order to minimize 1,3-acyl migration and, the resultant primary alcohol was oxidized using Jones reagent which afforded acid 112.

Example 109

Figure 53:
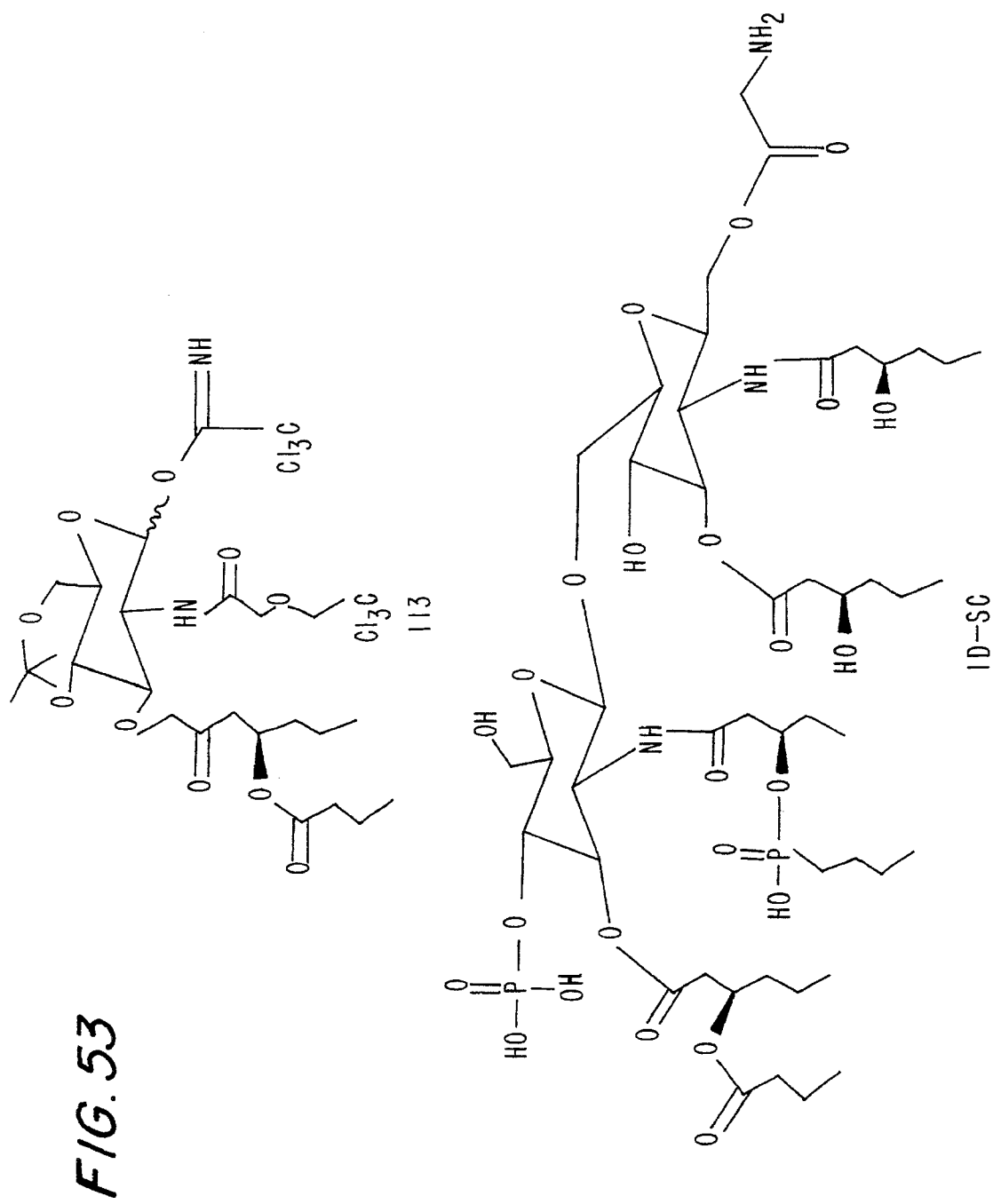

Preparation of Compound 1D-SC (FIG. 53)

The synthesis of 1D-SC (FIG. 53) followed essentially the same chemical steps as the synthesis of ID (Scheme 27). The difference in the two syntheses was the types of reagents used. For compound ID-SC., the acid 112 (Scheme 44) was used instead of compound 3 (Scheme 24), and for disaccharide formation, Compound 113 (shown in FIG. 53) was coupled to 107 rather than 41 (Scheme 25). For the acylation of the amino group of the disaccharide, compound 110 (Scheme 41) was used instead of 4 (Scheme 26). Confirmation of the synthesis was provided by $^1$H NMR analysis.

Having thus described in detail preferred embodiments of the present invention, it is to be understood that the invention defined by the appended claims is not to be limited by particular details set forth in the above-description as many apparent variations thereof are possible without departing from the spirit or scope of the present invention.

References

1. Maki, D. G., In *Nosocomial Infections*. R. E. Dixon (Ed.), p. 183–196, 1981.
2. Kreger, B. E., D. E. Craven, and W. R. McCabe. Am. J. Med. 68: 344–355, 1980.
3. Cohen, C. J., R. A. Janis, D. G. Taylor et al. In Calcium Antagonist and Cardiovascular Disease, 1984.
4. Waage, A., P. Brandtzaeg, A. Halstensen et al. J. Exp. Med. 169: 333–338, 1989.
5. Shenep, J. L., R. P. Barton and K. A. Mogan. J. Infect. Dis. 151: 1012–1018, 1985.
6. Ziegler, E. J., Fisher, C. J., Sprung, C. L., Straube, R. C., Sadoff, J. C., Foulke, G. E., Wortel, C. H., Fink, M. P., Dellinger, R. P., Teng, N. N. H., Allen, I. E., Berger, H. J., Knatterud, G. L., Lobuglio, A. F. & Smith, C. R. N Engl J Med 324,429–436 (1991).
7. Greenman, R. L., Schein, R. M. H., Martin, M. A., Wenzel, R. P., Macintyre, N. R., Emmanuel, G., Chmel, H., Kohler, R. B., arthy, M., Plouffe, J. & Russell, J. A. JAMA-J Am Med Assoc 266, 1097–1102 (1991).
8. Alving, C. R., (1991) J. Immunol. Meth. 140, 1–13.
9. Alving, C. R. & Richards, R. L. (1990) Immunol. Lett. 25, 275–280.
10. Schuster, B. G. et al. (1979) J. Immunol. 122, 900–905.
11. Frisch, B. et al. (1991) Eur. J. Immunol. 21, 185–193.
12. Mccafferty, J., Griffiths, A. D., Winter, G. & Chiswell, D. J. Nature 348, 552–554 (1990).
13. Clackson, T., Hoogenboom, H. R., Griffiths, A. D. & Winter, G. Nature 352, 624–628 (1991).
14. Huse, W., Sastry, L., Iverson, S., Kang, A., Altingmees, M., Burton, D., Benkovic, S. and Lerner, R Science 246, 1275–1281 (1989).
15. Pauling, L. Am. Sci. 36:51, 1948.
16. Jencks, W. P. Adv. Enzymol. 43:219, 1975.
17. Fersht, A. R., and A. J. Kirby. J. Am. Chem. Soc. 90:5833, 1968.
18. Lerner, R. A., Benkovic, S. J. & Schultz, P. G. Science 252. 659–667 (1991).
19. Buchner, H. Berl Klin Wochenschr 1980, 47, 1084.
20. Coley, W. B, Inoperable sarcoma cured by mixed toxins of erysipelas and Bacillus prodigiosus. *JAMA* 1988, 31, 389–95 & 456–65.
21. Westphal, O, Luderitz, O, Eichenberger, E, and Keiderling, W. Z, Naturforsch 1952, 76, 536.
22. Westphal, O, Luderitz, O, Eichenberger, E, and Neter, E, Chemistry and biology of Mucopolysaccharides 1958, 187.
23. Luderitz, O, Westphal, O, Staub, A. M, and Nikaido, H. Microbial Toxins 1971, 4, 145.
24. Galanos, C., Reitschel, E. T., Luderittz, O., Westphal, O., Kim, Y. B, and Watson, D. W., Biological activities of lipid A complexed with BSA, Eur, J. Biochem. 1972, 31, 230, 25. Galanos, C., Reitschel, E. T, Luderittz, O, and Westphal, O, Intern Rev Biochem, Biochemistry of Lipids II, T. W. Goodwin(ed) University Park Press 1977, 14, 239.
26. Nowotny, A., Beneficial effects of endotoxins. A Nowotny (Ed). Plenum Press: New York/London 1983, 1–55.
27. Inage, M., Chaki, H., Kusumoto, S., Shiba, T., Tai, A., Nakahata, M., Harada, T. and Izumi, Y. Chem. Lett. 980, 1373–6.
28. Kiso, M., Nishiguchi, H., Nishihori, K., Hasegawa, A. and Miura, I., Carbohydrate research. 1981, 88, C10.
29. Szabo, P., Sarfati, S, R., Diolez, C. and Szabo, L., Carbohydrate Res. 1983, 111, c9–c12
30. Charon, D. and Szabo Carbohydrate Res. 1983, 111, C9. Ibid 1983, 111, C13–C15.
31. Inage, M., Chaki, H., Kusumoto, S., and Shiba, T. Tetrahedron lett 1980, 21, 3889.
32. Inage, M., Chaki, H., Kusumoto, S., Shiba, T. Tetrahedron lett. 1981, 22, 2281.
33. Inage, M., Chaki, H., Imoto, M., Shimamoto, T., Kusumoto, S., and Shiba, T. Tetrahedron lett 1983, 24, 2011.
34. Erwin, L. A. and Munford, S. R., J. of Biol. Chem. 1990, 265, 16444.
35. Hall, C. L. and Munford, R. S. Proc. Nat. Acad. Sci. 1983, 80, 6671.
36. Munford, R. S. and Hall, C. L., Science 1986, 234, 203.
37. Munford, R. S. and Hall, C. L. (1985) Infect. Immun. 48, 464–473.
38. Luderitz, O. C., Galanos, C., and Rietschel, E., Pharmacology of Bacterial Toxins, Dolmer, F. and Drews, J. (Eds.) 1986.
39. Takayama, K., Quershi, N., Ribi, E., and Cantrell, J. L., Rev. Infec. Dis. 1984, 6, 439.
40. Kumazawa, Y., Takimoto, H., Yamamoto, A., Homma, J, Y., Ogawa, Y., Kiso, M., and Hasegawa, A., FEBS lett 1988, 239, 117.
41. Matsuura, M., Kojima, Y., Homma, J. Y., Kubota, Y., Shibukawa, N., Shibata, M., Inage, M., Kusumoto, S. and Shiba T. Eur. J. Biochem. 1983, 137, 639.
42. Matsuura, M., Kojima, Y., Homma, J. Y., Kumazawa, Y., Kubota, Y., Shiba, T and Kusumoto, S., Bacterial Endotoxin Chemical, Biological and Clinical Aspects, Homma, Y. J., et al 1984, 61. (verlag Chemie).
43. Kumazawa, Y., Matsuura, M., Nakatsuuru-Watanabe, Y., Fukumoto, M., Nishimura, C., Homma, J. Y., Inage, M., Kusumoto, S., and Shiba, T., Eur. J. Immunol, 1984, 14, 109.
44. Yasuda, T., Kanegasaki, S., Tsumita, T., Tadakuma, T., Ikewaki, N., Homma, J. Y., Inage, M., Kusumoto, S., and Shiba, T., Eur. J. Biochem. 1984, 140, 245.
45. Kotani, S., Takada, H., Tsujimoto, M., Ogawa, T., Mori, Y., Sakuta, M., Kawasaki, A., Inage M., Kusumoto, S., Shiba, T. and Kasai, N. Infec. Immunity. 1983, 41, 758.
46. Tanamoto, K., Zahringer, U., Mckenzie, G. R., Galanos, C., Rietschel, E. Th., Luderitz, O., Kusumoto, S., and Shiba, T., Infec. Immunity 1984, 44, 421.
47. Imoto, M., Kusumoto, S., Shiba, T., Naoki, H., Iwashita, T., Rietschel, E. T., Wollenweber, H. W., Galanos, C. and Luderitz, O. Tetrahedron Lett 1983, 24, 4017
48. Imoto M., Kusumoto, S., Shiba, T., Rietschel, E, T., Galanos, C., and Luderitz, O., Tetrahedron Lett 1985, 26, 907.
49. Strain S, m., Fesik, S, W., Armitage, I. M., J. Biol. Chem 1983, 258, 2906.
50. Kanegasaki, S., Kojima, Y., Matsuura, M., Homma, J. Y., Yamamoto, A., Kumazawa, Y., Tanamoto, K., Tsumita, T., Imoto, M., Yoshimura, H., Yamamoto, M., Shimamoto, T., Kusumoto, S., and Shiba, T., Eur. J. Biochem. 1984, 143, 237.
51. Kotani, S., Takada, H., Tsujimoto, M., Ogawa, T., Harada, K., Mori, Y., Kawasaki, A., Tanaka, A., Nagao, S., Tanaka, S., Shiba, T., Kusumoto, S., Imoto, M., Yoshimura, M., and Shimamoto, T., Infec. Immunity 1984, 45, 293.
52. Galanos, C., Lehman, V., Luderitz, O., Rietschel, E, T., Westphal, O., Brade, H., Brade, L., Freudenberg, M. A., Hansen-Hagge, T., Luderitz, T., Mckenzie, G., Schade, U., Strittmater, W., Tanamoto, K., Zahringer, U., Imoto, M., Yoshimura, H., Yamamoto, M., Shimamoto, T., Kusumoto, S., and Shiba, T., Eur J Biochem 1984, 140, 221.
53. Imoto, M., Yoshimura, H., Kusumoto, S., Shiba, T., Proc Jpn Acad 1984, 60B, 285.
54. Kusumoto, S., Yoshimura, H., Imoto, M., Shimamoto, T., and Shiba, T., Tetrahedron lett 1985, 26, 909.
55. Imoto, M., Yoshimura, H., Sekiguchi, N., Kusumoto, S., and Shiba, T., Tetrahedron lett 1985, 26, 1545.
56. Homma, J, Y., Matsuura, M., Kanegasaki, S., Kawakubo, Y-, Kojima, Y-, Shibukawa, N., Kumazawa, Y., Yamamoto, A., Tanamoto, K., Yasuda, T., Imoto, M., Yoshimura, H., Kusumoto, S., and Shiba, T., J. Biochem. 1985, 98, 395.
57. Kotani, S., Takada, H., Tsujimoto, m., Ogawa, T., Takahashi, I., Ikeda, T., Otsuka, K., Shimauchi, H., Kasai, N., Mashimo, J., Nagao, S., Tanaka, A., Tanaka, S., Harada, K., Nagaki, K., Kitamura, H., Shiba, T., Kusumoto, S., Imoto, M., and Yoshimura, H., Infec Immunity 1985, 49, 225.
58. Galanos, C., Luderitz, O., Rietschel, E, T., Westphal, O., Brade, H., Brade, L., Freudenberg, M., Schade, U., Imoto, M., Yoshimura, H., Kusumoto, S., and Shiba, T., Eur J Biochem 1985, 148, 1.
59. Kanegasaki, S., Tanamoto, K., Yasuda, T., Homma, J, Y., Matsuura, M., Nakatsuka, M., Kumazawa, Y., Yamamoto. A., Shiba, T., Kusumoto, S., Imoto, M., Yoshimura, H., and Shimamoto, T., J Biochem 1986, 99, 1203.
60. Takada, H., Kotani, S., Tanaka, S., Ogawa, T., Takahashi, I., Tsujimoto, M., Komuro, T., Shiba, T., Kusumoto, S., Kusunose, N., Hasegawa, A., and Kiso, M., Eur J Biochem 1988, 175, 573.
61. Kotani, S., Takada, H., Takahashi, I., Tsujimoto, M., Ogawa, T., Ikeda, T., Harada, K., Okamura, H., Tamura, T., Tanaka, S., Shiba, T., Kusumoto, S., Imoto, M., Yoshimura, H., and Kasai, N., Infect immunity 1986, 52, 872.
62. Galanos, C., Luderitz, O., Freudenberg, M., Brade, L., Schade, U., Rietschel, E, Th., Kusumoto, S., and Shiba, T., Eur J Biochem 1986, 160, 55.
63. Kiso, M., Ishida, H., and Hasegawa, A., Agri. Biol. Chem. 1984, 48, 251.
64. Kiso, M., and Hasegawa., Bacterial Endotoxin-Chemical, Biological And Clinical aspects, Homma, Y. J., Kanegasaki, O., Luderitz, O., Shiba, T., and Westphal (Eds), 1984, 39. (verlag Chemie)
65. Kiso, M., Tanaka, S., Tanahashi, M., Fujishima, Y., Ogawa, Y., and Hasegawa, A., Carbohydrate Research 1986, 148, 221.
66. Matsuura, M., Kojima, Y., Hommma, J, Y., Kubota, Y., Yamamoto, A., Kiso, M., and Hasegawa, FEBS lett 1984, 167, 226.
67. Kumazawa, Y., Matsuura, M., Homma, J. Y., Nakatsuru, Y., Kiso, M., and Hasegawa, A., Eur. J. Immunol 1985, 15, 199.
68. Matsuura, M., Yamamoto, A., Kojima, Y., Homma, J, Y., Kiso, M., Hasegawa, A., J. Biochem 1985, 98, 1229.
69. Matsuura, M., Kojima, Y., Homma, J, Y., Kumazawa, Y., Yamamoto, A., Kiso, M., and Hasegawa, A., J. Biochem 1986, 99, 1377.

70. Kumazawa, Y., Ikeda, S., Takimoto, H., Nishimura, C., Nakatsuka, M., Homma, J, Y., Yamamoto, A., Kiso, M., and Hasegawa, A., Eur. J. Immunol 1987, 17, 663.
71. Kumazawa, Y., Matsuura, M., Maruyama, T., Homma, J, Y., Kiso, M., and Hasegawa, A., Eur. J. Immunol 1986, 16, 1099.
72. Ikeda, S., Kumuzawa, Y., Nishimura, C., Nakatsuka, M., Homma, J. Y., Kiso, M., and Hasegawa, A., Antiviral Res 1988, 10, 167.
73. Kiso, M., Tanaka, S., Fujishima, M., Ogawa, Y., and Hasegawa, A., Carbohy. Res 1987, 162, 247.
74. Kumazawa, Y., Nakatsuka, M., Takimoto, H., Furuya, T., Nagumo, T., Homma, J, Y., Yamamoto, A., Inada, K., Yoshida, M., Kiso, M., and Hasegawa, A., Infec Immunity 1988, 56, 149.
75. Kiso, M., Tanaka, S., Fujita, M., Fujishima, Y., Ogawa, Y., Ishida, H., and Hasegawa, a., Carbohy. Res 1987, 162, 127.
76. Homma, J, Y., Matsuura, M., and Kumuzawa, Y., Drugs of the future 1989, 14, 645.
77. Ikeda, S., Nishimura, C., Nakatsuka, M., Homma, J, Y., Kiso, M., and Hasegawa., Antiviral Res 1988, 9, 37.
78. Ikeda, S., Kumazawa, Y., Nishimura, C., Nakatsuka, M., Homma, J, Y., Kiso, M., and Hasegawa, A., Int J Immunopharmacol 1988, 10, 331.
79. Nakatsuka, M., Kumazawa, Y., Ikeda, S., Yamamoto, A., Nishimura, C., Homma, J, Y., Kiso, M., and Hasegawa, A., J Cli Lab Immunol 1988, 26, 43.
80. Takayama, K., Qureshi, N., Mascagni, P., Anderson, L., and Raetz, C., R, H., J Biol Chem 1983, 258, 14245.
81. Shimizu, T., Akiyama, S., Masuzawa, T., Yanagihara, Y., Nakamoto, S., Takahashi, T., Ikeda, K., and Achiwa, K., Chem Pharm Bull 1986, 34, 5169.
82. Shimizu, T., Akiyama, S., Masuzawa, T., Yanagihara, Y., Nakamoto, S., Takahashi, T., Ikeda., K., Achiwa, K., Chem. Pharm. Bull. 1985, 33, 4621.
83. Shimizu, T., Akiyama, S., Masuzawa, T., Yanagihara, Y., Nakamoto, S., and Achiwa, K., Infec Immunity 1987, 55, 2287.
84. M., Fujita, M., Hayashi, E., and Hasegawa, A., J. Carbohy Chem 1987, 6, 691.
85. Kiso. M., Fujita, M., Tanahashi, M., Fujishima, Y., Ogawa, Y., and Hasegawa, A., Carbohy. Res 1988, 177, 51.
86. Brade, 1., Rietschel, E, Th., Kusumoto,. S., Shiba, T., and Brade, H., Infec Immunity 1986, 51, 110,
87. Brade, L., Bradenberg, K., Kuhn, H.-M., Kusumoto, S., Macher, I., Rietschel, E, T., and Brade, H., Infec. Immunity. 1987, 55, 2636.
88. Kasai, N., Arata, S., Mashimo, J., Okuda, K., Aihara, Y., Kotani, S., Takada, H., Shiba, T., and Kusumoto, S., Biochem. Biophys. Res. Commun 1985, 28, 607.
89. Kasai, N., Arata, S., Mashimo, J., Okuda, K., Aihara, Y., Kotani, S., Takada, H., Shiba, T., Kusumoto, S., Imoto, M., Yoshimura, H., and Shimamoto, T., Infec Immunity 1986, 51, 43.
90. Arata, S., Mashimo, J-, Kasai, N., Okuda, K., Aihara, Y., Hasegawa, A., and Kiso, M., FEMS Microbiol lett 1987, 44, 231.
91. Arata, S., Mashimo, J., Kasai, N., Okuda, K., Aihara, Y., Kotani, S., Takada, H., Shiba, T., Kusumoto, S., Shimamoto, T., and Kusunose, N., FEMS Microbiol lett 1988, 49, 479.
92. Adorini, L. et al. (1988) Proc. Natl. Acad. Sci. USA 85, 5181–5185.
93. Lemieux, U. R., and Ratcliffe, M. R., Can. J. Chem. 1979, 57, 1244.
94. Ketchan, Jambotkar, and Martinelli., J. Org. Chem. 1962, 27, 4666.
95. Nagaoka, H., and Kishi, Y., Tetrahedron 1981, 37, 3873.
96. Katsuki, T., and Sharpless., J. Am. Chem. Soc, 1980, 102, 5974.
97. Martin, S. V., Woodard, S. S., Katsuki, Y., Yamada, M., Ikeda, M., and Shapless, K. B., J. Am. Chem. Soc. 1981, 103, 6237.
Finam, M. J., and Kishi, Y., Tetrahedron lett, 1982, 23, 2714.
98. Inage, M., Chaki, H., Kusumoto, S., and Shiba, T., Chem. Lett 1982, 1281.
100. Carr, C. J. & Morison, D. Rev. Inf. Dis. 6, 497–500 (1984).
101. Galanos, C., Luderitz, O. & Westphal, O. Eur. J. Biochem. 24, 116–122 (1971).
102. Teng, N. H., Kaplan, H. S., Hebert, J. M., Moore, C., Douglas, H. & Braude, A. I. Proc. Natl. Acad. Sci. USA 82, 1970 (1985).
103. Nakatsuka, M., Ikeda, S., Kumazawa, Y., Matsuura, M., Nishimura, C., Homma, J. Y., Kiso, M. & Hasegawa, A. International Journal of Immunopharmacology 12, 599–603 (1990).)
104. Nakatsuka, M., Kumazawa, Y., Homma, J. Y., Kiso, M. & Hasegawa, A. Int J Immunopharmacol 13, 11–19 (1991).
105. Jeannin, J. F., Onier, N., Lagadec, P., Vonjeney, N., Stutz, P. & Liehl, E. Gastroenterology 101, 726–733 (1991).
106. Quereshi et al. (1991) Infecn. and Immun. 59, 441–444.
107. Flick and Gifford (1984) J. Immun. Meth. 68, 167–75
108. Golenbock, D. T., Hampton, R. Y., Qureshi, N., Takayama, K. & Raetz, C. R. H. J Biol Chem 266, 19490–19498 (1991).

We claim:

1. A compound of the formula wherein each of $R_a$, $R_b$, $R_c$, $R_d$, and $R_e$ and $R_f$, independent of each other, is a branched or linear, substituted or unsubstituted $C_{1-11}$ alkyl, alkene or alkyne group, and E is NH or O.

2. The compound of claim 1 wherein each of $R_a$, $R_b$, $R_c$, $R_d$, $R_e$ and $R_f$ is $C_{11}H_{23}$.

3. The compound of claim 2 wherein E is NH.

4. The compound of claim 2 wherein E is O.

5. A method for eliciting antibodies in an animal which bind to Lipid A or LPS comprising administering to the animal, as an immunogen a composition comprising a compound as claimed in any one of claims 1–4.

6. A composition comprising a suitable carrier and a compound as claimed in anyone of claims 1–4.

* * * * *